(12) United States Patent
Carey et al.

(10) Patent No.: US 7,527,942 B2
(45) Date of Patent: May 5, 2009

(54) TRANSCRIPTION AMPLIFICATION SYSTEM FOR MOLECULAR IMAGING

(75) Inventors: Michael F. Carey, Sherman Oaks, CA (US); Lily Wu, Northridge, CA (US); Sanjiv Gambhir, Los Angeles, CA (US); Meera Iyer, Newbury Park, CA (US); Joanne Zhang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 122 days.

(21) Appl. No.: 10/503,642

(22) PCT Filed: Feb. 7, 2003

(86) PCT No.: PCT/US03/03847

§ 371 (c)(1),
(2), (4) Date: May 21, 2005

(87) PCT Pub. No.: WO03/066883

PCT Pub. Date: Aug. 14, 2003

(65) Prior Publication Data
US 2006/0223141 A1    Oct. 5, 2006

Related U.S. Application Data

(60) Provisional application No. 60/355,300, filed on Feb. 8, 2002.

(51) Int. Cl.
C12P 21/02 (2006.01)
(52) U.S. Cl. .............. 435/69.1; 435/320.1; 435/252.33; 435/254.11; 435/325; 536/24.1
(58) Field of Classification Search .................. None
See application file for complete search history.

(56) References Cited

U.S. PATENT DOCUMENTS 6,432,705 B1    8/2002    Yee et al.

FOREIGN PATENT DOCUMENTS

| WO | WO 99/28469 A1 | 6/1999 |
|----|----------------|--------|
| WO | WO 00/31286 A1 | 6/2000 |

OTHER PUBLICATIONS

Burcin, Mark M. et al.; "Adenovirus-mediated regulable target gene expression in vivo"; 1999, *PNAS*, vol. 96, pp. 355-360.
Emami, K.H. et al., "A Synergistic Increase in Potency of a Multimerized VP16 Transcriptional Activation Domain," *The EMBO Journal*, 1992, vol. 11, No. 13, pp. 5005-5012.
Gambhir, S.S. et al., "Imaging of Adenoviral-Directed Herpes Simplex Virus Type 1 Thymidine Kinase Reporter Gene Expression in Mice With Radiolabeled Ganciclovir," *The Journal of Nuclear Medicine*, Nov. 1998, vol. 39, No. 11, pp. 2003-2011.
Gambhir, S.S. et al., "Imaging Adenoviral-Directed Reporter Gene Expression in Living Animals With Positron Emission Tomography," *Proc. Natl. Acad. Sci. USA*, Mar. 1999, vol. 96, pp. 2333-2338.
Ilagan, R. et al., "Imaging Androgen Receptor Function During Flutamide Treatment in the LAPC9 Xenograft Model," *Mol. Cancer Ther.*, Nov. 2005, vol. 4, No. 11, pp. 1662-1669.
Ilagan, R. et al., "Imaging Mitogen-Activated Protein Kinase Function in Xenograft Models of Prostate Cancer," *Cancer Research*, Nov. 15, 2006, vol. 66, No. 22, pp. 10778-10785.
Iyer, M. et al., "Two-Step Transcriptional Amplification as a Method for Imaging Reporter Gene Expression Using Weak Promoters," *PNAS*, Dec. 4, 2001, vol. 98, No. 25, pp. 14595-14600.
Iyer, M. et al., "Noninvasive Imaging of Enhanced Prostate-Specific Gene Expression Using a Two-Step Transcriptional Amplification-Based Lentivirus Vector," *Molecular Therapy*, Sep. 2004, vol. 10, No. 3, pp. 545-552.
Iyer, M. et al., "Applications of Molecular Imaging in Cancer Gene Therapy," *Current Gene Therapy*, 2005, vol. 5, No. 6, pp. 607-618.
Iyer, M. et al., "Non-Invasive Imaging of a Transgenic Mouse Model Using a Prostate-Specific Two-Step Transcriptional Amplification Strategy," *Transgenic Research*, 2005, vol. 14, pp. 47-55.
Köster, R.W. et al., "Tracing Transgene Expression in Living Zebrafish Embryos," *Developmental Biology*, 2001, vol. 233, pp. 329-346.
Latham, J.P.F. et al., "Prostate-Specific Antigen Promoter/Enhancer Driven Gene Therapy for Prostate Cancer: Construction and Testing of a Tissue-Specific Adenovirus Vector," *Cancer Research*, Jan. 15, 2000, vol. 60, pp. 334-341.
Nettelbeck, D.M. et al., "A Strategy for Enhancing the Transcriptional Activity of Weak Cell Type-Specific Promoters," *Gene Therapy*, 1998, vol. 5, pp. 1656-1664.
Nettelbeck, D.M. et al., "Gene Therapy Designer Promoters for Tumor Targeting," *TIG*, Apr. 2000, vol. 16, No. 4, pp. 174-181.
Potter, H. et al., "Enhancer-Dependent Expression of Human K Immunoglobulin Genes Introduced into Mouse Pre-B Lymphocytes by Electroporation," *Proc. Natl. Acad. Sci. USA*, Nov. 1984, vol. 81, pp. 7161-7165.
Ray, P. et al., "Monitoring Gene Therapy With Reporter Gene Imaging," *Seminars in Nuclear Medicine*, Oct. 2001, vol. XXXI, No. 4, pp. 312-320.
Ray, S. et al., "Novel Bidirectional Vector Strategy for Amplification of Therapeutic and Reporter Gene Expression," *Human Gene Therapy*, Jul. 2004, vol. 15, pp. 681-690.

(Continued)

*Primary Examiner*—James S Ketter
(74) *Attorney, Agent, or Firm*—Townsend and Townsend and Crew LLP

(57) ABSTRACT

The present invention provides a transcription amplification system, comprising an effector nucleic acid molecule and a reporter molecule, which work together to produce a heterologous gene product in a cell-type, specific manner. The present invention also relates to methods for producing, detecting, imaging, and monitoring the heterologous gene product in a cell or in a subject.

32 Claims, 60 Drawing Sheets

OTHER PUBLICATIONS

Rehemtulla, A. et al., "Rapid and Quantitative Assessment of Cancer Treatment Response Using In Vivo Bioluminescence Imaging," *Neoplasia*, 2000, vol. 2, No. 6, pp. 491-495.

Sadeghi, H. et al., "Transciptionally Targeted Adenovirus Vectors," *Current Gene Therapy*, 2005, vol. 5, No. 4, pp. 411-427.

Segawa, T. et al., "Prostate-Specific Amplification of Expanded Polyglutamine Expression: A Novel Approach for Cancer Gene Therapy," *Cancer Research*, Jun. 1, 1998, vol. 58, pp. 2282-2287.

Tjuvajev, J.G. et al., "Noninvasive Imaging of Herpes Virus Thymidine Kinase Gene Transfer and Expression: A Potential Method for Monitoring Clinical Gene Therapy," *Cancer Research*, Sep. 15, 1996, vol. 56, pp. 4087-4095.

Wang, Y. et al., "Noninvasive Indirect Imaging of Vascular Endothelial Growth Factor Gene Expression Using Bioluminescence Imaging in Living Transgenic Mice," *Physiol Genomics*, 2006, vol. 24, pp. 173-180.

Wu, J.C. et al., "Noninvasive Optical Imaging of Firefly Luciferase Reporter Gene Expression in Skeletal Muscles of Living Mice," *Molecular Therapy*, Oct. 2001, vol. 4, No. 4, pp. 297-306.

Wu, L. et al., "Chimeric PSA Enhancers Exhibit Augmented Activity in Prostate Cancer Gene Therapy Vectors," *Gene Therapy*, 2001, vol. 8, pp. 1416-1426.

Wu, L. et al., "Transcriptionally Targeted Gene Therapy to Detect and Treat Cancer," *Trends in Molecular Medicine*, Oct. 2003, vol. 9, No. 10, pp. 421-429.

Zhang, L. et al., "Molecular Engineering of a Two-Step Transcription Amplification (TSTA) System for Transgene Delivery in Prostate Cancer," *Molecular Therapy*, Mar. 2002, vol. 5, No. 3, pp. 223-232.

Zhang, L. et al., "Interrogating Androgen Receptor Function in Recurrent Prostate Cancer," *Cancer Research*, Aug. 1, 2003, vol. 63, pp. 4552-4560.

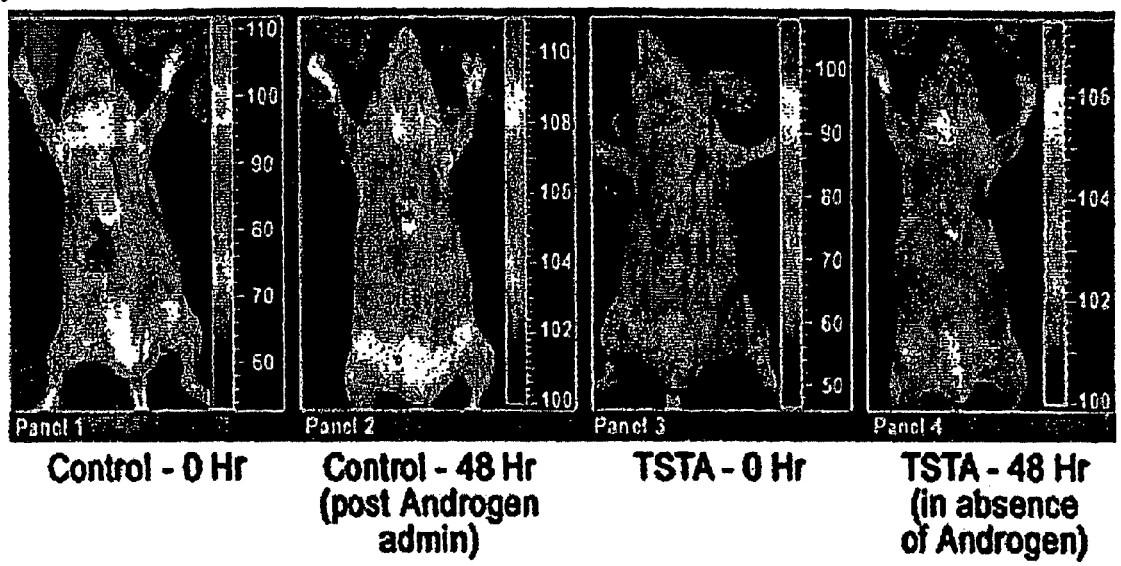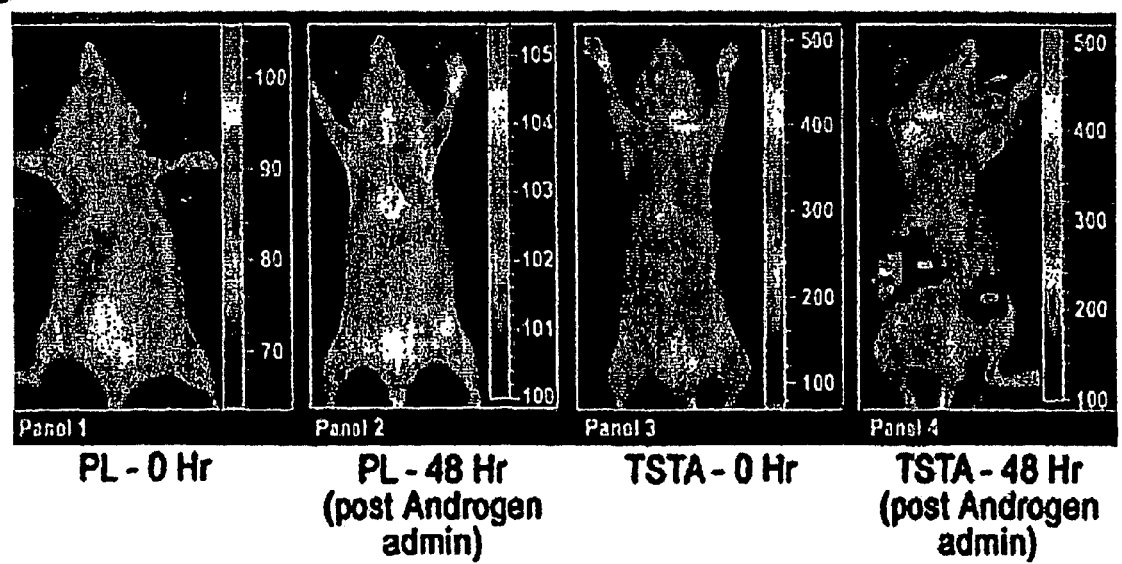
Fig. 4

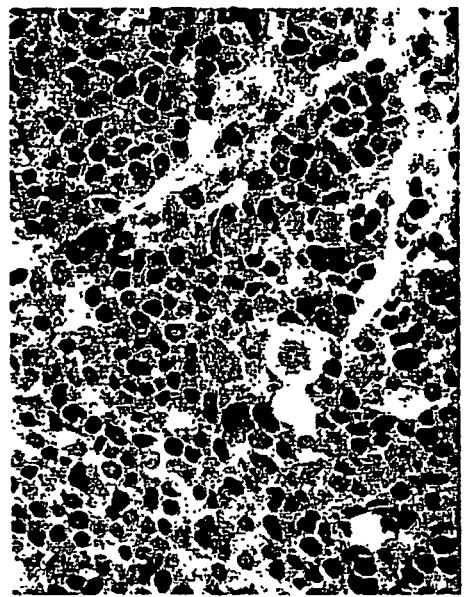
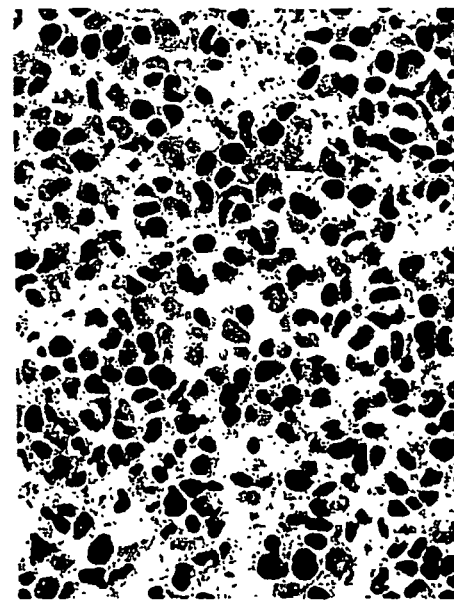
Fig. 17-1

Pbcvp2g5 (not-sal)

```
     KpnI
     Acc65I                              HindIII    SbfI
   1 GGTACCGAGC TCATTTAGGT GACACTATAG AATACAAGCT TGCATGCCTG

51 CAGGTCCGGA GGACAGTACT CCGCTCGGAG GACAGTACTC CGCTCGGAGG

101 ACAGTACTCC GCTCGGAGGA CAGTACTCCG CTCGGAGGAC AGTACTCCGA

XbaI  BamHI
 151 CTCTAGAGGA TCCCCAGTCC TATATATACT CGCTCTGCAC TTGGCCCTTT

BglII
                                                       XhoI
 201 TTTACACTGT GACTGATTGA GCTGGTGCCG TGTCGAGTGG TGTCTCGAGA

HindIII                             NcoI
 251 TCTGCGATCT AAGTAAGCTT GGCATTCCGG TACTGTTGGT AAAGCCACCA
                                                        M    Frame 3

SfoI
                         NarI
                         KasI
                         BbeI
 301 TGGAAGACGC CAAAAACATA AAGAAAGGCC CGGCGCCATT CTATCCGCTG
       E  D  A  K  N  I  K  K  G  P  A  P  F  Y  P  L     Frame 3

351 GAAGATGGAA CCGCTGGAGA GCAACTGCAT AAGGCTATGA AGAGATACGC
       E  D  G  T  A  G  E  Q  L  H  K  A  M  K  R  Y  A  Frame 3

401 CCTGGTTCCT GGAACAATTG CTTTTACAGA TGCACATATC GAGGTGGACA
       L  V  P  G  T  I  A  F  T  D  A  H  I  E  V  D  I  Frame 3

BstBI
 451 TCACTTACGC TGAGTACTTC GAAATGTCCG TTCGGTTGGC AGAAGCTATG
       T  Y  A  E  Y  F  E  M  S  V  R  L  A  E  A  M     Frame 3

501 AAACGATATG GGCTGAATAC AAATCACAGA ATCGTCGTAT GCAGTGAAAA
       K  R  Y  G  L  N  T  N  H  R  I  V  V  C  S  E  N  Frame 3

551 CTCTCTTCAA TTCTTTATGC CGGTGTTGGG CGCGTTATTT ATCGGAGTTG
       S  L  Q  F  F  M  P  V  L  G  A  L  F  I  G  V  A  Frame 3

601 CAGTTGCGCC CGCGAACGAC ATTTATAATG AACGTGAATT GCTCAACAGT
       V  A  P  A  N  D  I  Y  N  E  R  E  L  L  N  S     Frame 3

651 ATGGGCATTT CGCAGCCTAC CGTGGTGTTC GTTTCCAAAA AGGGGTTGCA
       M  G  I  S  Q  P  T  V  V  F  V  S  K  K  G  L  Q  Frame 3

701 AAAAATTTTG AACGTGCAAA AAAAGCTCCC AATCATCCAA AAAATTATTA
       K  I  L  N  V  Q  K  K  L  P  I  I  Q  K  I  I  I  Frame 3

BsrGI
 751 TCATGGATTC TAAAACGGAT TACCAGGGAT TTCAGTCGAT GTACACGTTC
```

Fig. 21A-1

```
                 M  D  S   K  T  D   Y  Q  G   F  Q  S   M  Y  T  F         Frame 3
 801 GTCACATCTC ATCTACCTCC CGGTTTTAAT GAATACGATT TTGTGCCAGA
      V  T  S  H   L  P  P   G  F  N   E  Y  D   F  V  P  E                 Frame 3
                                       BclI
 851 GTCCTTCGAT AGGGACAAGA CAATTGCACT GATCATGAAC TCCTCTGGAT
      S  F  D   R  D  K  T   I  A  L   I  M  N   S  S  G  S                 Frame 3

901 CTACTGGTCT GCCTAAAGGT GTCGCTCTGC CTCATAGAAC TGCCTGCGTG
      T  G  L   P  K  G   V  A  L  P   H  R  T   A  C  V                    Frame 3

951 AGATTCTCGC ATGCCAGAGA TCCTATTTTT GGCAATCAAA TCATTCCGGA
      R  F  S  H   A  R  D   P  I  F   G  N  Q   I  I  P  D                 Frame 3

1001 TACTGCGATT TTAAGTGTTG TTCCATTCCA TCACGGTTTT GGAATGTTTA
      T  A  I   L  S  V  V   P  F  H   H  G  F   G  M  F  T                 Frame 3

1051 CTACACTCGG ATATTTGATA TGTGGATTTC GAGTCGTCTT AATGTATAGA
      T  L  G   Y  L  I   C  G  F  R   V  V  L   M  Y  R                    Frame 3
              SapI
1101 TTTGAAGAAG AGCTGTTTCT GAGGAGCCTT CAGGATTACA AGATTCAAAG
      F  E  E   L  F  L   R  S  L   Q  D  Y  K   I  Q  S                    Frame 3

1151 TGCGCTGCTG GTGCCAACCC TATTCTCCTT CTTCGCCAAA AGCACTCTGA
      A  L  L   V  P  T  L   F  S  F   F  A  K   S  T  L  I                 Frame 3

1201 TTGACAAATA CGATTTATCT AATTTACACG AAATTGCTTC TGGTGGCGCT
       D  K  Y   D  L  S   N  L  H  E   I  A  S   G  G  A                   Frame 3

1251 CCCCTCTCTA AGGAAGTCGG GGAAGCGGTT GCCAAGAGGT TCCATCTGCC
      P  L  S  K   E  V  G   E  A  V   A  K  R  F   H  L  P                 Frame 3

1301 AGGTATCAGG CAAGGATATG GGCTCACTGA GACTACATCA GCTATTCTGA
      G  I  R   Q  G  Y  G   L  T  E   T  T  S   A  I  L  I                 Frame 3

1351 TTACACCCGA GGGGGATGAT AAACCGGGCG CGGTCGGTAA AGTTGTTCCA
       T  P  E   G  D  D   K  P  G  A   V  G  K   V  V  P                   Frame 3

1401 TTTTTTGAAG CGAAGGTTGT GGATCTGGAT ACCGGGAAAA CGCTGGGCGT
       F  F  E  A   K  V  V   D  L  D   T  G  K   T  L  G  V                Frame 3

1451 TAATCAAAGA GGCGAACTGT GTGTGAGAGG TCCTATGATT ATGTCCGGTT
       N  Q  R   G  E  L  C   V  R  G   P  M  I   M  S  G  Y                Frame 3

1501 ATGTAAACAA TCCGGAAGCG ACCAACGCCT TGATTGACAA GGATGGATGG
       V  N  N   P  E  A   T  N  A  L   I  D  K   D  G  W                   Frame 3

1551 CTACATTCTG GAGACATAGC TTACTGGGAC GAAGACGAAC ACTTCTTCAT
      L  H  S  G   D  I  A   Y  W  D   E  D  E  H   F  F  I                 Frame 3

1601 CGTTGACCGC CTGAAGTCTC TGATTAAGTA CAAAGGCTAT CAGGTGGCTC
       V  D  R   L  K  S  L   I  K  Y   K  G  Y   Q  V  A  P                Frame 3

1651 CCGCTGAATT GGAATCCATC TTGCTCCAAC ACCCCAACAT CTTCGACGCA
       A  E  L   E  S  I   L  L  Q  H   P  N  I   F  D  A                   Frame 3
```

Fig. 21A-2

```
                                   SgrAI
1701 GGTGTCGCAG GTCTTCCCGA CGATGACGCC GGTGAACTTC CCGCCGCCGT
       G   V  A    L   P   D    D  D  A    G  E  L    P  A  A  V       Frame 3

1751 TGTTGTTTTG GAGCACGGAA AGACGATGAC GGAAAAAGAG ATCGTGGATT
       V   V  L    E   H   G  K    T  M  T    E  K  E    I  V  D  Y    Frame 3

1801 ACGTCGCCAG TCAAGTAACA ACCGCGAAAA AGTTGCGCGG AGGAGTTGTG
         V  A  S    Q  V   T    T  A  K  K    L  R  G    G  V  V       Frame 3

1851 TTTGTGGACG AAGTACCGAA AGGTCTTACC GGAAAACTCG ACGCAAGAAA
       F   V  D  E    V  P    K  G  L  T    G  K  L    D  A  R  K      Frame 3

1901 AATCAGAGAG ATCCTCATAA AGGCCAAGAA GGGCGGAAAG ATCGCCGTGT
       I   R  E    I  L   I  K    A  K  K    G  G  K    I  A  V  *     Frame 3

XbaI            FseI
1951 AATTCTAGAG TCGGGGCGGC CGGCCGCTTC GAGCAGACAT GATAAGATAC

2001 ATTGATGAGT TTGGACAAAC CACAACTAGA ATGCAGTGAA AAAAATGCTT

2051 TATTTGTGAA ATTTGTGATG CTATTGCTTT ATTTGTAACC ATTATAAGCT

2101 GCAATAAACA AGTTAACAAC AACAATTGCA TTCATTTTAT GTTTCAGGTT

2151 CAGGGGGAGG TGTGGGAGGT TTTTTAAAGC AAGTAAAACC TCTACAAATG

SalI
                BamHI     AccI
2201 TGGTAAAATC GATAAGGATC CGTCGACCGA TGCCCTTGAG AGCCTTCAAC

2251 CCAGTCAGCT CCTTCCGGTG GGCGCGGGGC ATGACTATCG TCGCCGCACT

SapI
                                                            AfeI
2301 TATGACTGTC TTCTTTATCA TGCAACTCGT AGGACAGGTG CCGGCAGCGC

2351 TCTTCCGCTT CCTCGCTCAC TGACTCGCTG CGCTCGGTCG TTCGGCTGCG

2401 GCGAGCGGTA TCAGCTCACT CAAAGGCGGT AATACGGTTA TCCACAGAAT

2451 CAGGGGATAA CGCAGGAAAG AACATGTGAG CAAAAGGCCA GCAAAAGGCC

2501 AGGAACCGTA AAAAGGCCGC GTTGCTGGCG TTTTTCCATA GGCTCCGCCC

2551 CCCTGACGAG CATCACAAAA ATCGACGCTC AAGTCAGAGG TGGCGAAACC

BsssI
2601 CGACAGGACT ATAAAGATAC CAGGCGTTTC CCCCTGGAAG CTCCCTCGTG

2651 CGCTCTCCTG TTCCGACCCT GCCGCTTACC GGATACCTGT CCGCCTTTCT

2701 CCCTTCGGGA AGCGTGGCGC TTTCTCAATG CTCACGCTGT AGGTATCTCA

2751 GTTCGGTGTA GGTCGTTCGC TCCAAGCTGG GCTGTGTGCA CGAACCCCCC
```

Fig. 21A-3

```
2801 GTTCAGCCCG ACCGCTGCGC CTTATCCGGT AACTATCGTC TTGAGTCCAA

2851 CCCGGTAAGA CACGACTTAT CGCCACTGGC AGCAGCCACT GGTAACAGGA

2901 TTAGCAGAGC GAGGTATGTA GGCGGTGCTA CAGAGTTCTT GAAGTGGTGG

2951 CCTAACTACG GCTACACTAG AAGGACAGTA TTTGGTATCT GCGCTCTGCT

3001 GAAGCCAGTT ACCTTCGGAA AAAGAGTTGG TAGCTCTTGA TCCGGCAAAC

3051 AAACCACCGC TGGTAGCGGT GGTTTTTTTG TTTGCAAGCA GCAGATTACG

3101 CGCAGAAAAA AAGGATCTCA AGAAGATCCT TTGATCTTTT CTACGGGGTC

3151 TGACGCTCAG TGGAACGAAA ACTCACGTTA AGGGATTTTG GTCATGAGAT

3201 TATCAAAAAG GATCTTCACC TAGATCCTTT TAAATTAAAA ATGAAGTTTT

3251 AAATCAATCT AAAGTATATA TGAGTAAACT TGGTCTGACA GTTACCAATG
                                                   *  W  H    Frame 4

3301 CTTAATCAGT GAGGCACCTA TCTCAGCGAT CTGTCTATTT CGTTCATCCA
      K  I  L  S  A  G  I  E  A  I  Q  R  N  R  E  D      Frame 4

AhdI
3351 TAGTTGCCTG ACTCCCGTC GTGTAGATAA CTACGATACG GGAGGGCTTA
      M  T  A  Q  S  G  T  T  Y  I  V  V  I  R  S  P  K   Frame 4

3401 CCATCTGGCC CCAGTGCTGC AATGATACCG CGAGACCCAC GCTCACCGGC
      G  D  P  G  L  A  A  I  I  G  R  S  G  R  E  G  A   Frame 4

BglI
3451 TCCAGATTTA TCAGCAATAA ACCAGCCAGC CGGAAGGGCC GAGCGCAGAA
      G  S  K  D  A  I  F  W  G  A  P  L  A  S  R  L      Frame 4

AseI
3501 GTGGTCCTGC AACTTTATCC GCCTCCATCC AGTCTATTAA TTGTTGCCGG
      L  P  G  A  V  K  D  A  E  M  W  D  I  L  Q  Q  R   Frame 4

FspI
3551 GAAGCTAGAG TAAGTAGTTC GCCAGTTAAT AGTTTGCGCA ACGTTGTTGC
      S  A  L  T  L  L  E  G  T  L  L  K  R  L  T  T  A   Frame 4

3601 CATTGCTACA GGCATCGTGG TGTCACGCTC GTCGTTTGGT ATGGCTTCAT
      M  A  V  P  M  T  T  D  R  E  D  N  P  I  A ´E      Frame 4

3651 TCAGCTCCGG TTCCCAACGA TCAAGGCGAG TTACATGATC CCCCATGTTG
      N  L  E  P  E  W  R  D  L  R  T  V  H  D  G  M  N   Frame 4

3701 TGCAAAAAAG CGGTTAGCTC CTTCGGTCCT CCGATCGTTG TCAGAAGTAA
      H  L  F  A  T  L  K  P  G  I  T  T  L  L  L         Frame 4

3751 GTTGGCCGCA GTGTTATCAC TCATGGTTAT GGCAGCACTG CATAATTCTC
      N  A  A  T  N  D  S  M  T  I  A  A  S  C  L  E      Frame 4

3801 TTACTGTCAT GCCATCCGTA AGATGCTTTT CTGTGACTGG TGAGTACTCA
      R  V  T  M  G  D  T  L  H  K  E  T  V  P  S  Y  E   Frame 4
```

Fig. 21A-4

```
3851 ACCAAGTCAT TCTGAGAATA GTGTATGCGG CGACCGAGTT GCTCTTGCCC
      V  L  D   N  Q  S  Y   H  I  R   R  G  L    Q  E  Q  G    Frame 4

3901 GGCGTCAATA CGGGATAATA CCGCGCCACA TAGCAGAACT TTAAAAGTGC
      A  D  I   R  S  L    V  A  G    L  L  V    K  F  T        Frame 4

XmnI
3951 TCATCATTGG AAAACGTTCT TCGGGGCGAA AACTCTCAAG GATCTTACCG
      S  M  M  P   F  R  E   E  P  R   F  S  E   I  K  G        Frame 4

BssSI
4001 CTGTTGAGAT CCAGTTCGAT GTAACCCACT CGTGCACCCA ACTGATCTTC
      S  N  L   D  L  E  I   Y  G  V   R  A  G   L  Q  D  E     Frame 4

4051 AGCATCTTTT ACTTTCACCA GCGTTTCTGG GTGAGCAAAA ACAGGAAGGC
      A  D  K   V  K  V    L  T  E  P   H  A  F   V  P  L       Frame 4

4101 AAAATGCCGC AAAAAAGGGA ATAAGGGCGA CACGGAAATG TTGAATACTC
      C  F  A  A   F  P    I  L  A    V  R  F  H   Q  I  S      Frame 4

4151 ATACTCTTCC TTTTTCAATA TTATTGAAGC ATTTATCAGG GTTATTGTCT
      M  Frame 4

4201 CATGAGCGGA TACATATTTG AATGTATTTA GAAAAATAAA CAAATAGGGG

4251 TTCCGCGCAC ATTTCCCCGA AAAGTGCCAC CTGACGCGCC CTGTAGCGGC

4301 GCATTAAGCG CGGCGGGTGT GGTGGTTACG CGCAGCGTGA CCGCTACACT

4351 TGCCAGCGCC CTAGCGCCCG CTCCTTTCGC TTTCTTCCCT TCCTTTCTCG

4401 CCACGTTCGC CGGCTTTCCC CGTCAAGCTC TAAATCGGGG GCTCCCTTTA

4451 GGGTTCCGAT TTAGTGCTTT ACGGCACCTC GACCCCAAAA AACTTGATTA

DraIII
4501 GGGTGATGGT TCACGTAGTG GGCCATCGCC CTGATAGACG GTTTTTCGCC

AloI
          AloI
4551 CTTTGACGTT GGAGTCCACG TTCTTTAATA GTGGACTCTT GTTCCAAACT

4601 GGAACAACAC TCAACCCTAT CTCGGTCTAT TCTTTTGATT TATAAGGGAT

4651 TTTGCCGATT TCGGCCTATT GGTTAAAAAA TGAGCTGATT TAACAAAAAT

BglI
4701 TTAACGCGAA TTTTAACAAA ATATTAACGT TTACAATTTC CCATTCGCCA

FspI
4751 TTCAGGCTGC GCAACTGTTG GGAAGGGCGA TCGGTGCGGG CCTCTTCGCT

4801 ATTACGCCAG CCCAAGCTAC CATGATAAGT AAGTAATATT AAGGTACGGG

NotI
4851 AGGTACTTGG AGCGGCCGCG ATCCAGACAT GATAAGATAC ATTGATGAGT
```

Fig. 21A-5

```
4901 TTGGACAAAC CACAACTAGA ATGCAGTGAA AAAAATGCTT TATTTGTGAA

4951 ATTTGTGATG CTATTGCTTT ATTTGTAACC ATTATAAGCT GCAATAAACA

5001 AGTTAACAAC AACAATTGCA TTCATTTTAT GTTTCAGGTT CAGGGGGAGG

5051 TGTGGGAGGT TTTTTAAAGC AAGTAAAACC TCTACAAATG TGGTATGGCT

BclI
5101 GATTATGATC ATGAACAGAC TGTGAGGACT GAGGGGCCTG AAATGAGCCT

5151 TGGGACTGTG AATTTAAAAT ACACAAACAA TTAGAATCAG TAGTTTAACA

5201 CATTATACAC TTAAAAATTT TATATTTACC TTAGAGCTTT AAATCTCTGT

5251 AGGTAGTTTG TCCAATTATG TCACACCACA GAAGTAAGGT TCCTTCACAA
                      *    T  V  G    F  Y  P    E  K  V              Frame 4
                       XbaI
5301 AGATCCCAAG CTGTCGATCG ACATTTCTAG AGGATCTCGG ACCCGGGGAA
      F  I  G  L    Q  R  D    V  N  R    S  S  R  P    G  P  S        Frame 4

5351 TCCCCGTCCC CCAACATGTC CAGATCGAAA TCGTCTAGCG CGTCGGCATG
      D  G  D    G  L  M  D    L  D  F    D  D  L    A  D  A  H        Frame 4

BtrI
5401 CGCCATCGCC ACGTCCTCGC CGTCTAAGTG GAGCTCGTCC CCCAGGCTGA
      A  M  A    V  D  E    G  D  L  H    L  E  D    G  L  S           Frame 4

5451 CATCGGTCGG GGGGCGGAT CTCGGACCCG GGAATCCCC GTCCCCCAAC
      V  D  T  P    P  A  S    R  P  G    P  S  D    G  D  G  L        Frame 4

BtrI
5501 ATGTCCAGAT CGAAATCGTC TAGCGCGTCG GCATGCGCCA TCGCCACGTC
      M  D  L    D  F  D  D    L  A  D    A  H  A    M  A  V  D        Frame 4

5551 CTCGCCGTCT AAGTGGAGCT CGTCCCCCAG GCTGACATCG GTCGGGGGGG
      E  G  D    L  H  L    E  D  G  L    S  V  D    T  P  P           Frame 4

BamHI           EcoRI
5601 CGGATCCCCC GGGCTGCAGG AATTCCGGCG ATACAGTCAA CTGTCTTTGA
      A  S  G  G    P  Q  L    F  E  P    S  V  T    L  Q  R  Q        Frame 4

5651 CCTTTGTTAC TACTCTCTTC CGATGATGAT GTCGCACTTA TTCTATGCTG
      G  K  N    S  S  E  E    S  S  S    T  A  S    I  R  H  Q        Frame 4

5701 TCTCAATGTT AGAGGCATAT CAGTCTCCAC TGAAGCCAAT CTATCTGTGA
      R  L  T    L  P  M    D  T  E  V    S  A  L    R  D  T           Frame 4

BsrGI
5751 CGGCATCTTT ATTCACATTA TCTTGTACAA ATAATCCTGT TAACAATGCT
      V  A  D  K    N  V  N    D  Q  V    F  L  G    T  L  L  A        Frame 4

XhoI
5801 TTTATATCCT GTAAAGAATC CATTTTCAAA ATCATGTCAA GGTCTTCTCG
      K  I  D    Q  L  S  D    M  K  L    I  M  D    L  D  E  R        Frame 4
```

Fig. 21A-6

```
5851 AGGAAAAATC AGTAGAAATA GCTGTTCCAG TCTTTCTAGC CTTGATTCCA
        P  F  I    L  L  F    L  Q  E  L    R  E  L    R  S  E         Frame 4

5901 CTTCTGTCAG ATGTGCCCTA GTCAGCGGAG ACCTTTTGGT TTTGGGAGAG
        V  E  T  L    H  A  R    T  L  P    S  R  K  T    K  P  S     Frame 4

5951 TAGCGACACT CCCAGTTGTT CTTCAGACAC TTGGCGCACT TCGGTTTTTC
        Y  R  C    E  W  N  N    K  L  C    K  A  C    K  P  K  E     Frame 4

6001 TTTGGAGCAC TTGAGCTTTT TAAGTCGGCA AATATCGCAT GCTTGTTCGA
        K  S  C    K  L  K    K  L  R  C    I  D  C    A  Q  E        Frame 4

HindIII
6051 TAGAAGACAG TAGCTTCATC TTTCAGGAGG CTTGCTTCAA GCTTGGGGCT
        I  S  S  L    L  K  M    Frame 4

6101 GGGGAGCCTC CCCCAGGAGC CCTATAAAAC CTTCATTCCC CAGGACTCCG

BglI                                       BstXI
6151 CCCCTGCCCT GCTGGCACCC AGAGGCTGAC CAAGGCCCTC CCCATGCTGC

BstXI
6201 TGGAGGCTGG ACAACCCCCT CCCACACCCA GAGCTGTGGA AGGGGAGGGA

PsrI
        PsrI
6251 GAGCTAGTAC TTGCTGTTCT GCAATTACTA GATCACCCTG GATGCACCAG

6301 GCCCTGTGGC TCATGGAGAC TTCATCTAGG GGACAAAGGC AGAGGAGACA

6351 CGCCCAGGAT GAAACAGAAA CAGGGGGTGG GTACGATCCC CGATTCTTCA

PmlI
6401 TACAAAGCCT CACGTGCCTA GATCCTTTGC ACTCCAAGAC CCAGTGTGCC

6451 CTAAGACACC AGCACTCAGG AGATTGTGAG ACTCCCTGAT CCCTGCACCA

AloI
                 AloI
6501 CTCTGAGACC AGAAACTAGA ACTTTTATTC CTCATGCTCC TGAAATAGAT

6551 GTCTTGGCAT TTAGTACATT CTTTTCCTTG CACTCCCAAC CCAGAATCCA

AfeI
                                                  Bpu10I
6601 GCTCCACAGA TACATTGCTA CTGTCATCAT AAAAAGATCC TGAGCGCTGC

Tth111I
6651 CTTATTCTGG GTTTGGCAGT GGAGTGCTGC AGACACAGT CGATCGGGAC

6701 CTAGAACCTT GGTTAGGCAT AAAGAAGCAG GATGTGATAG AAGAAGTATT

6751 TAATGGTGGA ACGTTGAGAC TGTCCTGCAG ACAAGGGTGG AAGGCTCTGG

NcoI
6801 CTGAACAGCG TTGGGAGGCA ATTCTCCATG GTTCTGTCAC GTATCTGTGT
```

Fig. 21A-7

```
6851 GTCTTCTGAG CAAAGACAGC AACACCTTTT TTTTTCTGGA TTGTTGTTTC
                                         EcoRV
6901 AAGGATGTTT GTAAAGCAGG CATCCTTGCA AGATGATATC TCTCTCAGAT
6951 CCAGGCTTGC TTACTGTCCT AGATAATAAA GATAATGTCT CTTACAACAG
7001 ATTTGTTTAC TGTCAAGGAC AATCAATACA ATATGTTCCT CCAGAGTAGG
7051 TCTGTTTTCA ATCCAAGATC ATGAAGATAA TATCTTCATC AGAGACAAAG
7101 GCTGAGCAGG TTTGCAAGTT GTCCAGTAT AAGATTGAGG ATTCCTAATC
7151 TCAGGTTTCT CACCAGTGGC ACAAACCCCG TGTGCACAGC ATCCACCTAG
                NcoI
           BstEII
7201 ACTGCTCTGG TCACCATGGT TCTGTCACGT ATCTGTGTGT CTTCTGAGCA
7251 AAGACAGCAA CACCTTTTTT TCTGGATTGT TGTTTCAAGG ATGTTGTAAA
                          EcoRV
7301 GCAGGCATCC TTGCAAGATG ATATCTCTCT CAGATCCAGG CTTGCTTACT
7351 GTCCTAGATA ATAAAGATAA TGTCTCTTAC AACAGATTTG TTTACTGTCA
7401 AGGACAATCA ATACAATATG TTCCTCCAGA GTAGGTCTGT TTTCAATCCA
7451 AGATCATGAA GATAATATCT TCATCAGAGA CAAAGGCTGA GCAGGTTTGC
7501 AAGTTGTCCC AGTATAAGAT TGAGGATTCC TAATCTCAGG TTTCTCACCA
                                                    BstEII
7551 GTGGCACAAA CCCCGTGTGC ACAGCATCCA CCTAGACTGC TCTGGTCACC
7601 CTACAAGATT TGGGGGGGGC AAGGTGTACT AATGTGAACA TGAACCTCAT
7651 GCTGTCTGCT AAGCTGTGAG CAGTAAAAGC CTTTGCCTCT GACTCAGGAG
7701 TCTCATGGAC TCTGCCAGCA TTCACAAAAC TCTGGAAAGT TAGCTTATTT
7751 GTTTGCAAGT CAGTAAAATG TCAGCCCCTT CAGAGTTACT GACAAACAGG
                    MscI PvuII                SanDI
7801 TGGGCACTGA GACTGCACTG GCCAGCTGGG AATAGAGATA GGAGGGGACC
     PvuII
7851 CAGCTGGATG CAGTGGGCAG TGGGGGTCAT AGAGTCAAGA GGGTACAGAA
7901 TACAATGGGG TCCTAGTATC ATGGTGGAGG TCAGAAAGAG CCCTAAAAGA
7951 GAGGGTCAAG GTAGGAGGTT AGTGAAGGTC CACCTCCACC CTCTCCAGGA
                   AseI
8001 CAGGGACATC AGGCCACAAT TAATTTCTCT GCAGTTGGTG AGTGGTCATG
```

Fig. 21A-8

```
8051 GTCTCTGGAG TCCCCAGCAT CCAGAGTGTC CCTGGTCTAG TGGTCCCCCC

8101 TTTCTGAGCC ACAGCCACTT TCTCCATCAA ATGAGGCCAG TAATACCCAT

8151 CCCATAGTGA TGCTGTGAGG ATGAGATGAG CATCTGTAAG TGCTGAAGAT

8201 AATCCCTGAC ACATCCCAAG CATTCAGCAG TGCAAGCATA CACTTACACG

PmlI
8251 GCACTCCCCA GAGCCAGGCA TGTGCTGGTG CCTCATACAC GTGACCAcnt

8301 TTGATCGTCA CAATGACCCT GTGAGGGAGA CTGTGCAACA GAGGACTGAC

Bsu36I
8351 CTTGCTCAAA GACCTCAGGC GTTCCCCTC AGAGCCTGAG AGGTCATCTC

8401 TTTTTTTTTT TTTTTTTCCT TTCTTTCTTT TTCTTTTCCA TTTCTTTTTC

8451 TTTGCAAGAG GTCATCTCTA ATGCTTTGGA ATATCCTGCC AGATTAGAGT

8501 CCCTTTGTTC ACCTGAAGGT TTGGGCCACA CCAGATAGTC TAACGGTGTG

XbaI
8551 ATTTGTGCTG AAGGTTTTGA GCCACACTAT ATCAGCTAGA TTTCTAGAGC

FseI
8601 GGCCGGCCGC AATAAAATAT CTTTATTTTC ATTACATCTG TGTGTTGGTT

8651 TTTTGTGTGA ATCGATAGTA CTAACATACG CTCTCCATCA AACAAAACG

8701 AAACAAAACA AACTAGCAAA ATAGGCTGTC CCCAGTGCAA GTGCAGGTGC

8751 CAGAACATTT CTCTATCGAT A
```

Fig. 21A-9

ORIGINAL TSTA (aka Pbcvp2g5 -L)

Legend:
- G5 DNA BINDING SITES -(Magenta)
- E4TATA PROMOTER -((Red)
- LUCIFERASE+ CODING REGION -(Blue)
- VP2 (DUPLICATED VP16 ACTIVATION DOMAIN) -(Aqua)
- GAL4 DNA BINDING DOMAIN -(Green)
- PSA PROXIMAL PROMOTER -(Purple)
- PSA ENHANCER CORES (DUPLICATED)-(Yellow)

```
KpnI
    Acc65I                              HindIII    SbfI
  1 GGTACCGAGC TCATTTAGGT GACACTATAG AATACAAGCT TGCATGCCTG
    CCATGGCTCG AGTAAATCCA CTGTGATATC TTATGTTCGA ACGTACGGAC 51 CAGGTCCGGA GGACAGTACT CCGCTCGGAG GACAGTACTC CGCTCGGAGG
    GTCCAGGCCT CCTGTCATGA GGCGAGCCTC CTGTCATGAG GCGAGCCTCC 101 ACAGTACTCC GCTCGGAGGA CAGTACTCCG CTCGGAGGAC AGTACTCCGA
    TGTCATGAGG CGAGCCTCCT GTCATGAGGC GAGCCTCCTG TCATGAGGCT XbaI BamHI
151 CTCTAGAGGA TCCCCAGTCC TATATATACT CGCTCTGCAC TTGGCCCTTT
    GAGATCTCCT AGGGGTCAGG ATATATATGA GCGAGACGTG AACCGGGAAA BglII
                                                    XhoI
201 TTTACACTGT GACTGATTGA GCTGGTGCCG TGTCGAGTGG TGTCTCGAGA
    AAATGTGACA CTGACTAACT CGACCACGGC ACAGCTCACC ACAGAGCTCT HindIII                                NcoI
251 TCTGCGATCT AAGTAAGCTT GGCATTCCGG TACTGTTGGT AAAGCCACCA
    AGACGCTAGA TTCATTCGAA CCGTAAGGCC ATGACAACCA TTTCGGTGGT
                                                M    Frame 3

SfoI
                   NarI
                   KasI
                   BbeI
301 TGGAAGACGC CAAAAACATA AAGAAAGGCC CGGCGCCATT CTATCCGCTG
    ACCTTCTGCG GTTTTTGTAT TTCTTTCCGG GCCGCGGTAA GATAGGCGAC
      E  D  A  K  N  I  K  K  G  P  A  P  F  Y  P  L   Frame 3

351 GAAGATGGAA CCGCTGGAGA GCAACTGCAT AAGGCTATGA AGAGATACGC
    CTTCTACCTT GGCGACCTCT CGTTGACGTA TTCCGATACT TCTCTATGCG
      E  D  G  T  A  G  E  Q  L  H  K  A  M  K  R  Y  A  Frame 3

401 CCTGGTTCCT GGAACAATTG CTTTTACAGA TGCACATATC GAGGTGGACA
    GGACCAAGGA CCTTGTTAAC GAAAATGTCT ACGTGTATAG CTCCACCTGT
      L  V  P  G  T  I  A  F  T  D  A  H  I  E  V  D  I  Frame 3
```

Fig. 21B-1

```
                         BstBI
451 TCACTTACGC TGAGTACTTC GAAATGTCCG TTCGGTTGGC AGAAGCTATG
    AGTGAATGCG ACTCATGAAG CTTTACAGGC AAGCCAACCG TCTTCGATAC
     T  Y  A   E  Y  F   E  M  S  V   R  L  A   E  A  M         Frame 3

501 AAACGATATG GGCTGAATAC AAATCACAGA ATCGTCGTAT GCAGTGAAAA
    TTTGCTATAC CCGACTTATG TTTAGTGTCT TAGCAGCATA CGTCACTTTT
     K  R  Y   G  L  N  T   N  H  R   I  V  V   C  S  E  N      Frame 3

551 CTCTCTTCAA TTCTTTATGC CGGTGTTGGG CGCGTTATTT ATCGGAGTTG
    GAGAGAAGTT AAGAAATACG GCCACAACCC GCGCAATAAA TAGCCTCAAC
     S  L  Q   F  F  M  P   V  L  G   A  L  F   I  G  V  A      Frame 3

601 CAGTTGCGCC CGCGAACGAC ATTTATAATG AACGTGAATT GCTCAACAGT
    GTCAACGCGG GCGCTTGCTG TAAATATTAC TTGCACTTAA CGAGTTGTCA
     V  A  P   A  N  D   I  Y  N  E   R  E  L   L  N  S         Frame 3

651 ATGGGCATTT CGCAGCCTAC CGTGGTGTTC GTTTCCAAAA AGGGGTTGCA
    TACCCGTAAA GCGTCGGATG GCACCACAAG CAAAGGTTTT TCCCCAACGT
     M  G  I   S  Q  P  T   V  V  F   V  S  K  K   G  L  Q      Frame 3

701 AAAAATTTTG AACGTGCAAA AAAAGCTCCC AATCATCCAA AAAATTATTA
    TTTTTAAAAC TTGCACGTTT TTTTCGAGGG TTAGTAGGTT TTTTAATAAT
     K  I  L  N   V  Q  K   L  P  I  I   Q  K  I  I  I          Frame 3

BsrGI
751 TCATGGATTC TAAAACGGAT TACCAGGGAT TTCAGTCGAT GTACACGTTC
    AGTACCTAAG ATTTTGCCTA ATGGTCCCTA AAGTCAGCTA CATGTGCAAG
     M  D  S   K  T  D   Y  Q  G  F   Q  S  M   Y  T  F         Frame 3

801 GTCACATCTC ATCTACCTCC CGGTTTTAAT GAATACGATT TTGTGCCAGA
    CAGTGTAGAG TAGATGGAGG GCCAAAATTA CTTATGCTAA AACACGGTCT
     V  T  S  H   L  P  P   G  F  N   E  Y  D  F   V  P  E      Frame 3

BclI
851 GTCCTTCGAT AGGGACAAGA CAATTGCACT GATCATGAAC TCCTCTGGAT
    CAGGAAGCTA TCCCTGTTCT GTTAACGTGA CTAGTACTTG AGGAGACCTA
     S  F  D   R  D  K  T   I  A  L   I  M  N   S  S  G  S      Frame 3

901 CTACTGGTCT GCCTAAAGGT GTCGCTCTGC CTCATAGAAC TGCCTGCGTG
    GATGACCAGA CGGATTTCCA CAGCGAGACG GAGTATCTTG ACGGACGCAC
     T  G  L   P  K  G   V  A  L  P   H  R  T   A  C  V         Frame 3

951 AGATTCTCGC ATGCCAGAGA TCCTATTTTT GGCAATCAAA TCATTCCGGA
    TCTAAGAGCG TACGGTCTCT AGGATAAAAA CCGTTAGTTT AGTAAGGCCT
     R  F  S  H   A  R  D   P  I  F   G  N  Q  I   I  P  D      Frame 3

1001 TACTGCGATT TTAAGTGTTG TTCCATTCCA TCACGGTTTT GGAATGTTTA
     ATGACGCTAA AATTCACAAC AAGGTAAGGT AGTGCCAAAA CCTTACAAAT
      T  A  I   L  S  V  V   P  F  H   H  G  F   G  M  F  T     Frame 3

1051 CTACACTCGG ATATTTGATA TGTGGATTTC GAGTCGTCTT AATGTATAGA
     GATGTGAGCC TATAAACTAT ACACCTAAAG CTCAGCAGAA TTACATATCT
      T  L  G   Y  L  I   C  G  F  R   V  V  L   M  Y  R        Frame 3

SapI
1101 TTTGAAGAAG AGCTGTTTCT GAGGAGCCTT CAGGATTACA AGATTCAAAG
```

Fig. 21B-2

```
     AAACTTCTTC TCGACAAAGA CTCCTCGGAA GTCCTAATGT TCTAAGTTTC
       F  E  E     L  F  L     R  S  L     Q  D  Y     K  I  Q  S          Frame 3

1151 TGCGCTGCTG GTGCCAACCC TATTCTCCTT CTTCGCCAAA AGCACTCTGA
     ACGCGACGAC CACGGTTGGG ATAAGAGGAA GAAGCGGTTT TCGTGAGACT
       A  L  L     V  P  T     L  F  S     F  A  K     S  T  L  I          Frame 3

1201 TTGACAAATA CGATTTATCT AATTTACACG AAATTGCTTC TGGTGGCGCT
     AACTGTTTAT GCTAAATAGA TTAAATGTGC TTTAACGAAG ACCACCGCGA
       D  K  Y     D  L  S     N  L  H  E     I  A  S     G  G  A          Frame 3

1251 CCCCTCTCTA AGGAAGTCGG GGAAGCGGTT GCCAAGAGGT TCCATCTGCC
     GGGGAGAGAT TCCTTCAGCC CCTTCGCCAA CGGTTCTCCA AGGTAGACGG
       P  L  S  K     E  V  G     E  A  V     A  K  R  F     H  L  P       Frame 3

1301 AGGTATCAGG CAAGGATATG GGCTCACTGA GACTACATCA GCTATTCTGA
     TCCATAGTCC GTTCCTATAC CCGAGTGACT CTGATGTAGT CGATAAGACT
       G  I  R     Q  G  Y  G     L  T  E     T  T  S     A  I  L  I       Frame 3

1351 TTACACCCGA GGGGGATGAT AAACCGGGCG CGGTCGGTAA AGTTGTTCCA
     AATGTGGGCT CCCCCTACTA TTTGGCCCGC GCCAGCCATT TCAACAAGGT
       T  P  E     G  D  D     K  P  G  A     V  G  K     V  V  P          Frame 3

1401 TTTTTTGAAG CGAAGGTTGT GGATCTGGAT ACCGGGAAAA CGCTGGGCGT
     AAAAAACTTC GCTTCCAACA CCTAGACCTA TGGCCCTTTT GCGACCCGCA
       F  F  E  A     K  V  V     D  L  D     T  G  K  T     L  G  V       Frame 3

1451 TAATCAAAGA GGCGAACTGT GTGTGAGAGG TCCTATGATT ATGTCCGGTT
     ATTAGTTTCT CCGCTTGACA CACACTCTCC AGGATACTAA TACAGGCCAA
       N  Q  R     G  E  L  C     V  R  G     P  M  I     M  S  G  Y       Frame 3

1501 ATGTAAACAA TCCGGAAGCG ACCAACGCCT TGATTGACAA GGATGGATGG
     TACATTTGTT AGGCCTTCGC TGGTTGCGGA ACTAACTGTT CCTACCTACC
       V  N  N     P  E  A     T  N  A  L     I  D  K     D  G  W          Frame 3

1551 CTACATTCTG GAGACATAGC TTACTGGGAC GAAGACGAAC ACTTCTTCAT
     GATGTAAGAC CTCTGTATCG AATGACCCTG CTTCTGCTTG TGAAGAAGTA
       L  H  S  G     D  I  A     Y  W  D     E  D  E  H     F  F  I       Frame 3

1601 CGTTGACCGC CTGAAGTCTC TGATTAAGTA CAAAGGCTAT CAGGTGGCTC
     GCAACTGGCG GACTTCAGAG ACTAATTCAT GTTTCCGATA GTCCACCGAG
       V  D  R     L  K  S  L     I  K  Y     K  G  Y     Q  V  A  P       Frame 3

1651 CCGCTGAATT GGAATCCATC TTGCTCCAAC ACCCCAACAT CTTCGACGCA
     GGCGACTTAA CCTTAGGTAG AACGAGGTTG TGGGGTTGTA GAAGCTGCGT
       A  E  L     E  S  I     L  L  Q  H     P  N  I     F  D  A          Frame 3

SgrAI
1701 GGTGTCGCAG GTCTTCCCGA CGATGACGCC GGTGAACTTC CCGCCGCCGT
     CCACAGCGTC CAGAAGGGCT GCTACTGCGG CCACTTGAAG GGCGGCGGCA
       G  V  A  G     L  P  D     D  D  A     G  E  L  P     A  A  V       Frame 3

1751 TGTTGTTTTG GAGCACGGAA AGACGATGAC GGAAAAAGAG ATCGTGGATT
     ACAACAAAAC CTCGTGCCTT TCTGCTACTG CCTTTTTCTC TAGCACCTAA
       V  V  L     E  H  G  K     T  M  T     E  K  E     I  V  D  Y       Frame 3

1801 ACGTCGCCAG TCAAGTAACA ACCGCGAAAA AGTTGCGCGG AGGAGTTGTG
```

Fig. 21B-3

```
             TGCAGCGGTC AGTTCATTGT TGGCGCTTTT TCAACGCGCC TCCTCAACAC
              V  A  S   Q  V  T    I  A  K  K    L  R  G   G  V  V    Frame 3

1851 TTTGTGGACG AAGTACCGAA AGGTCTTACC GGAAAACTCG ACGCAAGAAA
            AAACACCTGC TTCATGGCTT TCCAGAATGG CCTTTTGAGC TGCGTTCTTT
              F  V  D   E  V  P  K   G  L  T    G  K  L   D  A  R  K    Frame 3

1901 AATCAGAGAG ATCCTCATAA AGGCCAAGAA GGGCGGAAAG ATCGCCGTGT
            TTAGTCTCTC TAGGAGTATT TCCGGTTCTT CCCGCCTTTC TAGCGGCACA
              I  R  E   I  L  I  K   A  K  K    G  G  K   I  A  V  *    Frame 3

XbaI           FseI
       1951 AATTCTAGAG TCGGGGCGGC CGGCCGCTTC GAGCAGACAT GATAAGATAC
            TTAAGATCTC AGCCCCGCCG GCCGGCGAAG CTCGTCTGTA CTATTCTATG

2001 ATTGATGAGT TTGGACAAAC CACAACTAGA ATGCAGTGAA AAAAATGCTT
            TAACTACTCA AACCTGTTTG GTGTTGATCT TACGTCACTT TTTTTACGAA

2051 TATTTGTGAA ATTTGTGATG CTATTGCTTT ATTTGTAACC ATTATAAGCT
            ATAAACACTT TAAACACTAC GATAACGAAA TAAACATTGG TAATATTCGA

2101 GCAATAAACA AGTTAACAAC AACAATTGCA TTCATTTTAT GTTTCAGGTT
            CGTTATTTGT TCAATTGTTG TTGTTAACGT AAGTAAAATA CAAAGTCCAA

2151 CAGGGGGAGG TGTGGGAGGT TTTTTAAAGC AAGTAAAACC TCTACAAATG
            GTCCCCCTCC ACACCCTCCA AAAAATTTCG TTCATTTTGG AGATGTTTAC

SalI
                         BamHI      AccI
       2201 TGGTAAAATC GATAAGGATC CGTCGACCGA TGCCCTTGAG AGCCTTCAAC
            ACCATTTTAG CTATTCCTAG GCAGCTGGCT ACGGGAACTC TCGGAAGTTG

2251 CCAGTCAGCT CCTTCCGGTG GGCGCGGGGC ATGACTATCG TCGCCGCACT
            GGTCAGTCGA GGAAGGCCAC CCGCGCCCCG TACTGATAGC AGCGGCGTGA

SapI
                                                             AfeI
       2301 TATGACTGTC TTCTTTATCA TGCAACTCGT AGGACAGGTG CCGGCAGCGC
            ATACTGACAG AAGAAATAGT ACGTTGAGCA TCCTGTCCAC GGCCGTCGCG

2351 TCTTCCGCTT CCTCGCTCAC TGACTCGCTG CGCTCGGTCG TTCGGCTGCG
            AGAAGGCGAA GGAGCGAGTG ACTGAGCGAC GCGAGCCAGC AAGCCGACGC

2401 GCGAGCGGTA TCAGCTCACT CAAAGGCGGT AATACGGTTA TCCACAGAAT
            CGCTCGCCAT AGTCGAGTGA GTTTCCGCCA TTATGCCAAT AGGTGTCTTA

2451 CAGGGGATAA CGCAGGAAAG AACATGTGAG CAAAAGGCCA GCAAAAGGCC
            GTCCCCTATT GCGTCCTTTC TTGTACACTC GTTTTCCGGT CGTTTTCCGG

2501 AGGAACCGTA AAAAGGCCGC GTTGCTGGCG TTTTTCCATA GGCTCCGCCC
            TCCTTGGCAT TTTTCCGGCG CAACGACCGC AAAAAGGTAT CCGAGGCGGG

2551 CCCTGACGAG CATCACAAAA ATCGACGCTC AAGTCAGAGG TGGCGAAACC
            GGGACTGCTC GTAGTGTTTT TAGCTGCGAG TTCAGTCTCC ACCGCTTTGG

BssSI
       2601 CGACAGGACT ATAAAGATAC CAGGCGTTTC CCCCTGGAAG CTCCCTCGTG
```

Fig. 21B-4

```
           GCTGTCCTGA TATTTCTATG GTCCGCAAAG GGGGACCTTC GAGGGAGCAC

2651  CGCTCTCCTG TTCCGACCCT GCCGCTTACC GGATACCTGT CCGCCTTTCT
      GCGAGAGGAC AAGGCTGGGA CGGCGAATGG CCTATGGACA GGCGGAAAGA

2701  CCCTTCGGGA AGCGTGGCGC TTTCTCAATG CTCACGCTGT AGGTATCTCA
      GGGAAGCCCT TCGCACCGCG AAAGAGTTAC GAGTGCGACA TCCATAGAGT

2751  GTTCGGTGTA GGTCGTTCGC TCCAAGCTGG GCTGTGTGCA CGAACCCCCC
      CAAGCCACAT CCAGCAAGCG AGGTTCGACC CGACACACGT GCTTGGGGGG

2801  GTTCAGCCCG ACCGCTGCGC CTTATCCGGT AACTATCGTC TTGAGTCCAA
      CAAGTCGGGC TGGCGACGCG GAATAGGCCA TTGATAGCAG AACTCAGGTT

2851  CCCGGTAAGA CACGACTTAT CGCCACTGGC AGCAGCCACT GGTAACAGGA
      GGGCCATTCT GTGCTGAATA GCGGTGACCG TCGTCGGTGA CCATTGTCCT

2901  TTAGCAGAGC GAGGTATGTA GGCGGTGCTA CAGAGTTCTT GAAGTGGTGG
      AATCGTCTCG CTCCATACAT CCGCCACGAT GTCTCAAGAA CTTCACCACC

2951  CCTAACTACG GCTACACTAG AAGGACAGTA TTTGGTATCT GCGCTCTGCT
      GGATTGATGC CGATGTGATC TTCCTGTCAT AAACCATAGA CGCGAGACGA

3001  GAAGCCAGTT ACCTTCGGAA AAAGAGTTGG TAGCTCTTGA TCCGGCAAAC
      CTTCGGTCAA TGGAAGCCTT TTTCTCAACC ATCGAGAACT AGGCCGTTTG

3051  AAACCACCGC TGGTAGCGGT GGTTTTTTTG TTTGCAAGCA GCAGATTACG
      TTTGGTGGCG ACCATCGCCA CCAAAAAAAC AAACGTTCGT CGTCTAATGC

3101  CGCAGAAAAA AAGGATCTCA AGAAGATCCT TTGATCTTTT CTACGGGGTC
      GCGTCTTTTT TTCCTAGAGT TCTTCTAGGA AACTAGAAAA GATGCCCCAG

3151  TGACGCTCAG TGGAACGAAA ACTCACGTTA AGGGATTTTG GTCATGAGAT
      ACTGCGAGTC ACCTTGCTTT TGAGTGCAAT TCCCTAAAAC CAGTACTCTA

3201  TATCAAAAAG GATCTTCACC TAGATCCTTT TAAATTAAAA ATGAAGTTTT
      ATAGTTTTTC CTAGAAGTGG ATCTAGGAAA ATTTAATTTT TACTTCAAAA

3251  AAATCAATCT AAAGTATATA TGAGTAAACT TGGTCTGACA GTTACCAATG
      TTTAGTTAGA TTTCATATAT ACTCATTTGA ACCAGACTGT CAATGGTTAC
                                                      *  W  H      Frame 4

3301  CTTAATCAGT GAGGCACCTA TCTCAGCGAT CTGTCTATTT CGTTCATCCA
      GAATTAGTCA CTCCGTGGAT AGAGTCGCTA GACAGATAAA GCAAGTAGGT
         K  I  L  S  A  G  I  E  A  I  Q  R  N   R  E  D     Frame 4

AhdI
3351  TAGTTGCCTG ACTCCCCGTC GTGTAGATAA CTACGATACG GGAGGGCTTA
      ATCAACGGAC TGAGGGGCAG CACATCTATT GATGCTATGC CCTCCCGAAT
         M  T  A  Q  S  G  T   T  Y  I  V  V  I  R   S  P  K     Frame 4

3401  CCATCTGGCC CCAGTGCTGC AATGATACCG CGAGACCCAC GCTCACCGGC
      GGTAGACCGG GGTCACGACG TTACTATGGC GCTCTGGGTG CGAGTGGCCG
         G  D  P  G  L  A  A  I  G  R  S  G   R  E  G  A     Frame 4

BglI
3451  TCCAGATTTA TCAGCAATAA ACCAGCCAGC CGGAAGGGCC GAGCGCAGAA
```

Fig. 21B-5

```
              AGGTCTAAAT AGTCGTTATT TGGTCGGTCG GCCTTCCCGG CTCGCGTCTT
                C  S  K    D  A  I    F  W  G    A  P  L    S  R  L       Frame 4

AseI
     3501 GTGGTCCTGC AACTTTATCC GCCTCCATCC AGTCTATTAA TTGTTGCCGG
          CACCAGGACG TTGAAATAGG CGGAGGTAGG TCAGATAATT AACAACGGCC
             L  P  G    A  V  K    D  A  E    M  W  D    I  L  Q  Q  R    Frame 4

FspI
     3551 GAAGCTAGAG TAAGTAGTTC GCCAGTTAAT AGTTTGCGCA ACGTTGTTGC
          CTTCGATCTC ATTCATCAAG CGGTCAATTA TCAAACGCGT TGCAACAACG
             S  A  L    T  L  L  E   G  T  L    L  K  R    L  T  T  A     Frame 4

3601 CATTGCTACA GGCATCGTGG TGTCACGCTC GTCGTTTGGT ATGGCTTCAT
          GTAACGATGT CCGTAGCACC ACAGTGCGAG CAGCAAACCA TACCGAAGTA
             M  A  V    P  M  T    T  D  R  E    D  N  P    I  A  E       Frame 4

3651 TCAGCTCCGG TTCCCAACGA TCAAGGCGAG TTACATGATC CCCCATGTTG
          AGTCGAGGCC AAGGGTTGCT AGTTCCGCTC AATGTACTAG GGGGTACAAC
             N  L  E  P   E  W  R    D  L  R    T  V  H  D   G  M  N      Frame 4

3701 TGCAAAAAAG CGGTTAGCTC CTTCGGTCCT CCGATCGTTG TCAGAAGTAA
          ACGTTTTTTC GCCAATCGAG GAAGCCAGGA GGCTAGCAAC AGTCTTCATT
             H  L  F    A  T  L  E    K  P  G    G  I  T    T  L  L  L    Frame 4

3751 GTTGGCCGCA GTGTTATCAC TCATGGTTAT GGCAGCACTG CATAATTCTC
          CAACCGGCGT CACAATAGTG AGTACCAATA CCGTCGTGAC GTATTAAGAG
             N  A  A    T  N  D    S  M  T  I    A  A  S    C  L  E       Frame 4

3801 TTACTGTCAT GCCATCCGTA AGATGCTTTT CTGTGACTGG TGAGTACTCA
          AATGACAGTA CGGTAGGCAT TCTACGAAAA GACACTGACC ACTCATGAGT
             R  V  T  M    G  D  T    L  H  K    E  T  V  P    S  Y  E    Frame 4

3851 ACCAAGTCAT TCTGAGAATA GTGTATGCGG CGACCGAGTT GCTCTTGCCC
          TGGTTCAGTA AGACTCTTAT CACATACGCC GCTGGCTCAA CGAGAACGGG
             V  L  D    N  Q  S  Y    H  I  R    R  G  L    Q  E  Q  G    Frame 4

3901 GGCGTCAATA CGGGATAATA CCGCGCCACA TAGCAGAACT TTAAAAGTGC
          CCGCAGTTAT GCCCTATTAT GGCGCGGTGT ATCGTCTTGA AATTTTCACG
             A  D  I    R  S  L    V  A  G  C    L  L  V    K  F  T       Frame 4

XmnI
     3951 TCATCATTGG AAAACGTTCT TCGGGGCGAA AACTCTCAAG GATCTTACCG
          AGTAGTAACC TTTTGCAAGA AGCCCCGCTT TTGAGAGTTC CTAGAATGGC
             S  M  M  P    F  R  E    E  P  R    F  S  E  L    I  K  G    Frame 4

BsssSI
     4001 CTGTTGAGAT CCAGTTCGAT GTAACCCACT CGTGCACCCA ACTGATCTTC
          GACAACTCTA GGTCAAGCTA CATTGGGTGA GCACGTGGGT TGACTAGAAG
             S  N  L    D  L  E  I    Y  G  V    R  A  G    L  Q  D  E    Frame 4

4051 AGCATCTTTT ACTTTCACCA GCGTTTCTGG GTGAGCAAAA ACAGGAAGGC
          TCGTAGAAAA TGAAAGTGGT CGCAAAGACC CACTCGTTTT TGTCCTTCCG
             A  D  K    V  K  V    L  T  E  P    H  A  F    V  P  L       Frame 4

4101 AAAATGCCGC AAAAAAGGGA ATAAGGGCGA CACGGAAATG TTGAATACTC
          TTTTACGGCG TTTTTTCCCT TATTCCCGCT GTGCCTTTAC AACTTATGAG
```

Fig. 21B-6

```
           C    F    A    A    F    F    P    I    L    A    V    R    F    H    Q    I    S        Frame 4
     4151 ATACTCTTCC TTTTTCAATA TTATTGAAGC ATTTATCAGG GTTATTGTCT
          TATGAGAAGG AAAAAGTTAT AATAACTTCG TAAATAGTCC CAATAACAGA
            M  Frame 4
     4201 CATGAGCGGA TACATATTTG AATGTATTTA GAAAAATAAA CAAATAGGGG
          GTACTCGCCT ATGTATAAAC TTACATAAAT CTTTTTATTT GTTTATCCCC 4251 TTCCGCGCAC ATTTCCCCGA AAAGTGCCAC CTGACGCGCC CTGTAGCGGC
          AAGGCGCGTG TAAAGGGGCT TTTCACGGTG GACTGCGCGG GACATCGCCG 4301 GCATTAAGCG CGGCGGGTGT GGTGGTTACG CGCAGCGTGA CCGCTACACT
          CGTAATTCGC GCCGCCCACA CCACCAATGC GCGTCGCACT GGCGATGTGA 4351 TGCCAGCGCC CTAGCGCCCG CTCCTTTCGC TTTCTTCCCT TCCTTTCTCG
          ACGGTCGCGG GATCGCGGGC GAGGAAAGCG AAAGAAGGGA AGGAAAGAGC 4401 CCACGTTCGC CGGCTTTCCC CGTCAAGCTC TAAATCGGGG GCTCCCTTTA
          GGTGCAAGCG GCCGAAAGGG GCAGTTCGAG ATTTAGCCCC CGAGGGAAAT 4451 GGGTTCCGAT TTAGTGCTTT ACGGCACCTC GACCCCAAAA AACTTGATTA
          CCCAAGGCTA AATCACGAAA TGCCGTGGAG CTGGGGTTTT TTGAACTAAT DraIII
     4501 GGGTGATGGT TCACGTAGTG GGCCATCGCC CTGATAGACG GTTTTTCGCC
          CCCACTACCA AGTGCATCAC CCGGTAGCGG GACTATCTGC CAAAAAGCGG AloI
                AloI
     4551 CTTTGACGTT GGAGTCCACG TTCTTTAATA GTGGACTCTT GTTCCAAACT
          GAAACTGCAA CCTCAGGTGC AAGAAATTAT CACCTGAGAA CAAGGTTTGA 4601 GGAACAACAC TCAACCCTAT CTCGGTCTAT TCTTTTGATT TATAAGGGAT
          CCTTGTTGTG AGTTGGGATA GAGCCAGATA AGAAAACTAA ATATTCCCTA 4651 TTTGCCGATT TCGGCCTATT GGTTAAAAAA TGAGCTGATT TAACAAAAAT
          AAACGGCTAA AGCCGGATAA CCAATTTTTT ACTCGACTAA ATTGTTTTTA BglI
     4701 TTAACGCGAA TTTTAACAAA ATATTAACGT TTACAATTTC CCATTCGCCA
          AATTGCGCTT AAAATTGTTT TATAATTGCA AATGTTAAAG GGTAAGCGGT FspI
     4751 TTCAGGCTGC GCAACTGTTG GGAAGGGCGA TCGGTGCGGG CCTCTTCGCT
          AAGTCCGACG CGTTGACAAC CCTTCCCGCT AGCCACGCCC GGAGAAGCGA 4801 ATTACGCCAG CCCAAGCTAC CATGATAAGT AAGTAATATT AAGGTACGGG
          TAATGCGGTC GGGTTCGATG GTACTATTCA TTCATTATAA TTCCATGCCC NotI
     4851 AGGTACTTGG AGCGGCCGCG ATCCAGACAT GATAAGATAC ATTGATGAGT
          TCCATGAACC TCGCCGGCGC TAGGTCTGTA CTATTCTATG TAACTACTCA 4901 TTGGACAAAC CACAACTAGA ATGCAGTGAA AAAAATGCTT TATTTGTGAA
          AACCTGTTTG GTGTTGATCT TACGTCACTT TTTTTACGAA ATAAACACTT
```

Fig. 21B-7

```
4951 ATTTGTGATG CTATTGCTTT ATTTGTAACC ATTATAAGCT GCAATAAACA
     TAAACACTAC GATAACGAAA TAAACATTGG TAATATTCGA CGTTATTTGT

5001 AGTTAACAAC AACAATTGCA TTCATTTTAT GTTTCAGGTT CAGGGGGAGG
     TCAATTGTTG TTGTTAACGT AAGTAAAATA CAAAGTCCAA GTCCCCCTCC

5051 TGTGGGAGGT TTTTTAAAGC AAGTAAAACC TCTACAAATG TGGTATGGCT
     ACACCCTCCA AAAAATTTCG TTCATTTTGG AGATGTTTAC ACCATACCGA

BclI
5101 GATTATGATC ATGAACAGAC TGTGAGGACT GAGGGGCCTG AAATGAGCCT
     CTAATACTAG TACTTGTCTG ACACTCCTGA CTCCCCGGAC TTTACTCGGA

5151 TGGGACTGTG AATTTAAAAT ACACAAACAA TTAGAATCAG TAGTTTAACA
     ACCCTGACAC TTAAATTTTA TGTGTTTGTT AATCTTAGTC ATCAAATTGT

5201 CATTATACAC TTAAAAATTT TATATTTACC TTAGAGCTTT AAATCTCTGT
     GTAATATGTG AATTTTTAAA ATATAAATGG AATCTCGAAA TTTAGAGACA

5251 AGGTAGTTTG TCCAATTATG TCACACCACA GAAGTAAGGT TCCTTCACAA
     TCCATCAAAC AGGTTAATAC AGTGTGGTGT CTTCATTCCA AGGAAGTGTT
                                                 *  L      Frame 6

SalI
             AccI      XbaI
5301 AGATCCCAAG CTGTCGACAT TTCTAGAGGA TCTCGGACCC GGGGAATCCC
     TCTAGGGTTC GACAGCTGTA AAGATCTCCT AGAGCCTGGG CCCCTTAGGG
        S  G  L  S  D  V  N  R  S  S  R  P  G  P  S  D     Frame 6

5351 CGTCCCCCAA CATGTCCAGA TCGAAATCGT CTAGCGCGTC GGCATGCGCC
     GCAGGGGGTT GTACAGGTCT AGCTTTAGCA GATCGCGCAG CCGTACGCGG
        G  D  G  L  M  D  L  D  F  D  D  L  A  D  A  H  A  Frame 6

BtrI
5401 ATCGCCACGT CCTCGCCGTC TAAGTGGAGC TCGTCCCCCA GGCTGACATC
     TAGCGGTGCA GGAGCGGCAG ATTCACCTCG AGCAGGGGGT CCGACTGTAG
        M  A  V  D  E  G  D  L  H  L  E  D  G  L  S  V  D  Frame 6

5451 GGTCGGGGGG GCGGATCTCG GACCCGGGGA ATCCCCGTCC CCCAACATGT
     CCAGCCCCCC CGCCTAGAGC CTGGGCCCCT TAGGGGCAGG GGGTTGTACA
        T  P  P  A  S  R  P  G  P  S  D  G  D  G  L  M     Frame 6

BtrI
5501 CCAGATCGAA ATCGTCTAGC GCGTCGGCAT GCGCCATCGC CACGTCCTCG
     GGTCTAGCTT TAGCAGATCG CGCAGCCGTA CGCGGTAGCG GTGCAGGAGC
        D  L  D  F  D  D  L  A  D  A  H  A  M  A  V  D  E  Frame 6

BamHI
5551 CCGTCTAAGT GGAGCTCGTC CCCCAGGCTG ACATCGGTCG GGGGGGCGGA
     GGCAGATTCA CCTCGAGCAG GGGGTCCGAC TGTAGCCAGC CCCCCGCCT
        G  D  L  H  L  E  D  G  L  S  V  D  T  P  P  A  S  Frame 6

EcoRI
5601 TCCCCCGGGC TGCAGGAATT CCGGCGATAC AGTCAACTGT CTTTGACCTT
     AGGGGGCCCG ACGTCCTTAA GGCCGCTATG TCAGTTGACA GAAACTGGAA
        G  G  P  Q  L  F  E  P  S  V  T  L  Q  R  Q  G     Frame 6
```

Fig. 21B-8

```
5651 TGTTACTACT CTCTTCCGAT GATGATGTCG CACTTATTCT ATGCTGTCTC
     ACAATGATGA GAGAAGGCTA CTACTACAGC GTGAATAAGA TACGACAGAG
        K  N  S  S    E  E  S    S  S  T    A  S  I    R    H  Q  R       Frame 6

5701 AATGTTAGAG GCATATCAGT CTCCACTGAA GCCAATCTAT CTGTGACGGC
     TTACAATCTC CGTATAGTCA GAGGTGACTT CGGTTAGATA GACACTGCCG
        L  T  L    P  M  D    T    E  V  S    A  L  R    D  T  V  A       Frame 6

BsrGI
5751 ATCTTTATTC ACATTATCTT GTACAAATAA TCCTGTTAAC AATGCTTTTA
     TAGAAATAAG TGTAATAGAA CATGTTTATT AGGACAATTG TTACGAAAAT
         D  K  N    V  N  D    Q  V  F    L    G  T    L  A  K            Frame 6

XhoI
5801 TATCCTGTAA AGAATCCATT TTCAAAATCA TGTCAAGGTC TTCTCGAGGA
     ATAGGACATT TCTTAGGTAA AAGTTTTAGT ACAGTTCCAG AAGAGCTCCT
         I  D  Q  L    S  D  M    K  L  I    M  D  L    E  R  P           Frame 6

5851 AAAATCAGTA GAAATAGCTG TTCCAGTCTT TCTAGCCTTG ATTCCACTTC
     TTTTAGTCAT CTTTATCGAC AAGGTCAGAA AGATCGGAAC TAAGGTGAAG
         F  I  L    L  F  L    Q    E  L  R    E  L  R    S  E  V  E      Frame 6

5901 TGTCAGATGT GCCCTAGTCA GCGGAGACCT TTTGGTTTTG GGAGAGTAGC
     ACAGTCTACA CGGGATCAGT CGCCTCTGGA AAACCAAAAC CCTCTCATCG
            T  L  H    A  R  T    L  P  S  R    K  T    P  S  Y           Frame 6

5951 GACACTCCCA GTTGTTCTTC AGACACTTGG CGCACTTCGG TTTTTCTTTG
     CTGTGAGGGT CAACAAGAAG TCTGTGAACC GCGTGAAGCC AAAAAGAAAC
         R  C  E  W    N  N  K    L  C  K    A  C  K  P    K  E  K        Frame 6

6001 GAGCACTTGA GCTTTTTAAG TCGGCAAATA TCGCATGCTT GTTCGATAGA
     CTCGTGAACT CGAAAAATTC AGCCGTTTAT AGCGTACGAA CAAGCTATCT
         S  C  K    L  K  K  L    R  C  I    D  C  A    Q  E  I  S        Frame 6

HindIII
6051 AGACAGTAGC TTCATCTTTC AGGAGGCTTG CTTCAAGCTT GGGGCTGGGG
     TCTGTCATCG AAGTAGAAAG TCCTCCGAAC GAAGTTCGAA CCCCGACCCC
         S  L  L    K  M    Frame 6

6101 AGCCTCCCCC AGGAGCCCTA TAAAACCTTC ATTCCCCAGG ACTCCGCCCC
     TCGGAGGGGG TCCTCGGGAT ATTTTGGAAG TAAGGGGTCC TGAGGCGGGG

BglI                                       BstXI
6151 TGCCCTGCTG GCACCCAGAG GCTGACCAAG GCCCTCCCCA TGCTGCTGGA
     ACGGGACGAC CGTGGGTCTC CGACTGGTTC CGGGAGGGGT ACGACGACCT

BstXI
6201 GGCTGGACAA CCCCCTCCCA CACCCAGAGC TGTGGAAGGG GAGGGAGAGC
     CCGACCTGTT GGGGGAGGGT GTGGGTCTCG ACACCTTCCC CTCCCTCTCG

PsrI
        PsrI
6251 TAGTACTTGC TGTTCTGCAA TTACTAGATC ACCCTGGATG CACCAGGCCC
     ATCATGAACG ACAAGACGTT AATGATCTAG TGGGACCTAC GTGGTCCGGG

6301 TGTGGCTCAT GGAGACTTCA TCTAGGGGAC AAAGGCAGAG GAGACACGCC
     ACACCGAGTA CCTCTGAAGT AGATCCCCTG TTTCCGTCTC CTCTGTGCGG
```

Fig. 21B-9

```
                                        PmlI
6351 CAGGATGAAA CAGAAACAGG GGGTGGGTAC GATCCCCGAT TCTTCATACA
     GTCCTACTTT GTCTTTGTCC CCCACCCATG CTAGGGGCTA AGAAGTATGT

6401 AAGCCTCACG TGCCTAGATC CTTTGCACTC CAAGACCCAG TGTGCCCTAA
     TTCGGAGTGC ACGGATCTAG GAAACGTGAG GTTCTGGGTC ACACGGGATT

6451 GACACCAGCA CTCAGGAGAT TGTGAGACTC CCTGATCCCT GCACCACTCT
     CTGTGGTCGT GAGTCCTCTA ACACTCTGAG GGACTAGGGA CGTGGTGAGA

AloI
                        AloI
6501 GAGACCAGAA ACTAGAACTT TTATTCCTCA TGCTCCTGAA ATAGATGTCT
     CTCTGGTCTT TGATCTTGAA AATAAGGAGT ACGAGGACTT TATCTACAGA

6551 TGGCATTTAG TACATTCTTT TCCTTGCACT CCCAACCCAG AATCCAGCTC
     ACCGTAAATC ATGTAAGAAA AGGAACGTGA GGGTTGGGTC TTAGGTCGAG

AfeI
                                            Bpu10I
6601 CACAGATACA TTGCTACTGT CATCATAAAA AGATCCTGAG CGCTGCCTTA
     GTGTCTATGT AACGATGACA GTAGTATTTT TCTAGGACTC GCGACGGAAT

Tth111I
6651 TTCTGGGTTT GGCAGTGGAG TGCTGCCAGA CACAGTCGAT CGGGACCTAG
     AAGACCCAAA CCGTCACCTC ACGACGGTCT GTGTCAGCTA GCCCTGGATC

6701 AACCTTGGTT AGGCATAAAG AAGCAGGATG TGATAGAAGA AGTATTTAAT
     TTGGAACCAA TCCGTATTTC TTCGTCCTAC ACTATCTTCT TCATAAATTA

6751 GGTGGAACGT TGAGACTGTC CTGCAGACAA GGGTGGAAGG CTCTGGCTGA
     CCACCTTGCA ACTCTGACAG GACGTCTGTT CCCACCTTCC GAGACCGACT

NcoI
6801 ACAGCGTTGG GAGGCAATTC TCCATGGTTC TGTCACGTAT CTGTGTGTCT
     TGTCGCAACC CTCCGTTAAG AGGTACCAAG ACAGTGCATA GACACACAGA

6851 TCTGAGCAAA GACAGCAACA CCTTTTTTTT TCTGGATTGT TGTTTCAAGG
     AGACTCGTTT CTGTCGTTGT GGAAAAAAAA AGACCTAACA ACAAAGTTCC

EcoRV
6901 ATGTTTGTAA AGCAGGCATC CTTGCAAGAT GATATCTCTC TCAGATCCAG
     TACAAACATT TCGTCCGTAG GAACGTTCTA CTATAGAGAG AGTCTAGGTC

6951 GCTTGCTTAC TGTCCTAGAT AATAAAGATA ATGTCTCTTA CAACAGATTT
     CGAACGAATG ACAGGATCTA TTATTTCTAT TACAGAGAAT GTTGTCTAAA

7001 GTTTACTGTC AAGGACAATC AATACAATAT GTTCCTCCAG AGTAGGTCTG
     CAAATGACAG TTCCTGTTAG TTATGTTATA CAAGGAGGTC TCATCCAGAC

7051 TTTTCAATCC AAGATCATGA AGATAATATC TTCATCAGAG ACAAAGGCTG
     AAAAGTTAGG TTCTAGTACT TCTATTATAG AAGTAGTCTC TGTTTCCGAC

7101 AGCAGGTTTG CAAGTTGTCC CAGTATAAGA TTGAGGATTC CTAATCTCAG
     TCGTCCAAAC GTTCAACAGG GTCATATTCT AACTCCTAAG GATTAGAGTC
```

Fig. 21B-10

```
7151  GTTTCTCACC AGTGGCACAA ACCCCGTGTG CACAGCATCC ACCTAGACTG
      CAAAGAGTGG TCACCGTGTT TGGGGCACAC GTGTCGTAGG TGGATCTGAC

NcoI
        BstEII
7201  CTCTGGTCAC CATGGTTCTG TCACGTATCT GTGTGTCTTC TGAGCAAAGA
      GAGACCAGTG GTACCAAGAC AGTGCATAGA CACACAGAAG ACTCGTTTCT

7251  CAGCAACACC TTTTTTTCTG GATTGTTGTT TCAAGGATGT TGTAAAGCAG
      GTCGTTGTGG AAAAAAAGAC CTAACAACAA AGTTCCTACA ACATTTCGTC

EcoRV
7301  GCATCCTTGC AAGATGATAT CTCTCTCAGA TCCAGGCTTG CTTACTGTCC
      CGTAGGAACG TTCTACTATA GAGAGAGTCT AGGTCCGAAC GAATGACAGG

7351  TAGATAATAA AGATAATGTC TCTTACAACA GATTTGTTTA CTGTCAAGGA
      ATCTATTATT TCTATTACAG AGAATGTTGT CTAAACAAAT GACAGTTCCT

7401  CAATCAATAC AATATGTTCC TCCAGAGTAG GTCTGTTTTC AATCCAAGAT
      GTTAGTTATG TTATACAAGG AGGTCTCATC CAGACAAAAG TTAGGTTCTA

7451  CATGAAGATA ATATCTTCAT CAGAGACAAA GGCTGAGCAG GTTTGCAAGT
      GTACTTCTAT TATAGAAGTA GTCTCTGTTT CCGACTCGTC CAAACGTTCA

7501  TGTCCCAGTA TAAGATTGAG GATTCCTAAT CTCAGGTTTC TCACCAGTGG
      ACAGGGTCAT ATTCTAACTC CTAAGGATTA GAGTCCAAAG AGTGGTCACC

BstEII
7551  CACAAACCCC GTGTGCACAG CATCCACCTA GACTGCTCTG GTCACCCTAC
      GTGTTTGGGG CACACGTGTC GTAGGTGGAT CTGACGAGAC CAGTGGGATG

7601  AAGATTTGGG GGGGGCAAGG TGTACTAATG TGAACATGAA CCTCATGCTG
      TTCTAAACCC CCCCCGTTCC ACATGATTAC ACTTGTACTT GGAGTACGAC

7651  TCTGCTAAGC TGTGAGCAGT AAAAGCCTTT GCCTCTGACT CAGGAGTCTC
      AGACGATTCG ACACTCGTCA TTTTCGGAAA CGGAGACTGA GTCCTCAGAG

7701  ATGGACTCTG CCAGCATTCA CAAAACTCTG GAAAGTTAGC TTATTTGTTT
      TACCTGAGAC GGTCGTAAGT GTTTTGAGAC CTTTCAATCG AATAAACAAA

7751  GCAAGTCAGT AAAATGTCAG CCCCTTCAGA GTTACTGACA AACAGGTGGG
      CGTTCAGTCA TTTTACAGTC GGGGAAGTCT CAATGACTGT TTGTCCACCC

PvuII
          MscI                                SanDI  PvuII
7801  CACTGAGACT GCACTGGCCA GCTGGGAATA GAGATAGGAG GGGACCCAGC
      GTGACTCTGA CGTGACCGGT CGACCCTTAT CTCTATCCTC CCCTGGGTCG

7851  TGGATGCAGT GGGCAGTGGG GGTCATAGAG TCAAGAGGGT ACAGAATACA
      ACCTACGTCA CCCGTCACCC CCAGTATCTC AGTTCTCCCA TGTCTTATGT

7901  ATGGGGTCCT AGTATCATGG TGGAGGTCAG AAAGAGCCCT AAAAGAGAGG
      TACCCCAGGA TCATAGTACC ACCTCCAGTC TTTCTCGGGA TTTTCTCTCC

7951  GTCAAGGTAG GAGGTTAGTG AAGGTCCACC TCCACCCTCT CCAGGACAGG
      CAGTTCCATC CTCCAATCAC TTCCAGGTGG AGGTGGGAGA GGTCCTGTCC
```

Fig. 21B-11

```
                         AseI
8001  GACATCAGGC CACAATTAAT TTCTCTGCAG TTGGTGAGTG GTCATGGTCT
      CTGTAGTCCG GTGTTAATTA AAGAGACGTC AACCACTCAC CAGTACCAGA

8051  CTGGAGTCCC CAGCATCCAG AGTGTCCCTG GTCTAGTGGT CCCCCCTTTC
      GACCTCAGGG GTCGTAGGTC TCACAGGGAC CAGATCACCA GGGGGGAAAG

8101  TGAGCCACAG CCACTTTCTC CATCAAATGA GGCCAGTAAT ACCCATCCCA
      ACTCGGTGTC GGTGAAAGAG GTAGTTTACT CCGGTCATTA TGGGTAGGGT

8151  TAGTGATGCT GTGAGGATGA GATGAGCATC TGTAAGTGCT GAAGATAATC
      ATCACTACGA CACTCCTACT CTACTCGTAG ACATTCACGA CTTCTATTAG

8201  CCTGACACAT CCCAAGCATT CAGCAGTGCA AGCATACACT TACACGGCAC
      GGACTGTGTA GGGTTCGTAA GTCGTCACGT TCGTATGTGA ATGTGCCGTG
                                              PmlI
8251  TCCCCAGAGC CAGGCATGTG CTGGTGCCTC ATACACGTGA CCACATTTGA
      AGGGGTCTCG GTCCGTACAC GACCACGGAG TATGTGCACT GGTGTAAACT

8301  TCGTCACAAT GACCCTGTGA GGGAGACTGT GCAACAGAGG ACTGACCTTG
      AGCAGTGTTA CTGGGACACT CCCTCTGACA CGTTGTCTCC TGACTGGAAC

Bsu36I
8351  CTCAAAGACC TCAGGCGTTT CCCCTCAGAG CCTGAGAGGT CATCTCTTTT
      GAGTTTCTGG AGTCCGCAAA GGGGAGTCTC GGACTCTCCA GTAGAGAAAA

8401  TTTTTTTTTT TTTCCTTTCT TTCTTTTTCT TTTCCATTTC TTTTTCTTTG
      AAAAAAAAAA AAAGGAAAGA AAGAAAAAGA AAAGGTAAAG AAAAAGAAAC

8451  CAAGAGGTCA TCTCTAATGC TTTGGAATAT CCTGCCAGAT TAGAGTCCCT
      GTTCTCCAGT AGAGATTACG AAACCTTATA GGACGGTCTA ATCTCAGGGA

8501  TTGTTCACCT GAAGGTTTGG GCCACACCAG ATAGTCTAAC GGTGTGATTT
      AACAAGTGGA CTTCCAAACC CGGTGTGGTC TATCAGATTG CCACACTAAA
                                           XbaI   NotI
8551  GTGCTGAAGG TTTTGAGCCA CACTATATCA GCTAGATTTC TAGAGCGGCC
      CACGACTTCC AAAACTCGGT GTGATATAGT CGATCTAAAG ATCTCGCCGG

8601  GCAATAAAAT ATCTTTATTT TCATTACATC TGTGTGTTGG TTTTTTGTGT
      CGTTATTTTA TAGAAATAAA AGTAATGTAG ACACACAACC AAAAAACACA

8651  GAATCGATAG TACTAACATA CGCTCTCCAT CAAAACAAAA CGAAACAAAA
      CTTAGCTATC ATGATTGTAT GCGAGAGGTA GTTTTGTTTT GCTTTGTTTT

8701  CAAACTAGCA AAATAGGCTG TCCCCAGTGC AAGTGCAGGT GCCAGAACAT
      GTTTGATCGT TTTATCCGAC AGGGGTCACG TTCACGTCCA CGGTCTTGTA

8751  TTCTCTATCG ATA
      AAGAGATAGC TAT
```

Fig. 21B-12

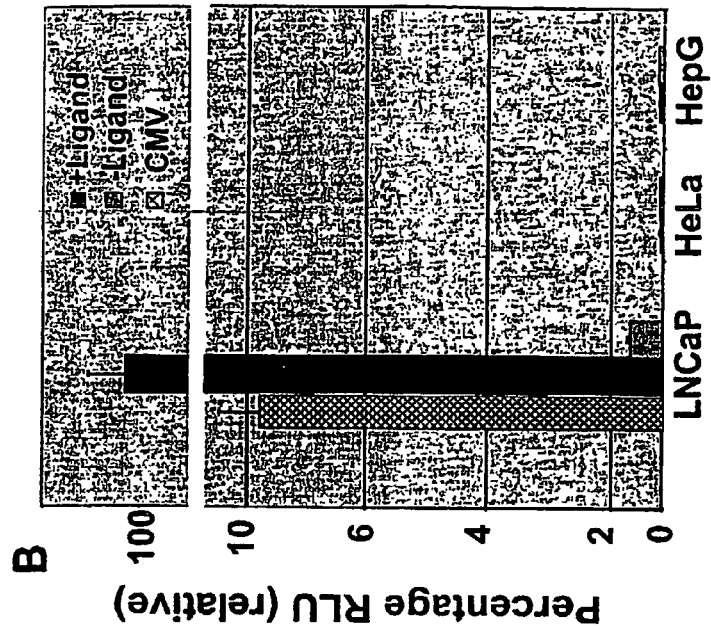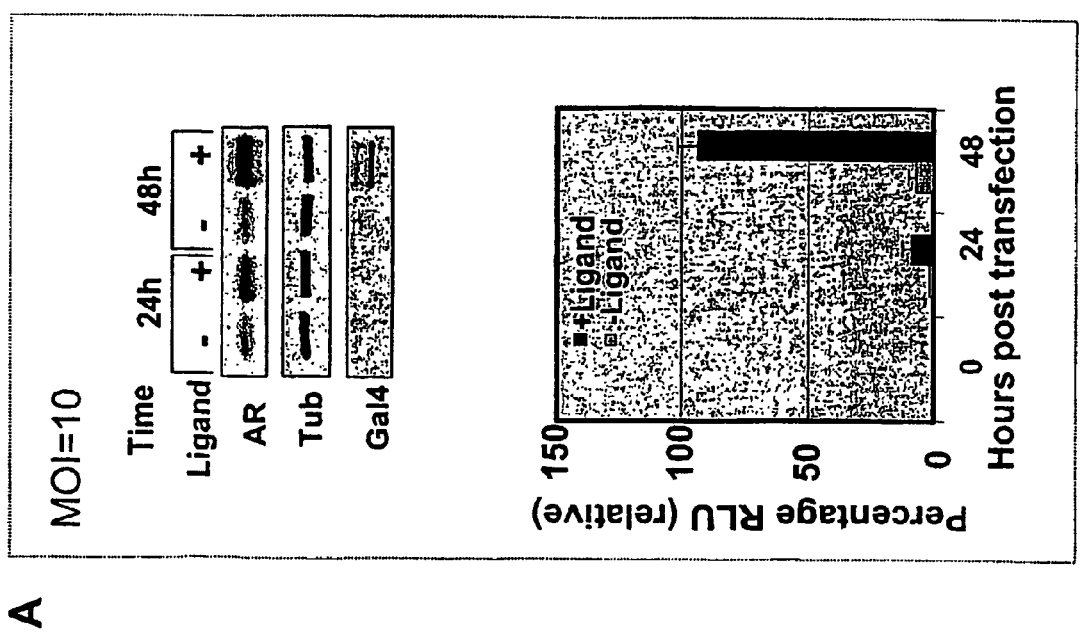
Fig. 23

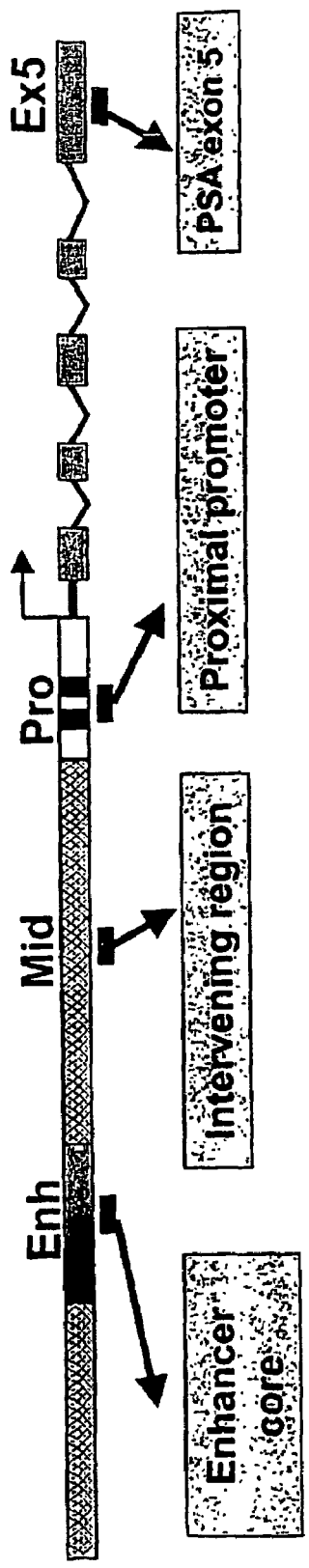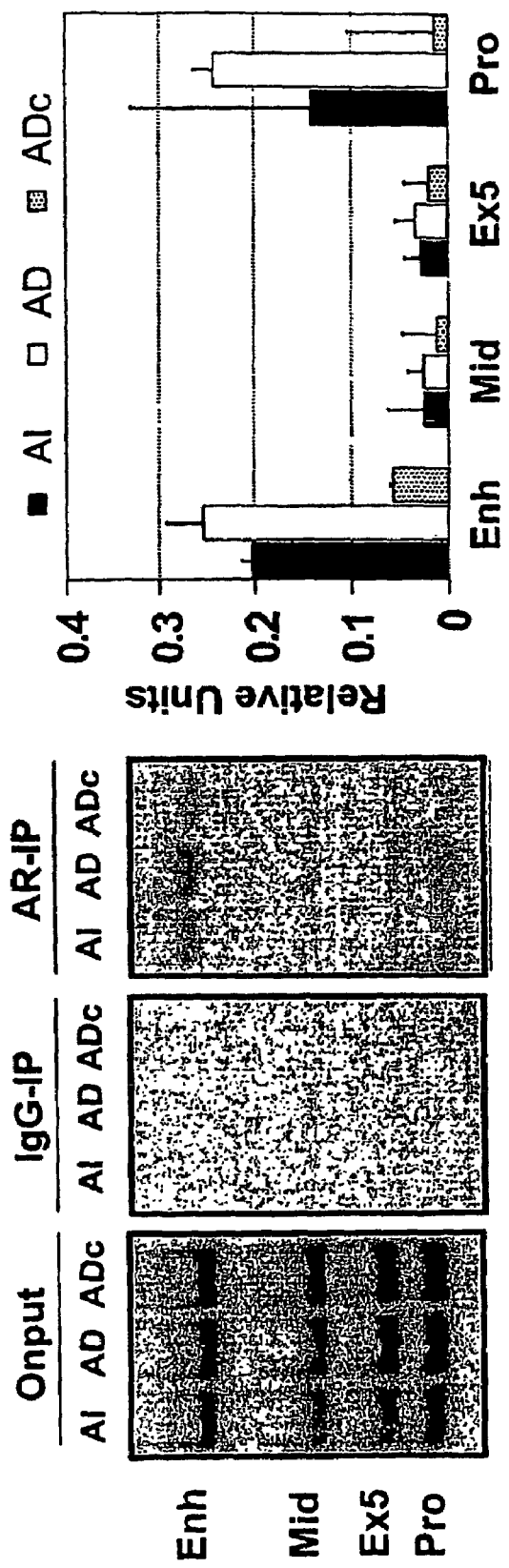
Fig. 27

SEQUENCE LISTING

```
<160> NUMBER OF SEQ ID NOS: 18

<210> SEQ ID NO 1
<211> LENGTH: 8771
<212> TYPE: DNA
<213> ORGANISM: Artificial Sequence
<220> FEATURE:
<223> OTHER INFORMATION: Description of Artificial Sequence:PBCVP2G5
      (not Sal) plasmid vector comprising effector and reporter
      sequences
<220> FEATURE:
<221> NAME/KEY: CDS
<222> LOCATION: (300)..(1952)
<223> OTHER INFORMATION: firefly luciferase (FL) from plasmid vector
      PBCVP2G5 (not Sal)
<220> FEATURE:
<221> NAME/KEY: CDS
<222> LOCATION: Complement((3292)..(4152))
<223> OTHER INFORMATION: beta lactamase, ampicillin resistance protein
      from plasmid vector PCBVP2G5 (not Sal)
<220> FEATURE:
<221> NAME/KEY: CDS
<222> LOCATION: Complement((5266)..(6069))
<223> OTHER INFORMATION: Gal4 DNA-binding domain/V16 transactivation
      domain fusion protein from plasmid vector PCBVP2G5 (not Sal)

<400> SEQUENCE: 1
ggtaccgagc tcatttaggt gacactatag aatacaagct tgcatgcctg caggtccgga      60
ggacagtact ccgctcggag gacagtactc cgctcggagg acagtactcc gctcggagga    120
```

-continued

| | |
|---|---|
| cagtactccg ctcggaggac agtactccga ctctagagga tccccagtcc tatatatact | 180 |
| cgctctgcac ttggcccttt tttacactgt gactgattga gctggtgccg tgtcgagtgg | 240 |
| tgtctcgaga tctgcgatct aagtaagctt ggcattccgg tactgttggt aaagccacc | 299 |

| | | |
|---|---|---|
| atg gaa gac gcc aaa aac ata aag aaa ggc ccg gcg cca ttc tat ccg<br>Met Glu Asp Ala Lys Asn Ile Lys Lys Gly Pro Ala Pro Phe Tyr Pro<br>1             5                 10              15 | | 347 |
| ctg gaa gat gga acc gct gga gag caa ctg cat aag gct atg aag aga<br>Leu Glu Asp Gly Thr Ala Gly Glu Gln Leu His Lys Ala Met Lys Arg<br>               20                 25              30 | | 395 |
| tac gcc ctg gtt cct gga aca att gct ttt aca gat gca cat atc gag<br>Tyr Ala Leu Val Pro Gly Thr Ile Ala Phe Thr Asp Ala His Ile Glu<br>       35                 40              45 | | 443 |
| gtg gac atc act tac gct gag tac ttc gaa atg tcc gtt cgg ttg gca<br>Val Asp Ile Thr Tyr Ala Glu Tyr Phe Glu Met Ser Val Arg Leu Ala<br>50                 55                 60 | | 491 |
| gaa gct atg aaa cga tat ggg ctg aat aca aat cac aga atc gtc gta<br>Glu Ala Met Lys Arg Tyr Gly Leu Asn Thr Asn His Arg Ile Val Val<br>65                 70                 75              80 | | 539 |
| tgc agt gaa aac tct ctt caa ttc ttt atg ccg gtg ttg ggc gcg tta<br>Cys Ser Glu Asn Ser Leu Gln Phe Phe Met Pro Val Leu Gly Ala Leu<br>               85                 90              95 | | 587 |
| ttt atc gga gtt gca gtt gcg ccc gcg aac gac att tat aat gaa cgt<br>Phe Ile Gly Val Ala Val Ala Pro Ala Asn Asp Ile Tyr Asn Glu Arg<br>              100                105              110 | | 635 |
| gaa ttg ctc aac agt atg ggc att tcg cag cct acc gtg gtg ttc gtt<br>Glu Leu Leu Asn Ser Met Gly Ile Ser Gln Pro Thr Val Val Phe Val<br>             115                120              125 | | 683 |
| tcc aaa aag ggg ttg caa aaa att ttg aac gtg caa aaa aag ctc cca<br>Ser Lys Lys Gly Leu Gln Lys Ile Leu Asn Val Gln Lys Lys Leu Pro<br>130                 135                140 | | 731 |
| atc atc caa aaa att att atc atg gat tct aaa acg gat tac cag gga<br>Ile Ile Gln Lys Ile Ile Ile Met Asp Ser Lys Thr Asp Tyr Gln Gly<br>145                 150                155              160 | | 779 |
| ttt cag tcg atg tac acg ttc gtc aca tct cat cta cct ccc ggt ttt<br>Phe Gln Ser Met Tyr Thr Phe Val Thr Ser His Leu Pro Pro Gly Phe<br>             165                170              175 | | 827 |
| aat gaa tac gat ttt gtg cca gag tcc ttc gat agg gac aag aca att<br>Asn Glu Tyr Asp Phe Val Pro Glu Ser Phe Asp Arg Asp Lys Thr Ile<br>              180                185              190 | | 875 |
| gca ctg atc atg aac tcc tct gga tct act ggt ctg cct aaa ggt gtc<br>Ala Leu Ile Met Asn Ser Ser Gly Ser Thr Gly Leu Pro Lys Gly Val<br>             195                200              205 | | 923 |
| gct ctg cct cat aga act gcc tgc gtg aga ttc tcg cat gcc aga gat<br>Ala Leu Pro His Arg Thr Ala Cys Val Arg Phe Ser His Ala Arg Asp<br>210                 215                220 | | 971 |
| cct att ttt ggc aat caa atc att ccg gat act gcg att tta agt gtt<br>Pro Ile Phe Gly Asn Gln Ile Ile Pro Asp Thr Ala Ile Leu Ser Val<br>225                 230                235              240 | | 1019 |
| gtt cca ttc cat cac ggt ttt gga atg ttt act aca ctc gga tat ttg<br>Val Pro Phe His His Gly Phe Gly Met Phe Thr Thr Leu Gly Tyr Leu<br>             245                250              255 | | 1067 |
| ata tgt gga ttt cga gtc gtc tta atg tat aga ttt gaa gaa gag ctg<br>Ile Cys Gly Phe Arg Val Val Leu Met Tyr Arg Phe Glu Glu Glu Leu<br>             260                265              270 | | 1115 |
| ttt ctg agg agc ctt cag gat tac aag att caa agt gcg ctg ctg gtg<br>Phe Leu Arg Ser Leu Gln Asp Tyr Lys Ile Gln Ser Ala Leu Leu Val<br>             275                280              285 | | 1163 |

```
cca acc cta ttc tcc ttc ttc gcc aaa agc act ctg att gac aaa tac      1211
Pro Thr Leu Phe Ser Phe Phe Ala Lys Ser Thr Leu Ile Asp Lys Tyr
    290             295                 300 gat tta tct aat tta cac gaa att gct tct ggt ggc gct ccc ctc tct      1259
Asp Leu Ser Asn Leu His Glu Ile Ala Ser Gly Gly Ala Pro Leu Ser
305                 310                 315                 320 aag gaa gtc ggg gaa gcg gtt gcc aag agg ttc cat ctg cca ggt atc      1307
Lys Glu Val Gly Glu Ala Val Ala Lys Arg Phe His Leu Pro Gly Ile
                325                 330                 335 agg caa gga tat ggg ctc act gag act aca tca gct att ctg att aca      1355
Arg Gln Gly Tyr Gly Leu Thr Glu Thr Thr Ser Ala Ile Leu Ile Thr
            340                 345                 350 ccc gag ggg gat gat aaa ccg ggc gcg gtc ggt aaa gtt gtt cca ttt      1403
Pro Glu Gly Asp Asp Lys Pro Gly Ala Val Gly Lys Val Val Pro Phe
        355                 360                 365 ttt gaa gcg aag gtt gtg gat ctg gat acc ggg aaa acg ctg ggc gtt      1451
Phe Glu Ala Lys Val Val Asp Leu Asp Thr Gly Lys Thr Leu Gly Val
    370                 375                 380 aat caa aga ggc gaa ctg tgt gtg aga ggt cct atg att atg tcc ggt      1499
Asn Gln Arg Gly Glu Leu Cys Val Arg Gly Pro Met Ile Met Ser Gly
385                 390                 395                 400 tat gta aac aat ccg gaa gcg acc aac gcc ttg att gac aag gat gga      1547
Tyr Val Asn Asn Pro Glu Ala Thr Asn Ala Leu Ile Asp Lys Asp Gly
                405                 410                 415 tgg cta cat tct gga gac ata gct tac tgg gac gaa gac gaa cac ttc      1595
Trp Leu His Ser Gly Asp Ile Ala Tyr Trp Asp Glu Asp Glu His Phe
            420                 425                 430 ttc atc gtt gac cgc ctg aag tct ctg att aag tac aaa ggc tat cag      1643
Phe Ile Val Asp Arg Leu Lys Ser Leu Ile Lys Tyr Lys Gly Tyr Gln
        435                 440                 445 gtg gct ccc gct gaa ttg gaa tcc atc ttg ctc caa cac ccc aac atc      1691
Val Ala Pro Ala Glu Leu Glu Ser Ile Leu Leu Gln His Pro Asn Ile
    450                 455                 460 ttc gac gca ggt gtc gca ggt ctt ccc gac gat gac gcc ggt gaa ctt      1739
Phe Asp Ala Gly Val Ala Gly Leu Pro Asp Asp Asp Ala Gly Glu Leu
465                 470                 475                 480 ccc gcc gcc gtt gtt gtt ttg gag cac gga aag acg atg acg gaa aaa      1787
Pro Ala Ala Val Val Val Leu Glu His Gly Lys Thr Met Thr Glu Lys
                485                 490                 495 gag atc gtg gat tac gtc gcc agt caa gta aca acc gcg aaa aag ttg      1835
Glu Ile Val Asp Tyr Val Ala Ser Gln Val Thr Thr Ala Lys Lys Leu
            500                 505                 510 cgc gga gga gtt gtg ttt gtg gac gaa gta ccg aaa ggt ctt acc gga      1883
Arg Gly Gly Val Val Phe Val Asp Glu Val Pro Lys Gly Leu Thr Gly
        515                 520                 525 aaa ctc gac gca aga aaa atc aga gag atc ctc ata aag gcc aag aag      1931
Lys Leu Asp Ala Arg Lys Ile Arg Glu Ile Leu Ile Lys Ala Lys Lys
    530                 535                 540 ggc gga aag atc gcc gtg taa ttctagagtc ggggcggccg gccgcttcga         1982
Gly Gly Lys Ile Ala Val
545                 550 gcagacatga taagatacat tgatgagttt ggacaaacca caactagaat gcagtgaaaa    2042
aaatgcttta tttgtgaaat ttgtgatgct attgctttat ttgtaaccat tataagctgc    2102
aataaacaag ttaacaacaa caattgcatt cattttatgt ttcaggttca ggggaggtg     2162 tgggaggttt tttaaagcaa gtaaaacctc tacaaatgtg gtaaaatcga taaggatccg    2222
tcgaccgatg cccttgagag ccttcaaccc agtcagctcc ttccggtggg cgcggggcat    2282
gactatcgtc gccgcactta tgactgtctt ctttatcatg caactcgtag gacaggtgcc    2342
```

```
ggcagcgctc ttccgcttcc tcgctcactg actcgctgcg ctcggtcgtt cggctgcggc    2402
gagcggtatc agctcactca aaggcggtaa tacggttatc cacagaatca ggggataacg    2462
caggaaagaa catgtgagca aaaggccagc aaaaggccag gaaccgtaaa aaggccgcgt    2522
tgctggcgtt tttccatagg ctccgccccc ctgacgagca tcacaaaaat cgacgctcaa    2582
gtcagaggtg gcgaaacccg acaggactat aaagatacca ggcgtttccc cctggaagct    2642
ccctcgtgcg ctctcctgtt ccgaccctgc cgcttaccgg atacctgtcc gcctttctcc    2702
cttcgggaag cgtggcgctt tctcaatgct cacgctgtag gtatctcagt tcggtgtagg    2762
tcgttcgctc caagctgggc tgtgtgcacg aaccccccgt tcagcccgac cgctgcgcct    2822
tatccggtaa ctatcgtctt gagtccaacc cggtaagaca cgacttatcg ccactggcag    2882
cagccactgg taacaggatt agcagagcga ggtatgtagg cggtgctaca gagttcttga    2942
agtggtggcc taactacggc tacactagaa ggacagtatt tggtatctgc gctctgctga    3002
agccagttac cttcggaaaa agagttggta gctcttgatc cggcaaacaa accaccgctg    3062
gtagcggtgg ttttttttgtt tgcaagcagc agattacgcg cagaaaaaaa ggatctcaag    3122
aagatccttt gatcttttct acggggtctg acgctcagtg gaacgaaaac tcacgttaag    3182 ggatttttggt catgagatta tcaaaaagga tcttcaccta gatcctttta aattaaaaat    3242
gaagttttaa atcaatctaa agtatatatg agtaaacttg gtctgacagt taccaatgct    3302
taatcagtga ggcacctatc tcagcgatct gtctatttcg ttcatccata gttgcctgac    3362
tccccgtcgt gtagataact acgatacggg agggcttacc atctggcccc agtgctgcaa    3422
tgataccgcg agacccacgc tcaccggctc cagatttatc agcaataaac cagccagccg    3482
gaagggccga gcgcagaagt ggtcctgcaa ctttatccgc ctccatccag tctattaatt    3542
gttgccggga agctagagta agtagttcgc cagttaatag tttgcgcaac gttgttgcca    3602
ttgctacagg catcgtggtg tcacgctcgt cgtttggtat ggcttcattc agctccggtt    3662
cccaacgatc aaggcgagtt acatgatccc ccatgttgtg caaaaaagcg gttagctcct    3722
tcggtcctcc gatcgttgtc agaagtaagt tggccgcagt gttatcactc atggttatgg    3782
cagcactgca taattctctt actgtcatgc catccgtaag atgcttttct gtgactggtg    3842
agtactcaac caagtcattc tgagaatagt gtatgcggcg accgagttgc tcttgcccgg    3902
cgtcaatacg ggataatacc gcgccacata gcagaacttt aaaagtgctc atcattggaa    3962
aacgttcttc ggggcgaaaa ctctcaagga tcttaccgct gttgagatcc agttcgatgt    4022
aacccactcg tgcacccaac tgatcttcag catcttttac tttcaccagc gtttctgggt    4082
gagcaaaaac aggaaggcaa aatgccgcaa aaaagggaat aagggcgaca cggaaatgtt    4142
gaatactcat actcttcctt tttcaatatt attgaagcat ttatcagggt tattgtctca    4202
tgagcggata catatttgaa tgtatttaga aaaataaaca ataggggtt ccgcgcacat    4262 ttccccgaaa agtgccacct gacgcgccct gtagcggcgc attaagcgcg gcgggtgtgg    4322
tggttacgcg cagcgtgacc gctacacttg ccagcgccct agcgcccgct cctttcgctt    4382
tcttcccttc ctttctcgcc acgttcgccg gctttccccg tcaagctcta aatcgggggc    4442
tccctttagg gttccgattt agtgctttac ggcacctcga ccccaaaaaa cttgattagg    4502
gtgatggttc acgtagtggg ccatcgccct gatagacggt ttttcgccct ttgacgttgg    4562
agtccacgtt ctttaatagt ggactcttgt tccaaactgg aacaacactc aaccctatct    4622
cggtctattc ttttgattta agggattt tgccgatttc ggcctattgg ttaaaaaatg    4682
```

```
agctgattta acaaaaattt aacgcgaatt ttaacaaaat attaacgttt acaatttccc    4742
attcgccatt caggctgcgc aactgttggg aagggcgatc ggtgcgggcc tcttcgctat    4802
tacgccagcc caagctacca tgataagtaa gtaatattaa ggtacgggag gtacttggag    4862
cggccgcgat ccagacatga taagatacat tgatgagttt ggacaaacca caactagaat    4922
gcagtgaaaa aaatgcttta tttgtgaaat tgtgatgct attgctttat ttgtaaccat     4982
tataagctgc aataaacaag ttaacaacaa caattgcatt cattttatgt ttcaggttca    5042 ggggaggtg tgggaggttt tttaaagcaa gtaaaacctc tacaaatgtg gtatggctga     5102
ttatgatcat gaacagactg tgaggactga ggggcctgaa atgagccttg ggactgtgaa    5162
tttaaaatac acaaacaatt agaatcagta gtttaacaca ttatacactt aaaaatttta    5222
tatttacctt agagctttaa atctctgtag gtagtttgtc caattatgtc acaccacaga    5282
agtaaggttc cttcacaaag atcccaagct gtcgatcgac atttctagag gatctcggac    5342
ccggggaatc cccgtccccc aacatgtcca gatcgaaatc gtctagcgcg tcggcatgcg    5402
ccatcgccac gtcctcgccg tctaagtgga gctcgtcccc caggctgaca tcggtcgggg    5462
gggcggatct cggacccggg gaatcccgt ccccaacat gtccagatcg aaatcgtcta     5522
gcgcgtcggc atgcgccatc gccacgtcct cgccgtctaa gtggagctcg tccccaggc    5582 tgacatcggt cggggggcg gatccccgg gctgcaggaa ttccggcgat acagtcaact     5642
gtctttgacc tttgttacta ctctcttccg atgatgatgt cgcacttatt ctatgctgtc    5702
tcaatgttag aggcatatca gtctccactg aagccaatct atctgtgacg gcatctttat    5762
tcacattatc ttgtacaaat aatcctgtta acaatgcttt tatatcctgt aaagaatcca    5822
ttttcaaaat catgtcaagg tcttctcgag gaaaaatcag tagaaatagc tgttccagtc    5882
tttctagcct tgattccact tctgtcagat gtgccctagt cagcggagac cttttggttt    5942
tgggagagta gcgacactcc cagttgttct tcagacactt ggcgcacttc ggttttctt     6002 tggagcactt gagcttttta agtcggcaaa tatcgcatgc ttgttcgata aagacagta    6062 gcttcatctt tcaggaggct tgcttcaagc ttggggctgg ggagcctccc ccaggagccc    6122
tataaaacct tcattcccca ggactccgcc cctgccctgc tggcacccag aggctgacca    6182
aggccctccc catgctgctg gaggctggac aaccccctcc cacacccaga gctgtggaag    6242
gggagggaga gctagtactt gctgttctgc aattactaga tcaccctgga tgcaccaggc    6302
cctgtggctc atggagactt catctagggg acaaaggcag aggagacacg cccaggatga    6362
aacagaaaca gggggtgggt acgatccccg attcttcata caaagcctca cgtgcctaga    6422
tcctttgcac tccaagaccc agtgtgccct aagacaccag cactcaggag attgtgagac    6482
tccctgatcc ctgcaccact ctgagaccag aaactagaac ttttattcct catgctcctg    6542
aaatagatgt cttggcattt agtacattct tttccttgca ctcccaaccc agaatccagc    6602
tccacagata cattgctact gtcatcataa aaagatcctg agcgctgcct tattctgggt    6662
ttggcagtgg agtgctgcca gacacagtcg atcgggacct agaaccttgg ttaggcataa    6722
agaagcagga tgtgatagaa gaagtattta atggtggaac gttgagactg tcctgcagac    6782
aagggtggaa ggctctggct gaacagcgtt gggaggcaat tctccatggt tctgtcacgt    6842
atctgtgtgt cttctgagca aagacagcaa caccttttt tttctggatt gttgtttcaa     6902
ggatgtttgt aaagcaggca tccttgcaag atgatatctc tctcagatcc aggcttgctt    6962
actgtcctag ataataaaga taatgtctct tacaacagat tgtttactg tcaaggacaa     7022 tcaatacaat atgttcctcc agagtaggtc tgttttcaat ccaagatcat gaagataata    7082
```

```
tcttcatcag agacaaaggc tgagcaggtt tgcaagttgt cccagtataa gattgaggat    7142
tcctaatctc aggtttctca ccagtggcac aaacccgtg tgcacagcat ccacctagac    7202
tgctctggtc accatggttc tgtcacgtat ctgtgtgtct tctgagcaaa gacagcaaca    7262
ccttttttc tggattgttg tttcaaggat gttgtaaagc aggcatcctt gcaagatgat    7322
atctctctca gatccaggct tgcttactgt cctagataat aaagataatg tctcttacaa    7382
cagatttgtt tactgtcaag gacaatcaat acaatatgtt cctccagagt aggtctgttt    7442
tcaatccaag atcatgaaga taatatcttc atcagagaca aaggctgagc aggtttgcaa    7502
gttgtcccag tataagattg aggattccta atctcaggtt tctcaccagt ggcacaaacc    7562
ccgtgtgcac agcatccacc tagactgctc tggtcaccct acaagatttg ggggggcaa    7622
ggtgtactaa tgtgaacatg aacctcatgc tgtctgctaa gctgtgagca gtaaaagcct    7682
ttgcctctga ctcaggagtc tcatggactc tgccagcatt cacaaaactc tggaaagtta    7742
gcttatttgt ttgcaagtca gtaaaatgtc agccccttca gagttactga caaacaggtg    7802
ggcactgaga ctgcactggc cagctgggaa tagagatagg aggggaccca gctggatgca    7862
gtgggcagtg ggggtcatag agtcaagagg gtacagaata caatgggtc ctagtatcat    7922
ggtggaggtc agaaagagcc ctaaaagaga gggtcaaggt aggaggttag tgaaggtcca    7982
cctccaccct ctccaggaca gggacatcag gccacaatta atttctctgc agttggtgag    8042
tggtcatggt ctctggagtc cccagcatcc agagtgtccc tggtctagtg gtccccctt    8102
tctgagccac agccactttc tccatcaaat gaggccagta ataccatcc catagtgatg    8162
ctgtgaggat gagatgagca tctgtaagtg ctgaagataa tccctgacac atcccaagca    8222
ttcagcagtg caagcataca cttacacggc actcccagga gccaggcatg tgctggtgcc    8282
tcatacacgt gaccacattt gatcgtcaca atgaccctgt gagggagact gtgcaacaga    8342
ggactgacct tgctcaaaga cctcaggcgt ttcccctcag agcctgagag gtcatctctt    8402
tttttttttt ttttccttt cttctttt ctttccatt tcttttctt tgcaagaggt    8462
catctctaat gctttggaat atcctgccag attagagtcc ctttgttcac ctgaaggttt    8522
gggccacacc agatagtcta acggtgtgat ttgtgctgaa ggttttgagc cacactatat    8582
cagctagatt tctagagcgg ccggccgcaa taaatatct ttattttcat tacatctgtg    8642
tgttggtttt ttgtgtgaat cgatagtact aacatacgct ctccatcaaa acaaaacgaa    8702
acaaaacaaa ctagcaaaat aggctgtccc cagtgcaagt gcaggtgcca gaacatttct    8762
ctatcgata                                                            8771
```

<210> SEQ ID NO 2
<211> LENGTH: 550
<212> TYPE: PRT
<213> ORGANISM: Artificial Sequence
<220> FEATURE:
<223> OTHER INFORMATION: Description of Artificial Sequence:firefly
      luciferase (FL) from plasmid vectors PBCVP2G5 (not Sal) and
      PBCVP2G5-L

<400> SEQUENCE: 2

```
Met Glu Asp Ala Lys Asn Ile Lys Lys Gly Pro Ala Pro Phe Tyr Pro
 1               5                  10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45
```

```
Val Asp Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460
```

```
Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ile Ala Val
545                 550

<210> SEQ ID NO 3
<211> LENGTH: 286
<212> TYPE: PRT
<213> ORGANISM: Artificial Sequence
<220> FEATURE:
<223> OTHER INFORMATION: Description of Artificial Sequence:beta
      lactamase, ampicillin resistance protein from plasmid vectors
      PCBVP2G5 (not Sal) and PCBVP2G5-L

<400> SEQUENCE: 3

Met Ser Ile Gln His Phe Arg Val Ala Leu Ile Pro Phe Phe Ala Ala
 1               5                  10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
```

```
                    260                 265                 270
Arg Gln Ile Ala Glu Ile Gly Ala Ser Leu Ile Lys His Trp
            275                 280                 285

<210> SEQ ID NO 4
<211> LENGTH: 267
<212> TYPE: PRT
<213> ORGANISM: Artificial Sequence
<220> FEATURE:
<223> OTHER INFORMATION: Description of Artificial Sequence:Gal4
      DNA-binding domain/V16 transactivation domain
      fusion protein from plasmid vector PCBVP2G5 (not Sal)

<400> SEQUENCE: 4

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Leu Gln Pro Gly Gly Ser Ala Pro Pro Thr
145                 150                 155                 160

Asp Val Ser Leu Gly Asp Glu Leu His Leu Asp Gly Glu Asp Val Ala
                165                 170                 175

Met Ala His Ala Asp Ala Leu Asp Asp Phe Asp Leu Asp Met Leu Gly
            180                 185                 190

Asp Gly Asp Ser Pro Gly Pro Arg Ser Ala Pro Pro Thr Asp Val Ser
        195                 200                 205

Leu Gly Asp Glu Leu His Leu Asp Gly Glu Asp Val Ala Met Ala His
    210                 215                 220

Ala Asp Ala Leu Asp Asp Phe Asp Leu Asp Met Leu Gly Asp Gly Asp
225                 230                 235                 240

Ser Pro Gly Pro Arg Ser Ser Arg Asn Val Asp Arg Gln Leu Gly Ile
                245                 250                 255

Phe Val Lys Glu Pro Tyr Phe Cys Gly Val Thr
            260                 265

<210> SEQ ID NO 5
<211> LENGTH: 8763
<212> TYPE: DNA
<213> ORGANISM: Artificial Sequence
<220> FEATURE:
<223> OTHER INFORMATION: Description of Artificial Sequence:PBCVP2G5-L
      plasmid vector comprising effector and reporter sequences
<220> FEATURE:
<221> NAME/KEY: CDS
<222> LOCATION: (300)..(1952)
```

```
<223> OTHER INFORMATION: firefly luciferase (FL) from plasmid vector
      PBCVP2G5-L
<220> FEATURE:
<221> NAME/KEY: CDS
<222> LOCATION: Complement((3292)..(4152))
<223> OTHER INFORMATION: beta lactamase, ampicillin resistance protein
      from plasmid vector PCBVP2G5-L
<220> FEATURE:
<221> NAME/KEY: CDS
<222> LOCATION: Complement((5295)..(6065))
<223> OTHER INFORMATION: Gal4 DNA-binding domain/V16 transactivation
      domain fusion protein from plasmid vector PCBVP2G5-L

<400> SEQUENCE: 5
ggtaccgagc tcatttaggt gacactatag aatacaagct tgcatgcctg caggtccgga     60
ggacagtact ccgctcggag gacagtactc cgctcggagg acagtactcc gctcggagga    120
cagtactccg ctcggaggac agtactccga ctctagagga tccccagtcc tatatatact    180
cgctctgcac ttggcccttt tttacactgt gactgattga gctggtgccg tgtcgagtgg    240
tgtctcgaga tctgcgatct aagtaagctt ggcattccgg tactgttggt aaagccacca    300
tggaagacgc caaaaacata agaaaggcc cggcgccatt ctatccgctg aagatggaa      360 ccgctggaga gcaactgcat aaggctatga agagatacgc cctggttcct ggaacaattg    420
cttttacaga tgcacatatc gaggtggaca tcacttacgc tgagtacttc gaaatgtccg    480
ttcggttggc agaagctatg aaacgatatg gctgaatac aaatcacaga atcgtcgtat     540
gcagtgaaaa ctctcttcaa ttctttatgc cggtgttggg cgcgttattt atcggagttg    600
cagttgcgcc cgcgaacgac atttataatg aacgtgaatt gctcaacagt atgggcattt    660
cgcagcctac cgtggtgttc gtttccaaaa aggggttgca aaaattttg aacgtgcaaa     720 aaaagctccc aatcatccaa aaattatta tcatggattc taaaacggat taccagggat    780
ttcagtcgat gtacacgttc gtcacatctc atctacctcc cggttttaat gaatacgatt    840
ttgtgccaga gtccttcgat agggacaaga caattgcact gatcatgaac tcctctggat    900
ctactggtct gcctaaaggt gtcgctctgc tcatagaac tgcctgcgtg agattctcgc     960
atgccagaga tcctattttt ggcaatcaaa tcattccgga tactgcgatt ttaagtgttg   1020
ttccattcca tcacggtttt ggaatgttta ctacactcgg atatttgata tgtggatttc   1080
gagtcgtctt aatgtataga tttgaagaag agctgtttct gaggagcctt caggattaca   1140
agattcaaag tgcgctgctg gtgccaaccc tattctcctt cttcgccaaa agcactctga   1200
ttgacaaata cgatttatct aatttacacg aaattgcttc tggtggcgct ccctctcta    1260 aggaagtcgg ggaagcggtt gccaagaggt tccatctgcc aggtatcagg caaggatatg   1320
ggctcactga gactacatca gctattctga ttacacccga gggggatgat aaaccgggcg   1380
cggtcggtaa agttgttcca tttttgaag cgaaggttgt ggatctggat accgggaaaa    1440
cgctgggcgt taatcaaaga gcgaactgt gtgtgagagg tcctatgatt atgtccggtt    1500
atgtaaacaa tccggaagcg accaacgcct tgattgacaa ggatggatgg ctacattctg   1560
gagacatagc ttactgggac gaagacgaac acttcttcat cgttgaccgc ctgaagtctc   1620
tgattaagta caaaggctat caggtggctc ccgctgaatt ggaatccatc ttgctccaac   1680
accccaacat cttcgacgca ggtgtcgcag gtcttcccga cgatgacgcc ggtgaacttc   1740
ccgccgccgt tgttgttttg gagcacggaa agacgatgac ggaaaaagag atcgtggatt   1800
acgtcgccag tcaagtaaca accgcgaaaa agttgcgcgg aggagttgtg tttgtggacg   1860
aagtaccgaa aggtcttacc ggaaaactcg acgcaagaaa aatcagagag atcctcataa   1920
```

```
aggccaagaa gggcggaaag atcgccgtgt aattctagag tcggggcggc cggccgcttc    1980
gagcagacat gataagatac attgatgagt ttggacaaac cacaactaga atgcagtgaa    2040
aaaaatgctt tatttgtgaa atttgtgatg ctattgcttt atttgtaacc attataagct    2100
gcaataaaca agttaacaac aacaattgca ttcattttat gtttcaggtt caggggagg     2160
tgtgggaggt tttttaaagc aagtaaaacc tctacaaatg tggtaaaatc gataaggatc    2220
cgtcgaccga tgcccttgag agccttcaac ccagtcagct ccttccggtg ggcgcggggc    2280
atgactatcg tcgccgcact tatgactgtc ttctttatca tgcaactcgt aggacaggtg    2340
ccggcagcgc tcttccgctt cctcgctcac tgactcgctg cgctcggtcg ttcggctgcg    2400
gcgagcggta tcagctcact caaaggcggt aatacggtta ccacagaat cagggggataa    2460
cgcaggaaag aacatgtgag caaaaggcca gcaaaaggcc aggaaccgta aaaaggccgc    2520
gttgctggcg ttttcccata ggctccgccc ccctgacgag catcacaaaa atcgacgctc    2580
aagtcagagg tggcgaaacc cgacaggact ataaagatac caggcgtttc ccctggaag    2640
ctccctcgtg cgctctcctg ttccgaccct gccgcttacc ggatacctgt ccgcctttct    2700
cccttcggga agcgtggcgc tttctcaatg ctcacgctgt aggtatctca gttcggtgta    2760
ggtcgttcgc tccaagctgg gctgtgtgca cgaacccccc gttcagcccg accgctgcgc    2820
cttatccggt aactatcgtc ttgagtccaa cccggtaaga cacgacttat cgccactggc    2880
agcagccact ggtaacagga ttagcagagc gaggtatgta ggcggtgcta cagagttctt    2940
gaagtggtgg cctaactacg gctacactag aaggacagta tttggtatct gcgctctgct    3000
gaagccagtt accttcggaa aaagagttgg tagctcttga tccggcaaac aaaccaccgc    3060
tggtagcggt ggttttttg tttgcaagca gcagattacg cgcagaaaaa aaggatctca    3120
agaagatcct ttgatctttt ctacggggtc tgacgctcag tggaacgaaa actcacgtta    3180
agggattttg gtcatgagat tatcaaaaag gatcttcacc tagatccttt taaattaaaa    3240
atgaagtttt aaatcaatct aaagtatata tgagtaaact tggtctgaca gttaccaatg    3300
cttaatcagt gaggcaccta tctcagcgat ctgtctattt cgttcatcca tagttgcctg    3360
actccccgtc gtgtagataa ctacgatacg ggagggctta ccatctggcc ccagtgctgc    3420
aatgataccg cgagacccac gctcaccggc tccagattta tcagcaataa accagccagc    3480
cggaagggcc gagcgcagaa gtggtcctgc aactttatcc gcctccatcc agtctattaa    3540
ttgttgccgg gaagctagag taagtagttc gccagttaat agtttgcgca acgttgttgc    3600
cattgctaca ggcatcgtgg tgtcacgctc gtcgtttggt atggcttcat tcagctccgg    3660
ttcccaacga tcaaggcgag ttacatgatc ccccatgttg tgcaaaaaag cggttagctc    3720
cttcggtcct ccgatcgttg tcagaagtaa gttggccgca gtgttatcac tcatggttat    3780
ggcagcactg cataattctc ttactgtcat gccatccgta agatgctttt ctgtgactgg    3840
tgagtactca accaagtcat tctgagaata gtgtatgcgg cgaccgagtt gctcttgccc    3900
ggcgtcaata cgggataata ccgcgccaca tagcagaact ttaaaagtgc tcatcattgg    3960
aaaacgttct cggggcgaaa actctcaag gatcttaccg ctgttgagat ccagttcgat    4020
gtaacccact cgtgcaccca actgatcttc agcatctttt actttcacca gcgtttctgg    4080
gtgagcaaaa acaggaaggc aaaatgccgc aaaaaaggga ataagggcga cacggaaatg    4140
ttgaatactc atactcttcc ttttttcaata ttattgaagc atttatcagg gttattgtct    4200
catgagcgga tacatatttg aatgtattta gaaaaataaa caaataggg ttccgcgcac    4260
atttccccga aaagtgccac ctgacgcgcc ctgtagcggc gcattaagcg cggcgggtgt    4320
```

```
ggtggttacg cgcagcgtga ccgctacact tgccagcgcc ctagcgcccg ctcctttcgc    4380
tttcttccct tcctttctcg ccacgttcgc cggctttccc cgtcaagctc taaatcgggg    4440
gctcccttta ggttccgat ttagtgcttt acggcacctc accccaaaa aacttgatta     4500
gggtgatggt tcacgtagtg ggccatcgcc ctgatagacg gttttcgcc ctttgacgtt    4560
ggagtccacg ttctttaata gtggactctt gttccaaact ggaacaacac tcaaccctat   4620
ctcggtctat tcttttgatt tataagggat tttgccgatt tcggctatt ggttaaaaaa   4680
tgagctgatt taacaaaaat ttaacgcgaa ttttaacaaa atattaacgt ttacaatttc   4740
ccattcgcca ttcaggctgc gcaactgttg ggaagggcga tcggtgcggg cctcttcgct   4800
attacgccag cccaagctac catgataagt aagtaatatt aaggtacggg aggtacttgg   4860
agcggccgcg atccagacat gataagatac attgatgagt ttggacaaac cacaactaga   4920
atgcagtgaa aaaatgctt tatttgtgaa atttgtgatg ctattgcttt atttgtaacc   4980
attataagct gcaataaaca agttaacaac aacaattgca ttcattttat gtttcaggtt   5040
caggggagg tgtgggaggt tttttaaagc aagtaaaacc tctacaaatg tggtatggct    5100
gattatgatc atgaacagac tgtgaggact gaggggcctg aaatgagcct tgggactgtg   5160
aatttaaaat acacaacaa ttagaatcag tagtttaaca cattatacac ttaaaaattt    5220
tatatttacc ttagagcttt aaatctctgt aggtagtttg tccaattatg tcacaccaca   5280
gaagtaaggt tccttcacaa agatcccaag ctgtcgacat ttctagagga tctcggaccc   5340
ggggaatccc cgtcccccaa catgtccaga tcgaaatcgt ctagcgcgtc ggcatgcgcc   5400
atcgccacgt cctcgccgtc taagtggagc tcgtccccca ggctgacatc ggtcggggg   5460
gcggatctcg gacccgggga atccccgtcc ccaacatgt ccagatcgaa atcgtctagc   5520
gcgtcggcat gcgccatcgc cacgtcctcg ccgtctaagt ggagctcgtc ccccaggctg   5580
acatcggtcg gggggcgga tccccgggc tgcaggaatt ccggcgatac agtcaactgt    5640
ctttgacctt tgttactact ctcttccgat gatgatgtcg cacttattct atgctgtctc   5700
aatgttagag gcatatcagt ctccactgaa gccaatctat ctgtgacggc atctttattc   5760
acattatctt gtacaaataa tcctgttaac aatgctttta tatcctgtaa agaatccatt   5820
ttcaaaatca tgtcaaggtc ttctcgagga aaaatcagta gaaatagctg ttccagtctt   5880
tctagccttg attccacttc tgtcagatgt gccctagtca gcggagacct tttggttttg   5940
ggagagtagc gacactccca gttgttcttc agacacttgg cgcacttcgg ttttctttg   6000
gagcacttga gcttttaag tcggcaaata tcgcatgctt gttcgataga agacagtagc    6060
ttcatctttc aggaggcttg cttcaagctt ggggctgggg agcctccccc aggagcccta   6120
taaaaccttc attccccagg actccgcccc tgccctgctg gcacccagag gctgaccaag   6180
gccctcccca tgctgctgga ggctggacaa ccccctccca cacccagagc tgtggaaggg   6240
gagggagagc tagtacttgc tgttctgcaa ttactagatc accctggatg caccaggccc   6300
tgtggctcat ggagacttca tctaggggac aaaggcagag gagacacgcc caggatgaaa   6360
cagaaacagg gggtgggtac gatccccgat tcttcataca aagcctcacg tgcctagatc   6420
ctttgcactc caagacccag tgtgcccctaa gacaccagca ctcaggagat tgtgagactc   6480
cctgatccct gcaccactct gagaccagaa actagaactt ttattcctca tgctcctgaa   6540
atagatgtct tggcatttag tacattcttt tccttgcact cccaacccag aatccagctc   6600
cacagataca ttgctactgt catcataaaa agatcctgag cgctgcctta ttctgggttt   6660
```

```
ggcagtggag tgctgccaga cacagtcgat cgggacctag aaccttggtt aggcataaag    6720
aagcaggatg tgatagaaga agtatttaat ggtggaacgt tgagactgtc ctgcagacaa    6780
gggtggaagg ctctggctga acagcgttgg gaggcaattc tccatggttc tgtcacgtat    6840
ctgtgtgtct tctgagcaaa gacagcaaca ccttttttt tctggattgt tgtttcaagg     6900
atgtttgtaa agcaggcatc cttgcaagat gatatctctc tcagatccag gcttgcttac    6960
tgtcctagat aataaagata atgtctctta caacagattt gtttactgtc aaggacaatc    7020
aatacaatat gttcctccag agtaggtctg ttttcaatcc aagatcatga agataatatc    7080
ttcatcagag acaaaggctg agcaggtttg caagttgtcc cagtataaga ttgaggattc    7140
ctaatctcag gtttctcacc agtggcacaa accccgtgtg cacagcatcc acctagactg    7200
ctctggtcac catggttctg tcacgtatct gtgtgtcttc tgagcaaaga cagcaacacc    7260
tttttttctg gattgttgtt tcaaggatgt tgtaaagcag gcatccttgc aagatgatat    7320
ctctctcaga tccaggcttg cttactgtcc tagataataa agataatgtc tcttacaaca    7380
gatttgttta ctgtcaagga caatcaatac aatatgttcc tccagagtag gtctgttttc    7440
aatccaagat catgaagata atatcttcat cagagacaaa ggctgagcag gtttgcaagt    7500
tgtcccagta taagattgag gattcctaat ctcaggtttc tcaccagtgg cacaaacccc    7560
gtgtgcacag catccaccta gactgctctg gtcaccctac aagatttggg gggggcaagg    7620
tgtactaatg tgaacatgaa cctcatgctg tctgctaagc tgtgagcagt aaaagccttt    7680
gcctctgact caggagtctc atggactctg ccagcattca caaaactctg gaaagttagc    7740
ttatttgttt gcaagtcagt aaaatgtcag cccttcaga gttactgaca aacaggtggg    7800
cactgagact gcactggcca gctgggaata gagataggag gggacccagc tggatgcagt    7860
gggcagtggg ggtcatagag tcaagagggt acagaataca atggggtcct agtatcatgg    7920
tggaggtcag aaagagccct aaaagagagg gtcaaggtag gaggttagtg aaggtccacc    7980
tccaccctct ccaggacagg gacatcaggc acaattaat ttctctgcag ttggtgagtg     8040
gtcatggtct ctggagtccc cagcatccag agtgtccctg gtctagtggt cccccttc     8100 tgagccacag ccactttctc catcaaatga ggccagtaat acccatccca tagtgatgct    8160
gtgaggatga gatgagcatc tgtaagtgct gaagataatc cctgacacat cccaagcatt    8220
cagcagtgca agcatacact tacacggcac tccccagagc caggcatgtg ctggtgcctc    8280
atacacgtga ccacatttga tcgtcacaat gaccctgtga gggagactgt gcaacagagg    8340
actgaccttg ctcaaagacc tcaggcgttt ccctcagag cctgagaggt catctctttt    8400
tttttttttt tttcctttct ttctttttct tttccatttc tttttctttg caagaggtca    8460
tctctaatgc tttggaatat cctgccagat tagagtccct ttgttcacct gaaggtttgg    8520
gccacaccag atagtctaac ggtgtgattt gtgctgaagg ttttgagcca cactatatca    8580
gctagatttc tagagcggcc gcaataaaat atctttattt tcattacatc tgtgtgttgg    8640 tttttgtgt gaatcgatag tactaacata cgctctccat caaaacaaaa cgaaacaaaa    8700
caaactagca aaataggctg tccccagtgc aagtgcaggt gccagaacat ttctctatcg    8760
ata                                                                 8763
```

<210> SEQ ID NO 6
<211> LENGTH: 256
<212> TYPE: PRT
<213> ORGANISM: Artificial Sequence
<220> FEATURE:
<223> OTHER INFORMATION: Description of Artificial Sequence:Gal4

DNA-binding domain/V16 transactivation domain
fusion protein from plasmid vector PCBVP2G5-L

<400> SEQUENCE: 6

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Pro Glu Phe Leu Gln Pro Gly Gly Ser Ala Pro Pro Thr
145                 150                 155                 160

Asp Val Ser Leu Gly Asp Glu Leu His Leu Asp Gly Glu Asp Val Ala
                165                 170                 175

Met Ala His Ala Asp Ala Leu Asp Asp Phe Asp Leu Asp Met Leu Gly
            180                 185                 190

Asp Gly Asp Ser Pro Gly Pro Arg Ser Ala Pro Pro Thr Asp Val Ser
        195                 200                 205

Leu Gly Asp Glu Leu His Leu Asp Gly Glu Asp Val Ala Met Ala His
    210                 215                 220

Ala Asp Ala Leu Asp Asp Phe Asp Leu Asp Met Leu Gly Asp Gly Asp
225                 230                 235                 240

Ser Pro Gly Pro Arg Ser Ser Arg Asn Val Asp Ser Leu Gly Ser Leu
                245                 250                 255

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:PCR
      amplification upstream primer with SacI site
      attached

<400> SEQUENCE: 7
cccgagctca tttaggtgac actatag                                              27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:PCR
      amplification downstream primer with XhoI site
      attached

<400> SEQUENCE: 8

```
cccctcgaga caccactcga cacggcacc                                    29
```

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:G5E4T PCR
      amplification primer

<400> SEQUENCE: 9

```
gactagatct acagcttgca tgcctgcag                                    29
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:G5E4T PCR
      amplification primer

<400> SEQUENCE: 10

```
gactgctagc tcgacacggc acca                                         24
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:Enhancer
      32P-labeled PCR primer

<400> SEQUENCE: 11

```
ggtgaccaga gcagtctagg tg                                           22
```

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Enhancer
      32P-labeled PCR primer

<400> SEQUENCE: 12

```
tgtttactgt caaggacaat cgat                                         24
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Promoter
      32P-labeled PCR primer

<400> SEQUENCE: 13

```
gtatgaagaa tcggggatcg t                                            21
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:Promoter
      32P-labeled PCR primer

<400> SEQUENCE: 14

```
gctcatggag acttcatcta g                                            21
```

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Middle
      32P-labeled PCR primer

<400> SEQUENCE: 15
tatgcttggg gacaccggat                                                    20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:Middle
      32P-labeled PCR primer

<400> SEQUENCE: 16
ttagagctgg agtggaagga tat                                                23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:Exon
      32P-labeled PCR primer

<400> SEQUENCE: 17
taatggtgtg cttcaaggta tcacg                                              25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:Exon
      32P-labeled PCR primer

<400> SEQUENCE: 18
gtgtccttga tccacttccg gtaat                                              25
```

US 7,527,942 B2

TRANSCRIPTION AMPLIFICATION SYSTEM FOR MOLECULAR IMAGING

This application claims priority to provisional application, U.S. Ser. No. 60/355,300, filed Feb. 8, 2002, the contents of which are hereby incorporated by reference in their entirety into this application.

Throughout this application, various publications are referenced within parentheses. The disclosures of these publications are hereby incorporated by reference herein in their entireties.

FIELD OF THE INVENTION

The present invention relates to a transcription amplification system, comprising an effector nucleic acid molecule and a reporter molecule, which work together to produce/express a heterologous gene product in a cell-type, specific manner. The present invention also relates to methods for use of the transcription system, including methods for producing, detecting, and/or imaging the heterologous gene product.

BACKGROUND OF THE INVENTION

Current gene therapy regimens used for treatment of cancer has many limitations, including lack of tissue-specificity, borderline efficacy, and inadequate delivery methods. Most attempts to optimize gene therapy have focused on delivery of the recombinant therapeutic gene to the target tumor and restricted expression of the therapeutic gene in the target tumor. Another limitation is the lack of reliable and non-invasive methods for detecting and monitoring delivery and expression of the therapeutic gene.

One strategy for optimizing gene therapy methods includes the two-component reporter gene system, or the so-called two-step transcription amplification system (Segawa, et al., 1998 Cancer Res. 58:2282-2287). In this system, the first step involves a tissue-specific or tumor-specific promoter to drive expression of a transcription activator. In the second step, the transcription activator induces expression of a reporter or therapeutic gene product.

SUMMARY OF THE INVENTION

The present invention provides isolated, recombinant nucleic acid molecules comprising effector sequences and reporter sequences. The effector and reporter molecules comprise a two-step transcription amplification system (TSTA) which can be used to express heterologous gene products in a cell-type specific manner. The effector and reporter nucleotide sequences can be used for in vivo and in vitro production of heterologous gene products. The present invention also provides methods for making and using the nucleic acid molecules having the effector and reporter nucleotide sequences.

The effector nucleotide sequences include an upstream regulatory region which permits expression of the effector gene product in a cell-type specific manner. The upstream regulatory region is operably linked to a nucleotide sequence encoding a chimeric, transactivator protein which includes a DNA-binding domain and a transcription trans-activator domain.

The reporter nucleotide sequences include a DNA-binding sequence and an upstream regulatory sequence. The upstream sequence can be a promoter which is operably linked to a heterologous gene sequence. The heterologous gene sequence can encode a reporter gene product, a therapeutic gene product, and/or an immunologically active protein.

The chimeric transactivator protein, produced by the effector molecule, is capable of binding to the DNA-binding sequence (part of the reporter molecule) and activating transcription of the heterologous sequence. Thus, the effector gene product (e.g., the transactivator protein) is capable of trans-activating transcription, and subsequently translation (e.g., expression), of the heterologous gene sequence.

The present invention also provides methods for producing/expressing heterologous gene products using the molecules of the TSTA system. The first step includes expression of the effector gene product (e.g., the chimeric transactivator protein) in a cell-specific manner. The second step includes expression of the heterologous gene product. The effector gene product causes expression of the heterologous gene product. The heterologous gene product is produced in a cell, in a cell in a subject, or in a donor cell implanted in a subject.

The present invention provides methods for detecting production of the heterologous gene product. Such detecting methods include using non-invasive techniques, including positron emission tomography (PET), single photon emission computed tomography, cooled charged coupled device (CCD) camera optical imaging, magnetic resonance imaging, bioluminescent optical imaging, and fluorescence optical imaging.

The effector and reporter nucleotide sequences of the present invention are DNA or RNA. Further, the invention includes nucleotides sequences that are identical or nearly identical (e.g., similar) with the effector and reporter nucleotide sequences of the invention. The invention additionally provides polynucleotide sequences that hybridize under stringent conditions to the effector and reporter nucleotide sequences of the invention. A further embodiment provides polynucleotide sequences which are complementary to the effector and reporter nucleotide sequences of the invention. Yet another embodiment provides effector and reporter nucleotide nucleic acid molecules that are labeled with a detectable marker. Another embodiment provides recombinant nucleic acid molecules, such as a vector or a fusion molecule, including the effector and reporter nucleotide sequences of the invention.

The present invention provides various effector and reporter nucleotide sequences, fragments thereof having essential gene activity, and related molecules such as antisense molecules, oligonucleotides, peptide nucleic acids (PNA), fragments, and portions thereof.

The present invention relates to the inclusion of the effector and reporter nucleotide sequences included in an expression vector. The expression vector can be used to transform host cells or organisms to produce transgenic hosts. The invention further provides host-vector systems and transgenic animals harboring the effector and reporter nucleotide sequences. Such transgenic hosts are useful for the production, detection, monitoring, imaging, and visualizing the expression of the heterologous gene product.

BRIEF DESCRIPTION OF THE FIGURES

FIG. 4: (A) In vivo optical CCD imaging of mice carrying transiently transfected LNCaP cells for control studies. All images shown are the visible light image superimposed on the optical CCD image with a scale in RLU/min as shown. (Panel 1) LNCaP cells were transiently transfected with only the L5 vector (control) and cells implanted i.p. The animal was then imaged after injection of D-luciferin (i.p.). (Panel 2) The same animal as in Panel 1 was imaged 48 h after implantation of androgen pellet by re-administering D-luciferin (i.p.). (Panel 3) LNCaP cells were transiently transfected with the PG and L5 vectors and cells implanted i.p. The mouse was imaged after i.p. injection of D-luciferin. (Panel 4) The same animal imaged in Panel 3 was re-imaged in the absence of androgen 48 h later after i.p. injection of D-luciferin. (B) In vivo optical CCD imaging of mice carrying transiently transfected LNCaP cells for comparison of one-step and TSTA. All images shown are the visible light image superimposed on the optical CCD image with a scale in RLU/min as shown. (Panel 1) LNCaP cells were transiently transfected with only the one-step PL vector and cells implanted i.p. The animal was then imaged after injection of D-luciferin (i.p.). (Panel 2) The same mouse in Panel 1 was re-imaged with i.p. injection of D-luciferin 48 h after implantation of an androgen pellet. (Panel 3) LNCaP cells were transiently transfected with the PG and L5 vectors (TSTA system) and cells implanted i.p. The mouse was then imaged after i.p. injection of D-luciferin. (Panel 4) The same animal imaged in Panel 3 was re-imaged with i.p. D-luciferin 48 h after implantation of an androgen pellet.

G5-L with or without androgen treatment. The samples were prepared, blotted and probed with GAL4-VP16 antibodies. (B) We seeded six human cell lines in six-well plates and transfected as described. The same molar amount of luciferase gene was transfected into all the cell types with a total DNA amount of 0.5 mg per well. We normalized all the RLU readings to the values obtained from the combination of SV40-VP2 and G5-L transfected into the same cell line. The SV40-VP2/G5-L value was set at 1 in the 3-D plot. We employed PBC-L as a control for promoter specificity of the effector and measured the background by transfection of G5-L alone.

Figure 11:
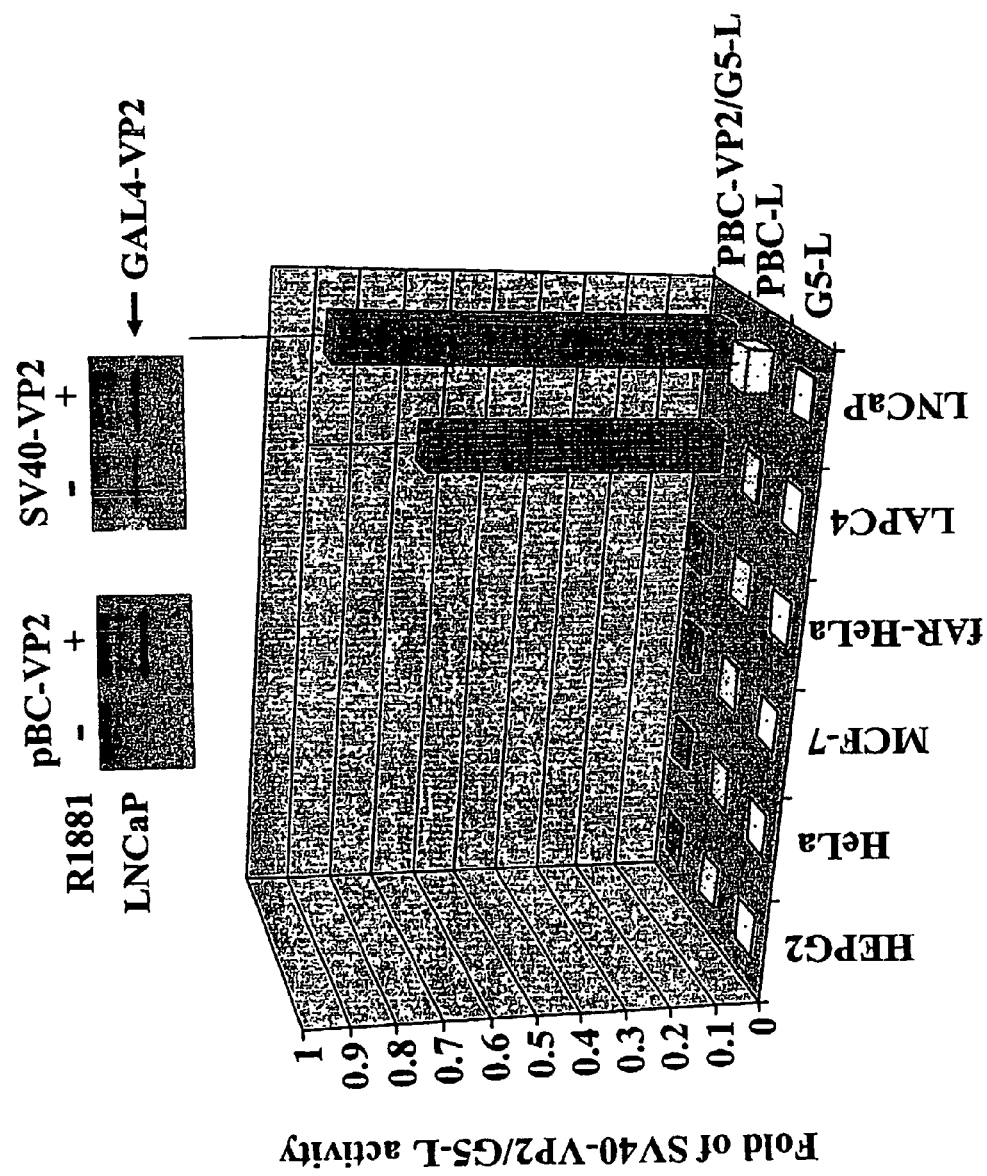
FIG. 11: Cell Specific Expression and Androgen Inducibility of the TSTA system. (A) Immunoblot analyses demonstrating the expression GAL4-VP2 from the optimized PBC-VP2 construct versus our benchmark SV40-VP2. We transfected LNCaP cells with PBC-VP2/G5-L or SV40-VP2/
Figure 12:
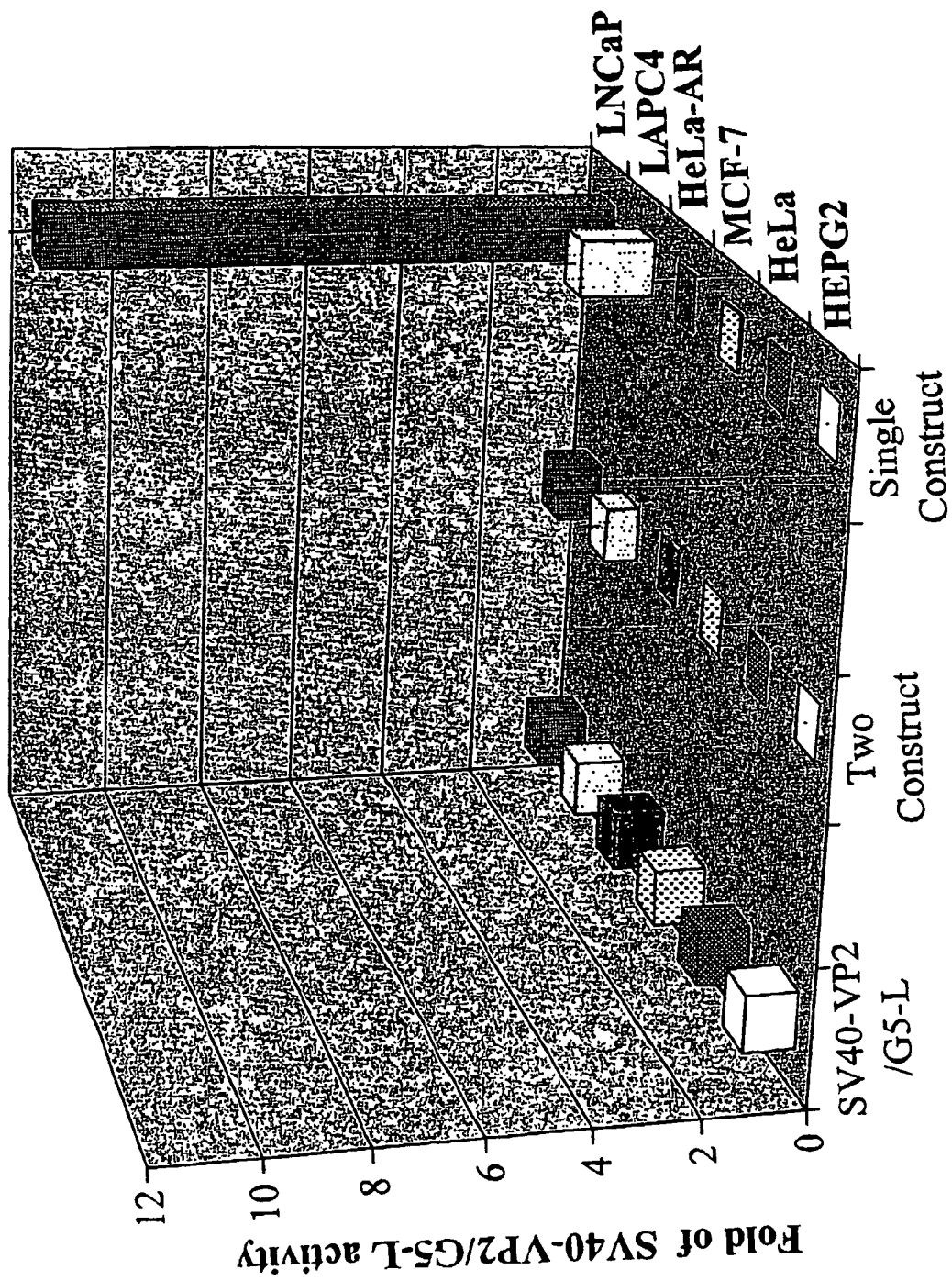

FIG. 12: Cell Specific Expression of the Single Construct. We transfected six human cell lines with SV40-VP2/G5-L, PBC-VP2/G5-L or the single construct. All the cells were transfected with the same molar amount of luciferase DNA. The cells were sampled, analyzed and graphed as in FIG. 11 except we switched the axes on the cell lines and transfected plasmids to simplify the presentation.

Figure 13:
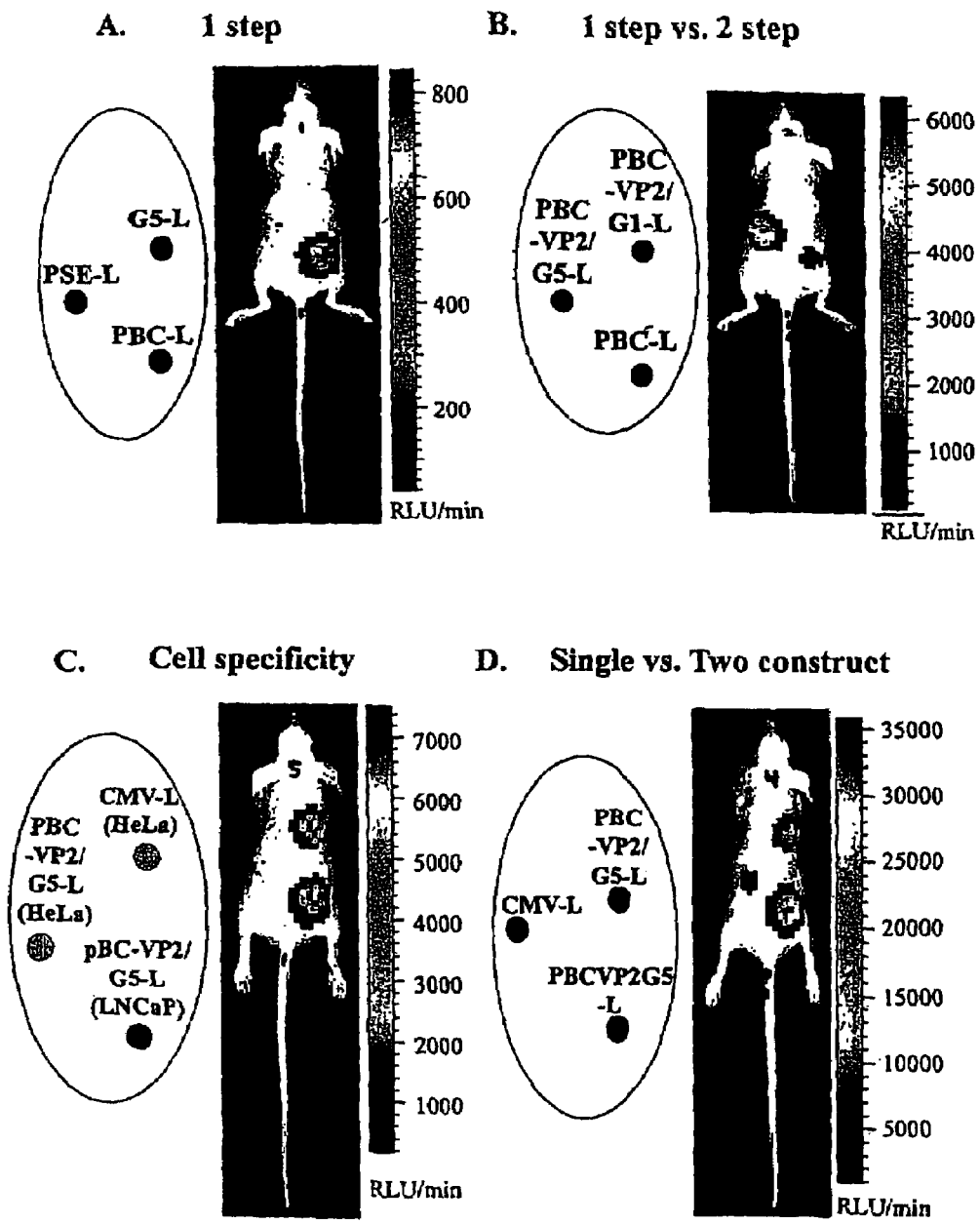

FIG. 13: Imaging of One-step and TSTA in Living Athymic Nude Mice. Pictures shown in the figure are bioluminescent color images superimposed upon the gray-scale mouse photographs. The color scale is in units of RLU/min and is to the right of each photo. Note that the scales vary among experiments. A map representing the dorsal surface of the mice is on the left; the circles denote the relative position of the three injection spots, with the transfected plasmids labeled over each circle. We also marked the needle points on the mouse with a red marker. A description of the group is shown on top of each panel and the acquisition time of the CCD camera for each image generated is in parentheses.

Figures 1, 14:
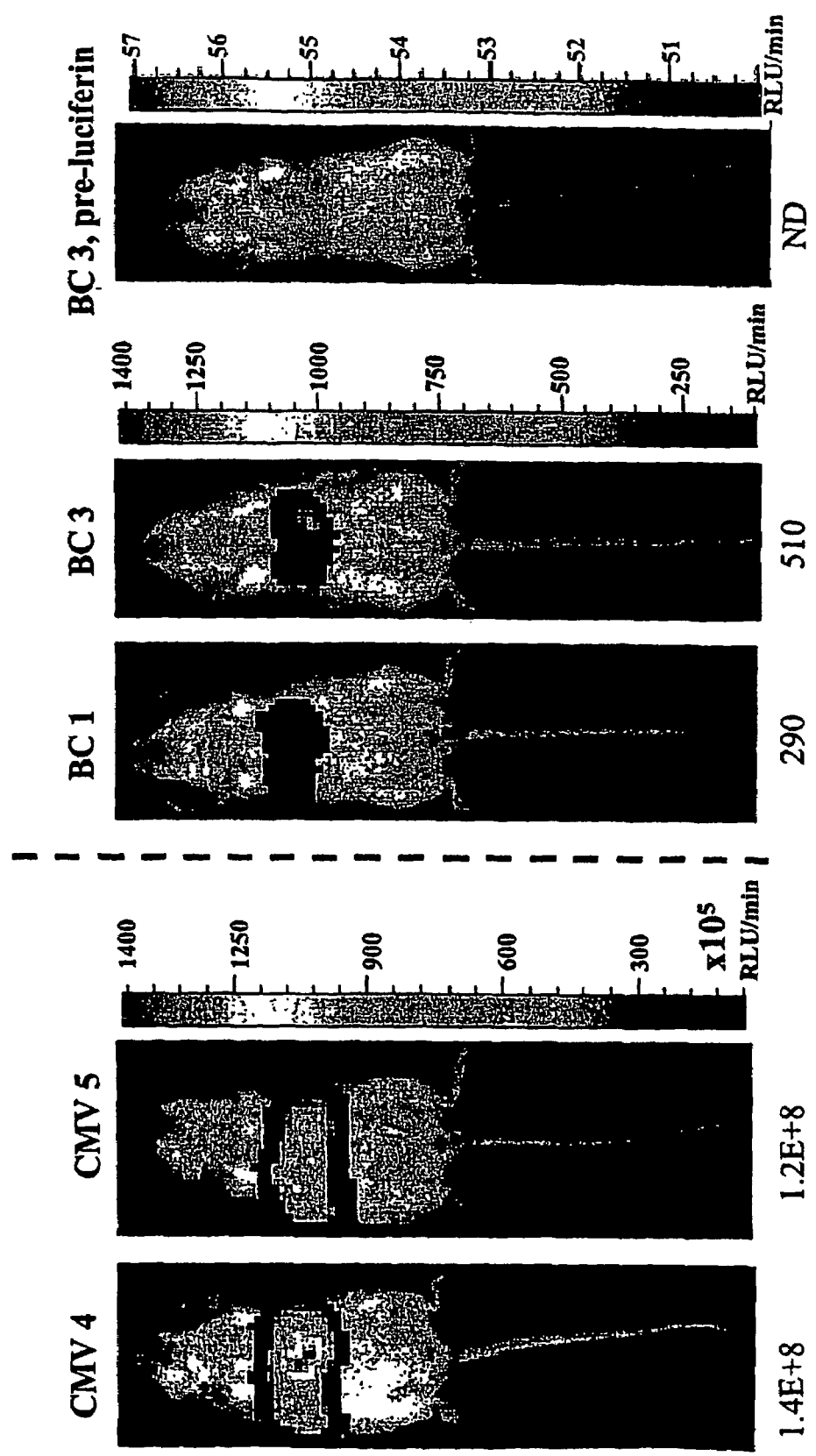
Figures 2, 14:
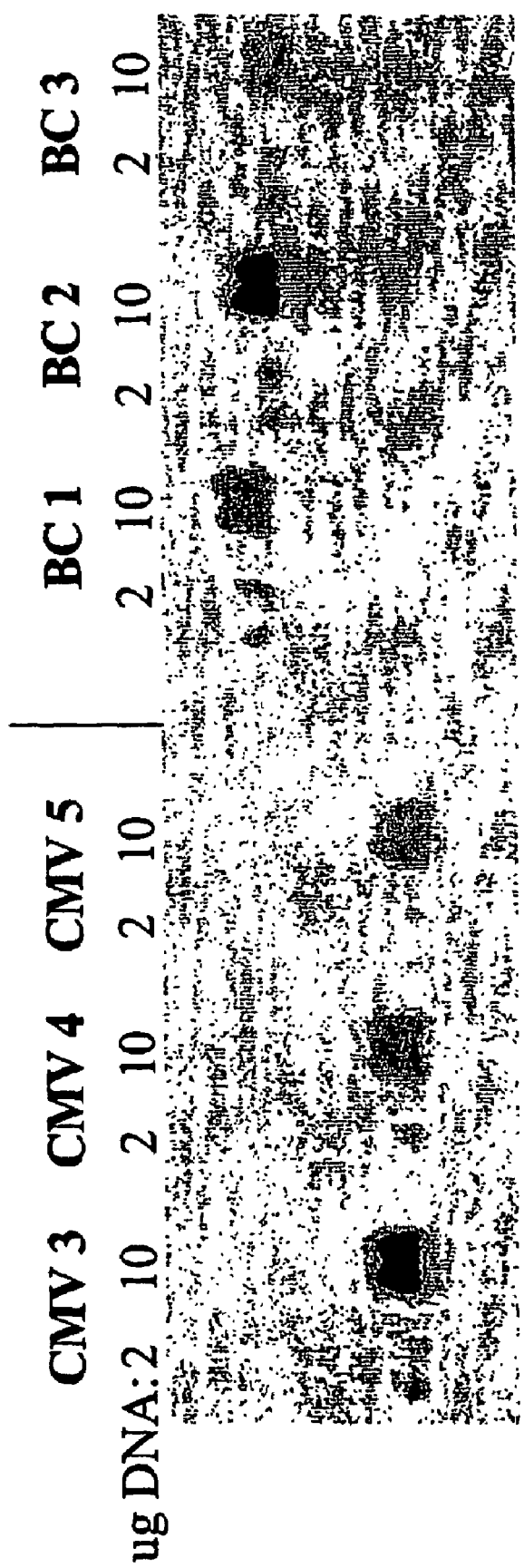

FIG. 14: Luciferase expression patterns in mice and adenoviral vector-mediated luciferase gene delivery to the liver after systemic administration. (A) CCD images of mice injected with either AdCMV-luc or the prostate-specific AdPSE-BC-luc via tail vein. The images for 2 representative animals from each cohort at 4 days post-injection are shown. The animal designation in each cohort is indicated above the images. BC1 and BC3 represent mouse #1 and #3, respectively, in the cohort that received AdPSC-BC-luc, and CMV4 and CMV5 indicate the AdCMV-luc injected animals. The relative light intensity (RLU/min) emitted from the animal was quantitated by computer image analysis software and represented by the color scale ranges from violet (least intense) to red (most intense), shown next to the images. The maximal signal intensity (maximum RLU/min) for each image is shown below each image. Liver signals in the AdCMV-luc cohort were more than 5 orders of magnitude higher than the AdPSE-BC-luc group. (B) Adenoviral gene transferred in livers of cohorts injected either with AdCMV-luc or AdPSE-BC-luc. Southern blot analysis of total cellular DNA, extracted from the livers of same animals in the 2 treatment cohorts, as in FIG. 14A, after imaging at 4 days post-injection. DNA (2 and 10 µg) of each sample was analyzed.

Figures 1, 15:
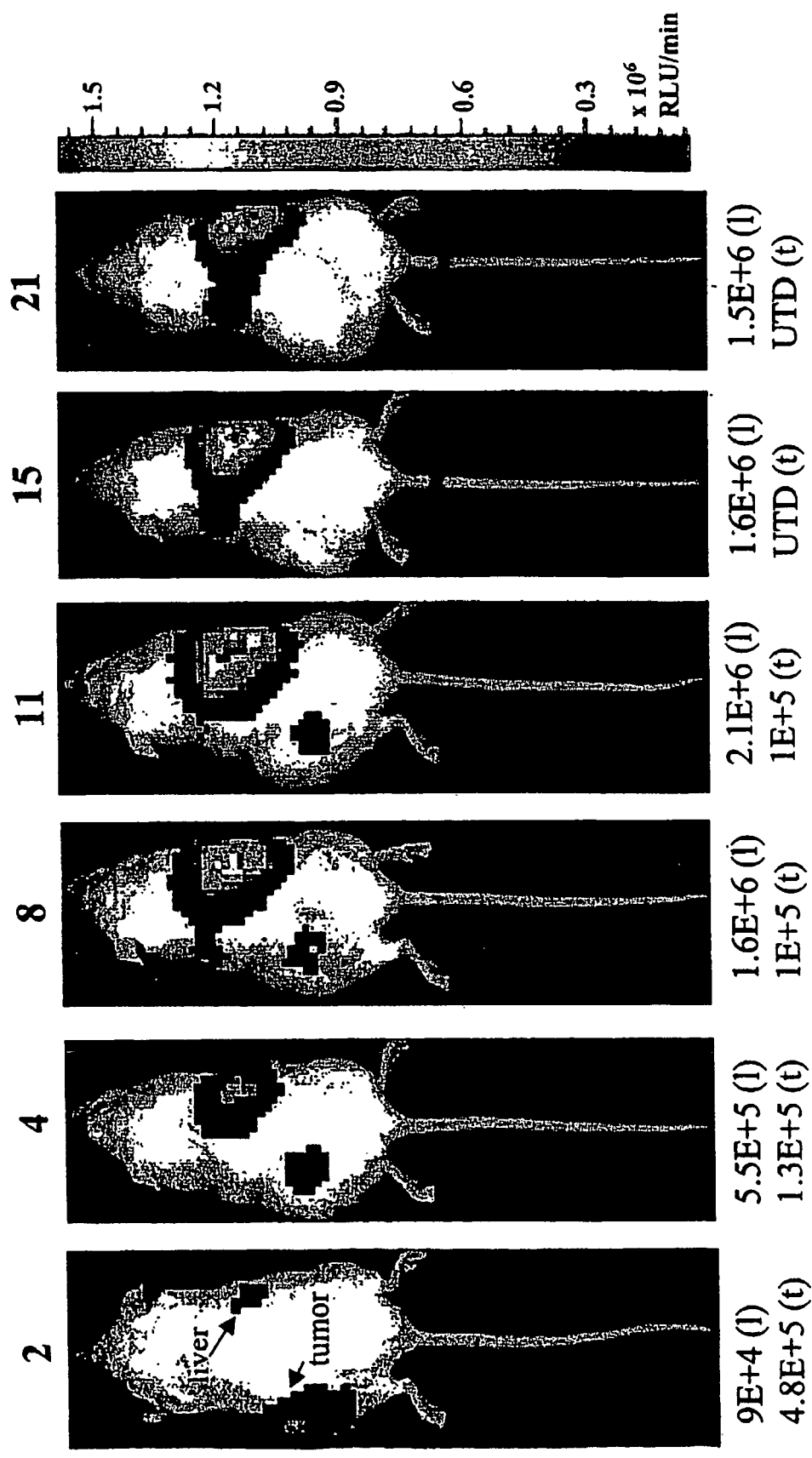
Figures 2, 15:
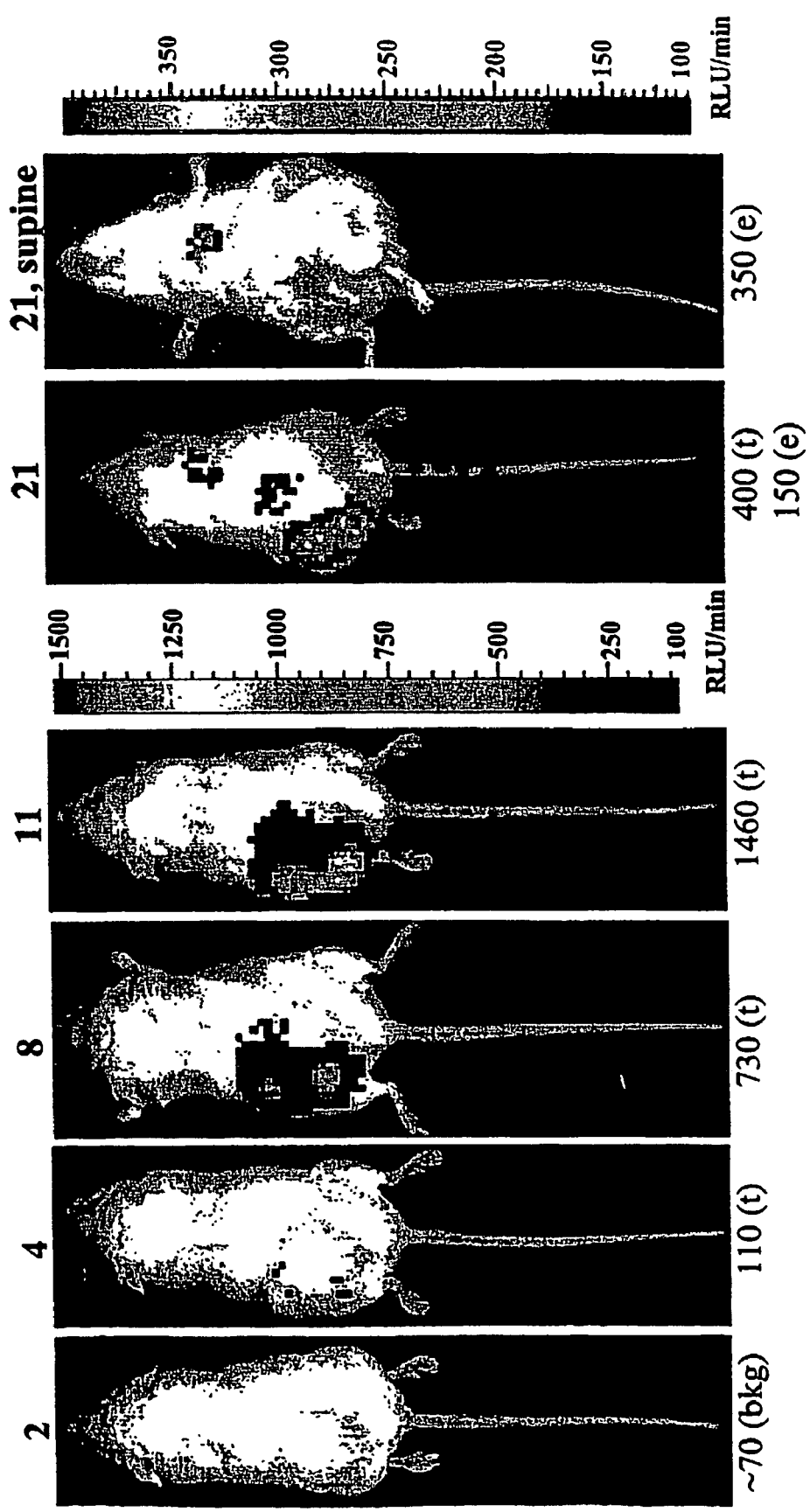
Figures 3, 15:
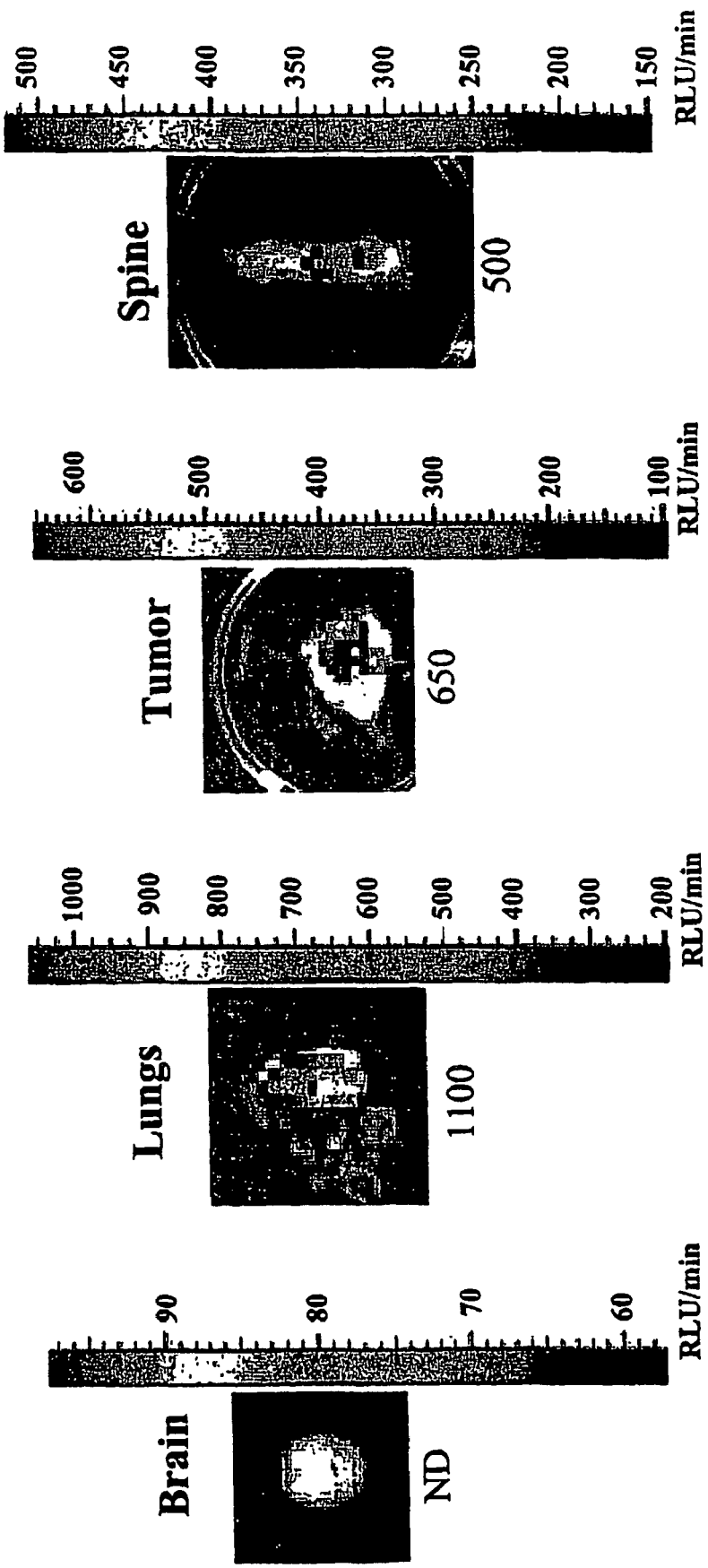

FIG. 15: Kinetics of transgene expression and detection of metastatic lesions in living mice bearing androgen-dependent (AD) LAPC-4 tumors. (A) Location and magnitude of luciferase expression over 3 weeks' duration after intra-tumoral injection of AdCMV-luc. The format of image display is similar to that described in FIG. 14A. However, all images are results of a single mouse, CMV1, monitored on sequential days after Ad injection (indicated at the top of each image). Two clear sites of luciferase expression detection are in the liver (indicated by (1) after signal intensity) and in the tumor (t). Tumor signals at 15 and 21 days post-injection were below the minimal scale (1E+5) set. Thus, using these imaging parameters the signals in the tumor was unable to be determined (UTD). (B) The in vivo luciferase expression profile of an AdPSE-BC-luc-injected animal (BC4). The in vivo luciferase expression was monitored at specific days post intra-tumoral injection (listed above the image). The signal intensity of the tumor (t) and of extra-tumoral lesions (e) is listed below the respective images. The signal in the animal at 2 days post-infection, before the onset of expression, served as background luminescence signal ($\leq$70). Extra-tumoral signals were detected at 21 days post-injection. (C) The CCD images of freshly isolated organs from mouse BC4. Individual organs of BC-4 (same as FIG. 15B) were isolated and re-imaged. Due to light signal attenuation contributed by the covering tissues, the isolated organs displayed higher signal intensities than in the intact living animal[12].

Figures 1, 16:
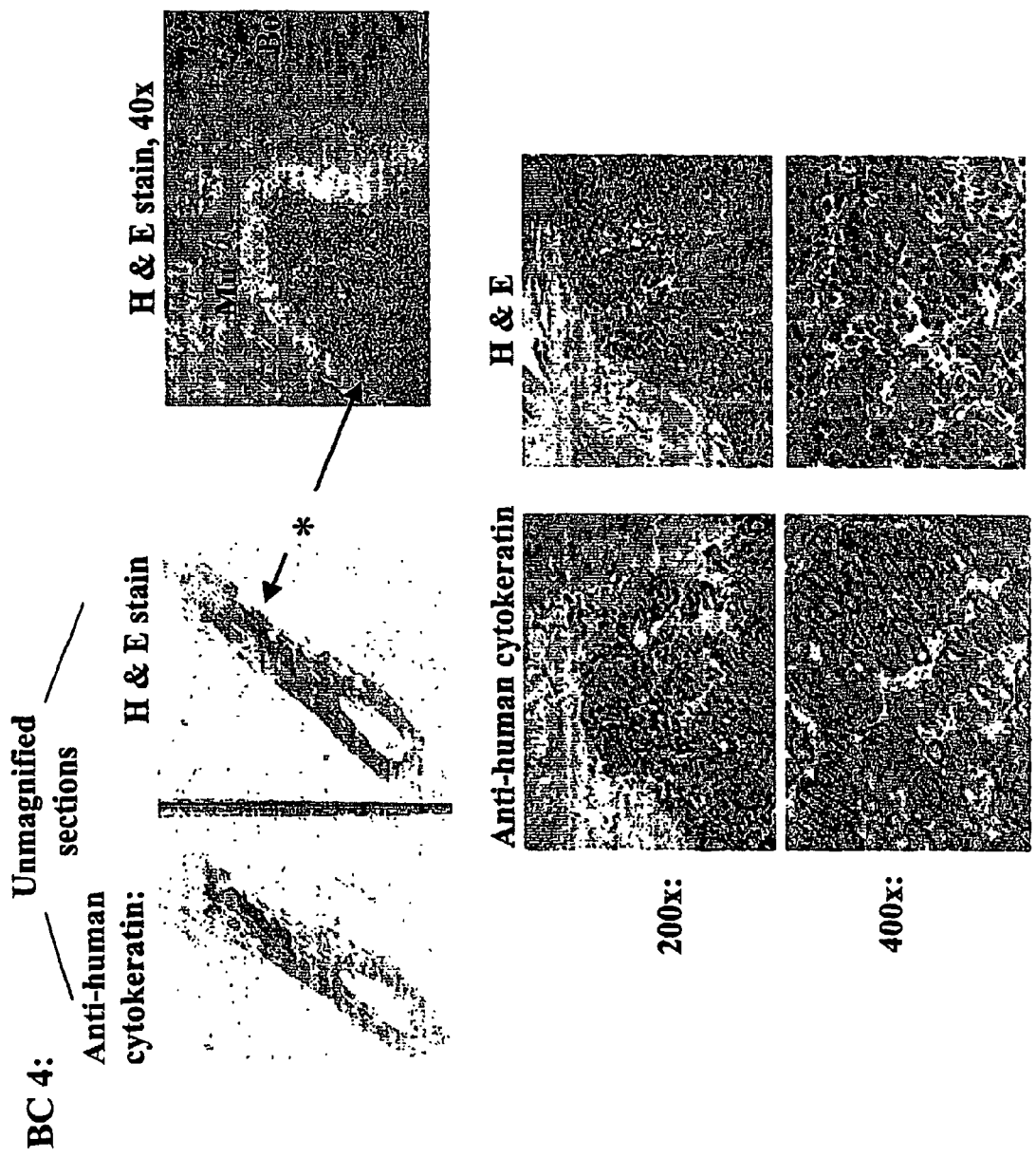
Figures 2, 16:
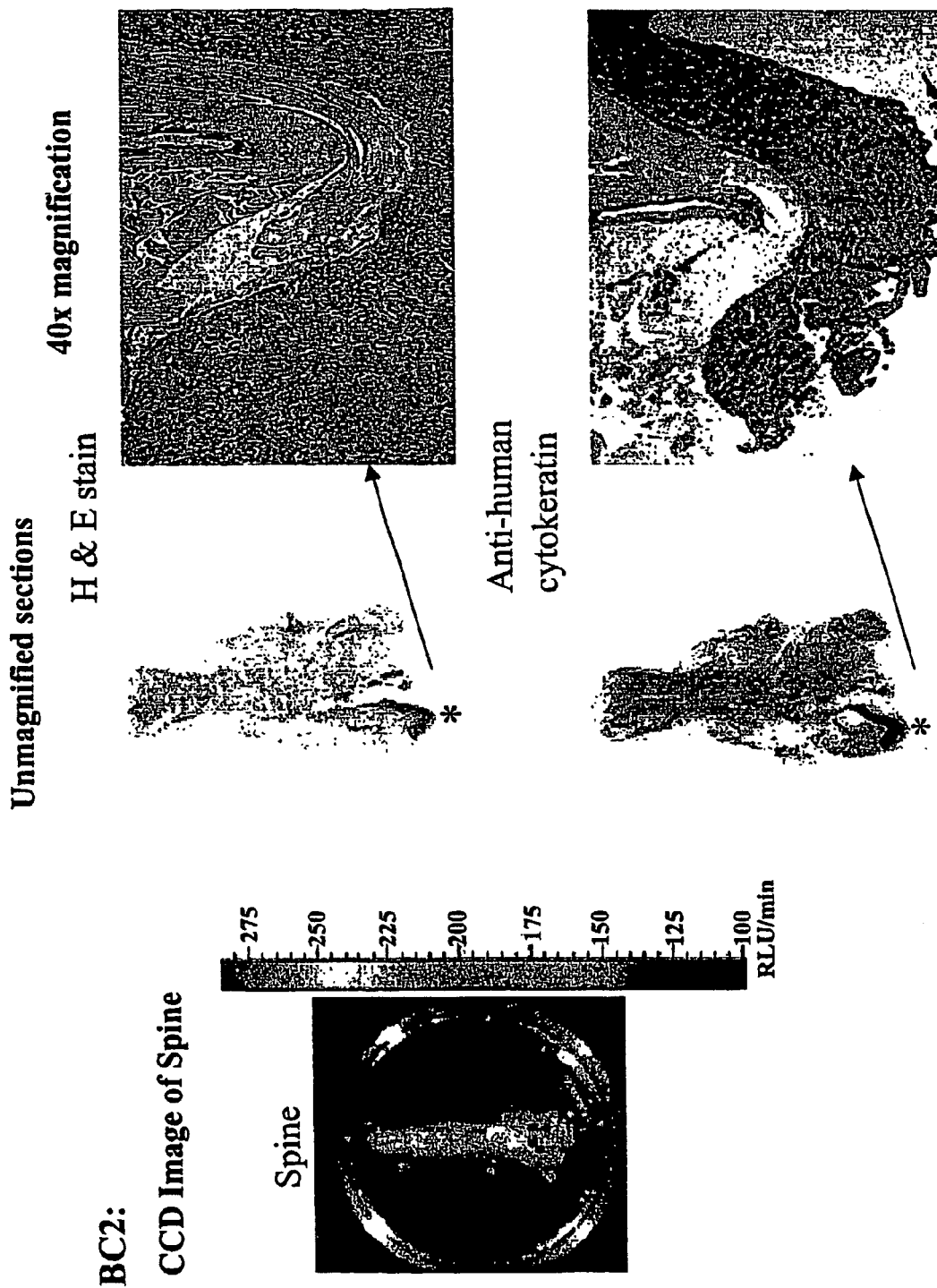
Figures 3, 16:
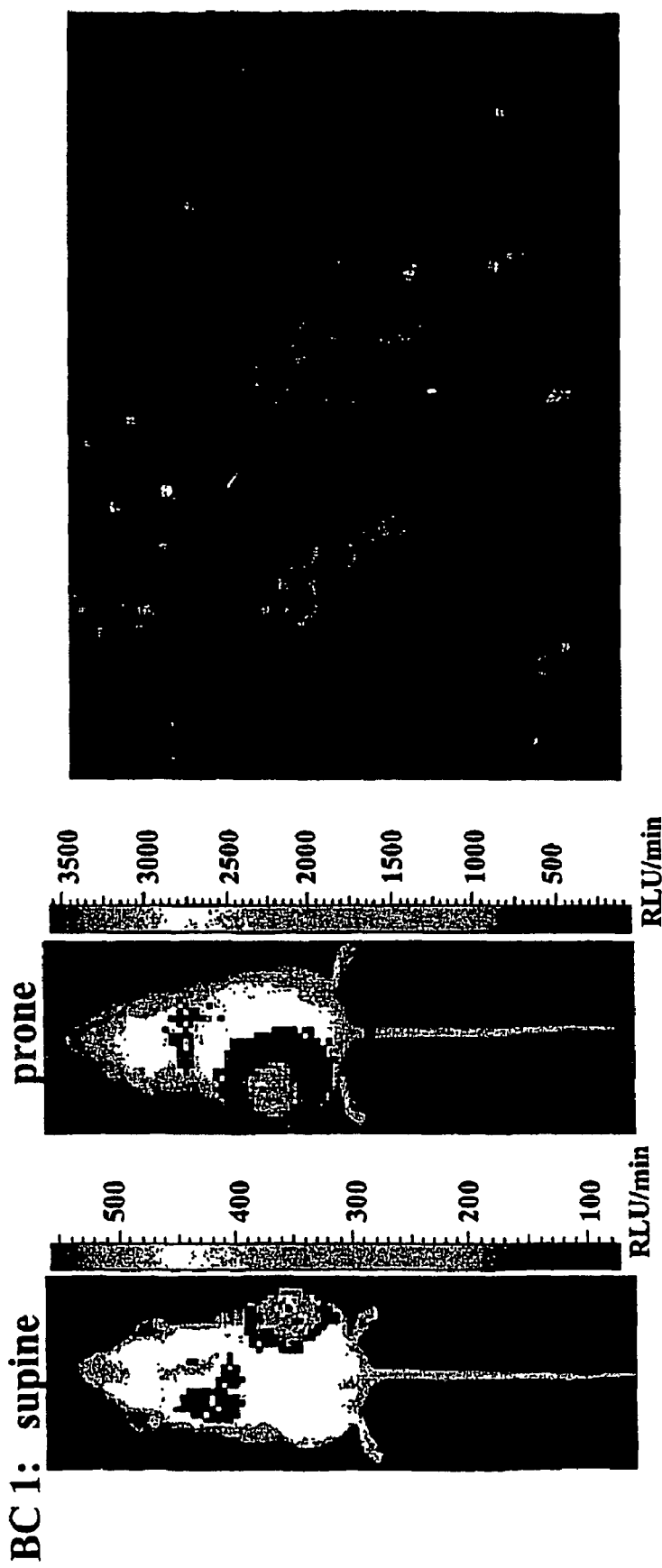

FIG. 16: Detailed histological analysis of spinal and lung metastatic lesions. (A) Histological analysis of the spine lesion of mouse BC4. 5-µm sections of spine were stained with hematoxylin/eosin (H&E) or with human-specific anti-cytokeratin antibody. Unmagnified sections show an elongated lesion in the mid-segment of the spine. A low-magnification (40×) micrograph showed the lesion was surrounded by muscle (Mu) and adjacent to bone (Bo). Higher magnifications (200× and 400×) of the lesion were displayed. Anti-human cytokeratin specifically stained the lesion with a characteristic intense ring of cytoplasmic staining. (B) Corresponding CCD signal and histological analysis of a spinal lesion in another mouse BC2. Procedures for the detection and identification of the lesion are as described above. (C) Detection of lung metastasis by CCD imaging in another animal, and definition of the lesion by confocal microscopy. Low-intensity upper chest signals, right>left, were detected in a LAPC4 AI tumor-bearing mouse (BC1) 21 days after intra-tumoral injection of AdPSE-BC-luc under the same conditions as in FIG. 15.

Figures 2, 17:
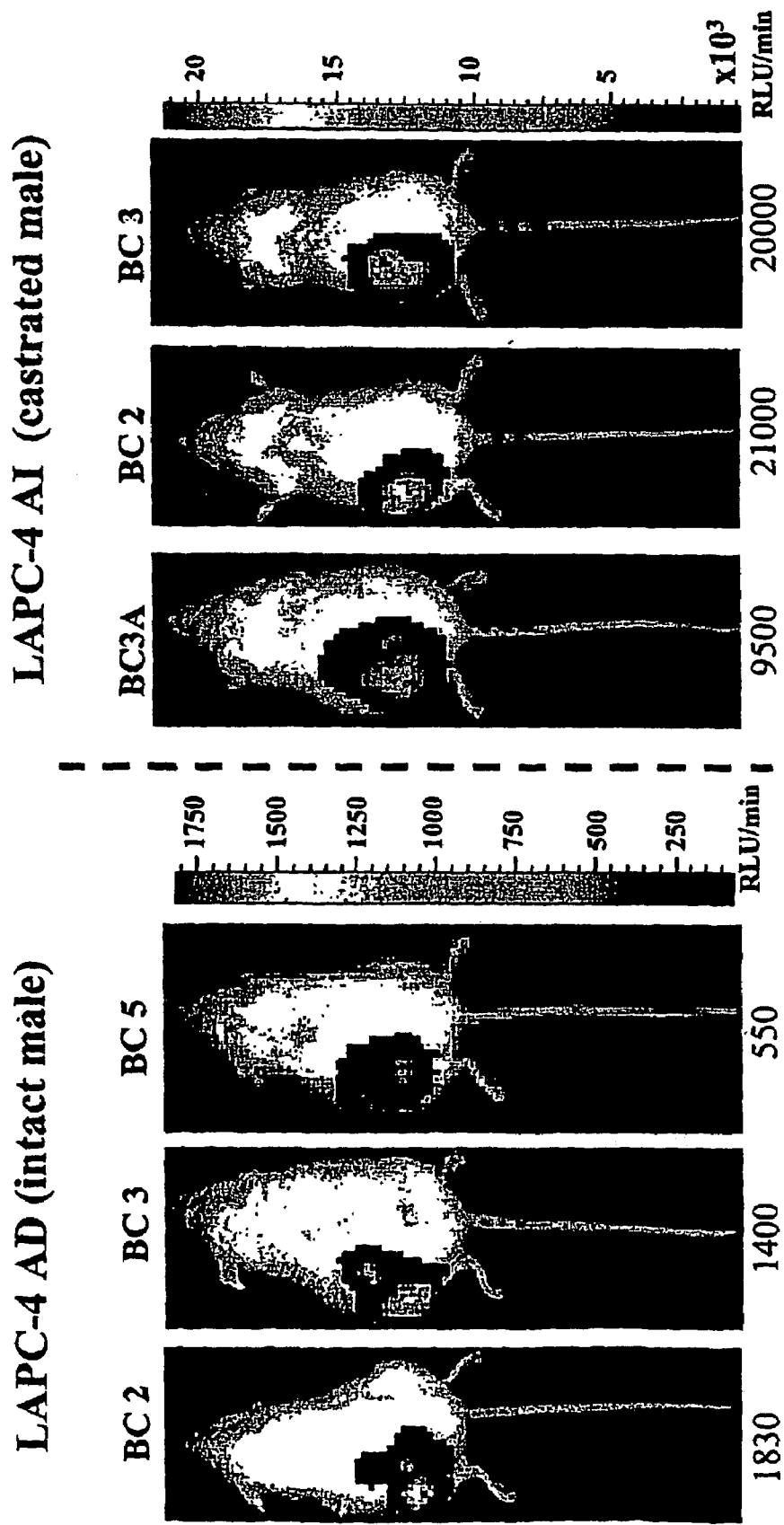
Figures 3, 17:
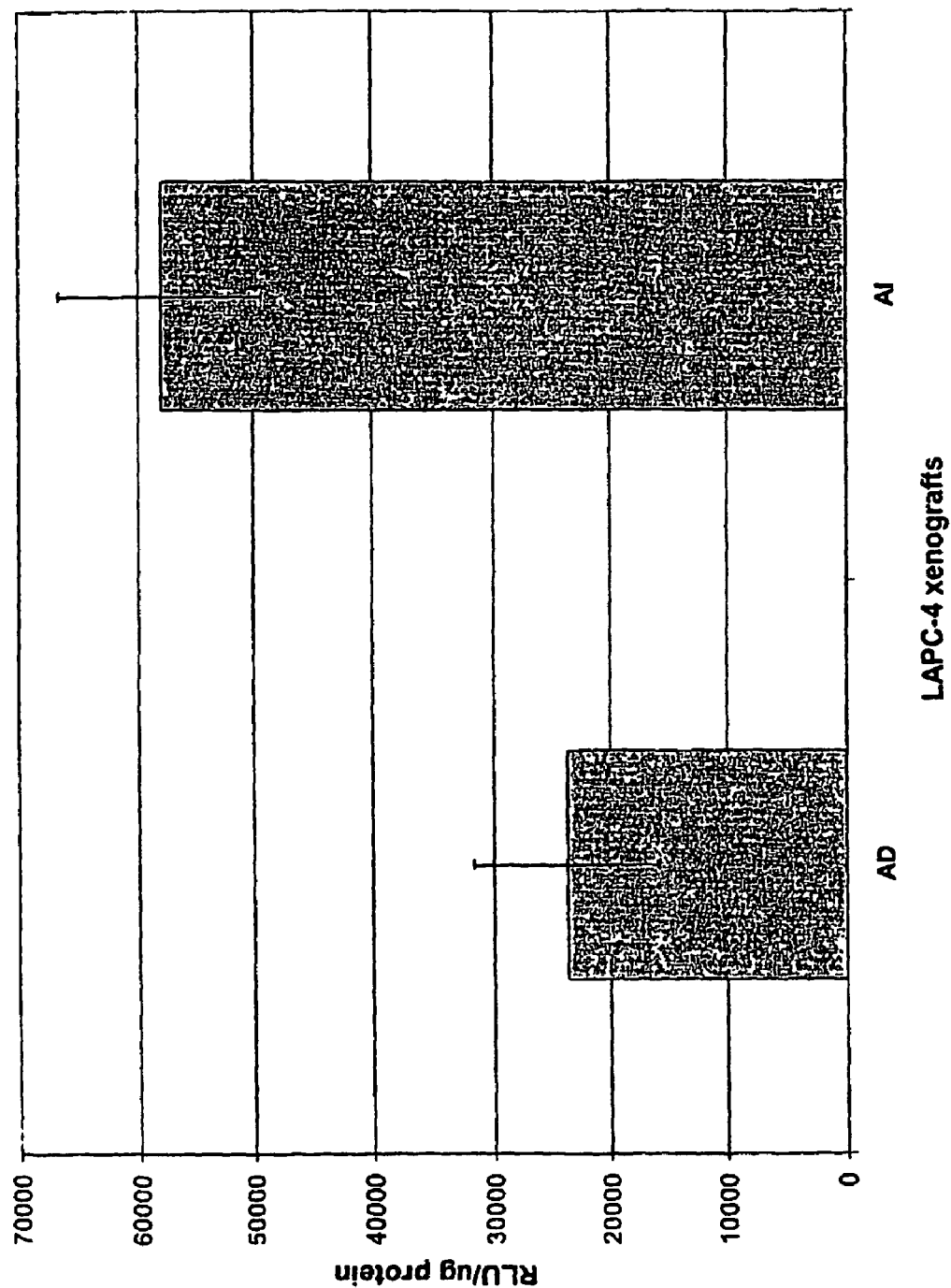

FIG. 17: Expression of endogenous and exogenous androgen receptor (AR)-regulated genes in an androgen-independent (AI) prostate tumor. (A) Endogenous AR and PSA expression in AD and AI LAPC-4 tumors. The brown staining indicates positive protein expression. PSA expression in AI tumor appears to be elevated compared to the AD LAPC-4 tumor. (B) CCD images of LAPC-4 AD or AI tumor-bearing mice 11 days after intra-tumoral injection. The images of 3 representative animals from each cohort are shown. The AI tumors are derived from two independent tumor passages. BC3A is a different passage from BC2 and BC3. (C) AdPSE-BC-luc-mediated luciferase expression in LAPC-4 AD and AI tumor cell suspensions after ex vivo infection. The graph displays the luciferase activity of infected cell extracts harvested at 3 days post-infection. Statistical analysis by t-test showed a significant difference (P=0.007) (two-tail). Single-cell suspension cultures were infected at 10 infectious units/cell and analyzed at three days post-infection[8].

Figure 18:
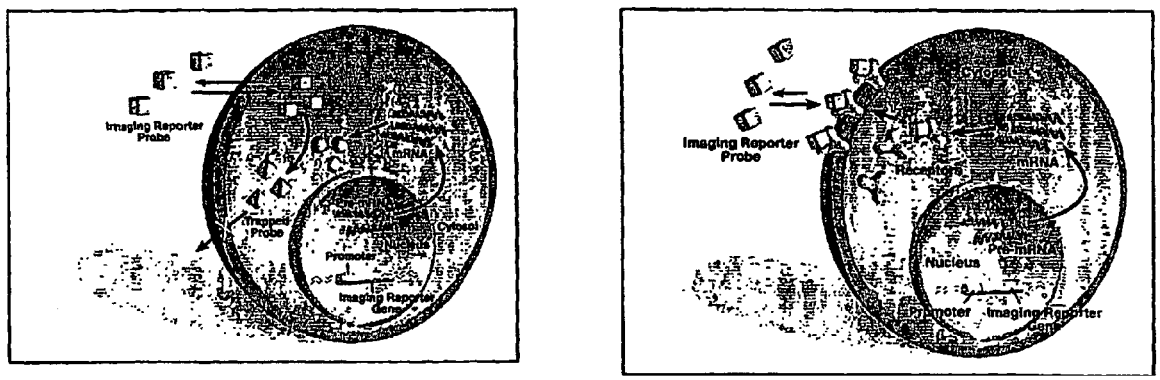

FIG. 18: Shows A schematic diagram is represented for two approaches for imaging of reporter gene expression using PET/SPECT. A reporter gene introduced into the cell can encode for (I) an enzyme (e.g., HSV1-TK) that leads to trapping of a radiolabeled probe (left panel) or (II) an intracellular and/or extra cellular receptor (e.g., $D_2R$), which would lead to trapping of a radiolabeled ligand (right panel). In both cases if the reporter gene is not expressed, then the radiolabeled probe is not retained.

Figure 19:
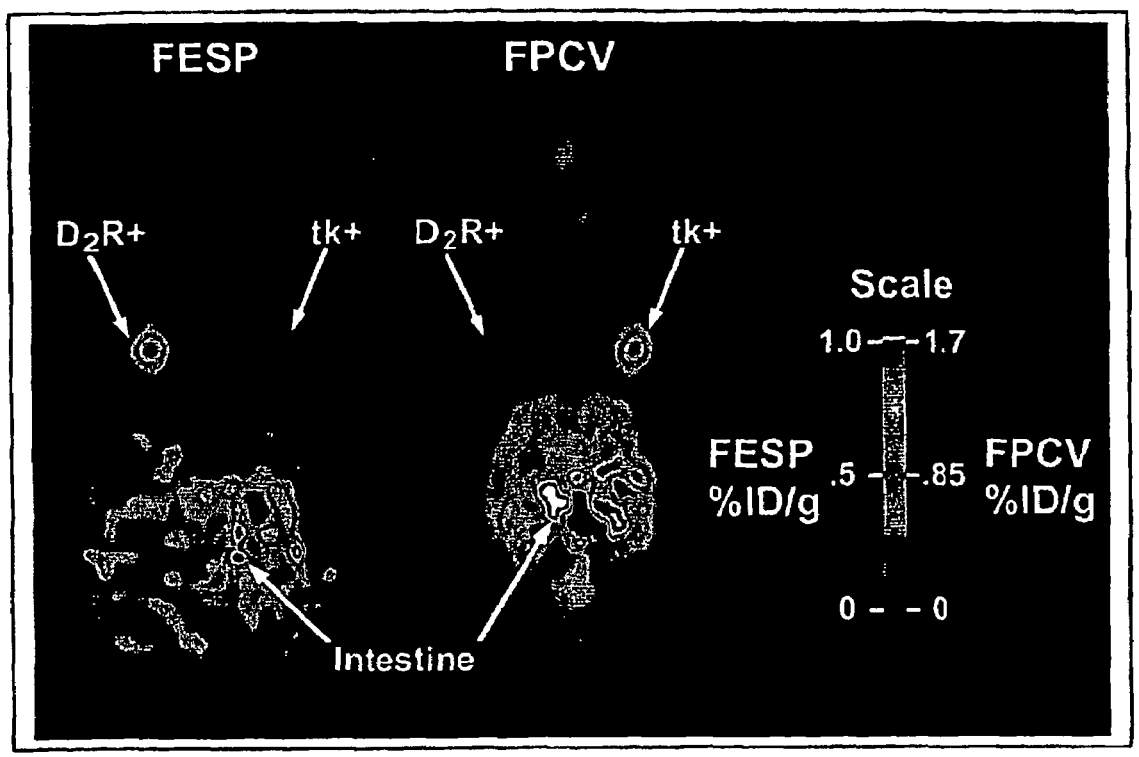

FIG. 19: Shows MicroPET imaging of two PET reporter genes (HSV1-tk and D2R) in the same mouse using two different reporter probes ($^{18}$F labeled FPCV and FESP) respectively. Specific accumulation of probes in a mouse carrying a tumor stably expressing HSV1-tk (right) and a separate tumor stably expressing $D_2R$ (left). The accumulation of [$^{18}$F]FPCV and [$^{18}$F]FESP in each tumor reflects trapping due to HSV1-tk and $D_2R$ expression respectively. Background signal in the intestinal tract is seen due to clearance of the probes via the hepatobiliary system. A separate scale for [$^{18}$F]FPCV and [$^{18}$F]FESP is shown (135).

Figure 20:
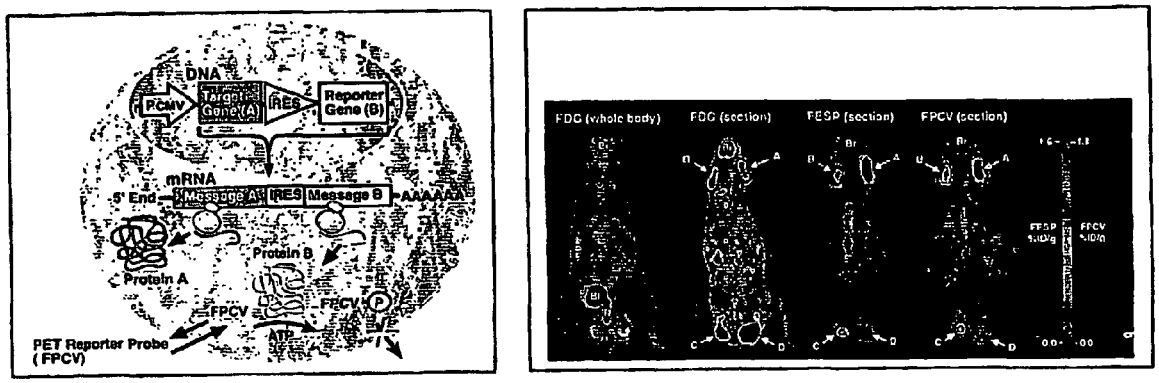

FIG. 20: Shows A schematic representation of imaging reporter gene expression by PET from a bi-cistronic vector containing an internal ribosomal entry site (IRES) (left panel). Both gene A and B are co-expressed from the same vector with the help of the IRES and expression of protein B (a PET reporter) can be imaged quantitatively by trapping of a PET reporter probe which will give an indirect measurement of expression of gene A. MicroPET imaging of bi-cistronic gene expression (pCMV-$D_2$R-IRES-sr39tk) where both the genes were imaged by using two different PET reporter probes ([$^{18}$F]FESP and [$^{18}$F]FPCV) in same animal (right panel). Three C6 cell lines stably transfected with pCMV-$D_2$R-IRES-sr39tk and the parental C6 control cell line were injected at 4 different sites in a single mouse. Sequential imaging of the tumors with [$^{18}$F]FDG, [$^{18}$F]FESP and [$^{18}$F]FPCV after 10 days showed specific accumulation of [$^{18}$F]FESP and [$^{18}$F]FPCV in the tumors with stably transfected cells while accumulation of [$^{18}$F]FDG is seen in all four tumors in the FDG section image. The [$^{18}$F]FDG (whole body) image shows the mouse outline and is provided for reference. The [$^{18}$F]FESP and [$^{18}$F]FPCV tumor images are highly correlated, illustrating that when one monitors one of the two genes, one can infer levels of the second gene (144).

FIG. 21: (A) Shows the nucleotide (SEQ ID NO: 1) and amino acid (SEQ ID NOS:2-4) sequences of a vector comprising the effector and reporter sequences (PBCVP2G5 (not Sal)). (B) Shows the nucleotide (SEQ ID NO:5) and amino acid (SEQ ID NOS:2, 3 and 6) sequences of a vector comprising the effector and reporter sequences (PBCVP2G5-L).

Figure 22:
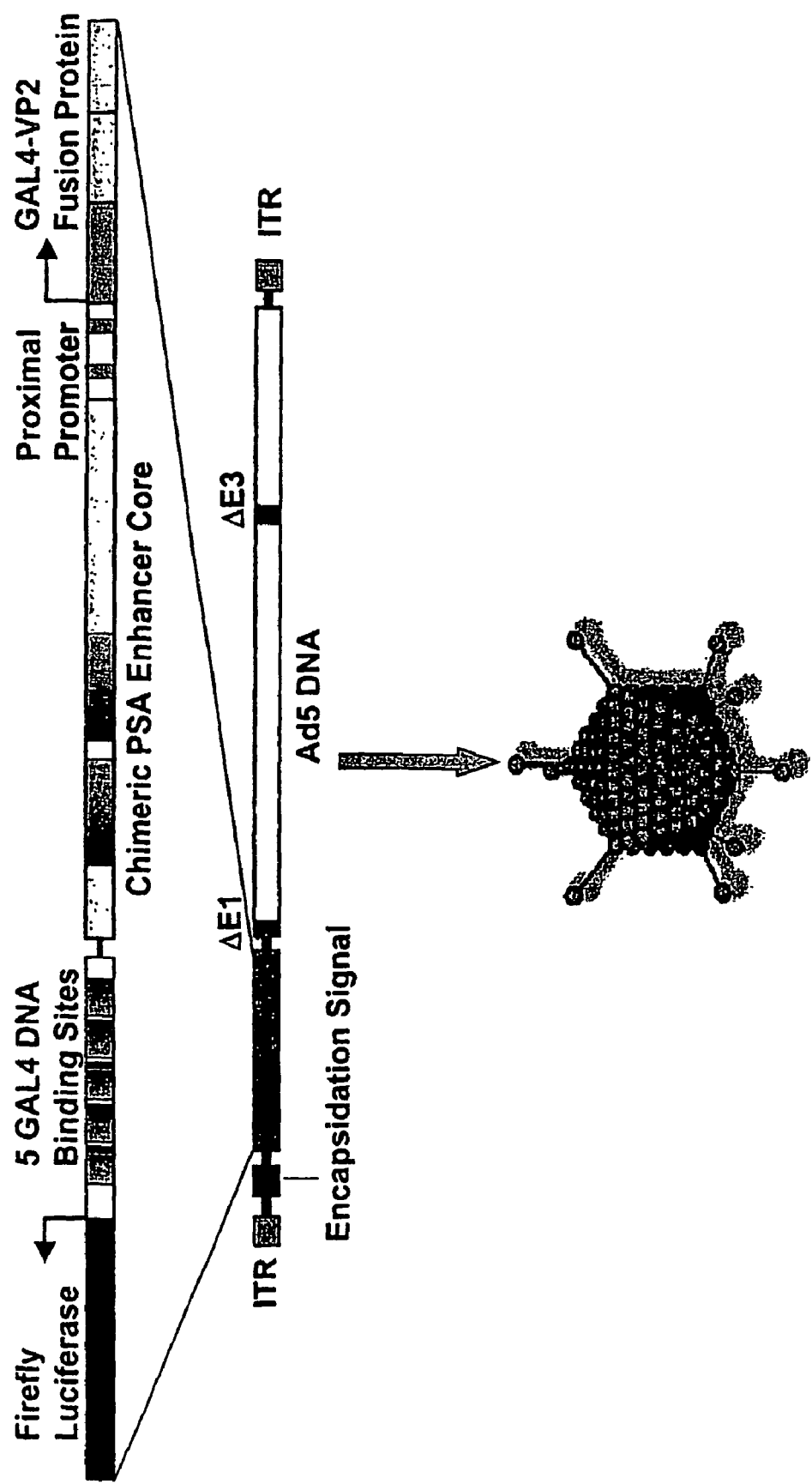

FIG. 22: The adenovirus two-step transcription activation (AdTSTA) imaging system. The upper portion of the diagram shows the TSTA imaging cassette. The PSA enhancer from −4326 to −3935 (purple) was duplicated (the chimeric enhancer core) within the upstream regulatory region from −5322 to −3744 and attached to the proximal promoter from −541 to 1. Each enhancer bears a cluster of six AREs and the promoter contains two AREs shown in blue. The PSA regulatory region is shown expressing GAL4-VP2 bearing two amino-terminal Herpes Simplex Virus 1 VP16 activation domains (amino acids 413-454) fused to the GAL4 DNA binding domain (amino acids 1-147). A GAL4-responsive promoter is fused in the divergent orientation to the PSA regulatory region. The GAL4-responsive promoter contains five 17-bp GAL4 sites upstream of the adenovirus E4 promoter driving firefly luciferase. The entire cassette was cloned into a shuttle vector and introduced into Ad5 deleted (.) for E1 and E3 using the AdEasy™ system. The virus was propagated in 293 cells, purified and titered. ITR Inverted terminal repeat. Bottom: simplified representation of Adenovirus serotype 5.

FIG. 23: AdTSTA activity in cancer cell lines. A. LNCaP cells were infected with AdTSTA at an MOI of 10 for 1 hour and treated with 10 nM R1881 (+Ligand) or vehicle (−Ligand). At the indicated time points, the cells were lysed with Reporter Lysis Buffer and firefly luciferase activity was analyzed either by luminometry (lower panel, Y-axis: Relative Luciferase Units/µg of total protein normalized to 100%) or by immunoblotting (Upper panel, AR: Anti-Androgen Receptor; Tub: Anti-Tubulin; GAL4: anti-GAL4-VP16). Samples were prepared in triplicate and the average reading with standard error is shown. The triplicate samples were mixed for immunoblot analysis. B. LNCaP, HeLa or HepG cells were infected with AdTSTA at an MOI of 0.1 for 1 hour followed by treatment with 10 nM R1881. The cells were harvested 48 hours later and luciferase levels were measured. Data are normalized to the ligand-induced signal in LNCaP (100%). The AdCMV (MOI 0.1) signal in LNCaP is shown in hatched bars for comparison of the AdTSTA and AdCMV luciferase activity.

Figure 24:
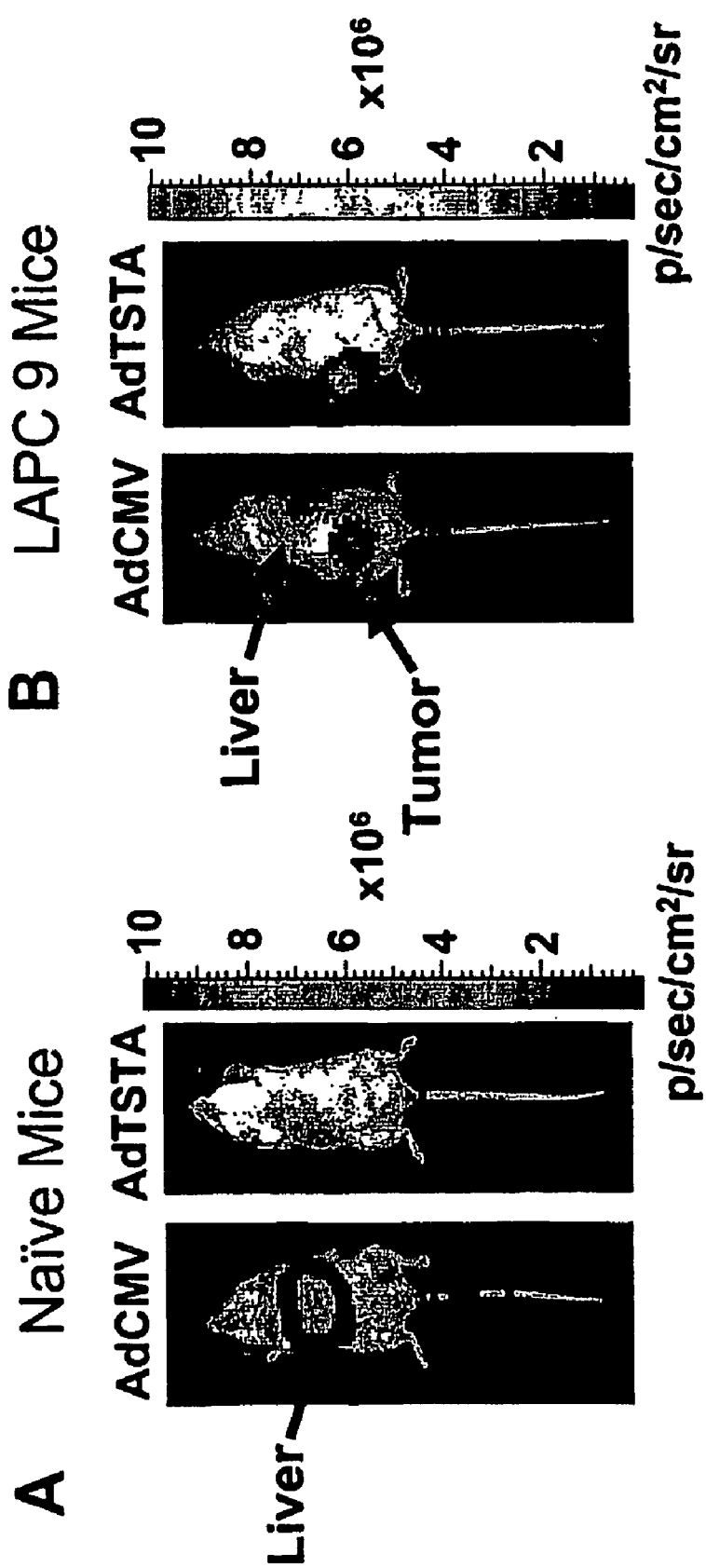

FIG. 24: AdTSTA specificity in animals. Left panel: 107 pfu of AdCMV or AdTSTA virus were injected through the tail vein into 3-month old male SCID mice and imaged by CCD. The pictures show a representative mouse in the supine position injected with AdCMV or AdTSTA on day 14. Right panel: LAPC9 AD xenografts were grown on the flanks of SCID mice. When tumors reached 0.5 cm diameter tumor size, AdCMV or AdTSTA were injected intratumorally and imaged by CCD. The picture shows representative mice in the prone position on day 14. For all studies, n>3 animals were used in each group. For each mouse, a pseudocolor image of the emitted light is superimposed over a gray scale photograph of the mouse. A colored bar, which indicates the intensity of the signals, is shown on the right of the panels, with units of photons (p) acquired per second (sec) per $cm^2$ per steridian (sr).

Figure 25:
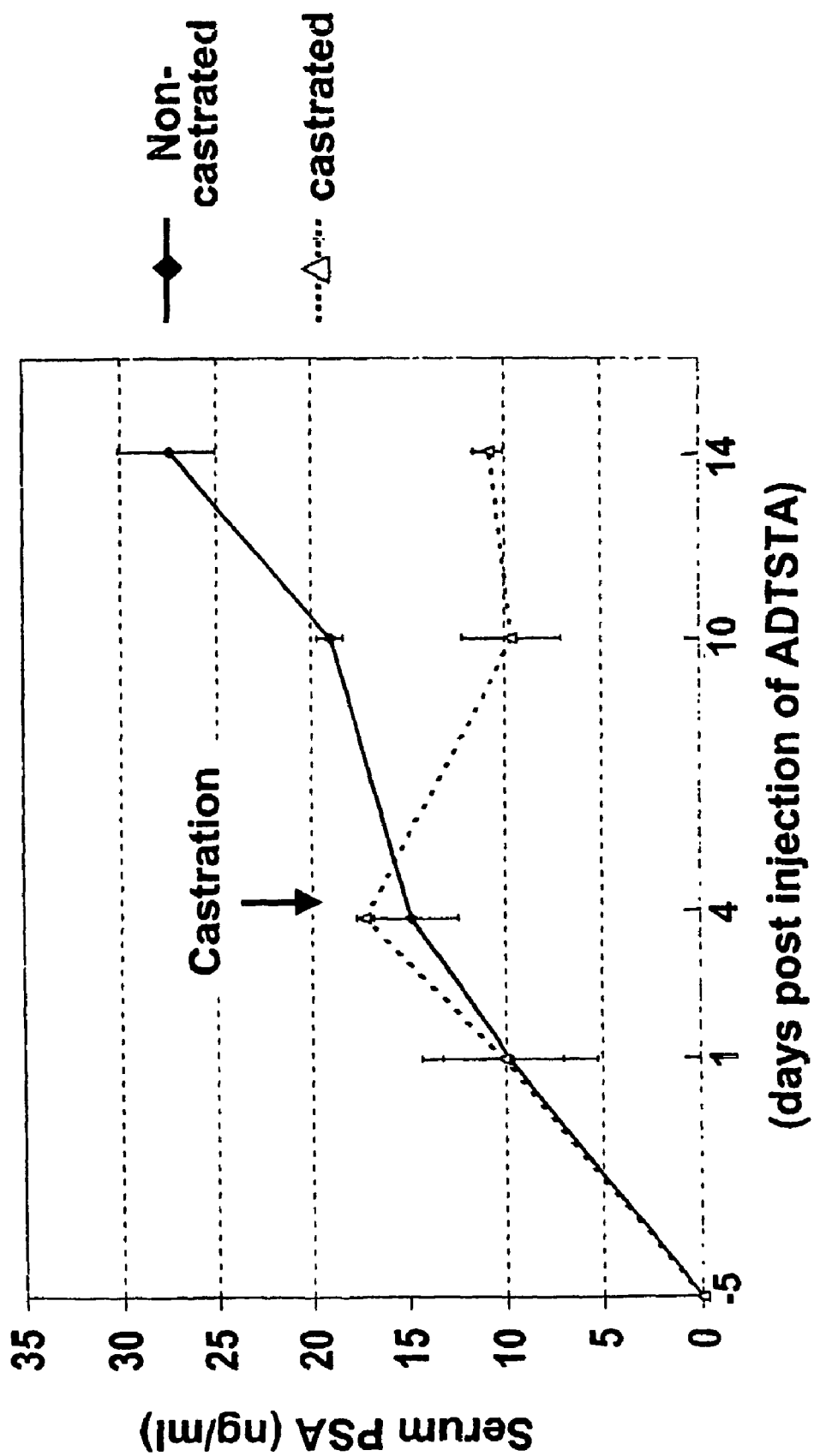

FIG. 25: Serum PSA Measurements for AD and Castrated Mice. Serum Elisa measurements of PSA at various time points during tumor growth. Values are in ng per ml.

Figure 26:
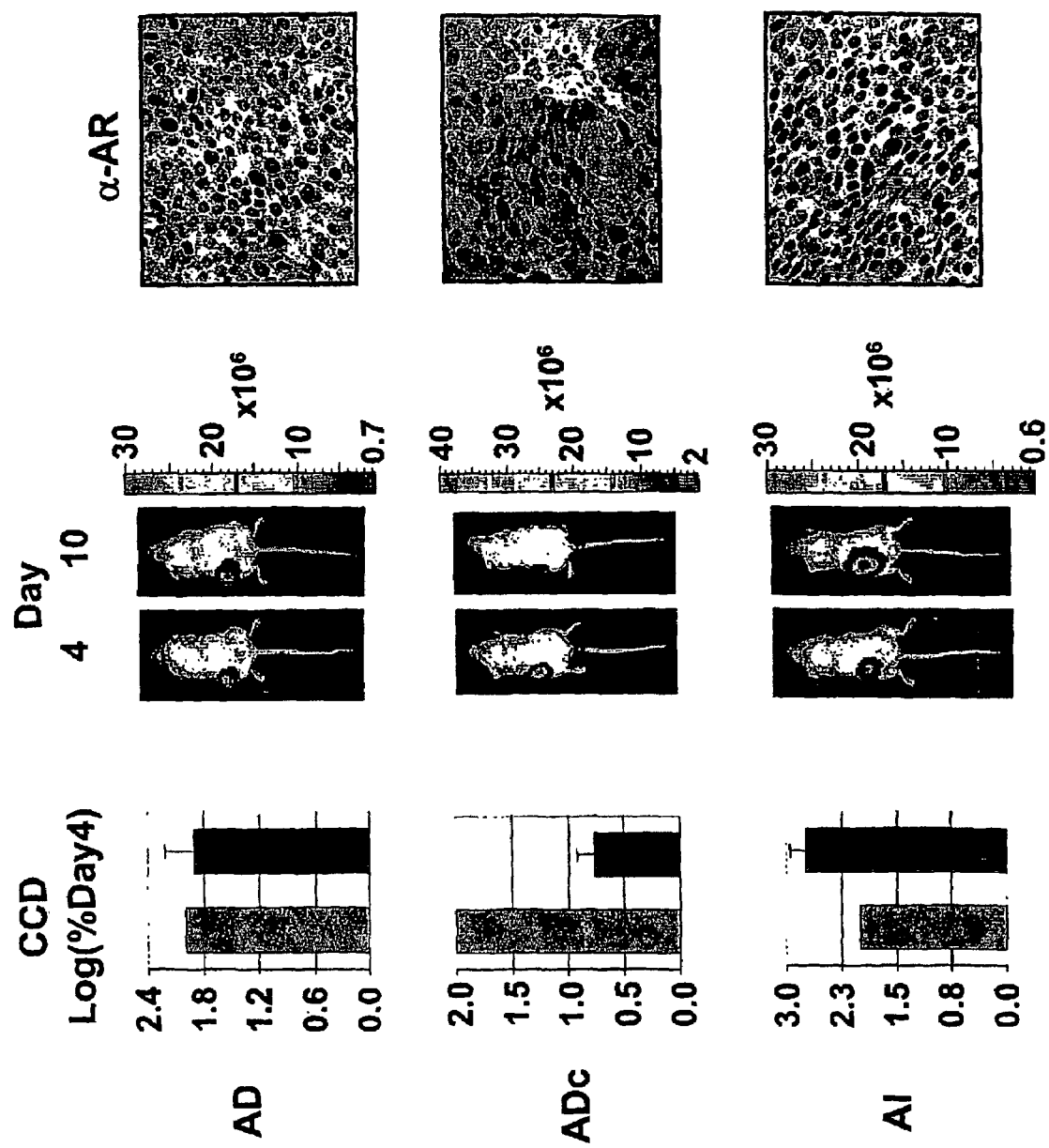

FIG. 26: AR signaling in LAPC 9 tumors. SCID mice implanted with LAPC9 xenografts grown to greater than 0.5 cm were injected with 107 pfu of AdTSTA and the mice were imaged every 3-4 days until day 14. Representative mice at day 4 and day 10 post virus injection from the AD group, the castrated (on day 4) AD group (ADc), and the stable AI group. The bar graph summarizes a cohort of three or more and summarizes the log of the % change in signal from day 4 (blue bars) to day 10 (purple bars). Day 4 is set at 2 (log of 100) in each case. The right panels show representative immunohistochemical localization of AR in the various tumors using anti-AR antibodies. AR stains brown against the blue-stained nuclei.

FIG. 27: Chromatin immunoprecipitation assays in LAPC9 tumors. The diagram describes the PSA regulatory region. Short black line underneath indicates the positions targeted by PCR. Enh: enhancer core; Mid: intermediate region; Pro: proximal promoter; Ex5: PSA exon 5 (for sequence coordinates see Methods). Tumors were isolated from mice sacrificed at day 10 (6 days post castration for ADc), minced, crosslinked with formaldehyde and immunoprecipitated with anti-AR. An autoradiograph of the multi-plex PCR reactions is shown for AD, AI and ADc tumors. Graph of Multiple Tumor ChIP Analyses. The band intensities were analyzed using ImageQuant. Background values from a mock (IgG) ChIP were subtracted from each band and normalized to the signal from onput DNA. Error bars shown are standard deviation of three values obtained in independent experiments.

Figure 28:
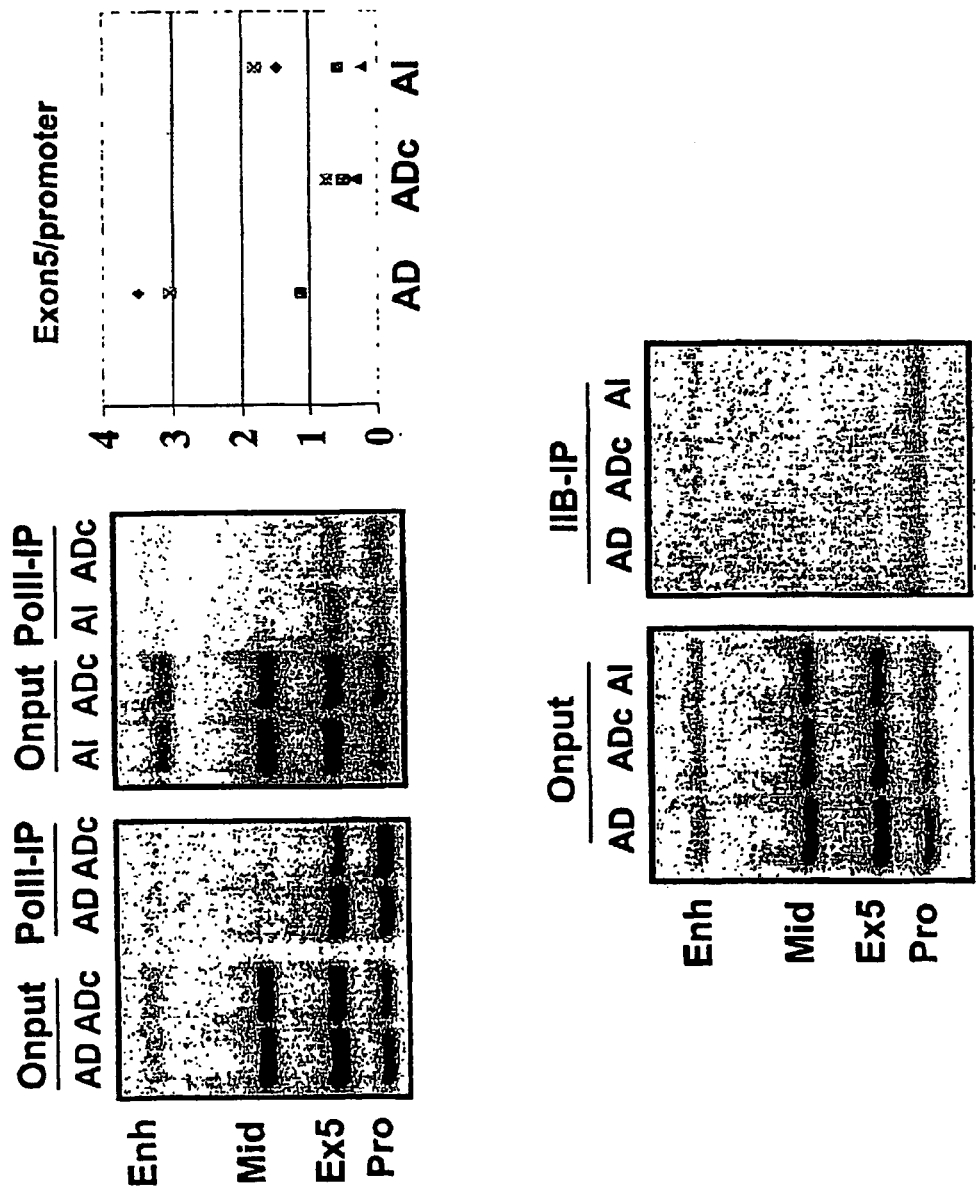

FIG. 28: ChIP analysis of RNA Polymerase II and TFIIB from LAPC9 tumors. The bands are described in the FIG. 27 legend. Representative experiments from AD, AI and ADc tumors are shown. The top panels are pol II and the bottom panels are TFIIB. The scatter plot represent the pol II binding from 4 experiments, where the ratios of pol II binding at exon 5 vs. the proximal promoter are shown.

Figure 29:
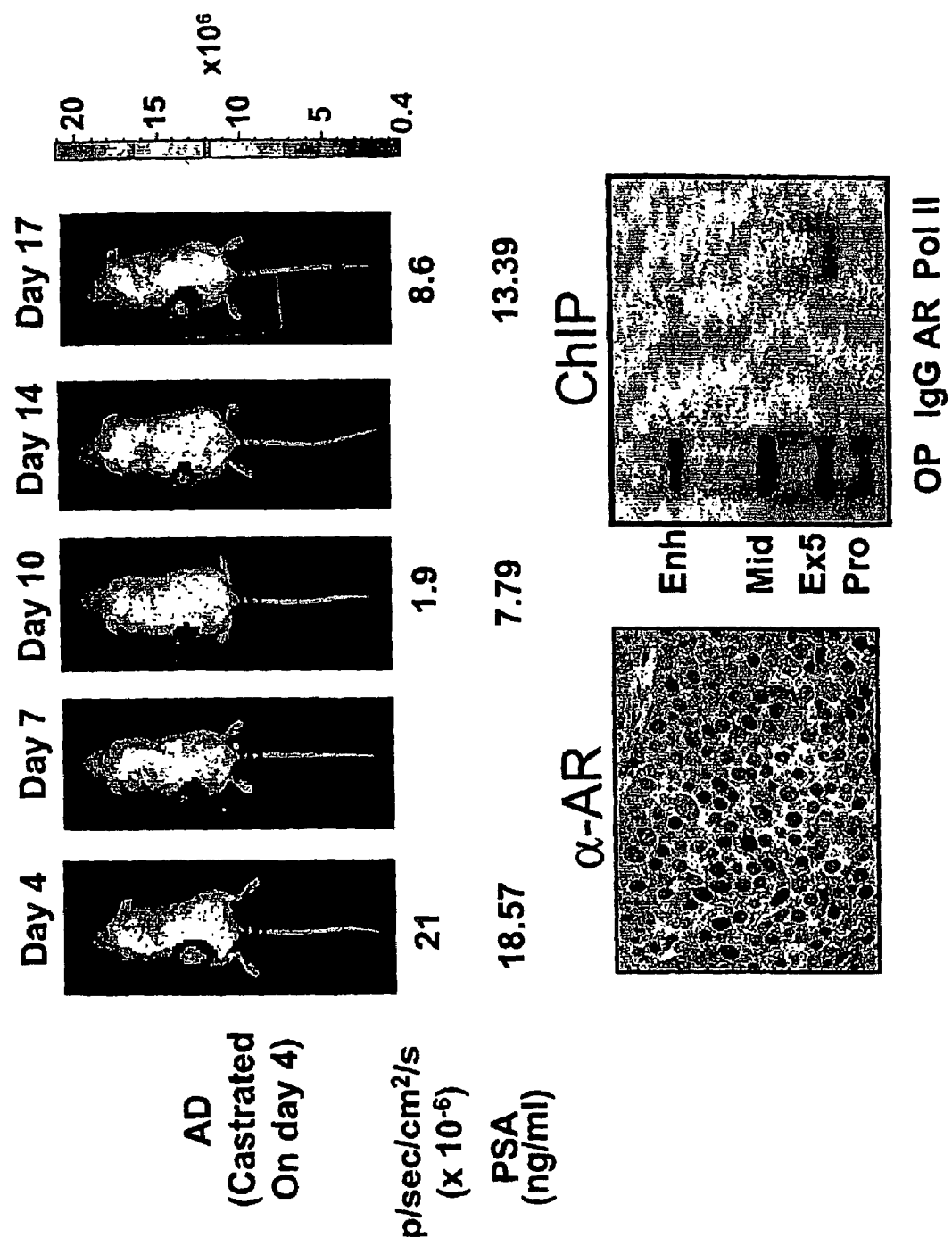

FIG. 29: Dynamic AR signaling. A SCID mouse bearing an LAPC9 AD tumor was injected with AdTSTA, imaged and castrated as described previously. The upper panel shows the entire time course with signals adjusted to the same color scale. Imaging measurements and PSA levels determined by Serum ELISA are shown below the images. Lower left panel: the tumors were extracted and subjected to immunohistological staining with AR antibodies. Lower right panel: a ChIP assay of the extracted tumors with IgG, AR and pol II antibodies.

Figure 30:
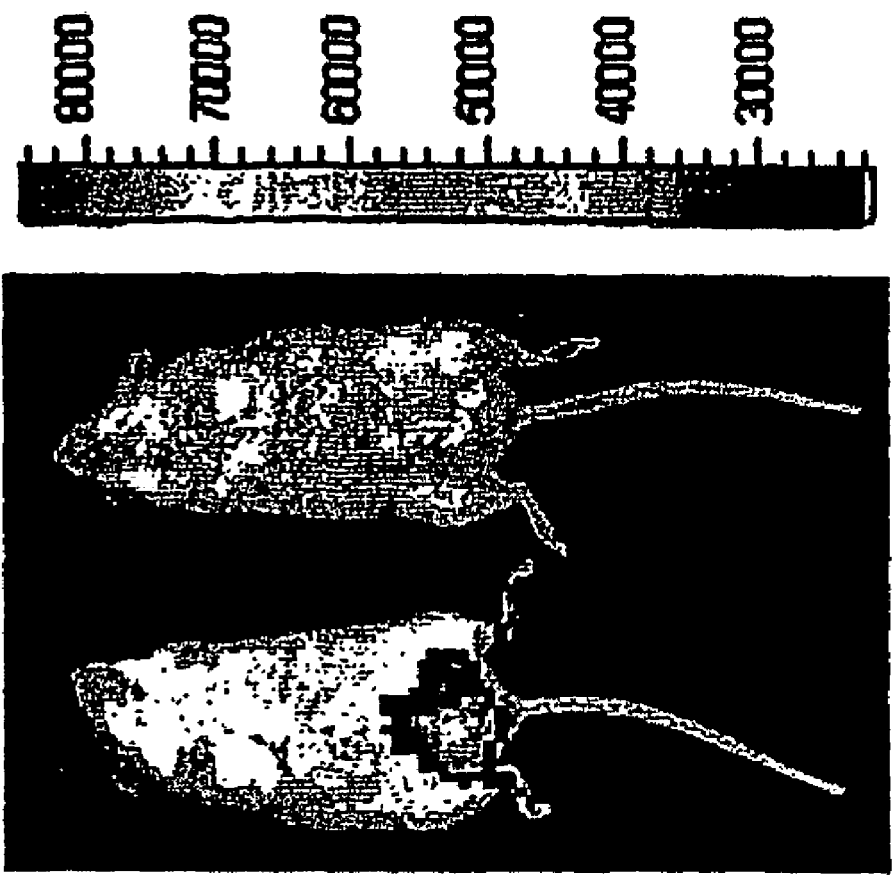

FIG. 30: Shown are a male transgenic mouse (left) and control mouse (right) imaged with D-Luciferin using a cooled CCD Camera. The color scale represents the relative light units for bioluminescence signal. Note the bioluminescence from the region of the prostate in the transgenic mouse. This illustrates the use of the TSTA approach in imaging prostate specific expression of a firefly luciferase optical reporter gene.

Figure 31:
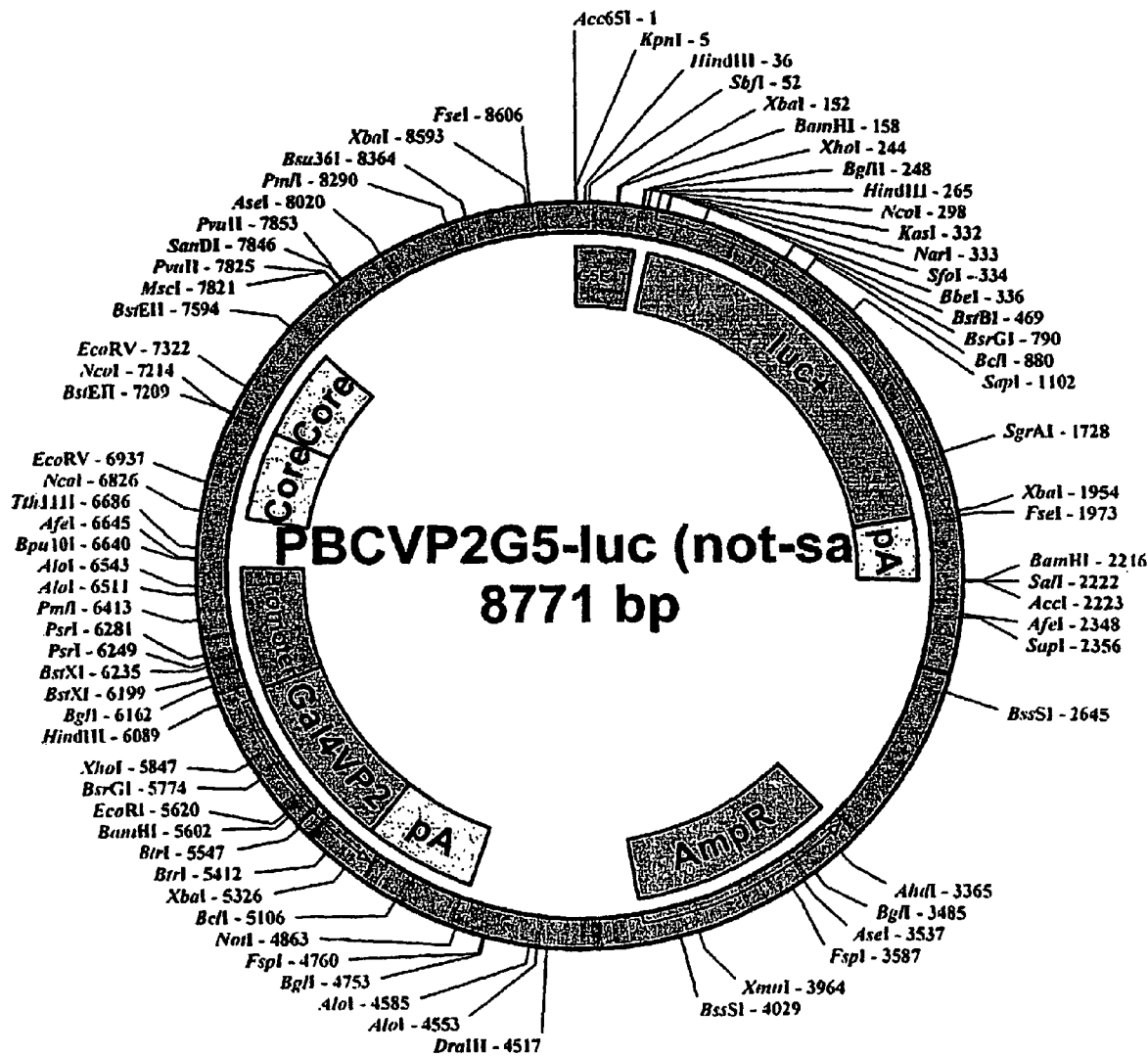

FIG. 31: A schematic diagram of a vector including the effector and reporter nucleotide sequences (PBCVP2G5-luc (not -sal)

Figure 32:
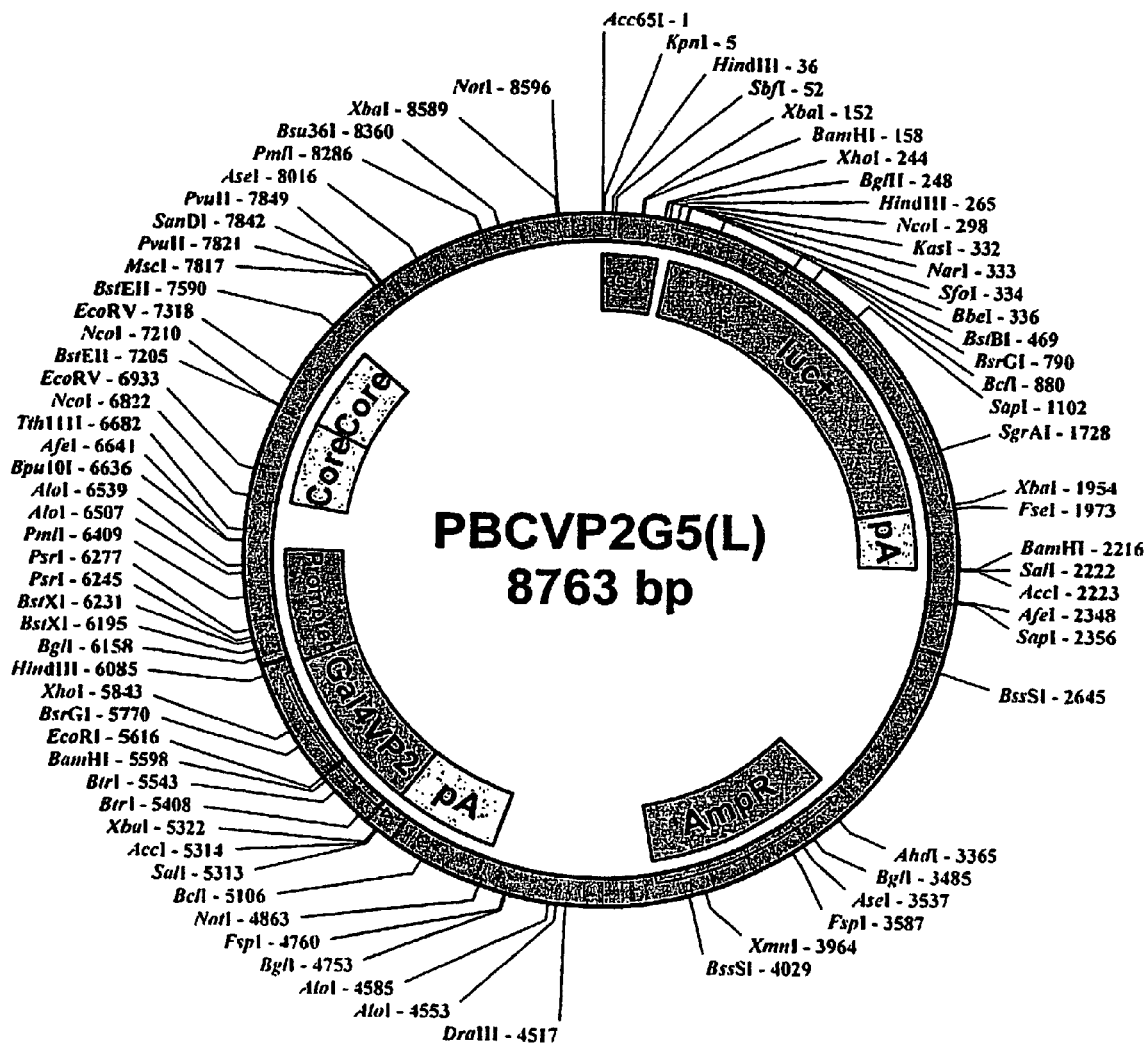

FIG. 32: A schematic diagram of a vector including the effector and reporter nucleotide sequences (PBCVP2G5(L)).

DETAILED DESCRIPTION OF THE INVENTION

In order that the invention herein described may be more fully understood, the following description is set forth.

The term "isolated" as used herein means a specific nucleic acid or polypeptide, or a fragment thereof, in which contaminants (i.e. substances that differ from the specific nucleic acid or polypeptide molecule) have been separated from the specific nucleic acid or polypeptide.

As used herein, a first nucleotide or amino acid sequence is said to have sequence "identity" to a second reference nucleotide or amino acid sequence, respectively, when a comparison of the first and the reference sequences shows that they are exactly alike.

As used herein, a first nucleotide or amino acid sequence is said to be "similar" to a second reference sequence when a comparison of the two sequences shows that they have few sequence differences (i.e., the first and second sequences are nearly identical). For example, two sequences are considered to be similar to each other when the percentage of nucleotides or amino acids that differ between the two sequences may be between about 60% to 99.99%.

The term "complementary" refers to nucleic acid molecules having purine and pyrimidine nucleotides which have the capacity to associate through hydrogen bonding to form double stranded nucleic acid molecules. The following base pairs are related by complementarity: guanine and cytosine; adenine and thymine; and adenine and uracil. Complementary applies to all base pairs comprising two single-stranded nucleic acid molecules, or to all base pairs comprising a single-stranded nucleic acid molecule folded upon itself. Molecules may be fully or partially complementary to the molecules of the invention.

The term "fragment" of an effector or a reporter nucleic acid molecule refers to a portion of the effector or reporter nucleotide sequences of the invention. A fragment of an effector or reporter molecule, is therefore, a nucleotide sequence having fewer nucleotides than and/or modified from the effector or reporter nucleotide sequences of the invention.

The term "operably linked" as used herein refers to two or more nucleotide sequences which are juxtaposed so as to permit function. For example, a promoter sequence operably linked to a nucleotide sequence encoding a gene product refers to the promoter sequence juxtaposed to the nucleotide gene sequence so that the promoter is capable of controlling the transcription of the gene sequence.

Effector Sequences

The present invention provides effector nucleic acid molecules including an upstream regulatory sequence operably linked to a nucleotide sequence encoding a chimeric, transcription activator protein (e.g., transactivator protein). The upstream regulatory sequence can include one or more of promoters and/or enhancers or any combination thereof.

The enhancer or promoter sequences can include portions having functions, such as nucleotide sequences that are known to bind cellular proteins or agents. The enhancer or promoter sequence function to mediate transcription of any operably linked gene sequence. These portions can be arranged within the enhancer or promoter sequences in a wild-type arrangement, or in a modified arrangement. For example, a modified enhancer or promoter sequence can include repeat sequences of a particular portion that bind cellular proteins or agents. Alternatively, the modified enhancer or promoter sequence can include repeat sequences of two or more portions. The repeat sequences can be arranged in a head-to-head or in a head-to-tail orientation. The cell-specific, upstream regulatory sequence can be intact (e.g., wild-type) or modified to include insertions, deletions, substitutions, or mutations.

The regulatory sequence can be a cell-specific regulatory sequence isolated from various cell types including: blood, prostate, brain, lung, stomach, bladder, pancreas, colon, breast, ovary, uterus, cervix, liver, muscle, skin, or bone.

The regulatory sequence can be isolated from various tissue-specific genes, including transferrin, tyrosinase and tyrosinase-related genes (melanocytes), albumin (liver), muscle creatinine kinase (muscle), myelin basic protein (oligodendrocytes and glial cells), glial fibrilllary acidic protein (glial cells), and NSE (neurons).

The tumor-specific, regulatory sequence can be isolated from various tumor-specific genes, including VEGF, KDR, E-selectin, endoglin, AFP (liver tumor), CEA (various adenocarcinomas), erbB2 (breast and pancreatic cancer), muc-1 (DF3) (breast cancer), ALA (breast cancer), BLG (breast cancer), osteocalcin (osteosarcoma and prostate cancer), SLP1 (ovarian and cervical cancer), HRE (solid tumors), Grp78(BIP) (solid tumors), L-plastin (cancer cells), and hexokinase II (cancer cells).

The regulatory sequences can be isolated from treatment responsive genes (egr-1, t-PA, mdr-1, hsp70) or from cell cycle-regulated genes (E2F-1, cycline A, and cdc25C). See Nettelbeck for a review (Trends in Genetics (2000) 16:174-181).

The regulatory sequences can be from any viral source, including adenvirus, adenovirus-associated virus, retrovirus, and lentivirus.

The regulatory sequences can be constitutive or inducible. A constitutive regulatory sequence includes CMV (cytomegalovirus), SV40 (Simian virus) and RSV (rous sarcoma virus), yeast beta-factor, alcohol oxidase and PGH.

The regulatory sequences can be inducible which are regulated by environmental stimuli or the growth medium of the cells, including those from the genes for heat shock proteins, alcohol dehydrogenase 2, isocytochrome C, acid phosphatase, enzymes associated with nitrogen catabolism, and enzymes responsible for maltose and galactose utilization.

In one embodiment, the cell-specific, upstream regulatory sequence can include a Prostate Specific Antigen (PSA) promoter (Pang, et al., 1995 Hum. Gene Ther. 6:1417-1426; Lee, et al., 1996 Anticancer Res. 16:1805-1811; Martiniello, et al., 1998 Hum. Gene Ther. 9:1617-1626; Pang, et al., 1997 Cancer Research 57:495-499; L Wu, et al., 2001 Gene Therapy 8:1416-1426).

In another embodiment, the cell-specific regulatory sequence can include a Prostate Specific Cell Antigen (PSCA) promoter (Watabe, et al., 2002 Proc. Natl. Acad. Sci. USA 99:401-406; Bahrenberg, et al., 2001 Cancer Lett. 168: 37-43; Jain, A., Lam, A., Carey, M. and Reiter, R. (2002) Indentification of an Androgen-Dependent Enhancer Within the Prostate Stem Cell Antigen Gene. *Molecular Endocrinology* 16:2323-2337.).

In another embodiment, the cell-specific regulatory sequence can include a human Kallikrien 2 (hK2) promoter (Song, et al., 1996 Immunopharmacology 32:105-107; Song, et al., 1997 Human Genet. 99:727-734; Wang, et al., 1997 Immunopharmacology 36:221-227; Chao and Chao 1997 Immunopharmacology 36:229-236; Xiong, et al., 1997 Biochem. J. 325(Pt 1):111-116; Zhang, et al., 1999 Endocrinology 140:1665-1671; Xie, et al., 2001 Hum Gene Ther. 12:549-561).

The cell-specific, upstream regulatory sequence can be isolated from various organisms including prokaryote or eukaryote organisms, such as bacteria, virus, yeast, plant, insect, or mammal. The mammals include mouse, rat, rabbit, dog, cat, horse, cow, goat, pig, fish, monkey, ape or human. In one embodiment, the upstream regulatory sequence is an intact, human PSA enhancer sequence including nucleotides −5824 through −2855, linked to an intact human PSA promoter sequence including −541 through +12.

The upstream regulatory sequence is operably linked, to control transcription of the nucleotide sequence encoding a transactivator protein. The transactivator protein includes a DNA-binding domain, linked in-frame, with a transcription activation domain. The DNA-binding domain can include the DNA-binding domain of yeast GAL4, or bacterial LexA The transcription activation domain can include the transactivator domain of herpes simplex VP-16 (Sadowski, et al., 1988 Nature 335:563-564) or forkhead in rhabdomycosarcoma (FKHR) (Massuda, et al., 1997 Proc. Natl. Acad. Sci. USA 94:14701-14706). Other transcriptional activator domains can be used (Ma and Ptashne 1987 Cell 48:847-853; Ma and Ptashne 1987 Cell 51:113-119; Brent and Ptashne 1985 Cell 43:729-736; Hope and Struhl 1986 Cell 46:885-894 (e.g., GCN4); Gill and Ptashne 1987 Cell 51:121-126). Other transcriptional activator domains include MAPK-responsive ELK-1, steroid receptors, and those from the Ets family.

In one embodiment, the effector sequence includes between 1 through 4 copies of VP-16. In another embodiment, the nucleotide sequence encoding the transactivator protein includes a DNA-binding domain of yeast GAL4 and between 1 through 4 copies of a transactivator domain of herpes simplex VP-16 (Emami and Carey 1992 The EMBO Journal 11:5005-5012).

In a preferred embodiment, the effector nucleotide sequence includes: an intact upstream regulatory sequence of a human PSA enhancer sequence including nucleotides −5824 through −2855, linked to an intact human PSA promoter sequence including −541 through +12, operably linked to a nucleotide sequence encoding the transactivator protein includes a DNA-binding domain of yeast GAL4 and a transactivator domain of herpes simplex VP-16.

In a more preferred embodiment, the effector nucleotide sequence includes: a modified upstream regulatory sequence including two copies of a human PSA enhancer sequence including nucleotides −4326 through −3935 (Pang, et al., 1997 Cancer Res. 57:495-499), with an intervening 890 bp sequence from −3743 through −2855 between the enhancer and promoter deleted, linked to an intact human PSA promoter sequence including −541 through +12, operably linked to a nucleotide sequence encoding the transactivator protein includes a DNA-binding domain of yeast GAL4 (encoding amino acids 1-147) and between 1 through 4 copies of a transactivator domain of herpes simplex VP-16 (encoding amino acids 413-454).

The most preferred embodiment of the effector nucleotide sequence includes 2 copies of the transactivator domain of VP16, encoding amino acids 413-454.

Reporter Sequences

The present invention provides reporter nucleotide sequences including 1 through 9 copies of a DNA-binding sequence. In one embodiment, the DNA-binding sequences can be isolated from yeast GAL4 or bacterial LexA or from PAX3 paired box gene 3 (PAX3) (Massuda, et al., 1997 Proc. Natl. Acad. Sci. USA 94:14701-14706). The DNA-binding sequence is linked to a promoter sequence. The promoter sequence can be a minimal promoter sequence. The promoter sequence includes sequences necessary for core promoter function. The promoter sequence can include a TATA box sequence. The promoter sequence can be isolated from any source including bacteria, virus, yeast, plant, insect, or mammal. In particular, the minimal promoter can be isolated from any virus including adenovirus, adenoviral-associated, retrovirus, lentivirus, herpes simplex virus, or retrovirus. In one embodiment, the promoter is isolated from any serotype of adenovirus, including serotypes A through F. In another embodiment, the promoter is isolated from any adenoviral early region, including E1a, E1b, E2a, E2b, E3, and E4. In a preferred embodiment, the promoter includes the TATA box sequence from adenoviral E4 gene.

In reporter nucleotide sequence invention includes a promoter operably linked to a heterologous nucleotide sequence encoding a heterologous gene product. In one embodiment, the reporter nucleotide sequence includes a minimal promoter operably linked to a chimeric heterologous gene sequence encoding two or more different heterologous gene products. In this embodiment, the different heterologous gene sequences are joined to form a fusion sequence which is operably joined in-frame, or the different heterologous sequences are arranged in a bi-cistronic construct (141-143). Other constructs include a multiple promoter construct where the different heterologous sequences are joined to a different promoter sequence. The reporter nucleotide sequence includes a bi-directional promoter sequence operably linked to two different heterologous gene sequences (148). Alternatively, two or more different reporter nucleotide sequences can be introduced to a cell, where the different reporter nucleotide sequences comprise a promoter operably linked to a heterologous nucleotide sequence encoding a heterologous gene product.

The heterologous gene product can encode a reporter gene product, a therapeutic gene product, and/or an immunologically active protein comprising a domain that binds a target.

The reporter gene product includes proteins that are detectable via various methods including colorimetric, fluorescence, optical, biochemical assays, or radiotracing. The reporter gene sequence can encode beta-galactosidase, luciferase, chloramphenicol acetyl-transferase, dopamine type-2 receptor ($D_2R$) or mutant forms including $D_2R80A$ and $D_2R194A$, and somatostatin receptor type-2 (SSTR2), or beta-lactamase. The reporter gene sequence can encode green fluorescent protein (GFP), or derivatives thereof such as YFP (yellow fluorescent protein), CFP (cyan fluorescent protein) or RFP (red fluorescent protein).

Alternatively, the heterologous gene sequence encodes proteins having therapeutic function such as cytotoxic function. The heterologous gene product having therapeutic function includes, but is not limited to, a toxin, a cytokine, an antibody, lymphokine, oncostatin, enzyme, or an enzyme that converts a prodrug into a cytotoxic drug.

Examples of therapeutic gene products include, but are not limited to ricin, ricin A-chain, diphteria toxin, *Pseudomonas* exotoxin (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, or maytansinoids.

Therapeutic gene products which convert a prodrug into a cytotoxic drug (e.g., pro-drug activating enzymes), including thymidine kinase (Oldfield 1993 Hum. Gene Therapy 4: 39-69). Thymidine kinase converts prodrugs acyclovir (9-((2-hydroxyethoxy)methyl)guanine)) or its analog ganciclovir (9-((2-hydroxy-1-(hydroxymethyl)ethoxy)methyl)guanine) into intermediates capable of inhibiting DNA synthesis of a cell. Cells that express thymidine kinase are susceptible to cell killing upon administration of the prodrug.

Other examples of therapeutic gene products that convert a prodrug into a cytotoxic drug include cytosine deaminase (Huber 1993 Cancer Res. 53: 4619-4626), nitroreductase (Green 1995 British J. Surgery 82: 1546), carboxypeptidase A (Hamstra 1999 Hum. Gene Therapy 10:235-248); linmarase (Cortes 1998 Gene Therapy 5:1499-1507); xanthine-guanine phospho-ribosyltransferase (Mrox 1993 Hum. Gene Therapy 4:589-595); beta-lactamase (Shepard 1991 Bioorg. Med. Chem. Lett. 1:21-26); alkaline phosphatase (Senter 1988 Proc. Natl. Acad. Sci. 85:48424846); carboxypeptidase G2 (Bagshawe 1991 Dis Markers 9:233-238); DT diaphorase (Knox 1993 Cancer Metasta. Rev. 12:195-212); and beta-glucuronidase (Roffler 1991 Biochem. Pharmacol. 42:2062-2065).

Other examples of pro-drug activating enzymes include mutant forms of the pro-drug activating enzymes. A mutant form of thymidine kinase, HSV1sr-39TK) utilizes ganciclovir and penciclovir substrates effectively than thymidine compared to wild type thymidine kinase (Gambhir 2000 Proc. Natl. Acad. Sci. 97:2785-2790).

The heterologous sequence can be a nucleotide sequence encoding an immunologically active protein comprising a domain capable of binding a target. The immunologically active protein can be a single-chain, immunologically active protein. The domain can include an antigen-binding site of an antibody that binds the target. The protein domain can include at least one complement determining region of an antibody that binds the target.

The target can be a target protein, a cell-surface antigen, or a cell-surface receptor. For example, the target protein can be tyrosinase, tyrosinase-related protein, albumin, muscle creatinine kinase, myelin basic protein, glial fibrilllary acidic protein, NSE, KDR, E-selectin, endoglin, AFP, CEA, erbB2, muc-1 (DF3), ALA, BLG, osteocalcin, SLP1, HRE, Grp78 (BIP), L-plastin, and hexokinase II, egr-1, t-PA, mdr-1, hsp70, E2F-1, cycline A, or cdc25C).

The immunologically active protein can bind to a target protein, including PSA, PSCA, or Kallikrien 2 (hK2).

The methods for producing the immunologically active proteins of the invention, synthesis of oligonucleotides, PCR, transforming cells, constructing vectors, expression systems, and the like, are well known in the art (Sambrook et al., eds., Molecular Cloning, A Laboratory Manual, 2nd Edition, Cold Spring Harbor Laboratory Press (1989); U.S. Pat. No. 5,637, 481 issued to Ledbetter et al).

The nucleotide sequences encoding the immunologically active protein may be expressed in a variety of systems. An expression vector, encoding the immunologically active protein is introduced (e.g, transformed) into suitable host cells, such as a bacterial cell (Chaudhary et al., 1987 Proc. Natl. Acad. Sci. USA 84:4538-4542; Cohen, 1971 Proc. Natl. Acad. Sci. USA (1972) 69:2110). The expression vector may be introduced into mammalian host cells using DEAE-dextran mediated transfection, calcium phosphate co-precipitation, lipofection, electroporation, protoplast fusion, or other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

The production of the immunologically active protein can be detected using Coomassie stained SDS-PAGE and/or immunoblotting using anti-idiotypic antibodies that bind to the immunologically active protein.

The heterologous gene product, including the reporter gene product, the therapeutic gene product, or the immunologically active protein, can be joined to a cytotoxic agent thereby forming a conjugated molecule.

Techniques for conjugating or joining cytotoxic agents to antibodies are well known and can be adapted for joining cytotoxic agents to the heterologous gene products (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982); Vitetta, E. S. et al., 1993, Immunotoxin therapy, in DeVita, Jr., V. T. et al., eds, Cancer: Principles and Practice of Oncology, 4th ed., J.B. Lippincott Co., Philadelphia, 2624-2636).

Examples of cytotoxic agents include, but are not limited to ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, maytansinoids, and glucocorticoid and other chemotherapeutic agents, as well as radioisotopes such as $^{212}$Bi, $^{131}$I, $^{131}$In, $^{90}$Y, and $^{186}$Re.

The heterologous gene products, including the reporter gene product, the therapeutic gene product, or the immunologically active protein, can be joined to a detectable label, including a radioisotope, a fluorescent compound, a bioluminescent compound, chemiluminescent compound, a metal chelator or an enzyme.

Recombinant Nucleic Acid Molecules

Also provided are recombinant DNA molecules that include the effector and/or the reporter nucleic acid molecules of the invention, or a fragment thereof. As used herein, a recombinant DNA molecule is a DNA molecule that has been subjected to molecular manipulation in vitro. Methods for generating rDNA molecules are well known in the art, for example, see Sambrook et al., *Molecular Cloning* (1989). In the preferred recombinant DNA molecules of the present invention, the effector and/or the reporter sequences, or fragments thereof, are operably linked to one or more expression control sequences and/or vector sequences.

Vectors

The nucleic acid molecules of the invention may be recombinant molecules each comprising the sequence, or portions thereof, of an effector of reporter nucleotide sequence. The term vector includes, but is not limited to, plasmids, cosmids, and phagemids. The effector and reporter nucleotide sequences can be joined to a single vector or to two different vectors. The effector and reporter nucleotides sequences can be arranged in a head-to-head or head-to-tail orientation on a single vector.

The vector of the invention can be an autonomously replicating vector comprising a replicon that directs the replication of the recombinant DNA within the appropriate host cell. Alternatively, the vector directs integration of the recombinant vector into the host cell. Various viral vectors may be used, such as, for example, a number of well known retroviral and adenoviral vectors (Berkner 1988 Biotechniques 6:616-629).

The vectors include, for example, a vector derived from herpes simplex virus that targets neuronal cells (Battleman et al., J. Neurosci. 13:941-951 (1993), an immunodeficiency virus that targets hematopoietic cells (Carroll et al., J. Cell. Biochem. 17E:241 (1993), and recombinant adeno-associated viral vectors having general or tissue-specific promoters (Lebkowski et al. U.S. Pat. No. 5,354,678). Recombinant adeno-associated viral vectors can be used to integrate the nucleic acid molecules of the invention into the genome of a cell (Lebkowski et al., Mol. Cell. Biol. 8:3988-3996 (1988).

Retroviral vectors can be used to produce the heterologous gene product. These vectors have broad host and cell type ranges, integrate into random sites in the host genome, express genes stably and efficiently, and under most conditions do not kill or obviously damage their host cells.

Retroviral vectors contain retroviral long terminal repeats (LTRs) and packaging (psi) sequences, as well as plasmid sequences for replication in bacteria and may include other sequences such as the SV40 early promoter and enhancer for potential replication in eukaryotic cells. Much of the rest of the viral genome is removed and replaced with other promoters and heterologous gene sequences. Modified (defective) retroviruses can be made in which at least one of the genes required for replication is replaced by the gene to be transferred. Vectors are packaged as RNA in virus particles following transfection of DNA constructs into packaging cell lines. These include psi2 which produce viral particles that can infect rodent cells and psiAM and PA 12 which produce particles that can infect a broad range of species. Methods of preparation of retroviral vectors have been described (Moolten & Wells, J. Natl. Cancer Inst., 82:297-300 (1990); Wolff et al., Proc. Natl. Acad. Sci. USA 84:3344-3348 (1987); Yee et al., Cold Spring Harbor Symp. on Quant. Biol. Vol. LI, pp. 1021-1026 (1986); Wolff et al., Proc. Natl. Acad. Sci. U.S.A. 84:3344-3348 (1987); Jolly et al., Meth. in Enzymol. 149:10-25 (1987); Miller et al., Mol. Cell. Biol. 5:431-437 (1985); and Miller, et al., Mol. Cell. Biol. 6:2895-2902 (1986) and Eglitis et al., Biotechniques 6:608-614 (1988).

The effector and reporter molecules of the invention can be introduced into herpes viruses (e.g. HSV-1). Herpes viruses are capable of establishing a latent infection and an apparently non-pathogenic relationship with some neural cells.

Other virus vectors that may be used for gene transfer into cells for treatment of brain tumors include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); paramyxoviruses; vaccinia; rabies and poliovirus and other human and animal viruses.

The nucleic acid molecules can be introduced into a cell or subject using retroviral vectors, or infectious viral particles, or non-infectious particles (e.g., helper-dependent). The virus vector can be modified so that it maintains the necessary genes, regulatory sequences and packaging signals to synthesize new viral proteins and RNA but lacks genes conferring oncogenic potential.

In the case of non-infectious viral vectors, a helper virus genome is required to provide the structural genes necessary to encode viral structural proteins. The helper virus lacks the viral packaging signal required to encapsulate the helper viral RNA into viral particles. Thus, only the helper-dependent viral vector carrying the heterologous gene sequence and a functional packaging signal, but lacking viral structural genes can be incorporated into a virus particle. The helper and helper-dependent vectors are used to infect a target cell and produce no further infectious virus can be produced since there are no viral structural genes provided. Methods for constructing and using viral vectors are well known in the art and reviewed, for example, in Miller and Rosman, Biotechniques 7:980-990 (1992) and Davison and Elliot, Molecular Virology: A Practical Approach (IRL Press, New York, 1993).

The viral or other vector can include a constitutive promoter for constitutive transcription of the transactivator sequence. Examples of constitutive promoters include the cytomegalovirus promoter (Boshart, M. et al., 1985 Cell 41:521-530). Viral vectors can include tissue-specific or tumor specific transcription or regulatory sequences to regulate the type of cell that expresses the heterologous gene product by incorporating a tissue-specific promoter or enhancer into the vector (Dai et al., Proc. Natl. Acad. Sci. USA 89:10892-10895 (1992).

The preferred vectors permit transcription and translation of the effector and/or reporter sequences in prokaryotic or eukaryotic host cells.

The efficiency of expression may be enhanced by the inclusion of enhancers appropriate to the cell system in use (Scharf, D., et al, 1994 *Results Probl. Cell. Differ.* 20:125-62; Bittner, et al., 1987 *Methods in Enzymol.* 153:516-544). The enhancers, transcriptional elements, and initiation codons can be of various origins, both natural and synthetic.

The vectors having the effector or reporter sequences include expression vectors which are compatible with prokaryotic host cells. Prokaryotic cell expression vectors are well known in the art and are available from several commercial sources. For example, pET vectors (e.g., pET-21, Novagen Corp.), BLUESCRIPT phagemid (Stratagene, LaJolla, Calif.), pSPORT (Gibco BRL, Rockville, Md.), or ptrp-lac hybrids for expression in bacterial host cells.

Alternatively, the vectors having the effector or reporter sequences are expression vectors which are compatible with eukaryotic host cells. The more preferred vectors are those compatible with vertebrate cells. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), and similar eukaryotic expression vectors.

Methods for generating a recombinant vector including the effector or reporter sequences are well known in the art, and can be found in Maniatis, T., et al., (1989 in: "Molecular Cloning, A Laboratory Manual", Cold Spring Harbor Laboratory, Cold Spring Harbor, N.Y.) and Ausubel et al. (1989 in: "Current Protocols in Molecular Biology", John Wiley & Sons, New York N.Y.).

The vector can include at least one selectable marker gene that encodes a gene product that confers drug resistance such as resistance to kanamycin, neomycin, tetracycline, or ampicillin. The selectable markers can include dihydrofolate reductase or glutamine synthetase. The vector also comprises multiple endonuclease restriction sites that enable convenient insertion of exogenous DNA sequences.

Host-Vector Systems

The invention further provides a host-vector system comprising a vector, plasmid, phagemid, or cosmid comprising the effector or reporter nucleotide sequence, or a fragment thereof, introduced into a suitable host cell. In one embodiment, the host cell is introduced with a vector comprising both the effector and reporter nucleotide sequences of the invention. In another embodiment, the host cell is introduced with two or more vectors (preferably two) where one vector comprises the effector nucleotide sequences of the invention and another vector comprises the reporter nucleotide sequences of the invention.

A variety of expression vector/host systems may be utilized to carry and express the effector or reporter sequences. The host-vector system can be used to transcribe and translate express (e.g., produce) the effector transactivator protein or the reporter heterologous gene product. The host cell can be either prokaryotic or eukaryotic. Examples of suitable prokaryotic host cells include bacteria strains from genera such as *Escherichia, Bacillus, Pseudomonas, Streptococcus*, and *Streptomyces*. Examples of suitable eukaryotic host cells include yeast cells, plant cells, or animal cells such as mammalian cells. A preferred embodiment provides a host-vector system comprising the pBCVP2G5-L vector (Example 2) in mammalian cells. A most preferred embodiment provides a host-vector system comprising the pBCVP2G5-L vector (Example 2) in human prostate cancer cells.

Introduction of the recombinant DNA molecules or vectors of the present invention into an appropriate host cell is accomplished by well known methods that depend on the type of vector used and host system employed. For example, host cells are introduced (e.g., transformed) with nucleic acid molecules by electroporation or salt treatment methods, see for example, Cohen et al., 1972 Proc Acad Sci USA 69:2110; Maniatis, T., et al., 1989 in: "Molecular Cloning, A Laboratory Manual", Cold Spring Harbor Laboratory, Cold Spring Harbor, N.Y. Host cells can also be introduced with nucleic acid molecules by various methods, including liposomes, cationic lipid, salt treatment (Graham et al., 1973 Virol 52:456; Wigler et al., 1979 Proc Natl Acad Sci USA 76:1373-76), diethyaminoethyl dextran, or viral infection. Alternatively, particle bombardment can be used to introduce the vectors of the invention into a host cell (Williams et al., Proc. Natl. Acad. Sci. USA 88:2726-2730 (1991).

Successfully transformed cells, i.e., cells that harbor the vector of the present invention, can be identified by techniques well known in the art. For example, cells resulting from the introduction of the vector are selected and cloned to produce single colonies. Cells from those colonies are harvested, lysed and their DNA content examined for the presence of the rDNA using a method such as that described by Southern, J Mol Biol (1975) 98:503, or Berent et al., Biotech (1985) 3:208, or the proteins produced from the cell assayed via a biochemical assay or immunological method.

In bacterial systems, a number of expression vectors may be selected depending upon the use intended for the effector or reporter nucleotide sequences. The vectors include, but are not limited to, the multifunctional *E. coli* cloning and expression vectors such as BLUESCRIPT (Stratagene), pIN vectors (Van Heeke & Schuster (1989) J Biol Chem 264:5503-5509), and the like. The pGEX vectors (Promega; Madison, Wis.) may also be used to express fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned protein of interest can be released from the GST moiety at will.

In yeast, *Saccharomyces cerevisiae*, a number of vectors containing constitutive or inducible promoters such as beta-factor, alcohol oxidase and PGH may be used. For reviews, see Ausubel et al (1989 in: "Current Protocols in Molecular Biology", John Wiley & Sons, New York N.Y.) and Grant et al (1987) Methods in Enzymology 153:516-544.

In cases where plant expression vectors are used, the vectors having the effector or reporter sequences of the invention can include viral promoters such as the 35S and 19S promoters of CaMV (Brisson, et al., (1984) Nature 310:511-514), or the omega leader sequence from TMV (Takamatsu, et al., (1987) EMBO J. 6:307-311). Alternatively, plant promoters such as the small subunit of RUBISCO (Coruzzi et al (1984) EMBO J. 3:1671-1680; Broglie et al (1984) Science 224:838-843); or heat shock promoters (Winter J and Sinibaldi R M (1991) Results Probl Cell Differ 17:85-105) can be used. These constructs can be introduced into plant cells by direct DNA transformation or pathogen-mediated transfection. For reviews of such techniques, see Hobbs, S. in: "McGraw Yearbook of Science and Technology" 1992 McGraw Hill New York N.Y., pp 191-196; or Weissbach and Weissbach 1988 in: "Methods for Plant Molecular Biology", Academic Press, New York N.Y., pp 421-463.

An alternative expression system that can be used to express the effector and reporter sequences is an insect system. In one such system, *Autographa californica* nuclear polyhedrosis virus (AcNPV) can be used as a vector to express the effector transactivator and reporter heterologous gene product in *Spodoptera frugiperda* cells or in *Trichoplusia larvae*. The effector or reporter sequence can be cloned into a nonessential region of the virus, such as the polyhedrin gene, and placed under control of the polyhedrin promoter. Successful insertion of the effector or reporter sequence will render the polyhedrin gene inactive and produce recombinant virus lacking coat protein. The recombinant viruses can then used to infect *S. frugiperda* cells or *Trichoplusia larvae* in which the effector transactivator or the reporter heterologous gene product can be expressed (Smith et al 1983 J Virol 46:584; Engelhard E. K., et al, 1994 Proc Nat Acad Sci 91:3224-7).

In mammalian host cells, a number of viral-based expression systems can be utilized. In cases where an adenovirus is used as an expression vector, the effector or reporter sequence can be ligated into an adenovirus transcription/translation vector consisting of the late promoter and tripartite leader sequence. Insertion in a nonessential E1 or E3 region of the viral genome results in a viable virus capable of expressing the effector transactivator or the reporter heterologous gene product in infected host cells (Logan and Shenk 1984 Proc Natl Acad Sci 81:3655-59). In addition, transcription enhancers, such as the rous sarcoma virus (RSV) enhancer, can be used to increase expression in mammalian host cells.

The host cell may be isolated from various animal sources including equine, porcine, bovine, murine, canine, feline, or avian. The host cell may also be isolated from any mammalian source including monkey, ape, or human. The host cell may be isolated from various cell or organ sources including blood, prostate, brain, lung, stomach, bladder, pancreas, colon, breast, ovary, uterus, cervix, liver, muscle, skin, or bone.

In addition, a host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a precursor form of a protein (e.g., a prepro protein) may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the effector or reporter gene products.

For long-term, high-yield production of the effector transactivator or the reporter heterologous gene product, stable expression is preferred. For example, cell lines that stably express the effector or the reporter gene product can be transformed using expression vectors that contain viral origins of replication or endogenous expression elements and a selectable marker gene. Following the introduction of the vector, cells can be grown in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate for the cell type used.

Any number of selection systems may be used to recover transformed cell lines. These include, but are not limited to, the herpes simplex virus thymidine kinase (Wigler, M., et al., 1977 Cell 11:223-32) and adenine phosphoribosyltransferase (Lowy, I. et al., 1980 Cell 22:817-23) which can be employed in tk-minus or aprt-minus cells, respectively. Also, anti-metabolite, antibiotic or herbicide resistance can be used as the basis for selection; for example, dhfr which confers resistance to methotrexate (Wigler, M., et al., 1980 Proc Natl Acad Sci 77:3567-70); npt, which confers resistance to the aminoglycosides neomycin and G-418 (Colbere-Garapin, F., et al., 1981 J. Mol. Biol. 150:1-14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (Hartman, S. C. and R. C. Mulligan 1988 Proc. Natl. Acad. Sci. 85:8047-51). Recently, the use of visible markers has gained popularity with such markers as anthocyanins, β-glucuronidase and its substrate, GUS, and luciferase and its substrate, luciferin, being widely used not only to identify transformants, but also to quantify the amount of transient or stable protein expression attributable to a specific vector system (Rhodes, C. A., et al., 1995 Methods Mol. Biol. 55:121-131).

Nucleic Acid Molecules

In its various aspects the present invention provides recombinant nucleic acid molecules, transformed host cells harboring the nucleic acid molecules, generation methods, and assays.

The nucleic acid molecules of the invention are preferably in isolated form, where the nucleic acid molecules are substantially separated from contaminant nucleic acid molecules having sequences other than the effector or reporter sequences. A skilled artisan can readily employ nucleic acid isolation procedures to obtain isolated effector or reporter sequences, see for example Sambrook et al., in: "Molecular Cloning" (1989). The present invention also provides for isolated effector or reporter sequences generated by recombinant DNA technology or chemical synthesis methods.

The isolated nucleic acid molecules include DNA, RNA, DNA/RNA hybrids, and related molecules, nucleic acid molecules complementary to the effector or reporter sequences or a portion thereof, and those which hybridize to the effector or reporter sequences. The preferred nucleic acid molecules have nucleotide sequences identical to or nearly identical (e.g., similar) to the nucleotide sequences disclosed herein. Specifically contemplated are DNA, cDNA, RNA, ribozymes, and antisense molecules.

Identical and Variant Sequences

The present invention provides isolated nucleic acid molecules having a polynucleotide sequence identical or similar to the effector or reporter sequences disclosed herein. Accordingly, the polynucleotide sequences may be identical to a particular effector or reporter sequence. Alternatively, the polynucleotide sequences may be similar to the disclosed sequences.

One embodiment of the invention provides nucleic acid molecules that exhibit sequence identity or similarity with the effector or reporter nucleotide sequences, such as molecules that have at least 60% to 99.9% sequence similarity and up to 100% sequence identity with the sequences of the invention. A preferred embodiment provides nucleic acid molecules that exhibit between about 75% to 99.9% sequence similarity, a more preferred embodiment provides molecules that have between about 86% to 99.9% sequence similarity, and the most preferred embodiment provides molecules that have 100% sequence identity with the effector or reporter sequences of the invention.

Complementary Sequences

The invention also provides nucleic acid molecules that are complementary to the effector or reporter sequences of the invention. Complementarity may be full or partial. When it is fully complementary that means complementarity to the entire sequence. When it is partially complementary that means complementarity to only portions of the sequences of the invention.

Nucleotide Sequences which Hybridize

The present invention further provides nucleotide sequences that selectively hybridize to the effector or reporter nucleotide sequences of the invention under high stringency hybridization conditions. Typically, hybridization under standard high stringency conditions will occur between two complementary nucleic acid molecules that differ in sequence complementarity by about 70% to about 100%. It is readily apparent to one skilled in the art that the high stringency hybridization between nucleic acid molecules depends upon, for example, the degree of identity, the stringency of hybridization, and the length of hybridizing strands. The methods and formulas for conducting high stringency hybridizations are well known in the art, and can be found in, for example, Sambrook, et al., in: "Molecular Cloning" (1989).

In general, stringent hybridization conditions are those that: (1) employ low ionic strength and high temperature for washing, for example, 0.015M NaCl/0.0015M sodium titrate/

0.1% SDS at 50 degrees C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 degrees C.

Another example of stringent conditions include the use of 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 mg/ml), 0.1% SDS, and 10% dextran sulfate at 42 degrees C., with washes at 42 degrees C. in 0.2×SSC and 0.1% SDS. A skilled artisan can readily determine and vary the stringency conditions appropriately to obtain a clear and detectable hybridization signal.

Fragments

The invention further provides nucleic acid molecules having fragments of the effector or reporter sequences of the invention. The size of the fragment will be determined by its intended use. For example, if the fragment is chosen to be used as a nucleic acid probe or PCR primer, then the fragment length is chosen to obtain a relatively small number of false positives during a probing or priming procedure.

The nucleic acid molecules, fragments thereof, and probes and primers of the present invention are useful for a variety of molecular biology techniques including, for example, hybridization screens of libraries, or detection and quantification of mRNA transcripts as a means for analysis of gene transcription and/or expression. The probes and primers can be DNA, RNA, or derivative molecules including peptide nucleic acids (PNAs). A probe or primer length of at least 15 base pairs is suggested by theoretical and practical considerations (Wallace, B. and Miyada, G. 1987 in: "Oligonucleotide Probes for the Screening of Recombinant DNA Libraries" in: "Methods in Enzymology", 152:432-442, Academic Press).

Fragments of the effector or reporter sequences that are particularly useful as selective hybridization probes or PCR primers can be readily identified from the effector or reporter nucleotide sequences, using art-known methods. For example, sets of PCR primers that detect a portion of the effector or reporter transcripts can be made by the PCR method described in U.S. Pat. No. 4,965,188. The probes and primers of this invention can be prepared by methods well known to those skilled in the art (Sambrook, et al. supra). In a preferred embodiment the probes and primers are synthesized by chemical synthesis methods (ed: Gait, M. J. 1984 in: "Oligonucleotide Synthesis", IRL Press, Oxford, England).

One embodiment of the present invention provides nucleic acid primers that are complementary to effector or reporter sequences, which allow the specific amplification of nucleic acid molecules of the invention or of any specific portions thereof. Another embodiment provides nucleic acid probes that are complementary for selectively or specifically hybridizing to the effector or reporter sequences or to any portion thereof.

Codon Usage Variants

The present invention provides isolated codon-usage variants that differ from the disclosed effector or reporter nucleotide sequences, yet do not alter the predicted polypeptide sequence or biological activity of the effector gene product (e.g. the transactivator protein) or the reporter gene product (e.g., the heterologous gene product). For example, a number of amino acids are encoded by more than one codon triplet. Codons that specify the same amino acid, or synonyms may occur due to degeneracy in the genetic code. Examples include nucleotide codons CGT, CGG, CGC, and CGA encoding the amino acid, arginine (R); or codons GAT, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
| --- | --- | --- | --- |
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The codon-usage variants may be generated by recombinant DNA technology. Codons may be selected to optimize the level of production of the effector or reporter transcript, or the effector or reporter gene product in a particular prokaryotic or eukaryotic expression host, in accordance with the frequency of codon utilized by the host cell. Alternative reasons for altering the nucleotide sequence encoding an effector or reporter transcript include the production of RNA transcripts having more desirable properties, such as an extended half-life or increased stability. A multitude of variant effector or reporter nucleotide sequences that encode the respective effector or reporter gene products may be isolated, as a result of the degeneracy of the genetic code. Accordingly, the present invention provides selecting every possible triplet codon to generate every possible combination of nucleotide sequences that encode the disclosed effector or reporter gene products, or that encode the gene products having the biological activity of the effector or reporter gene products. This particular embodiment provides isolated nucleotide sequences that vary from the sequences of the invention, such that each variant nucleotide sequence encodes a polypeptide having sequence identity with the amino acid sequences of the invention.

Derivative Nucleic Acid Molecules

The nucleic acid molecules of the invention also include derivative nucleic acid molecules which differ from DNA or RNA molecules, and anti-sense molecules. Derivative molecules include peptide nucleic acids (PNAs), and non-nucleic acid molecules including phosphorothioate, phosphotriester, phosphoramidate, and methylphosphonate molecules, that bind to single-stranded DNA or RNA in a base pair-dependent manner (Zamecnik, P. C., et al., 1978 Proc. Natl. Acad. Sci. 75:280284; Goodchild, P. C., et al., 1986 Proc. Natl. Acad. Sci. 83:4143-4146). Peptide nucleic acid molecules comprise a nucleic acid oligomer to which an amino acid residue, such as lysine, and an amino group have been added. These small molecules, also designated anti-gene agents, stop transcript elongation by binding to their complementary (template) strand of nucleic acid (Nielsen, P. E., et al., 1993 Anticancer Drug Des 8:53-63). Reviews of methods for synthesis of DNA, RNA, and their analogues can be found in: "Oligonucleotides and Analogues", eds. F. Eckstein, 1991, IRL Press, New York; "Oligonucleotide Synthesis", ed. M. J. Gait, 1984, IRL Press, Oxford, England. Additionally, methods for antisense RNA technology are described in U.S. Pat. Nos. 5,194,428 and 5,110,802. A skilled artisan can readily obtain these classes of nucleic acid molecules using the herein described effector and reporter sequences (see for example "Innovative and Perspectives in Solid Phase Synthesis" (1992) Egholm, et al. pp 325-328 or U.S. Pat. No. 5,539,082).

RNA Molecules

The present invention provides nucleic acid molecules that encode the effector or reporter gene products. In particular, the RNA molecules of the invention may be isolated full-length or partial-length RNA molecules or RNA oligomers that encode the effector or reporter gene products.

The RNA molecules of the invention also include antisense RNA molecules, peptide nucleic acids (PNAs), or non-nucleic acid molecules such as phosphorothioate derivatives, that specifically bind in a base-dependent manner to the sense strand of DNA or RNA, having the effector or reporter sequences, in a base-pair manner. A skilled artisan can readily obtain these classes of nucleic acid molecules using the effector or reporter sequences described herein.

Labeled Nucleic Acid Molecules

Embodiments of the effector or reporter nucleic acid molecules of the invention include DNA and RNA primers, which allow the specific amplification of the effector or reporter sequences, or of any specific parts thereof, and probes that selectively or specifically hybridize to the effector or reporter sequences or to any part thereof. The nucleic acid probes can be labeled with a detectable marker. Examples of a detectable marker include, but are not limited to, a radioisotope, a fluorescent compound, a bioluminescent compound, a chemiluminescent compound, a metal chelator or an enzyme. Technologies for generating labeled DNA and RNA probes are well known, see, for example, Sambrook et al., in "Molecular Cloning" (1989).

Methods for Producing the Heterologous Gene Product

The present invention provides methods for producing the heterologous gene product. These methods utilize a cell introduced with the effector and reporter nucleic acid molecules of the invention. The cell can be introduced with nucleic acid molecules of the invention inserted into a vector that permits transcription of the effector transactivator and the heterologous gene sequence. The cell, harboring the nucleic acid molecules of the invention, is induced to produce the heterologous gene product. Alternatively, the cell produces the heterologous gene product constitutively. The heterologous gene product, produced by these methods, can be detected and/or imaged in the cell or in the subject.

In one embodiment, the steps include: introducing a cell with the nucleic acid molecules of the invention; and culturing the introduced cell under conditions suitable for production of the heterologous gene product. The conditions which are suitable for production of the heterologous gene product include contacting the cell with an agent that induces transcription of the effector transactivator. The transcript is translated into the transactivator protein which activates transcription of the reporter nucleic acid molecule and translation of the heterologous gene product.

The agent includes agents that are capable of causing transcription of the transcription regulatory sequences in the effector molecule. For example, the inducing agent can be an androgen that mediates transcription of the effector molecule having a prostate-specific or prostate tumor-specific promoter and/or enhancer. The inducing androgen can be natural or synthetic.

In another embodiment, the methods for producing the heterologous gene product include: introducing the nucleic acid molecules of the invention into a subject under conditions that permit production of the heterologous gene product.

The nucleic acid molecules are introduced into the subject via various routes, including intravenous, intraperitoneal, intramuscular, intratumoral, intradermal, subcutaneous, and the like. The nucleic acid molecules of the invention can be introduced at a site distal from a target site, such as a tumor. The heterologous gene product produced by the nucleic acid molecules of the invention can migrate to the target site. For example, the nucleic acid molecules of the invention can be introduced into the subject intramuscularly and the heterologous gene product can migrate to the target tumor via the circulatory system. Alternatively, the nucleic acid molecules of the invention can be introduced at the target site, such as in or proximal to the tumor.

The conditions which are suitable for production of the heterologous gene product include contacting the cell, so introduced, with an agent that induces transcription of the effector transactivator. The transcript is translated into the transactivator protein which activates transcription of the reporter nucleic acid molecule and translation of the heterologous gene product.

The present invention also provides methods for producing the heterologous gene product which include: implanting a donor cell into a subject under conditions that permit production of the heterologous gene product, where the donor cell harbors the nucleic acid molecules of the invention. The conditions which are suitable for production of the heterologous gene product include contacting the donor cell, so implanted, with an agent that induces transcription of the effector transactivator. The transcript is translated into the transactivator protein which activates transcription of the reporter nucleic acid molecule and translation of the heterologous gene product.

The donor cells can be introduced into the subject as a cell suspension or as a solid clump of cells. The donor cells can be introduced into the subject via various routes, including intravenous, intraperitoneal, intramuscular, intratumor, intradermal, subcutaneous, and the like. The donor cells can be implanted at a site distal to the target site, such as a tumor. In such cases, the heterologous gene product is produced by the donor cell and can migrate to the target site. For example, the donor cell can be implanted into the subject intramuscularly and the heterologous gene product can migrate to a prostate tumor target site via the circulatory system. Alternatively, the donor cells can be implanted in or proximal to the target site.

The donor cell can be a cell from a the subject (e.g., autologous cells) or from a different subject (e.g., non-autologous). Donor cells which harbor the molecules of the invention include any cell from a subject, including blood, prostate, brain, lung, stomach, bladder, pancreas, colon, breast, ovary, uterus, cervix, liver, muscle, skin, or bone. Cells which harbor the molecules of the invention include any cell from any animal including mouse, rat, rabbit, dog, cat, horse, cow, goat, pig, fish, monkey, ape or human. Non-autologous cells such as allogeneic cells also can be used provided they share histocompatibility antigens with the subject to be introduced.

Methods for preparing donor cells and implanting donor cells harboring recombinant retroviral vectors carrying a heterologous gene sequence have been described (Gage et al., Ch. 86, in: "Progress in Brain Research", Vol. 78, pp. 651-658, 1988; U.S. Pat. No. 5,529,774).

A variety of methods can be used to introduce the nucleic acid molecules of the invention into a cell, into a subject, or into a donor cell which is implanted into a subject.

The molecules of the invention can be introduced as naked nucleic acid molecules (with or without a linked vector), liposomes, virus vectors, viruses, or receptor-mediated agents.

In one embodiment, introduction of naked nucleic acid molecules or liposomes (e.g, cationic) can be used for stable gene transfer of the nucleic acid molecules. The nucleic acid molecules can be introduced into non-dividing or dividing cells in vivo (Ulmer et al., Science 259:1745-1748 (1993). In addition, the nucleic acid can be transferred into a variety of tissues in vivo using the particle bombardment method (Williams et al., Proc. Natl. Acad. Sci. USA 88:2726-2730 (1991).

The nucleic acid molecules can be encapsulated into liposomes using hemagglutinating viruses including the Japan Sendai virus (Z strain). In one embodiment, the nucleic acid molecules are linked to a vector encapsulated into a liposome HVJ construct prior to injection. Alternatively, the liposomes can be produced using Lipofectamine™. The nucleic acid molecules can be introduced into a cell or a subject via viral vectors or viruses. The selection of a viral vector will depend, in part, on the cell type to be targeted. Specialized viral vectors are well known in the art that can target specific cell types.

The molecules of the invention can be introduced into a cell or a subject using receptor-mediated delivery methods. The nucleic acid molecules of the invention can be complexed with a tissue-specific ligand. The ligand can be an agent that binds a cell receptor. Alternatively, the ligand can be an antibody that binds a cell receptor. The nucleic acid molecules of the invention can be complexed with the ligand by a covalent, or non-covalent link such as a bridging molecule (Curiel et al., Hum. Gene Ther. 3:147-154 (1992); Wu and Wu, J. Biol. Chem. 262:4429-4432 (1987).

Methods for Detecting Production of the Heterologous Gene Product

The present invention provides methods for detecting the production of the heterologous gene product. The methods of the invention comprise introducing the effector and reporter nucleic acid molecules of the invention into a cell (e.g., transfected cell) under conditions suitable for production of the heterologous gene product; and detection of the heterologous gene product. The detecting methods of the invention are performed using a cultured transfected cell, a cell transfected in a subject, or a donor cell implanted in a subject.

The heterologous gene product, which is produced by these transfected cells, is detected using non-invasive radionuclide and/or non-radionuclide techniques that permit detection of the location, magnitude and time variation of the heterologous gene product (P. Ray, et al., 2001 Semin. Nucl. Med. 31:312-320).

The detecting step includes non-invasive techniques such as positron emission tomography (e.g., PET) (S. Gambhir, et al., 1999 Proc. Natl. Acad. Sci. USA 96:2333-2338; J G Tjuvajev, et al., 1998 Cancer Res 58:4333-4341; S R Cherry, et al., 1997 IEEE Transactions on Nuclear Science 44:1161-1166; M E Phelps, 1991 Neurochemical Research 16:929-994; S R Cherry and S S Gambhir 2001 Inst. Lab. Anim. Res. J. 42:219-232), single photon emission computed tomography (J G. Tjuvajev, et al., 1996 Cancer Res. 45:4087-4095; K R Zinn, et al., 2000 J. Nucl. Med. 41:887-895), cooled charged coupled device (CCD) camera optical imaging (Honigman, et al., 2001 Mol. Ther. 4:239-249); magnetic resonance imaging (A H Louie, et al., 2000 Nat. Biotechnol. 18:321-325; R. Weissleder, et al., 2000 Nat. Med. 6:351-355), bioluminescent optical imaging (P R Contag, et al., 1998 Nat. Med. 4:245-247; A Honigman, et al., 2001 Mol. Ther. 4:239-249; J C Wu, et al., 2001 Mol. Ther. 4:297-306; M Iyer, et al., 2001 Proc. Natl. Acad. Sci. USA 98:14595-14600), and fluorescence optical imaging (M Yang, et al., 2001 Proc. Natl. Acad. Sci USA 98:2616-2621).

The type of non-invasive technique used to detect the heterologous gene product is selected based on the type of gene product produced. For example, bioluminescent optical imaging (P R Contag, et al., 1998 Nat. Med. 4:245-247; J C Wu, et al., 2001 Mol. Ther. 4:297-306) has been used to detect production of luciferase.

Alternatively, cooled charge-coupled device camera has been used to detect luciferase in whole animals (A Honigman, et al., 2001 Mol. Ther. 4:239-249; M Iyer, et al., 2001 Proc. Natl. Acad. Sci. USA 98:14595-14600).

In other cases, positron emission tomography or micro PET and radiolabeled tracers have been used to detect a thymidine kinase or a mutant version of thymidine kinase, HSV-sr39tk (S R Cherry, et al., 1997 IEEE Transactions on Nuclear Science 44:1161-1166; S. Gambhir, et al., 1999 Proc. Natl. Acad. Sci. USA 96:2333-2338; S S Gambhir, et al., 1998 J. Nucl. Med. 39:2003-2011; D C MacLaren, et al., 1999 Gene Ther. 6:785-79; M Iyer, et al., 2001 J. Nucl. Med. 42:96-105; S S Gambhir, et al., 2000 Proc. Natl. Acad. Sci. USA 97:2785-2790; S S Gambhir, et al., 1999 Journal of Nuclear Cardiology 6:219-233).

Positron emission tomography and radiolabeled spiperone ({(3-(2'[$^{18}$F]-fluorethyl)spiperone (FESP)}has also been used to detect dopamine type 2 receptor ($D_2R$) (D C MacLaren, et al., 1998 Journal of Nuclear Medicine 39:35P; D C MacLaren, et al., 1999 Gene Therapy 6:785-791).

In one case, production of thymidine kinase and dopamine type 2 receptor have been simultaneously detected using microPET (M. Iyer, et al., 2001 Journal of Nuclear Medicine 42:96-105).

Magnetic resonance spectroscopy has been used to detect production of the pro-drug enzyme cytosine deaminase (L D Stegman, et al., 1999 Proc. Natl. Acad. Sci. USA 96:9821-9826; U Habrerkorn, et al., 1996 Journal of Nuclear Medicine 37:87-94).

The production of somatostatin receptor subtype II (SSTr2) has been detected using radiolabeled octreotide (B E Rogers, et al., 2000 Quarterly Journal of Nuclear Medicine 44:208-223).

The following examples are intended to illustrate, but not limit, the scope of the invention.

EXAMPLE 1

The following example provides description of a two-step transcriptional amplification as a method for imaging reporter gene expression using weak promoters.

Assays for imaging reporter gene expression are very useful for visualizing molecular events in living animals. Noninvasive imaging of reporter gene expression by using radionuclide and non-radionuclide techniques allows the monitoring of the location, magnitude, and time variation of gene expression in living animals and, in some cases, humans. Applications of reporter genes include: (i) optimization of gene therapy vectors that contain a reporter gene, (ii) imaging cell trafficking by marking cells with a reporter gene ex vivo, and (iii) monitoring endogenous gene expression through the use of reporter genes coupled to endogenous promoters in transgenic models. All of these applications should benefit from repetitive, noninvasive monitoring of reporter gene expression.

Methods to image reporter gene expression in living animals include positron emission tomography (PET) (1, 2), single photon emission computed tomography (3, 4), magnetic resonance imaging (5, 6), bioluminescent optical imaging with firefly luciferase (fl) (7-9), and fluorescence optical imaging with green fluorescent protein (10). A detailed review of the different approaches for imaging reporter genes is reported elsewhere (11).

The cooled charge-coupled device (CCD) camera offers a convenient, cost-effective, and reproducible method to image fl expression in small living animals (7-9). Recently, real-time monitoring of fl reporter gene expression in various tissues has been evaluated in rodents by using a cooled CCD camera (8). In this article, the authors have demonstrated that injection of adenovirus, AdHIV/fl (the fl expression is driven by the HIV-long-terminal repeat promoter) results in fl expression in the region over the testis in male mice. Transgenic mice with the human bone γ-carboxyglutamate protein promoter driving fl led to gene expression in bones and teeth. The use of tissue-specific promoters in these limited applications was possible, but in many applications specific promoters may not lead to sufficient levels of fl expression. In other cases, enhancement of observable signal may benefit from amplification.

The advantage of PET over optical approaches is the ability to obtain tomographic and quantitative information with high sensitivity. With appropriate corrections for photon attenuation, scatter, and object size, concentrations of radiolabeled tracers can be reliably estimated (12). Furthermore, unlike optical methods, small animal imaging with microPET (13) directly translates to human studies with clinical PET scanners. We have previously developed methods to monitor adenoviral-mediated herpes simplex virus type 1 thymidine kinase (HSV1-tk) expression in vivo by using 18 F-labeled acycloguanosine analogs and microPET (1, 14). We have studied cell lines stably transfected ex vivo with various PET reporter genes and implanted in mice for imaging with microPET (15, 16). We also have validated the use of a mutant HSV1-sr39tk with enhanced imaging sensitivity (17). In our earlier approaches, the expression of the PET reporter gene was driven by relatively strong promoters [e.g., cytomegalovirus (CMV)] that achieve a constitutive, high level of transcription. In many therapeutic applications, targeted approaches to enhance safety and specificity are highly desirable. To this end, transcriptional targeting by using tissue-specific promoters to limit expression of potential cytotoxic transgenes to the tissue of interest has been frequently used (18-20). In applications where a relatively weak, cellular promoter drives the expression of a reporter gene, one has to contend with weaker transcriptional activity that, in turn, limits the ability to image reporter gene expression in vivo. In such cases, it is essential to find ways to enhance the transcriptional activity of such promoters. Several potential methods can be used to increase levels of reporter protein. These include (i) increased transcription by using chimeric promoters that retain tissue specificity (20, 21), (ii) enhancement at the posttranscriptional level (22-24), or (iii) transcriptional amplification approaches discussed next.

Figure 1:
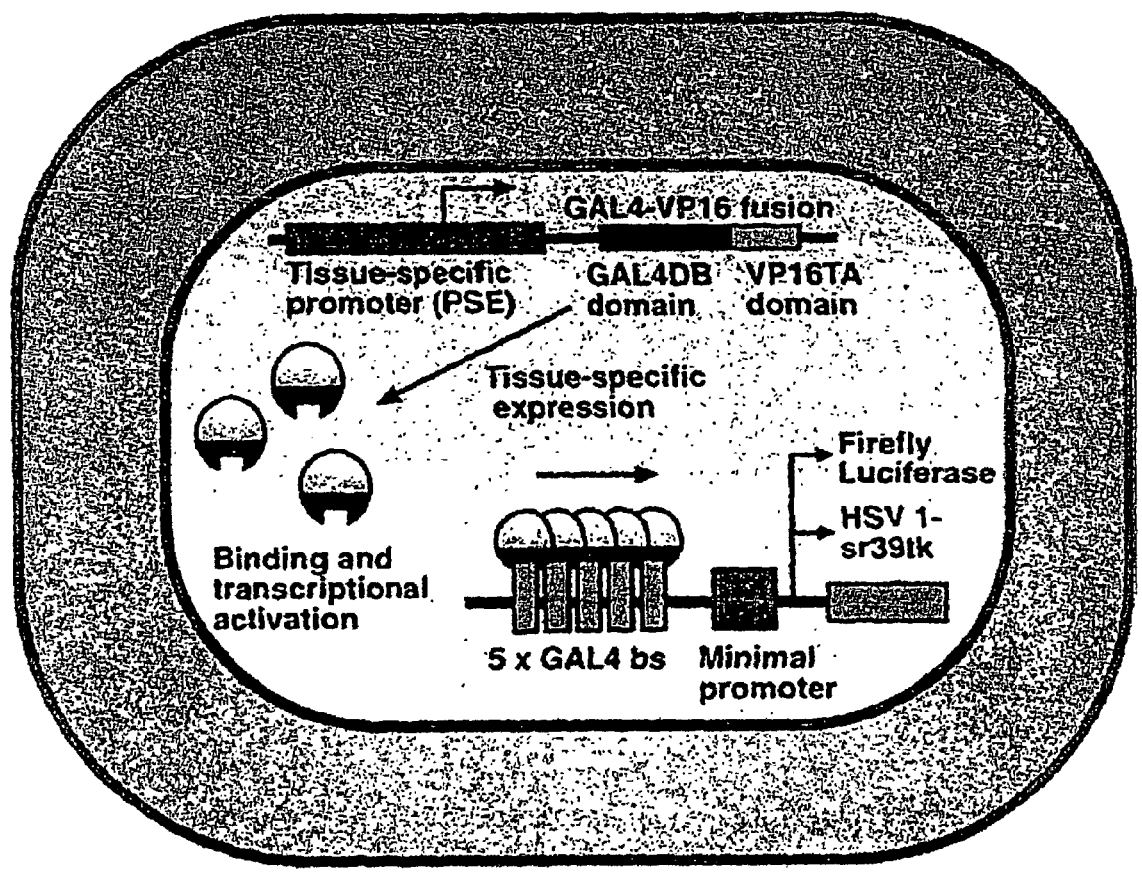
FIG. 1: Shows schematic diagram of the TSTA system. The first step involves the tissue-specific (e.g., PSE) expression of the GAL4-VP16 fusion protein. In the second step, GAL4-VP16, in turn, drives target gene expression under the control of GAL4 response elements in a minimal promoter [shown are five GAL4 binding sites (bs)]. Transcription of the reporter gene, either fl or HSV1-sr39tk, leads to reporter protein, which in turn leads to a detectable signal in the presence of the appropriate reporter probe. The use of the GAL4-VP16 fusion protein can potentially lead to amplified levels of the reporter protein (FL or HSV1-sr39TK) and therefore an increase in imaging signal.

One of the amplification approaches referred to as a two-step transcriptional amplification (activation) (TSTA) approach that can potentially be used to augment the transcriptional activity of cellular promoters uses the GAL4-VP16 fusion protein (25, 26) (FIG. 1). This approach is also referred to as a recombinant transcriptional activation approach (27). The yeast GAL4 gene expression system is one of the most widely studied eukaryotic transcriptional regulatory systems (28).

We are presently evaluating methods to non-invasively image reporter gene expression driven by cellular promoters. We chose to evaluate the prostate-specific antigen promoter (named PSE in this article) as it has been well characterized, determined to be tissue-specific, and is expressed after androgen administration in cell culture and in vivo (29). In this study, we chose to take advantage of the strong transactivating properties of the GAL4-VP16 fusion protein to achieve prostate-specific amplification by using the PSE promoter to drive expression of fl or HSV1-sr39tk in an LNCaP prostate cancer cell line. We also validated the system for monitoring reporter gene expression in living mice implanted with LNCaP cells transiently expressing fl by using a cooled CCD optical imaging system.

Materials and Methods

TSTA Experimental Strategy

The HSV1 VP16 immediate early transactivator contains a highly potent activation domain that, when fused to the GAL4 DNA binding domain, elicits a robust response on a GAL4-responsive promoter (referred to as a minimal promoter in this work) bearing multiple tandem copies of the 17 bp near consensus DNA binding site (25, 26). The VP16 activation domain amino acids 411-490 can be subdivided further into N- and C-terminal subdomains. The C-terminal domain is sometimes toxic to cells and elicits a transcriptional inhibitory phenomenon called squelching (30). GAL4-VP16 is a fusion of the N-terminal portion of the VP16 activation domain from amino acids 413-454 and the GAL4 DNA binding domain amino acids 1-147. It is a potent activator that squelches less effectively than the intact activation domain.

Chemicals

Methyltrienolone (R1881) was purchased from NEN. Tfx-50 transfection reagent and luciferase assay kit were purchased from Promega. D-Luciferin for use with in vivo fl imaging was obtained from Xenogen (Alameda, Calif.). [8-$^3$H]Penciclovir (17.6 Ci/mmol) was purchased from Moravek Biochemicals (Brea, Calif.). Testosterone pellets (0.007 mg, 6-h release) were obtained from Innovative Research of America. Matrigel was purchased from BD Biosciences (Bedford, Mass.). Cell Culture. The human prostate cancer cells, LNCaP (provided by C. Sawyers, University of California, Los Angeles), were grown in RPMI 1640 supplemented with 10% FBS and 1% penicillin/streptomycin solution. The C6 rat glioma cells were kindly provided by Margaret Black (Washington State University, Pullman) and were grown in deficient DMEM, supplemented with 5% FBS and 1% penicillin/streptomycin/L-glutamine. HeLa cells (American Type Culture Collection) were grown in DMEM with 10% FBS and 1% penicillin/streptomycin.

Construction of Plasmids/Vectors

The parental construct, PSE, derived from plasmid PSAR2.4k-PCPSA-P-Lux (29), consisted of a 2.4-kb enhancer fragment (−5322 to −2855) and the proximal promoter region from −541 to +12, upstream of an fl reporter gene. PSE was chosen to be the baseline construct because the 2.4-kb enhancer fragment generates the maximal transcriptional and androgen-responsive activity, comparable to the entire 6-kb regulatory region of the prostate-specific antigen gene (20, 31). The construction of PSE plasmid has been described (20). To construct pBS-PSEGAL4VP16, the HindIII to XbaI GAL4VP16 fragment was excised from pSP72-SV40-GAL4VP16 and inserted into PSE plasmid. The minimal promoter, G5E4TATA (G5E4T) contained templates bearing five 17-bp GAL4 binding sites positioned 23 bases from the TATA box of the E4 gene of adenovirus (32). TheG5E4T-fl construct was made by PCR amplification of the relevant GAL4 sites and E4TATA from the pGEM3 G5E4T vector by using an upstream primer with a SacI site attached (cccgagctcatttaggtgacactatag; SEQ ID NO:7) and a downstream primer with a XhoI site attached (cccctcgagacac-cactcgacacggcacc; SEQ ID NO:8). The PCR fragments were digested with SacI and XhoI and cloned into the pGL3 basic vector. TheG5E4T-sr39tk plasmid was constructed by excising the G5E4T fragment from pSP72-G5E4T-CAT and cloning into pcDNA3.1 vector. The G5E4T sequence was PCR-amplified by using primer pair 5'-gactagatctacagcttgcatgcctgcag-3' (SEQ ID NO:9) and 5'-gactgctagctcgacacg-gcacca-3' (SEQ ID NO:10) and cloned into the BglII/NheI sites upstream of sr39tk in the main vector, pcDNA3.1. For the sake of convenience, PSE-GAL4-VP16 is abbreviated as PG, and the re-porter plasmid GSE4T-fl is abbreviated as L5. The reporter template GSE4T-sr39tk is referred to as T5. The constructs PSE-fl, PSE-HSV1-sr39tk, and SV40-GAL4-VP16 are abbreviated as PL, PT, and SG, respectively.

Cell Transfections and Enzyme Assays

On day 1, LNCaP cells were plated in 6-well plates in RPMI 1640 containing charcoal-stripped FBS. Transient transfections were performed 24 h later by using Tfx-50 transfection reagent (Promega). Each transfection mix consisted of 0.5 micro grams of the effector and reporter plasmids or reporter plasmid alone. One hour after transfection, methyltrienolone (R1881) in ethanol was added to the medium at a concentration of 1 nM/well, and the cells were incubated for 48 h. For FL activities (fl refers to the gene and FL to the enzyme), the cells were harvested and assayed for FL activity by using the dual-reporter luciferase assay system (Promega) and a luminometer (Lumat 9507, Berthold, Germany) with an integration time of 10 s. LNCaP cells were also transfected by using CMV-fl plasmid (as a positive control). For the TK assay, the cells were harvested 48 h after transfection and assayed for HSV1-sr39TK enzyme activity (tk refers to the gene and TK to the enzyme) as described (14). For androgen inducibility experiments, LNCaP cells were transiently transfected with PG and T5 constructs in the presence of different concentrations of androgen. After 48 h, the cells were assayed for HSV1-sr39TK activity.

In Vivo Optical Imaging of Fl Expression Using a Cooled CCD Camera

LNCaP cells were transiently transfected with the effector and reporter plasmids or reporter plasmid alone as described earlier. The cells were harvested 48 h after transfection and resuspended in PBS. An aliquot of $1\times10^6$ cells was mixed with Matrigel and injected i.p. in female nude mice. Five minutes after injection of the cells, the mice were anesthetized (ketaminexylazine, 4:1), and 200 μl of D-luciferin (15 mg/ml) was injected (i.p.) 10 min before imaging. After the first scan, the mice were s.c. implanted with 0.007-mg sustained release testosterone pellets and imaged again after 24 h and 48 h. A total of five mice were used for the experiment, and one mouse in each group did not receive the androgen pellet.

The mice were imaged by using a cooled CCD camera (Xenogen IVIS, Alameda, Calif.) with an acquisition time of 5 min. The animals were placed supine in a light-tight chamber, and a gray scale reference image was obtained under low-level illumination. Photons emitted from cells implanted in the mice were collected and integrated for a period of 5 min. Images were obtained by using LIVING IMAGE software (Xenogen) and IGOR IMAGE analysis software (WaveMetrics, Lake Oswego, Oreg.). For quantitation of measured light, regions of interest were drawn over the peritoneal region, and maximum relative light units (RLU) per min were obtained as validated (9).

Results

Figure 2:
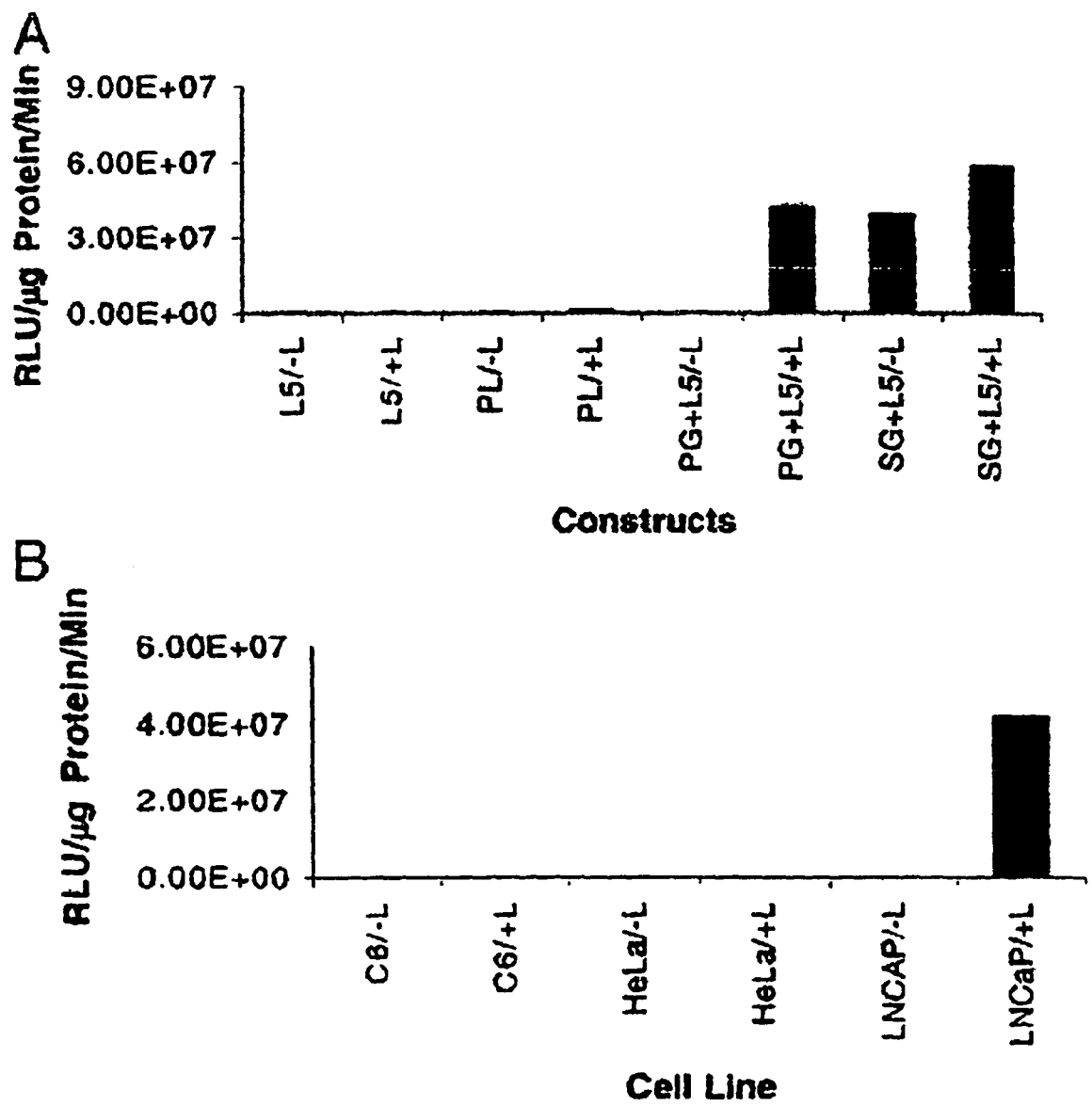
FIG. 2: (A) TSTA system-mediated amplification of fl expression. LNCaP cells were transiently transfected in the absence (−L) and presence (+L) of androgen with (i) reporter construct alone (L5), (ii) PL (one-step), (iii) PG/L5 (two-step), and (iv) SG/L5 (control) constructs. The cells were harvested 48 h after transfection and assayed for FL activity. The error bars represent SEM for triplicate measurements. (B) Cell-type specificity of the TSTA system (fl). C6, HeLa, and LNCaP cells were transiently transfected in the absence (−L) and presence (+L) of androgen with effector construct, PG, and reporter construct, L5. The cells were harvested 48 h after transfection and assayed for FL activity. The error bars represent SEM for triplicate measurements.

TSTA System Mediates Prostate-Specific Amplification of Fl Expression in LNCaP Cells and Demonstrates Cell-Type Specificity In transient transfection into LNCaP cells, when GAL4-VP16 was placed under the control of the PSE promoter, it activated poorly in the absence of androgen, but the response in the presence of androgen was significantly higher than that observed by using the reporter template alone (L5) (FIG. 2A). The maximal level of fl expression is observed by using five binding sites upstream of the adenovirus E4 promoter (L5) on the reporter template vs. one or two binding sites. The TSTA system-driven amplification of fl expression in the presence of androgen is similar to the SG-activated expression of a GAL4-responsive fl reporter in the absence and presence of androgen stimulation (−L/+L, FIG. 2A). These results validate the concept that the tissue-specific, ligand-responsive PSE promoter could be substituted for a strong viral one to elicit similar levels of GAL4-VP16 functional activity. When CMV-fl was compared with the TSTA system, the FL activity by using the TSTA system was observed to be 2- to 3-fold lower than that driven by the CMV promoter. A comparison of fl expression by using both the one-step and the TSTA systems reveals a ~50-fold gain (P<0.01) with the TSTA system when compared with the one-step system (FIG. 2A). To determine whether the TSTA system-mediated amplification is restricted to prostate cells alone, we studied the levels of fl expression in two non-prostate cell lines, C6 and HeLa. Firefly luciferase reporter gene expression after androgen administration is minimal in both the cell lines tested, indicating the tissue-specific nature of the PSE promoter (FIG. 2B). The results indicate a strong stimulatory effect on transcription exerted by the GAL4-VP16 fusion protein while maintaining tissue specificity.

Figure 3:
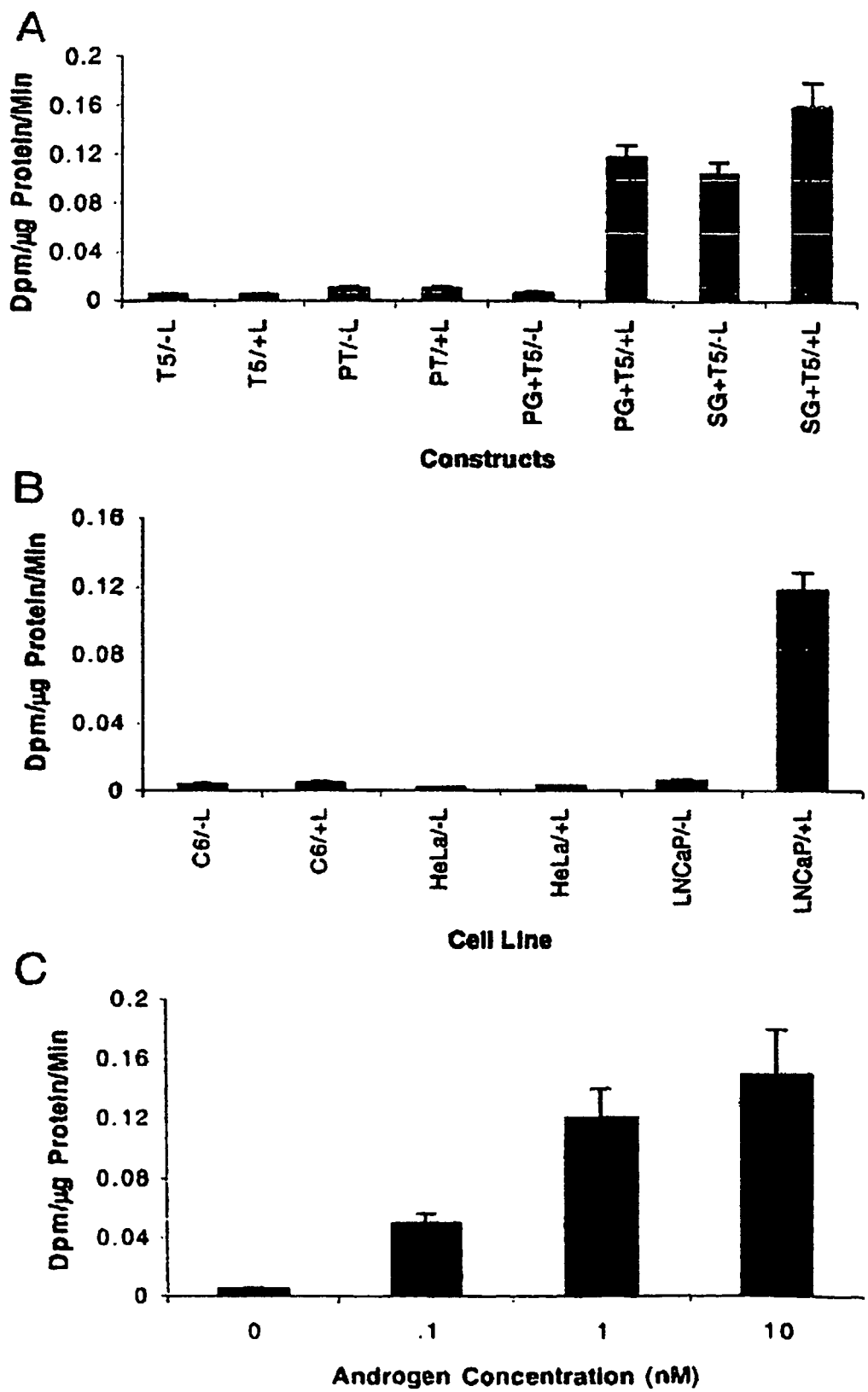
FIG. 3: (A) TSTA system-mediated amplification of HSV1-sr39tk expression. LNCaP cells were transiently transfected in the absence (−L) and presence (+L) of androgen with (i) reporter construct alone (T5), (ii) PT (one-step), (iii) PG/T5 (two-step), and (iv) SG/T5 (control) constructs. The cells were harvested 48 h after transfection and assayed for HSV1-sr39TK activity. The error bars represent SEM for triplicate measurements. (B) Cell-type specificity of the TSTA system (HSV1-sr39tk). C6, HeLa, and LNCaP cells were transiently transfected in the absence (−L) and presence (+L) of androgen with the effector construct, PG, and reporter construct, T5. The cells were harvested 48 h after transfection and assayed for HSV1-sr39TK activity. The error bars represent SEM for triplicate measurements. (C) Effect of androgen concentration on HSV1-sr39tk expression. LNCaP cells were transiently transfected in the absence (−L) and presence (+L) of androgen with PG and T5. The androgen concentration varied from 0.1 to 10 nM. The cells were harvested 48 h after transfection and assayed for HSV1-sr39TK activity. The error bars represent SEM for triplicate measurements.

TSTA System Mediates Prostate-Specific Amplification of HSV1-sr39tk Expression in LNCaP Cells, Demonstrates Cell-Type Specificity, and Expression Increases with Androgen Dose To test the HSV1-sr39tk reporter system, we used the T5 reporter construct with PG for transient transfections in LNCaP cells. The results with HSV1-sr39tk were similar to that observed by using fl. After androgen treatment, HSV1-sr39tk expression mediated by the TSTA system is significantly greater (~24-fold) (P<0.01) when compared with the expression in cells transfected with the reporter template only (T5) (FIG. 3A). Further, the TSTA system-mediated amplification of HSV1-sr39tk expression levels are ~12-fold greater than those driven by PT alone (one-step) (FIG. 3A) in the presence of androgen. Although the gain in amplification for HSV1-sr39tk is lower than fl, it is nevertheless highly significant (P<0.01). To determine whether the TSTA system-mediated reporter gene amplification is cell-type specific, we studied the levels of HSV1-sr39tk expression in two non-prostate cell lines, C6 and HeLa. HSV1-sr39tk expression level after androgen administration is minimal in both the cell lines tested, demonstrating that the TSTA system-mediated activation from the PSE promoter is highly cell-type specific (FIG. 3B). We further evaluated the effects of androgen response in LNCaP cells by using HSV1-sr39tk. In the absence of androgen, HSV1-sr39tk expression levels are similar to the values obtained by using the reporter template alone (minimal). A concentration-dependent increase in HSV1-sr39TK activity is observed with increasing androgen concentration, indicating that androgen treatment greatly enhances the TSTA system-mediated activation from the PSE promoter (FIG. 3C).

TSTA System Mediates Prostate-Specific Amplification of Fl Expression in Vivo

Figure 5:
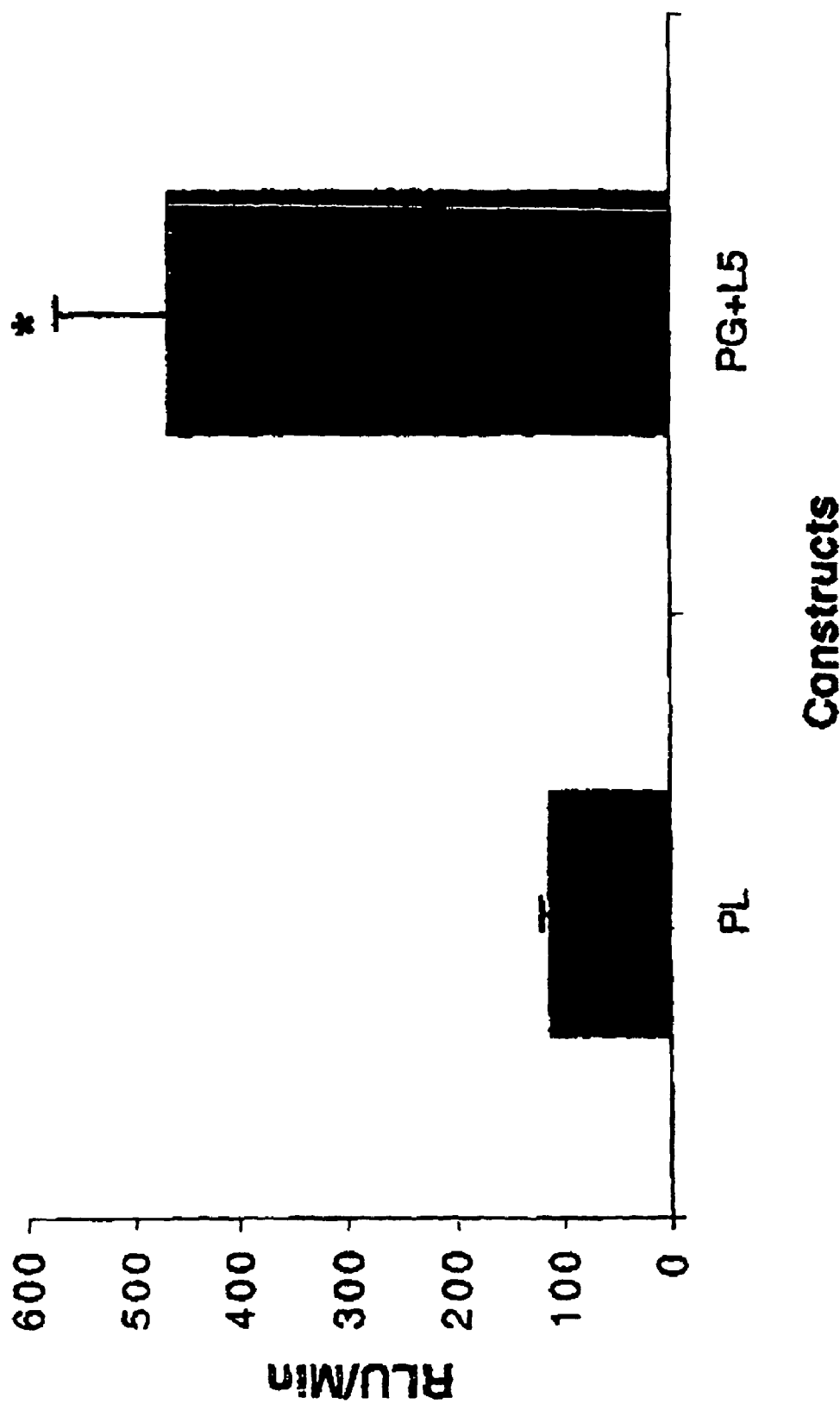
FIG. 5: Shows comparison of transcriptional activation in vivo using the TSTA system versus the one-step system. Shown are results of mean±SEM RLU/min in five nude mice in each group. The first group had LNCaP cells transiently transfected with PL (one-step), and the second group had LNCaP cells transiently transfected with PG and L5 vectors (two-step). The cells were implanted i.p. in the mice. The mice were then implanted with androgen pellets and imaged again after 24 and 48 h. There is a significant difference (*P<0.05) between the two groups.

To further test the utility of the TSTA system in vivo, we injected transiently transfected LNCaP cells (transfected with PG and L5 plasmids, L5 plasmid alone, and PL plasmid) i.p. in female nude mice. Optical CCD imaging of all mice 15 min after injection of transfected LNCaP cells reveals basal levels of fl expression (RLU/min<100). The mice were scanned again 24 h and 48 h after the implantation of androgen pellets. The results of the 24-h imaging were similar to those observed at 48 h. Forty-eight hours after pellet implantation, the control mice (L5 plasmid alone) again show minimal levels of fl expression (RLU/min<100) (FIG. 4A). In the mice representing the TSTA system, fl expression is observed to be much higher (RLU/min ~500) when compared with the control and the one-step system (RLU/min<100) (FIG. 4B). Mice representing the TSTA system that did not receive androgen pellets displayed basal levels of fl expression at 48 h (FIG. 4A). This is indicative of the specificity of androgen in activating the PSE promoter in vivo. The results were found to be reproducible between experimental groups. The induction of transcriptional activation upon androgen administration across five mice in each of two groups is illustrated in FIG. 5. The TSTA system-mediated amplification in fl expression shows a ~5-fold gain when compared with the one-step system (P<0.05). These results demonstrate the ability to image in vivo the expression of fl driven by a weak, tissue-specific promoter in a mammalian system by using the TSTA approach. The TSTA system mediates tissue-specific expression of fl in a mammalian system.

Discussion

We have previously demonstrated that adenoviral-mediated HSV1-tk expression can be non-invasively imaged by using acycloguanosine analogs and microPET (1, 14). We have been evaluating methods to non-invasively image reporter gene expression driven by weak promoters such as the PSE promoter. Several of the known weak promoters also demonstrate tissue specificity (33). In the present study, we describe a strategy to overcome the weak transcriptional activity of the PSE promoter for use in tissue-specific imaging applications. We used a two-step transcriptional amplification (activation) approach where, in the presence of androgen, a relatively weak PSE promoter activates a GAL4-VP16 fusion protein, which, in turn, drives reporter gene expression under the control of GAL4 response elements in a minimal promoter.

In the present study, we observed the TSTA system-mediated amplification of fl expression to be 50-fold higher than the one-step system in LNCaP cells in the presence of androgen. We have also demonstrated the TSTA system to be highly tissue-specific. Similar results were obtained when we changed the reporter gene from fl to the HSV1-sr39tk, although the fold gain in HSV1-sr39tk expression levels was lower than f. The differences in degree of amplification between fl and HSV1-sr39tk may be attributed to different levels of mRNA amplification and differences in the two enzymes to act on their corresponding substrates. The TSTA system, however, does lead to a statistically significant increase in amplification for both the fl and HSV1-sr39tk in a tissue-specific manner.

The TSTA system-mediated activation of the PSE promoter depends highly on the levels of androgen as evidenced by the dose-dependent increase in HSV1-sr39tk expression. The system seems to function in a continuous manner (as opposed to a binary on/off fashion). There also does not seem to be a threshold effect. As more androgen becomes available, levels of GAL4-VP16 fusion protein increase, thereby increasing the ability to bind to GAL4 binding sites on the reporter template, resulting in greater levels of fl and therefore greater imaging signal. Finally, although we did not see full saturation, higher levels of GAL4-VP16 have previously been reported to inhibit transcription (referred to as squelching) (30, 34, 35).

We further tested the utility of the GAL4-VP16 induction system in vivo to non-invasively image tissue-specific amplification of reporter gene expression. To validate this system in vivo, several issues needed consideration. These included the development of (i) LNCaP and non-prostate cell lines stably expressing both the effector and reporter constructs and (ii) construction of adenoviral vectors containing the two components of the TSTA system. Both of these approaches require considerable time before they can be tested in vivo. To expedite the process of in vivo evaluation, we injected transiently transfected LNCaP cells (using fl as the reporter gene in the absence of androgen) in female nude mice. The mice were imaged by using a sensitive cooled CCD camera before and after implantation of testosterone pellets. All mice displayed basal levels of fl expression in the absence of androgen. Twenty-four to 48 h after androgen administration, the mice representing the TSTA system showed a significantly greater level of fl expression when compared with the control and one-step mice. We observed similar high levels of induction across several mice with a ~5-fold gain for the TSTA system over the one-step system. In fact, in the absence of the TSTA system, the fl expression was close to background, and there-fore cells could not be imaged. These initial results are aimed at non-invasively imaging reporter gene expression in a mammalian system by augmenting the transcriptional activity of a weak promoter by using the TSTA system. The level of TSTA amplification in vivo depends on the pharmacokinetics of androgen availability to cells, and it is possible that the in vivo signal can potentially be higher than observed based on the imaging time after androgen induction. Future studies will need to address the exact correlation between levels of androgen in blood and the levels of induction in vivo.

Fang et al. (36) have examined the functionality of the GAL4-VP16 transactivator to evaluate phosphoglycerate kinase (PGK) promoter activities in vivo by using adenoviral vectors. Nettelbeck et al. (33) have used recombinant transcriptional activation to establish a positive feedback loop initiated by transcriptional activation from a von Willebrand factor promoter. The GAL4-VP16 fusion protein was used to achieve target gene amplification from a prostate-specific antigen promoter (37). Both of these approaches were targeted at increasing the expression of transgenes for use in cancer gene therapy protocols. Further, the GAL4-VP16 responsive TSTA system has been recently used in conjunction with zebrafish tissue-specific promoters with green fluorescent protein reporters (35). In this study, the GAL4-VP16 was injected transiently into fish embryos that developed with minimal toxicity, permitting imaging of specific tissue in adult fish.

It is important that any reporter gene-imaging approach not significantly perturb the cells/animal models being studied. There is potential for the GAL4-VP16 system to be toxic to cells (35, 38). In zebrafish, low levels of injected GAL4-VP16 were apparently not deleterious to development, whereas higher levels were (35). However, in the current study, only transiently transfected cells were used, so toxicity is not practical to detect. Future studies with stable cell lines, gene therapy vectors, and transgenic animal models will require strict characterization of potential toxicities of the TSTA approach. It may be the case that levels of GAL4-VP16 will need to be modulated to strike a balance between amplification and any potential toxicity.

The approaches validated in the current study should lead to better vectors for imaging gene therapy, study of tumor growth and regression following pharmacological intervention, as well as development of transgenic models with enhanced reporter gene expression. Applications and extensions of the TSTA approach include: (i) imaging PET reporter genes (e.g., HSV1-sr39tk) and other in vivo reporter genes; (ii) enhancing reporter gene expression by modifying the regulatory components of the PSE promoter and building a single vector that incorporates both components of the TSTA system; (iii) replacement of the PSE promoter with other weak promoters, thereby enabling one to target site-specific genes in vivo; (iv) the study of multiple endogenous genes by driving expression of GAL-4-A from one promoter and B-VP-16 from a separate promoter where genes A and B can be chosen so that their respective proteins interact (this procedure should allow the expression of a reporter gene if and only if both promoters are activated); (v) imaging of protein-protein interactions in vivo using inducible two-hybrid mammalian expression systems; and (vi) amplification of both therapeutic and reporter genes by modifying the reporter template.

EXAMPLE 2

The following provides descriptions of molecular engineering of a two-step transcription amplification (TSTA) system for transgene delivery in prostate cancer.

The concept of tissue specific gene therapy and imaging has been hampered by lack of specificity, borderline efficacy and inadequate delivery methods. Improvements in all three areas must occur to translate the promise of gene therapy into meaningful clinical applications [39]. In prostate cancer, the most common strategy to control specificity of transgene expression is to employ the regulatory region of a prostate gene product such as the prostate specific antigen (PSA) (reviewed in [40]). In order to achieve optimal therapeutic efficacy, one goal of the field has been to achieve prostate specific promoter activities similar in magnitude to those of ubiquitously active viral enhancers such as Simian Virus 40 (SV40) and Cytomegalovirus (CMV) [41]. A logical and systematic approach to improve the PSA regulatory regions for combating prostate cancer involves several steps. Novel promoter constructs are engineered and their activity in cell-based transfection studies is evaluated. The most promising constructs are cloned into recombinant adenoviral vectors or other efficient in vivo gene delivery vehicles) and tested in pre-clinical models [42, 43].

Our labs have recently initiated such studies for prostate cancer. We initially reported a strategy to augment the specificity and activity of the PSA enhancer by exploiting the synergistic nature of androgen receptor (AR) action. The key regulatory elements of the PSA enhancer include a proximal promoter (−541 to +12) comprising two binding sites for the androgen receptor (AREI and II) and a distal enhancer, which contains a 390-bp androgen-responsive core region [44, 45]. The core region contains a cluster of closely spaced androgen response elements (AREs) and sites for other transcription factors [46, 44, 47, 45, 48, 49]. The enhancer is active in both androgen-dependant (AD) and androgen independent (AI) cancer cells [49]. AR binds cooperatively to the enhancer and mediates synergistic transcription [48]. Other factors within and outside of the enhancer contribute to prostate specificity [50-52, 49]. We found that molecular engineering of the PSA enhancer by duplication of the core or fusion to multiple AREs generated 20-fold higher activities than the parental constructs yet retained androgen inducibility and tissue specificity [53]]. Furthermore, we showed that the enhanced activity, inducibility and specificity of the chimeric constructs were maintained in an adenoviral vector expressing firefly luciferase (FL) [53].

The PSA enhancer contains a natural androgen inducible subregion centered 4.2-kb upstream from the transcription start site. We reasoned that by combining this region with an artificial enhancer, or by duplicating the region, we could create a chimera with increased activity while retaining prostate specificity. To create the artificial enhancer, we multimerized the ARE I site found in the proximal PSA promoter region. We hypothesized that this ARE4 should function synergistically with the enhancer core when transposed directly adjacent to it.

The parental construct, PSE, consisted of the 2.4-kb enhancer fragment (−5322 to −2855) and the proximal promoter region from −541 to 12, upstream of a luciferase gene. PSE was chosen to serve as the baseline construct because the 2.4-kb enhancer fragment generates the maximal transcriptional and androgen responsive activity, comparable to the entire 6-kb regulatory region of the PSA gene. The androgen inducible core region bearing four natural AREs is defined by two flanking restriction sites, BstEII and NcoI (−4326 to −3935). We constructed the following reporter gene variants: one lacking the core enhancer (PSA-ARE0); one containing ARE4 in place of the core (PSE-ARE1); one in which ARE4 was inserted immediately downstream of the enhancer core at −3935 (PSE+A); and finally, a construct bearing a duplicated core region, where an additional copy of the core was placed upstream at −4326 (PSE+C). We also postulated that removing the sequence between the enhancer and promoter would increase activity further. This set of constructs is termed the PSE-B series.

The native PSA enhancer and promoter confer prostate-specific expression when inserted into adenovirus vectors capable of efficient in vivo gene delivery, although the transcriptional activity is low. By exploiting properties of the natural PSA control regions, the activity and specificity of the prostate-specific PSA enhancer for gene therapy and imaging applications has been improved. Previous studies have established that androgen receptor (AR) molecules bind cooperatively to AREs in the PSA enhancer core (−4326 to −3935)

and act synergistically with AR bound to the proximal promoter to regulate transcriptional output. To exploit the synergistic nature of AR action we generated chimeric enhancer constructs by (1) insertion of four tandem copies of the proximal ARBI element; (2) duplication of enhancer core; or (3) removal of intervening sequences (−3744 to −2855) between the enhancer and promoter. By comparing to the baseline construct, PSE, containing the PSA enhancer (−5322 to −2855) fused to the proximal promoter (−541 to +12), the three most efficacious chimeric constructs, PSE-BA (insertion of ARE4), PSE-BC (duplication of core) and PSE-BAC (insertion of core and ARE4), are 7.3-, 18.9-, and 9.4-fold higher, respectively. These chimeric PSA enhancer constructs are highly androgen inducible and retain a high degree of tissue discriminatory capability. Initial biochemical studies reveal that the augmented activity of the chimeric constructs in vivo correlates with their ability to recruit AR and critical co-activators in vitro. The enhanced activity, inducibility and specificity of the chimeric constructs are retained in an adenoviral vector. (see, Gene Therapy (2001) 8, 1416-1426).

The two-step transcriptional activation system (TSTA) is another strategy for augmenting PSA transgene expression [54]. In the TSTA system, a potent transcriptional activator, which is driven by a cell-specific promoter, acts on a second expression plasmid, which encodes the reporter/therapeutic protein. This two-step approach results in cell-specific amplification of expression. The activator is often GAL4-VP16, a fusion protein comprising the DNA binding domain from the yeast transcription activator GAL4 and the activation domain from the Herpes Simplex Virus 1 activator VP16. GAL4-VP16 assumes a unique specificity and potency that does not naturally exist in the mammalian cells [55, 56]. The cell specific TSTA approach is based on the original "enhancer trap" methodology employed in Drosophila to study developmental regulation of gene expression [57, 58].

In one application of the TSTA approach to prostate cancer, Segawa and colleagues attached the 5.3-kb intact PSA regulatory region to GAL4-VP16 and demonstrated androgen-dependant activation of a FL reporter gene bearing upstream GAL4 binding\sites and ablation of cancer cells using a TSTA-driven toxic gene [59]. Our groups employed a similar TSTA expression approach but coupled it to imaging of prostate cancer in living mice. Prostate cancer cells injected into live mice were visualized using a cooled Charge Coupled Device (CCD) optical imaging camera by using a streamlined 2.4-kb PSA enhancer-promoter attached to a FL reporter, [60]. In both cases, the TSTA system maintained androgen responsiveness, yet substantially amplified the signal versus the reporters driven directly by the PSA regulatory region.

In the current study, we sought to optimize the TSTA system for molecular imaging with eventual applications to therapy. Noninvasive molecular imaging with reporter genes can be used for imaging tumors and metastases, to monitor the therapeutic efficacy of drugs, cell trafficking, gene delivery and expression, as well as the study of various transgenic models [61]. Our objective was to augment the promoter activity and generate a titratable system. Augmented activity will be required to transition the FL-based CCD approach to clinically relevant methodologies such as positron emission tomography (PET). Titratability of expression, on the other hand, is an important safeguard in gene therapy. Often, the untoward side effects of introducing and expressing exogenous genes in animals and patients can not be fully predicted by in vitro or tissue culture experimentation. In addition, titratability is necessary because tumors and cell lines display varying AR responses [62, 63]. For example, biphasic effects of androgen on AR activity have been observed and excess levels of androgen inhibit PSA production and cell growth [64]. A study on the LNCaP subline also suggests that chronic androgen treatment induces reversible cell adaptation to the stimulant [65]. An additional complexity is that excess GAL4-VP16 exhibits a transcriptional inhibitory effect called squelching [66], which can generate cell toxicity and might confound TSTA under certain conditions (see, for example, [67]).

The concept of adjusting transgene expression by controlling the activator and promoter potency is detailed in older studies by one of us on GAL4-derived activators [56]. In a subsequent study, a wide range of activities was generated by exploiting the synergistic behavior observed by varying the number of activation domains on the GAL4-derived activator and GAL4 binding sites on the reporter plasmid [68]. Here we combine the modified GAL4 system with natural and chimeric PSA enhancers to create a highly active, robust expression system for prostate cancer gene imaging and therapy. We demonstrate the cell specificity, efficacy and utility of this system by imaging living mice using cooled CCD optical technology.

Results

The Chimeric TSTA System

Figures 1, 6:
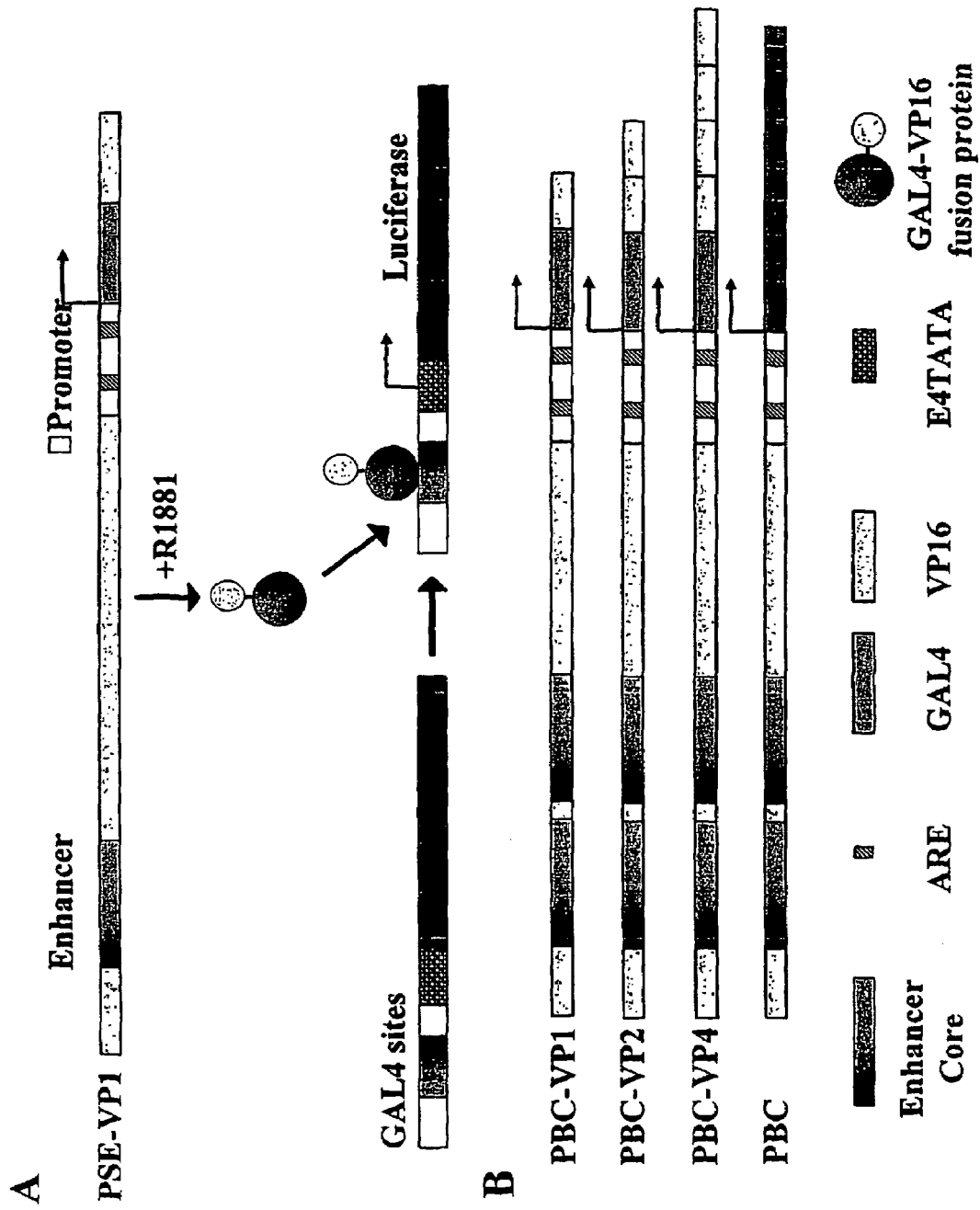
FIG. 6: Components of the Chimeric TSTA System. This figure illustrates the theory and design of the TSTA system. (A) Depiction of the two-step transcriptional activation process. In the first step, GAL4-VP16 derivatives (oval circles) are expressed in prostate cancer cells in the presence of androgen (R1881), which activates the PSA enhancer, PSE. In the second step, GAL4-VP16 binds to a GAL4-responsive promoter, and activates expression of luciferase. (B) This panel illustrates the effector plasmids used in our analysis. We describe the detailed composition in Results and in Materials and Methods. The abbreviations denote the components: GAL4: GAL4 DNA Binding Domain. VP16 AD: VP16 activation domain. Enhancer refers to the 390-bp core region bearing multiple AREs [10]; AREI and II are proximal AREs found in the promoter described by Trapman and colleagues [44]; the GAL4-VP1 to -VP4 derivatives are as described [68]. E4TATA contains the adenovirus E4 minimal promoter from −38 to +38 relative to the start site. (C) The FL reporters used in the analysis (described in Results). (D) The single construct comprises the G5-L plasmid with the PBC-VP2 fragment inserted into the NotI site.
Figures 2, 6:
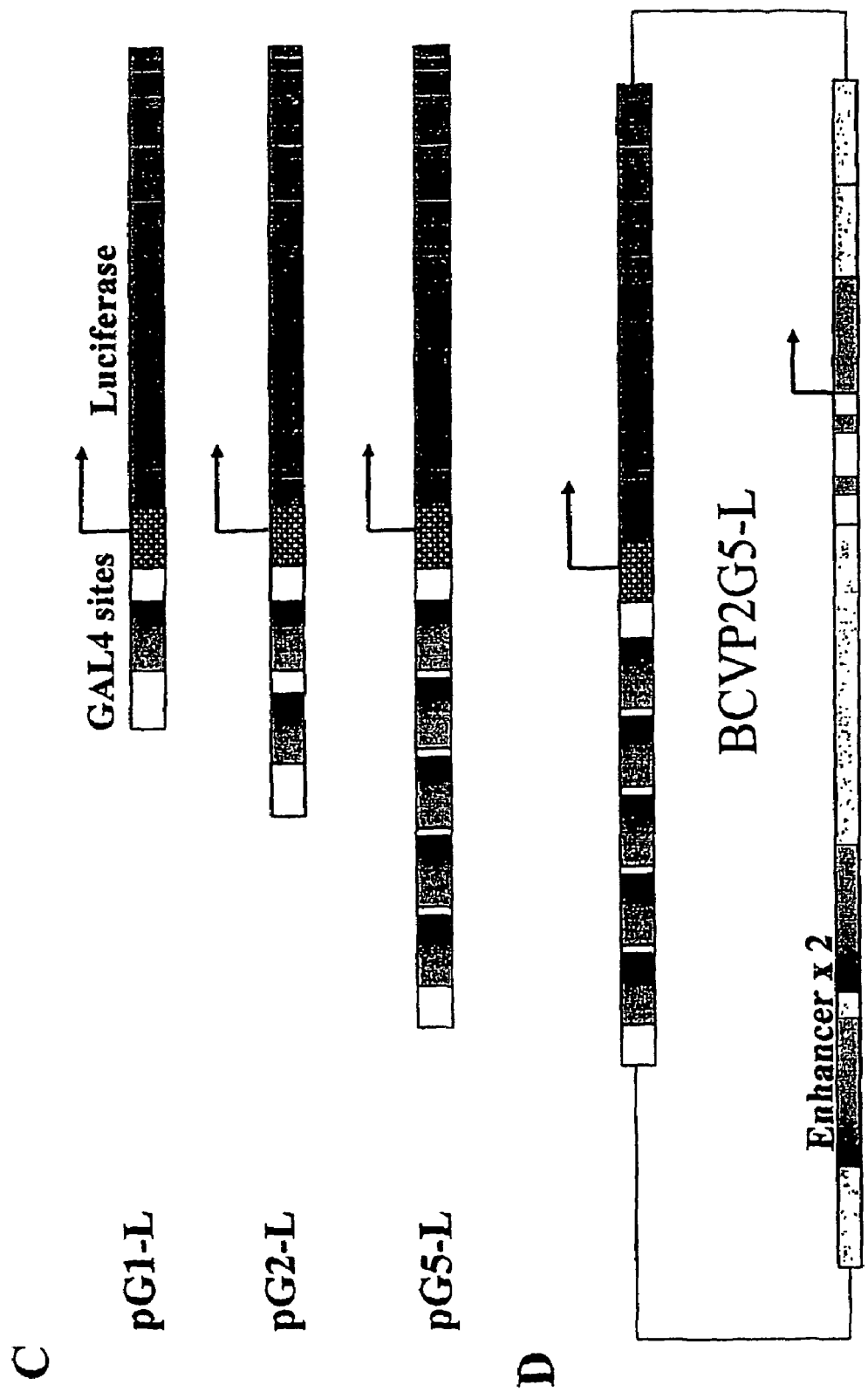

We outline the TSTA rationale in FIG. 6A. There are four primary variables in our system: i. The potency of the prostate specific promoter driving GAL4-VP16 (the effector) (FIG. 6B); ii. the number of GAL4 binding sites proximal to the FL reporter gene (FIG. 6C); iii. the potency of the GAL4-VP16 derivative (FIG. 6B); and iv. The presence of the effector and reporter genes on the same plasmid (FIG. 6D). Each variable offers a unique opportunity to modulate gene expression.

We employed two variants of the tissue specific PSA promoter (FIG. 6B). The first is PSE, which contains a 2.4 kb fragment (−5824 to −2855), encompassing the 390 bp core PSA enhancer core region (−4326 to −3935), linked to the proximal PSA promoter (−541 to +12). The second, PSE-BC ([53], abbreviated as PBC here), contains the PSA enhancer with a duplicated 390-bp core but a deletion of an 890 bp intervening sequence between the enhancer and promoter (−3743 to −2855). These modifications augmented androgen-responsive expression 20-fold in cell culture [53].

The reporter templates contain the FL gene under the control of 1, 2 or 5 copies of the 17 bp GAL4 binding sites positioned 23 bp upstream of a minimal promoter containing the adenovirus E4 gene TATA box (FIG. 6C) [68]. The resulting plasmids are termed G1-L, G2-L and G5-L. We used PSE and PBC to express recombinant GAL4-VP16 variants to generate a series of effector plasmids that display a gradient of activities (FIG. 6B). PSE expresses the 147 amino acid GAL4 DNA binding domain (DBD) bearing a single copy of the 42 amino acid VP16 activation subdomain (amino acids 413-454), PSE-VP1 [68]. We engineered PBC to express GAL4 DBD fusion proteins containing 1, 2 or 4 copies of the VP16 subdomain. We abbreviated the resultant plasmids as PSE-VP1, PBC-VP1, PBC-VP2 and PBC-VP4 and cloned the optimal combination of PBC-VP2 and G5-L into a single plasmid termed PBCVP2G5-L.

We expressed the parental plasmids GAL4-VP1, -VP2 and -VP4 from the SV40 enhancer as positive controls to provide a benchmark for comparison. As an additional benchmark, we used a FL construct driven by the CMV enhancer termed CMV-L. We systematically evaluated the TSTA constructs by co-transfection assays into the androgen-responsive prostate cancer cell line, LNCaP, in the presence of 10 nM R1881. We normalized each experiment using either CMV-L or the SV40 constructs and graphed representative individual experiments. Subsequently, we tested several cell lines to evaluate cell specificity. For ease of comparison with the TSTA system, we will refer to PSE or PBC directly driving FL expression as the one-step system.

Evaluation of the Variables

We evaluated the variables to determine i. the relative efficacies of the one-versus the two-step systems; ii. the use of PSE versus PBC to drive GAL4-VP16 expression; iii. the effect of varying the number of GAL4 binding sites; and iv. the effect of varying the number of VP16 activation domains.

Figure 7:
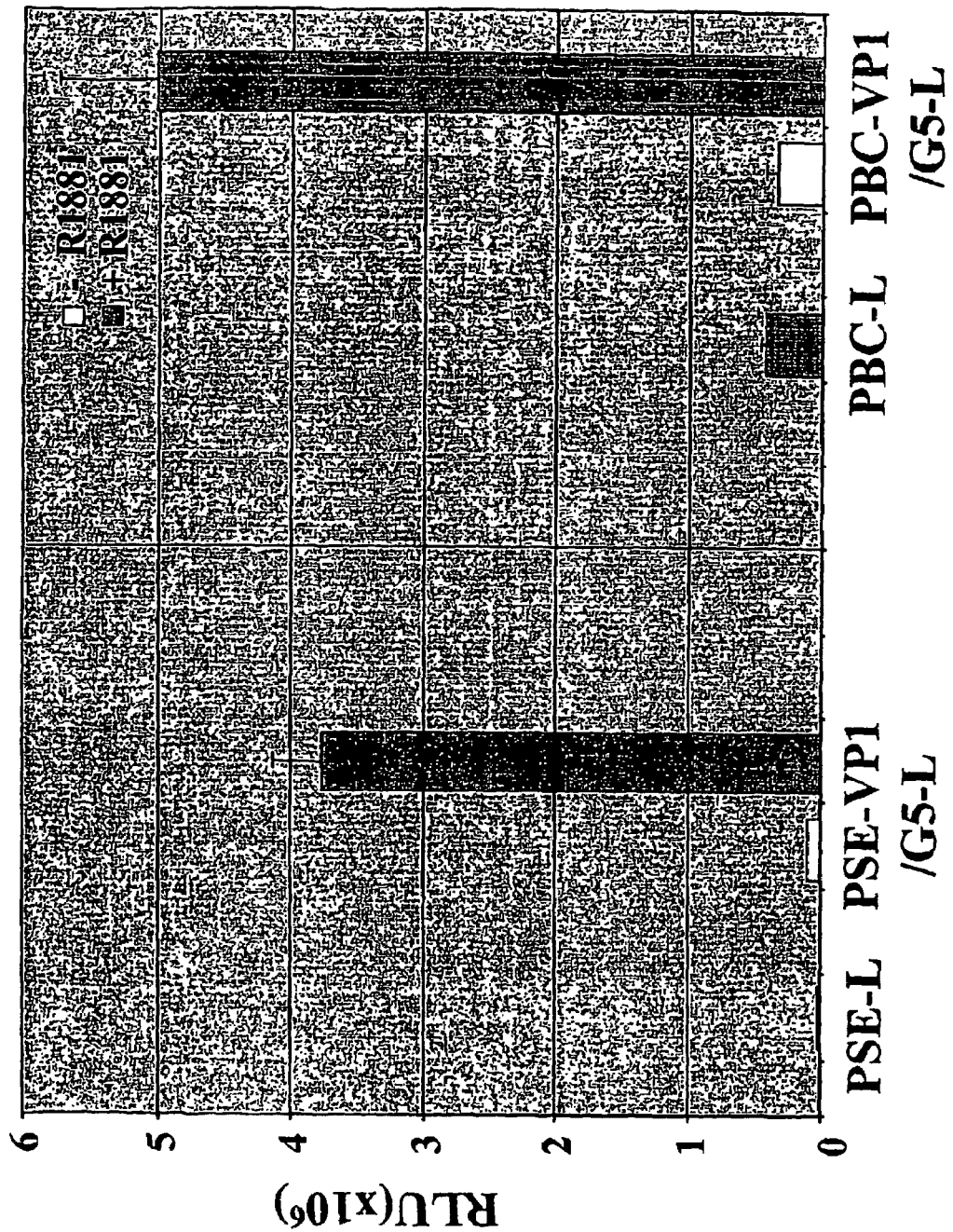
FIG. 7: Comparison of Two-step vs. One-step. We grew LNCaP cells in 6-well tissue culture plates and transiently transfected them with G5-L reporter and PSE/PBC-driven GAL4-VP1 (two-step), or with luciferase reporter driven directly by PSE/PBC (one-step). We added 10 nM R1881 (synthetic androgen) to the "+ligand" samples one hour after transfection, and measured the luciferase activities 48 hours after stimulation. The experiments were repeated multiple times in triplicate. The measurements shown here are average values of a representative experiment. The vertical axis shows the relative light unit (RLU) reading from the luminometer. The error bars represent standard deviation.

The TSTA system displayed enhanced activity and androgen inducibility versus the one-step system in transfection assays. Co-transfection of PSE-VP1 and G5-L resulted in an activated level in cell culture that was 250-fold greater than the PSE-L one-step construct (FIG. 7). Further, the TSTA system retained strong androgen-responsiveness (compare + and −R1881). However, the PBC-VP1/G5-L combination exhibited an induced activity only 15-fold better than the PBC-L. Comparison of PSE-VP1 and PBC-VP1 on G5-L revealed only a 1.5-fold difference, which is not considered significant (P=0.1). This value was much less than the 20-fold difference observed between PSE-L and PBC-L [15] suggesting that despite the augmented potency of PBC, the FL levels in LNCaP cells begin to saturate with G5-L as a reporter.

Figure 8:
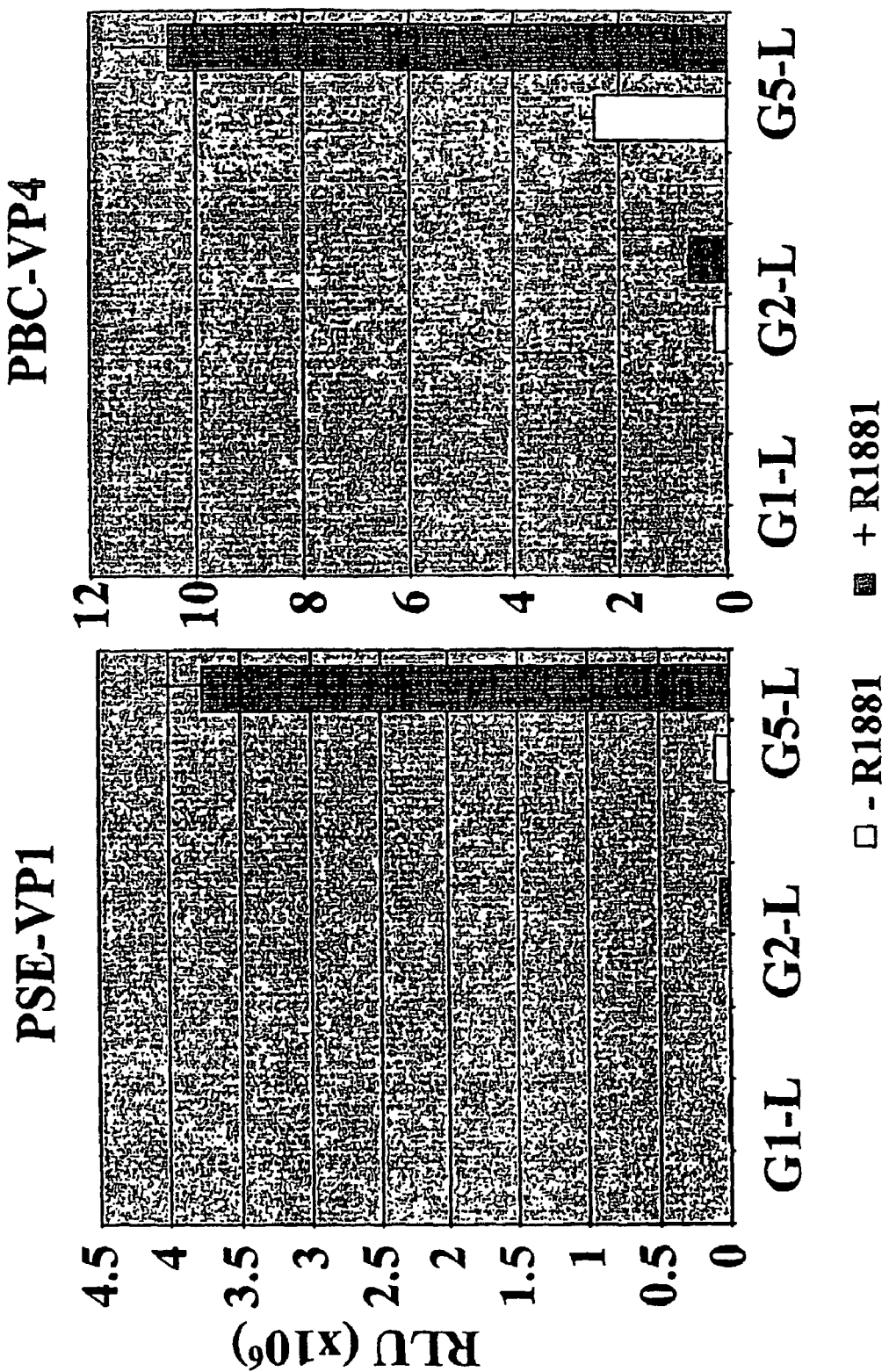
FIG. 8: Increasing the Number of GAL4 Sites and VP16 Domains Augments Activity. We transfected LNCaP cells with PSE-VP1 (left panel) or PBC-VP4 (right panel) and G1-, G2- and G5-L. We treated and measured the cells as in FIG. 7. The measurements shown in the two panels are from a side-by-side experiment.

Variation of the number of GAL4 binding sites contributed to the titratability (FIG. 8). The activity with PSE-VP1 increased nearly 8 fold after increasing the number of sites from one (G1-L) to two (G2-L). However, raising the number of sites from two (G2-L) to five (G5-L) increased the activity an additional 60-fold. The pattern changed when examining the combination of a stronger promoter, PBC, and a more potent activator, GAL4-VP4. In this example, the largest increase in activity, 30-fold was observed from G1-L to G2-L. From G2-L to G5-L there was only a 15-fold increase. The activity appears to saturate at five GAL4 sites because G9-L exhibited the same activity as G5-L with PBC-VP2 as an effector. In summary, PSE-VP1 and PBC-VP4 both increase transcription activation synergistically as the number of activator binding sites increases. The magnitude of the synergy and the absolute level of activation, however, are related to the potency of the effector plasmid, providing a strategy to further adjust the expression levels in this system.

Figure 9:
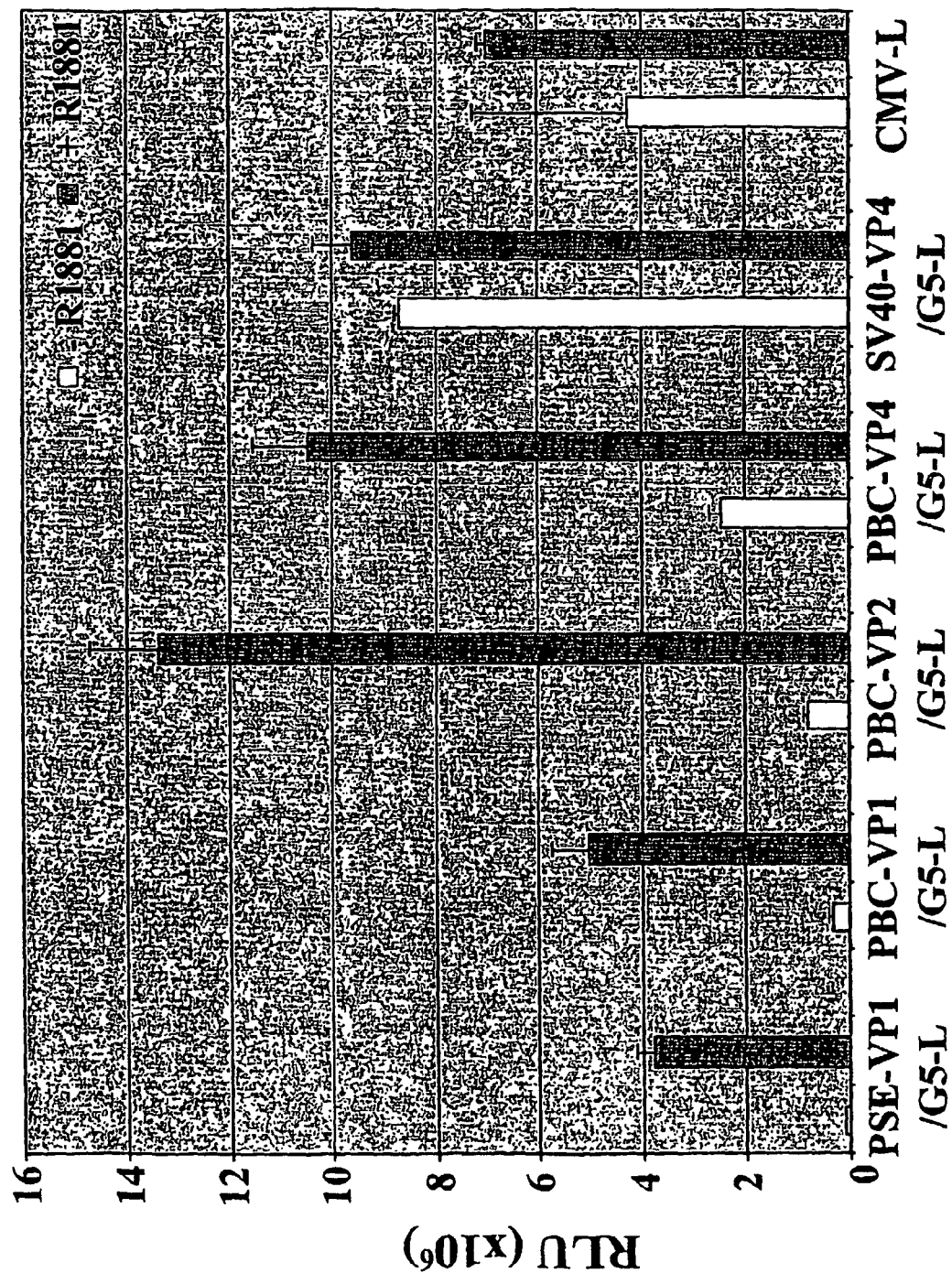
FIG. 9: Comparing Different Numbers of Activation Domains. We transfected LNCaP cells with G5-L and either GAL4-VP1, -VP2 or -VP4 expression vectors driven by the PSE or chimeric (PBC) PSA enhancer-promoter. SV40-VP4/G5-L and CMV-L serve as benchmarks. We adjusted the DNA concentrations so that the transfections contained comparable molar amounts of the FL gene.
Figure 10:
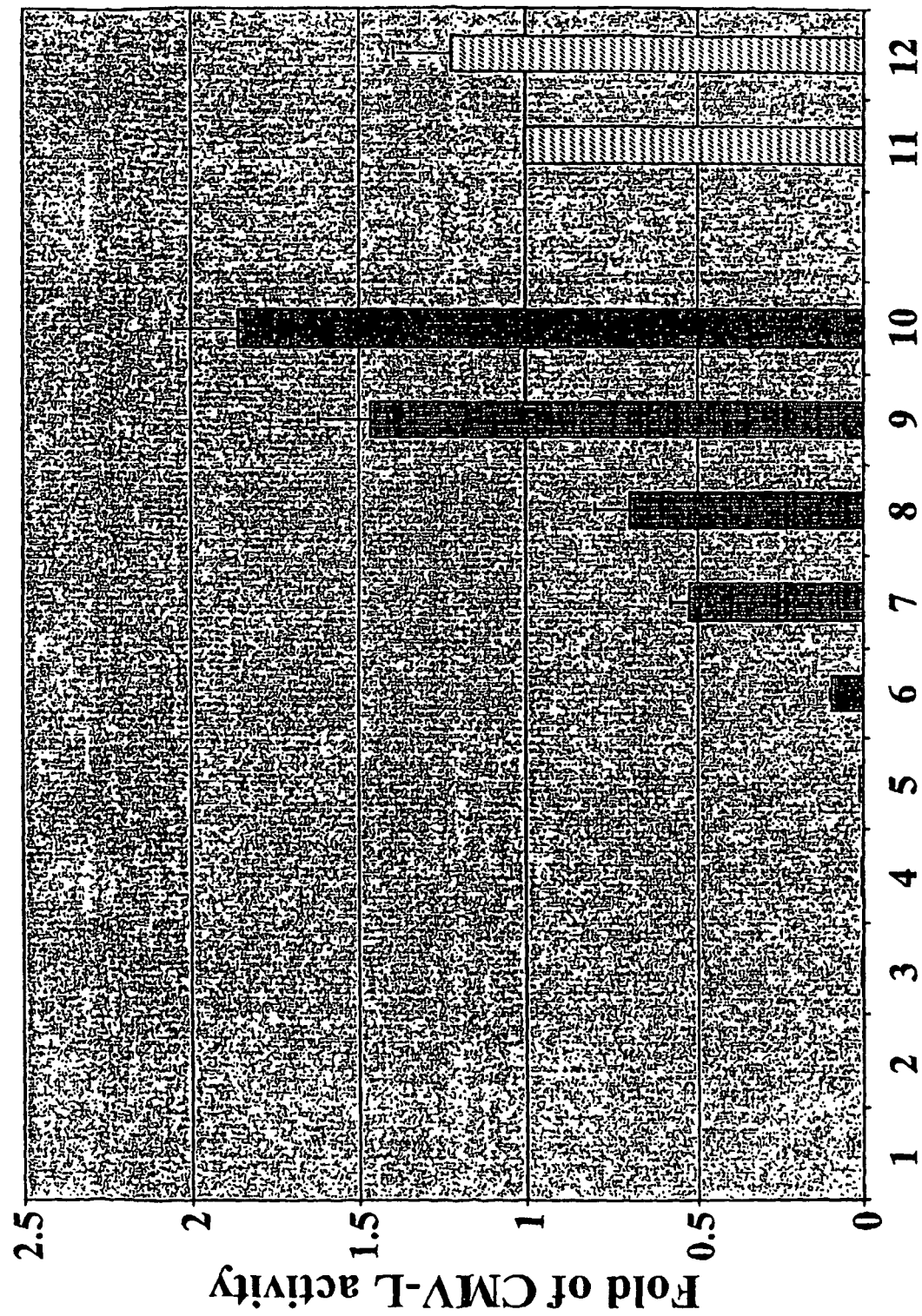
FIG. 10: The Spectrum of Activities Generated by the TSTA System. We plotted results of the previous experimental combinations side-by-side for direct comparison. We normalized the measurements to CMV-L activity in the presence of R1881. CMV-L was assigned a value of 1. The samples are aligned by their activities. 1. PSE-L 2. PSE-VP1/G1-L 3. PBC-VP4/G1-L 4. PBC-L 5. PSE-VP1/G2-L 6. PBC-VP4/G2-L 7. PSE-VP1/G5-L 8. PBC-VP1/G5-L 9. PBC-VP4/G5-L 10. PBC-VP2/G5-L 11. CMV-L 12. SV40-VP4/G5-L.

The final parameter we measured was the effect of multimerizing the VP16 activation domain (FIG. 9). With G5-L as reporter, PBC-VP2 displayed a 3-fold greater activity than PBC-VP1 (P=0.0007). Surprisingly, PBC-VP2 is modestly better than PBC-VP4 (P=0.02), possibly because PBC-VP4 is causing an inhibitory phenomenon called squelching [66]). Nevertheless, the hallmark was the combination of PBC-VP2 and G5-L, where the level of activated expression reproducibly exceeded the activity of both benchmarks (CMV-L and the combination of SV40-VP4 with G5-L). FIG. 10 illustrates the full spectrum of expression levels observed in our system, with an 800-fold variation from the weakest one-step to the strongest two-step system.

Tissue/Cell Specificity of the TSTA System

We chose the TSTA combination of PBC-VP2 and G5-L for analysis of tissue specificity (FIG. 11). We compared prostate and non-prostate lines, and cell lines expressing and lacking AR to assess authentic prostate specificity and distinguish it from simple androgen responsiveness. The LAPC4 cell line is an advanced prostate cancer cell (tumor cells from patient with refractory/metastatic prostate cancer) line that expresses AR and displays modest androgen-responsiveness as measured by PSA induction [69]. The mammary carcinoma cell line MCF-7 also expresses AR but not PSA. The human cervical cancer cell line HeLa cell is negative for AR and PSA. fAR-HeLa expresses flag-tagged human AR but not PSA [48]. Finally, we included the human hepatic cell line HepG to test for potential activity in liver.

During our initial tests we discovered that CMV-L responds to androgen stimulation (FIG. 9). We employed SV40-driven GAL4-VP2 and G5-L as a benchmark to properly normalize experiments in different cell types. The SV40-VP2/G5-L displayed a similar activity as CMV-L in LNCaP and was not significantly affected by androgen in any cell lines tested. In LNCaP cells, we consistently observed that, in the presence of androgen, the combination of PBC-VP2 and G5-L had an activity that was similar to that of SV40-VP2 and G5-L. This observation was consistent with immunoblotting results (FIG. 11, panel B) where PBC and SV40 expressed GAL4-VP2 at similar levels. However, PBC expression was androgen-dependent whereas SV40 expression was not influenced by androgen.

As shown in FIG. 11 we found that the TSTA system displayed activities comparable to the SV40 benchmark only in the prostate cancer cell lines, LNCaP and LAPC4 (>90% and 75%, respectively). In contrast, we found that the activities of the TSTA system relative to the benchmark were 0.2% in HepG cells, 0.7% in HeLa cells and 1.5% in MCF-7 cells. In a system where AR was overexpressed, fAR-HeLa cells, the TSTA system elicited 2% the activity of our benchmark. The difference between HeLa and fAR HeLa was significant (P=0.4).

The Effector and Reporter on the Same Plasmid

A single plasmid bearing both the effector and reporter greatly increased activity but maintained cell selectivity (FIG. 12). The construct, referred to as PBCVP2G5-L, contains a 3.5-kb PBC-VP2 NotI fragment inserted into the G5-L (FIG. 6D) in a "head to head" orientation, with 170-bp between G5 and the 5' end of the distal copy of the PSA core enhancer. Transfection of the single construct PBCVP2G5-L into LNCaP cells yielded an activated FL activity 10-fold higher than that seen with the same molar amount of the two-construct PBC-VP2/G5-L TSTA system. The single construct did not display as much activity relative to the benchmark in LAPC4 cells, possibly due to the reduced androgen dependency of LAPC4. Nevertheless, PBCVP2G5-L maintained tissue selectivity as illustrated by its low activity in HeLa, fAR-HeLa, HepG2, and MCF7 cells. When we cloned the PBC-VP2 NotI fragment in the "head-to-tail" orientation with G5-L to generate a single construct, we discovered that PBCVP2G5-L(R) displayed greatly reduced activity versus the head-to head orientation. We do not understand the cause of this effect.

Application of the Chimeric-TSTA System to Imaging FL Reporter Gene Expression in Living Mice We show that the chimeric-TSTA system displays robust expression in imaging studies in live mice. To validate the potential of the modified TSTA for imaging we determined whether the differences in activity could be reproduced qualitatively in an animal imaging system. A cooled charge coupled device (CCD) camera converts bioluminescent photons to quantifiable electronic signals. The luminescence is recorded and graphically displayed by superimposing a colored topographic pseudoimage on a photograph of the animal. Previous studies had established that within the proper time frame, the RLU signals acquired by the camera are linear to exposure time and amount of FL activity as assayed by luminometry [70]. We transfected LNCaP cells or HeLa cells with our optimal TSTA constructs, treated with R1881, and implanted the cells subcutaneously onto the dorsal surface of the mice. We separated the mice into 4 groups. Within each group we injected three types of transfected cells. To eliminate positional artifacts, we performed the experiments in triplicate; we rotated each group of cells through all three implantation sites. FIG. 13 shows pictures of representative mice from each group. In group 1 (FIG. 13A), the G5-L negative control showed no detectable signal and the signal generated by PSE-L was barely above the background. In contrast the signal for the one-step vector PBC-L was evident and equal to 800 RLU/min at the maximum intensity. When we analyzed the two-step system (FIG. 13B), signals of over 6500 RLU/min were obtained with the optimal two-construct TSTA system.

The signals appeared to be both ligand- and cell-specific. HeLa cells transfected with PBC-VP2/G5-luc (FIG. 13C), or LNCaP cells grown without R1881 did not display a signal above background. Remarkably, we estimated the maximum signal from PBCVP2G5-L, the single construct, to be 55,000 RLU/min, which is nearly 10-fold greater than the signal generated by the two-construct TSTA system (FIG. 13C). CMV-luc exhibited a similar signal in both LNCaP and HeLa cells. In summary, we have presented here our initial effort to apply the augmented TSTA system to molecular imaging and we discuss the potential applications of this system below.

Discussion

Use of the Chimeric TSTA System to Modulate Expression

We have modulated the activity of the TSTA system by introducing potent PSA enhancers and potent derivatives of GAL4-VP16. Remarkably, the largest increases in activity came not from increasing the potency of the PSA promoter but from either increasing the potency of the activator or by placing the TSTA components on a single plasmid. As shown in FIG. 8, increasing the number of activator binding sites from G1 to G5 greatly amplifies the activity by 240 to 450 fold, depending on the activator expressed (PSE-VP1 or PBC-VP4). Moreover, duplication of the activation domain from PBC-VP1 to PBC-VP2 resulted in a 3-fold enhancement of activity. These results reinforce the concept of synergistic activation of transcription and its use in varying the activity of an expression system.

We observed the single most dramatic increase in activity by placing the TSTA system on a single plasmid. Comparison in LNCaP cells of the single construct, PBCVP2G5-L, with the combination, PBC-VP2 and G5-L, revealed a striking 10-fold difference. The positioning of the two components on the same DNA molecule may generate a feed forward loop, where GAL4-VP16 drives G5-L and raises its own expression level by binding upstream of PBC. Similar loops have been described [71]

There are numerous combinations that could still be tested. The effects of the PSE-VP2 or -VP4 series have not been compared with PBC-VP2 and -VP4. Additionally, certain conditions, such as the R1881 concentration, have not been adjusted; this was performed in an earlier study [60]. However, the values will likely fall within the ranges we observed. The study has indicated that we have reached, or are close to, the limit of amplification using the present TSTA components.

Others have explored the concept of TSTA in imaging and gene therapy. The Fraser group used a TSTA system, which employed a GFP effector, and achieved enhanced, tissue specific bioluminescent signals to study Zebra fish development [67]. Segawa and colleagues combined the PSA wild type enhancer-promoter with GAL4-VP16 for gene therapy in prostate cancer [59] and our groups recently employed an early version of TSTA in imaging.

Remarkable progress has been reported by others, who have explored the optimization of prostate specific promoters. For example, the prostate specific PSA and human Kallikrein 2 (hK2) promoter/enhancers have been modified to generate potent androgen-responsive expression systems analogous to our chimeric enhancers [72, 73]. A direct comparison of the studies is difficult because of differences in enhancers, reporters (GFP vs. FL), minimal promoters, positive benchmarks (different CMV constructs) or methods of DNA transduction. We emphasize that our study was geared towards the same endpoint as the others but we focused on increasing potency and signal flexibility for use in imaging and therapy. By employing transient transfection assays we demonstrated the amplitude, titratability and specificity of our system over an 800-fold range. We tested certain points within this range and they maintained the same approximate activities by a cooled CCD imaging approach. The strongest constructs repeatedly exceeded the activities of multiple benchmarks.

Activity, Inducibility and Specificity

The current methodology prohibits us from drawing conclusions about the absolute degree of androgen inducibility. Basal expression increased as the activity of the system increased from the one-step to the most potent two-step constructs. We believe that much of the increase in basal expression is a consequence of incomplete depletion of steroids from the cultured cells. The argument is based on two observations: i. The basal activity of the PSA enhancer constructs in charcoal-stripped serum can be further reduced by addition of the anti-androgen casodex. ii. The small amount of residual androgen in charcoal-stripped medium will likely result in the same amount of activator being synthesized when comparing different GAL4-VP16 derivatives expressed from a similar promoter such as PBC. This point is supported by our result showing that the 3-fold increase in potency of activators, i.e., PBC-VP1 vs. PBC-VP2, is observed both in the presence and absence of R1881. Nevertheless, the system still displayed cell type specificity. Ultimately, the most rigorous test of true androgen responsiveness and tissue specific expression will be to perform transgenic animal studies or to employ viruses stably expressing the TSTA system to infect xenografts or other animal models; this is the current focus of our research.

Applications to in vivo Imaging

The cooled CCD optical imaging belongs to a new generation of in vivo imaging technologies that use fluorescent or bioluminescent reporter genes to produce a signal from within a living animal. The CCD approach detects low levels of luminescence consistently and reproducibly from fur-covered animals without the need for an external light source. [74, 70].

Luciferase monitoring of transgene expression is still in its infancy and is limited to small animals due to significant absorption and scatter of visible light within the animal [70]. Positron emission tomography (PET) is a technology currently employed in clinical settings [75-77]. PET utilizes molecular probes labeled with positron emitting isotopes and produces dynamic signals measurable by a circular array of detectors. PET generates tomographic images reflecting the concentration and location(s) of probes in a living subject of any size. Successful PET imaging has been performed with the Herpes Simplex-Virus-1 (HSV-1) Thymidine Kinase (TK) reporter gene expressed from a CMV enhancer [75, 77]. TK utilizes $_{18}$F-labeled ganciclovir/penciclovir to generate a signal primarily in cells expressing the reporter gene. However, for some applications PET may have a lower sensitivity than bioluminescence imaging [70]. A significant improvement in sensitivity, in order to image the least number of cells, is necessary to make reporter gene-based PET methods viable for imaging prostate cancer progression in pre-clinical and clinical models. The modifications reported in our current system are aimed at improving a prostate-specific PET-based reporter gene methodology.

Extensions of the TSTA System

The TSTA system can be manipulated for use in targeting cancer in different ways. New cell and promoter specific regulatory elements can be introduced to further up- or down-regulate expression [54]. Replacement of the VP16 activation domain with domains responsive to unique signals can be employed to identify novel cellular signaling pathways. Furthermore, other prostate cancer promoters can be utilized and novel reporter or therapeutic genes can be added. These additions will increase the utility and regulatability of TSTA. Although androgen and AR are central to early prostate cancer progression, later stages of proliferation gradually utilize cross-talk among AR and signaling cascades including MAPK, PI3K, PKA, EGFR, IGFR and TGF-$\beta$ [78, 79, 69, 80, 81]. The concept of TSTA can be readily applied to understanding the ramifications and activity of these cellular pathways during cancer progression.

In conclusion the major advances of TSTA are its cell selectivity, activity and robustness relative to cell specific promoters. Its flexibility will permit widespread utility in cancer research.

Materials and Methods

Cell Culture

We grew the human prostate cancer cell line LNCaP in RPMI 1640 supplemented with 10% Fetal Bovine Serum and 1% Penicillin/Streptomycin solution. We grew HeLa, fAR-HeLa [48], and the human hepatic line HepG cells (ATCC) in DMEM with 10% Fetal Bovine Serum and 1% Penicillin/Streptomycin. We grew the human prostate cancer line LAPC4 [69] in IMDM (GIBCO) with 10% Fetal Bovine Serum and 1% Penicillin/Streptomycin. Prior to transfection, we transferred the cells for 24 hours into media that contains 5% charcoal stripped serum.

Plasmids

The baseline PSA promoter construct termed PSE and the chimeric PSE-BC (abbreviated here as PBC) are as previously described [53]. To construct pPSE-VP1, the HindIII-XbaI fragment was excised from pSV40-VP1 and inserted downstream of the 2.4 Kb PSA promoter PSE. We generated the other effectors, PBC-VP1, PBC-VP2 and PBC-VP4 using similar strategies [53]. We constructed G1, G2 and G5-L as described [60]. We cloned the NotI Fragment bearing the PBC promoter and GAL4-VP2 gene into the NotI site of G5-L generating a single vector termed PBCVP2G5-L that contained both components of the TSTA system.

Cell Transfection

On day 1, we plated LNCaP cells in 6-well plates in RPMI 1640 containing charcoal stripped FBS. We performed transient transfections 24 hours later using Tfx-50 (Promega) with a lipid:DNA ratio of 4:1. Each transfection mixture contained 0.5 µg of the effector and reporter plasmids or reporter plasmid alone with pGL3B carrier DNA. Methylen-etrienolone (R1881; NEN Life Science Products, Boston, Mass.) was added to the medium at a concentration of 10 nM/well one hour following transfection, and the cells were incubated for 48 h. The cells were harvested and lysed using the passive lysis buffer provided in the assay kit for measuring FL activities (Dual-Reporter Luciferase Assay System, Promega). FL activities of 5% of the cell lysates with 100 ml of substrate D luciferin were measured using a luminometer (Lumat 9507, Berthod Germany) with an integration time of 10 sec.

Immunoblot Analysis of GAL4-VP16 Expression

LNCaP cells were grown in 10-cm dishes and transfected with select plasmids expressing the TSTA components. We harvested and lysed the treated cells using RIPA lysis buffer (10 mM Tris-HCl, 150 mM NaCl, 0.1% SDS, 1% DOC, 1 mM EDTA and 1% NP40). We normalized extracts by protein concentration (Bio-Rad Dc protein assay Kit), the samples were fractionated on 4-15% gradient acrylamide gels (Bio-Rad) and subjected to immunoblot analysis with rabbit polyclonal antibodies generated against intact GAL4-VP16 [82].

In vivo Studies

We treated transiently transfected LNCaP and HeLa cells with 10 mM R1881, harvested 40 hours post-transfection and resuspended in phosphate buffered saline (PBS). We anesthetized female nu/nu mice with 40 µl of ketamine-xylazine (4:1) solution. To allow time for tissue distribution, a solution of D-luciferin (Xenogen, CA) in PBS (200 ml, 15 mg/ml) was injected into the peritoneal cavity prior to implanting cells. After 5 min, $1\times10^6$ cells were suspended in 50 µl PBS, combined with 50 µl of Matrigel (BD Biosciences, Bedford Mass.) and injected subcutaneously onto the dorsal side of the mice. Each mouse bore injections at 3 sites. Twenty minutes after intra-peritoneal injection of D-luciferin, we imaged the mice using a cooled CCD camera (Xenogen IVIS, Xenogen Corp., Alameda, Calif.). At the time of injection into animals, an aliquot of the cells was also analyzed for FL activity using a luminometer as described above. All studies were performed with full approval from the UCLA Animal Research Committee (ARC).

CCD Imaging and Quantitation

We placed the mice prone in a light-tight chamber and a gray scale reference photograph was obtained under low-level illumination. We collected photons emitted from within the mouse and transmitted through tissue and integrated them for an acquisition time of 1 to 5 min. We obtained images and analyzed them using Living Image Software v4.02 A (Xenogen Corporation, Alameda, Calif.) v2.11 and Igor Image Analysis Software Wavemetrics, Seattle, Wash.). We drew regions of interest (ROI) over the visible light signal to quantitate the light. We normalized the maximum relative light unit (RLU) signals measured to acquisition time to obtain maximum (RLU/min). We calibrated the system as described earlier [70].

EXAMPLE 3

The following provides descriptions of visualization of advanced human prostate cancer lesions in living mice by a targeted gene transfer vector and optical imaging.

Continued improvements in screening, early detection, and treatment of localized disease have led to a steady decline in prostate cancer mortality over the past ten years (83-85). Despite these advancements, prostate cancer continues to be the second highest cause of cancer deaths in American men. Endocrine therapy, employing castration and/or anti-androgens, is the only effective treatment for advanced, metastatic disease (86, 87). Even though these patients continue endocrine therapy, prostate cancers invariably relapse within a mean time of 18-36 months (88), after which they are considered androgen-independent (AI), and are unresponsive to existing treatments. Vector-based prostate delivery of therapeutic transgenes represents a potential alternative or adjuvant to existing therapies, such as chemo- or radiotherapy, for the treatment of AI disease. As with other emerging therapies, vector-based approaches are challenged with achieving acceptable levels of efficacy and safety. Use of strong constitutive viral promoters, such as those of cytomegalovirus (CMV) and Rous sarcoma virus (RSV), enables high levels of therapeutic transgene expression, but could result in accompanying damage to healthy tissues (89). To improve the activity and specificity of prostate-targeted gene expression, we recently developed enhanced promoters designed to augment prostate-specific transgene expression by multimerizing key regulatory elements in the prostate-specific antigen (PSA) enhancer and promoter (90). One such promoter, PSE-BC, was 20-fold more active than the native PSA enhancer/promoter in cell-based firefly luciferase expression studies. Furthermore, when incorporated into an adenovirus vector (AdPSE-BC-luc), the promoter exhibited greatly enhanced transcriptional activity in LNCaP prostate cancer cells and restricted transgene expression in several non-prostate cell lines and mouse tissues (90).

To further advance the concept of prostate-targeted expression, we tested our approaches in several recently developed human prostate cancer (CaP) xenograft models, designated the Los Angeles Prostate Cancer (LAPC) series, which was derived from clinical tissues obtained from patients with advanced CaP and grafted into severe combined immune deficient (SCID) mice. The models retain characteristics of clinical disease, including androgen receptor (AR) and PSA expression, the requirement for androgens, and metastatic potential (91, 92). One of the models, LAPC-4, initially requires androgen for growth, but similar to clinical disease progression, tumors regress upon castration and an AI tumor emerges (91). Demonstration of the utility of our approaches in clinically relevant models suggests that they may be applicable in clinical settings.

The application of a non-invasive imaging modality in a CaP-targeted gene therapy model may greatly aid in accurate assessment of in vivo vector-mediated gene transduction and therapeutic efficacy. The recently developed cooled charged coupled device (CCD) camera for optical imaging is a sensitive approach for detecting bioluminescence emitted from luciferin reacting with firefly luciferase in living animals (93-95). The advantages of a targeted gene transfer approach coupled with non-invasive imaging include the ability to localize diseased tissue, and importantly, to accurately monitor the kinetics and levels of transgene expression in diseased and healthy tissues. In this study, we employed CCD imaging to achieve those ends in several mouse models of human CaP.

Results

Discriminatory Expression Capability of a Prostate Specific Gene Delivery Vector We first assessed the in vivo transcriptional targeting capability of AdPSE-BC-luc in comparison to the strong constitutive AdCMV-luc (94). After systemic tail vein injection of either Ad, luciferase expression was monitored. The CCD signals are dependent on the administration of D-luciferin substrate, as omission of luciferin results in weak background signals (FIG. 14A). The magnitudes of light signals (maximum relative light units, RLU) are linearly proportional to the image acquisition time (94). This important feature of cooled CCD camera allows the signal intensity to be normalized to the acquisition time and be reported as maximum RLU/min, represented by the color scale. The acquisition times were reduced to offset strong signal intensities that saturate the CCD camera (e.g., liver signal in CMV cohorts; FIG. 14A). Despite comparable gene delivery to the liver in both groups (FIG. 14B), AdPSE-BC-luc-mediated expression in the liver was less than $10^{-5}$ that of AdCMV-luc, as measured by CCD imaging and luminometry of tissue extracts from isolated livers (FIG. 14A and Table 1). These data confirmed that AdPSE-BC-luc has high specificity for prostate tissue (90), as indicated by its poor expression in liver, the major site of expression for AdCMV-luc. Furthermore, this non-invasive imaging modality correlates well with current in vitro biochemical analysis of luciferase activity (94).

The prostate-specific transcriptional activity of AdPSE-BC-luc was evaluated by direct injection of Ad into several human CaP tumors implanted into murine subcutaneous tissues in the lower back. The results from AD LAPC-4 models are shown in FIG. 15. The activity of AdPSE-BC-luc in LAPC-9 tumors was similar to that observed in LAPC-4. Based on the activity seen 8 days post-injection, AdPSE-BC-luc displayed 72-fold lower expression in AD LAPC-4 tumors than AdCMV-luc (FIG. 15 and Table 1). By comparing the ratio of activity in LAPC-4 tumors to that in livers, AdPSE-BC-luc exhibited ~1000 fold higher preferential expression in CaP tumors than AdCMV-luc (FIGS. 14 and 15, and Table 1).

Kinetics of Transgene Expression in Living Mice Bearing Human Prostate Tumors

One major advantage of the CCD non-invasive imaging system is the ability for repetitive monitoring of Ad-based luciferase gene transfer and expression in the same animal over time. Because the experiment was carried out entirely in the same animal, and without any variation in the genetic background or in gene delivery, smaller study cohorts could be used. Luciferase expression was evaluated in mice bearing AD LAPC-4 tumors spanning a 3-week period after intra-tumoral injections of AdCMV-luc (FIG. 15A) or AdPSE-BC-luc (FIG. 15B). The intra-tumoral signals in the AdCMV-luc injected mouse (CMV1) displayed the highest activity between 2 and 4 days post-injection, and diminished thereafter (FIG. 15A). Leakage of AdCMV-luc into the circulation after intra-tumoral injections was observed in LAPC-4 tumors, as indicated by the signals appearing in the liver (FIG. 15A). In fact, after 4 days, the liver signals exceeded those in the tumor, and gradually increased over time (FIG. 15A and Table 1). The intra-tumoral signals continued to decrease to a level below the minimum scale of $1 \times 10^5$ RLU/min at 15 days post-injection, whereas the liver signal remained robust at $\sim 1.5 \times 10^6$ RLU/min in this animal (CMV1).

By comparison with Ad-CMV-luc, the time course of intra-tumoral AdPSE-BC-luc expression was delayed (FIGS. 15A and 15B). The majority of the AdPSE-BC-luc injected tumors expressed negligible luciferase at 2 days post-injection (3/5 mice). All 5 mice in the cohort start to display signals at 4 days, and peaked signals between 8 to 11 days post-injection (FIG. 15B and Table 1). The delayed course of Ad-PSE-BC-luc-mediated expression may be attributed to its lower transcriptional activity relative to AdCMV-luc. In the AdPSE-BC-luc-injected cohort of 5 mice, only signals emitted from the tumors were detected at time points on or before 15 days post-injection (FIG. 15B). However, at 21 days post-injection, low-magnitude extra-tumoral signals were visible (FIG. 15B) in 3 out of 5 animals. These low-magnitude signals (~200 RLU/min; FIG. 15B) were distinguishable from background luminescence because CCD imaging of the same animal at 2 days post-injection, a time point just prior to initiation of expression, revealed the background to be ≦70

RLU/min. To localize the origin of light emission, we isolated organs from the BC4 mouse and re-imaged at the time of sacrifice (FIG. 15C). The signals in the upper chest and lower back emanated from the animal's lung and spine, respectively (FIGS. 15B and 15C).

Detection and Localization of Human Prostate Cancer Metastatic Lesions

We undertook detailed histological evaluation of the isolated organs to determine whether metastatic lesions were in fact detected by our methodology. The elongated spinal signal was well-localized within the length of the spinal column (FIG. 15C), so we processed this specimen for further histological and immunohistochemical analysis. Higher magnifications revealed a large, elongated metastatic lesion embedded in spinal musculature, characterized by large pleomorphic nuclei and a high mitotic rate consistent with neoplasia (FIGS. 16A and 16B). Immunohistochemistry performed with an anti-human pan-cytokeratin antibody confirmed that the lesion was of human origin (FIGS. 16A and 16B). The spinal lesion of another animal in the cohort (BC2) also demonstrated the same histological characteristics and a clear correspondence of CCD signal and lesion location at the caudal end of the spine (FIG. 16B). In another animal with lung signals (FIG. 16C), we processed the lung for immunofluorescent evaluation by confocal microscopy, using the human cytokeratin antibody. Evaluation of lung sections revealed specific cytoplasmic localization of the human pan-cytokeratin antibody, which was identical to that seen in cells of the xenograft and metastatic spinal lesion (FIG. 16C). The staining was undetectable in the lungs of non-tumor-bearing mice used as negative controls. Tumor cells in the lung were detected as micrometastatic nodules of 9 to 74 cells in several independent locations that occupied 377 $\mu m^3$ of the right lung and 46 $\mu m^3$ of the left lung. The predominant localization of micrometastasis in the right lung of this animal corresponded well with the CCD imaging result (FIG. 16C).

Elevated PSA-based Expression in Advanced Androgen Independent Tumors

To determine whether AdPSE-BC-luc would be active in AI tumors grown in the absence of testicular androgen, we first evaluated whether there were obvious differences between either endogenous AR or PSA expression in the AD and AI LAPC-4 xenografts. This result would offer insights regarding the expression of the exogenously introduced luciferase gene. FIG. 17A shows that neither protein is down-regulated in AD and AI tumors. In contrast, PSA protein expression appeared to increase in the AI subline. This up-regulated endogenous PSA expression paralleled the exogenously introduced luciferase expression mediated by AdPSE-BC-luc (FIG. 17B and Table 1). The CCD images of 3 animals from both AD and AI LAPC-4 tumor-bearing cohorts, 11 days after intratumoral injection, are shown in FIG. 17B. At this time point, 9.8-fold higher activity was observed in AI as compared to AD tumors (FIG. 17B and Table 1). Uneven vector distribution and gene transfer are known to occur in intra-tumoral injections[14]. To rule out this limitation as a reason for higher gene expression in AI versus AD tumors, we performed ex vivo infection of single-cell suspensions derived from the AD and AI xenografts. Both CaP tumor cell types were easily infected by Ads, but there was higher luciferase expression in AI than in AD LAPC-4 tumor cells (FIG. 17C).

Discussion

Hormone therapy for prostate cancer has changed little since its introduction 30 years ago, yet it continues to be the only effective treatment for advanced disease (97). As a result, gene-based therapeutic strategies, covering a broad spectrum of approaches, have emerged as promising alternatives or adjuvant to existing modalities, including replacement of defective tumor suppressors, cytotoxic enzyme-prodrug therapy (suicide gene therapy), suppression of tumor-angiogenesis, and up-regulation of immune-mediated tumor surveillance (98). However, the design and application of vector-based cancer gene therapies must address issues of both efficacy and safety.

Efficacy in vector-based gene therapy is dependent in part on the ability of a vector to infect and transduce cells of the target tissue. Our results demonstrate that our prostate-specific Ad was capable of transducing both the AD LAPC-4 and LAPC-9 prostate cancer xenografts. This study also showed that as LAPC-4 tumors progressed from AD to AI, the AI tumor cells continued to express AR, PSA, and the luciferase gene, despite the complete absence of testicular androgen (FIG. 17). Remarkably, not only was the PSA-based Ad transcriptionally active in AI prostate tumors, it displayed nearly 10-fold higher activity than in AD LAPC-4 tumors. As all of the models retain important features of advanced clinical disease (91, 92), these data support the possibility that a prostate-specific vector capable of transducing prostate cells in human patients can be developed to treat advanced disease.

One interesting observation that we noted in the AR immunohistochemical analysis was that positive AR staining appeared to be more diffuse and less nuclear localized in the AI than in AD tumor sections (FIG. 17A). This observation is consistent with our current understanding that nuclear translocation of AR is mediated in part by androgen binding to the receptor (99). When testicular androgen is depleted as in the LAPC-4 AI model, AR nuclear translocation is impeded but not completely inhibited (FIG. 17A). Both the mechanism of AR translocation and the functional role of nuclear localized AR in this setting may be key to understanding transcriptional regulation in AI prostate cancer cells. Due to the largely qualitative nature of immunohistochemical analysis we need to fully characterize the AR localization and functional activity in the LAPC-4 model at the molecular level. However, many studies provide evidence that AR can function in AI disease. The evidence includes AR mutations that confer expanded ligand specificity (100), AR gene amplification and over-expression (101), cross-talk between other signaling cascades and AR pathways (102, 103) and increased expression of the nuclear receptor transcriptional co-activator, TIF2 (104). In fact, over-expression of Her-2/neu has been implicated in AI progression of both the LAPC-4 model (103) and clinical cases (105). Regardless of the precise mechanism(s), a better understanding of the critical transcriptional regulatory pathways operative in advanced AI prostate cancer should enable the development of even more effective approaches for targeting this disease in the future.

One prominent, serendipitous discovery that arose from our study was detection of metastatic lesions. Although the precise transduction mechanism of the metastatic lesions is unclear at this time, we postulated that intra-tumoral injection of AdPSE-BC-luc leaked to the systemic circulation, in a route similar to the case in AdCMV-luc, and infected metastatic lesions. No discernable liver signal was detected in the AdPSE-BC-luc cohorts, because the tissue specificity of the PSE-BC promoter prevented expression in the liver. This hypothesis is supported by our recent preliminary results showing that metastatic lesions can be detected by systemic tail vein injection of AdPSE-BC-luc. The alternative explanation for detecting metastasis could be the dissemination of a transduced cell(s) from the primary tumor. This hypothesis is less likely, especially in the case of the large spinal lesions (FIGS. 16A and 16B), because Ad-mediated expression is known to be transient, and expansion from a single cell to the large lesion would likely have resulted in loss of expression. However, lung micrometastases could have originated from transduced cancer cells in the xenografts.

Although CCD imaging can sensitively and specifically monitor luciferase expression in small animal models, it lacks the ability to provide detailed tomographic information (93-95). On the other hand, Positron Emission Tomography (PET) is a clinically utilized imaging modality that can provide quantitative, three-dimensional localization of imaging signals. In fact, we have demonstrated that high-resolution micro-positron emission tomography (microPET) can track Ad mediated herpes simplex virus thymidine kinase gene expression in the livers (106) and tumors (96) of living mice. Currently, studies to optimize parameters of imaging of PET reporter transgene in human volunteers have been initiated (107). In preparation for the transition to clinical applications, it will be important to validate our vector-mediated cancer targeting approaches utilizing microPET in animal models. Appropriate resolution of the issues discussed should continue to improve the design, efficacy, and safety of prostate cancer gene-based diagnostic and therapeutic strategies.

Methods

Mice and LAPC Xenograft Propagation

SCID (scid/scid) mice were bred and maintained as previously described (91). Male mice of approximately 3 months of age were utilized in our studies. Mice were anesthetized as described (94) for all surgical or imaging procedures. LAPC-4 and LAPC-9 seed tumor cells from frozen stocks were generously provided by Dr. Charles Sawyers (91, 92). Xenografts were initiated by implanting ~$10^6$ viable cells subcutaneously with Matrigel (Collaborative Research, Bedford, Mass.), 50:50 by volume totaling 100 µl. Once tumors were established, further expansion and propagation of tumors were accomplished by implanting tumor fragments of 1-2 $mm^3$, and the AI sublines were grown and passaged several rounds in surgically castrated male mice (91). The viral injections were performed when the tumors reached a diameter of ~5-7 mm, which required about 3-4 weeks of tumor growth from the initial time of tumor passage. Single cell suspension transient cultures of xenografts were generated as described (92).

Adenoviral Vectors and Southern Hybridization

AdCMV-luc and AdPSE-BC-luc were generated as previously described (90, 94). The Ads were titered by plaque assays on 293 monolayer cells (i.e. infectious units=plaque forming units). Total cellular DNA was extracted from the livers of two treatment cohorts at 4 days post Ad injection. The Southern blot conditions were as previously described (90). The liver tissues were homogenized and lysed by proteinase K, and total DNA was purified by phenol/chloroform extraction, followed by ethanol precipitation. DNA was digested with Not I, subjected to agarose gel electrophoresis. NotI restriction digestion liberated a 2.8 kb CMV-luc and a 4.6 kb PSE-BC-luc expression cassette. Non-radioactive digoxigenin (Roche Co. Germany) labeled luciferase DNA fragment was used as probe (90).

CCD Imaging to Detect in vivo Luciferase Expression

The same total dose of $1.8 \times 10^9$ infectious units were injected either systemically via tail vein or intra-tumorally. For intra-tumoral injections, Ad were given in 6 doses of 10 µl each into 3 sites on 2 consecutive days. The procedures for animal imaging studies were performed as described (94). At the specified days post-injection, the CCD images were acquired using the Xenogen In Vivo Imaging System (Xenogen IVIS™, Alameda Calif.), adapted with a cooled CCD camera. Image analysis was performed using IGOR software (Wavemetrics, Lake Oswego, Oreg.). The increase in RLU is linearly proportional to the increase in acquisition time (94). Therefore, we normalized the signal intensity to the image acquisition time (RLU/min), such that an expanded range of comparative values beyond the saturation limit of 65,000 maximum RLU could be achieved. The image analysis software can quantify signal intensities by integrating over a region of interest (ROI) represented by RLU/pixel/min. We found, however, that due to the great range of signal intensities and light deflection properties, the pixel values can vary significantly, depending on the ROI region drawn. This limitation makes comparison between different experimental conditions difficult. Thus, we used the maximum RLU/min within a ROI, not integrated over the pixels, as the unit to compare the CCD signals, and the results correlated very well with luminometer readings of tissue extracts (Table I) (90, 94).

Confocal Microscopy Study of Lung Metastasis

Mice with signal in the lungs were evaluated by confocal microscopy to determine whether the signal from the reporter gene reflected metastatic events. Animals were perfused with 2% paraformaldehyde, and lungs were inflated with 3% agarose. Specimens were subsequently fixed by immersion in the same fixative, washed in PBS, and embedded on 7% agarose. Fragments from the tumor were used as positive control. Sections of 500 µm were obtained with a vibratome, and stained with human-specific anti-keratin antibody (AM273-5M, BioGenex, San Ramon, Calif.) and a CY-3-conjugated secondary antibody. Observation was performed on a confocal microscope (BioRad 1024 confocal microscope, Hercules, Calif.), and ImagePro4.0 software was used for quantification of serial sections.

Immunohistochemical Analysis of Tumor Sections

Immunohistochemistry was performed according to Leav et al. (108). Briefly, tissue sections were deparaffinized, and antigen retrieval was achieved by boiling in 0.1M sodium citrate pH 6.0 for 15 min. Tissue sections were incubated at 4 degrees C. overnight with respective antibodies, alpha-cytokeratin cocktail AM273-5M (BioGenex, San Ramon, Calif.), AR-beta 5 micro g/ml (UpState, Lake Placid, N.Y.), or PSA 1:40 (Novocastra, Ontario L7N 3J5, Canada). Stringent blocking and washing procedures were carried out to reduce background staining, prior to adding multilink 1:20 (BioGenex, San Ramon, Calif.) and AP label 1:20 at room temperature for 20 min each. Finally, sections were washed again before color development with DAB (BioGenex, San Ramon, Calif.). The micrographs were visualized with an Olympus BX41 microscope, and images captured by an Olympus Camedia C-3030 digital camera.

TABLE 1

Table 1. Summary of CCD image signal intensities and luminometry results of luciferase expression in mice.

| Naive Animals a | days p.i. | Systemic Injections | | | | CMV/ PSE-BC b |
|---|---|---|---|---|---|---|
| | | CMV | (n) | PSE-BC | (n) | |
| | | Max. CCD Imaging Signal (RLU/min) in liver | | | | |
| | 4 | 7.6E+7 | 7 | 402 | 7 | 1.9E+5 |
| | 11 | 6.0E+7 | 3 | 952 | 3 | 6.3E+4 |
| | | Luminometry Readings (RLU/ug protein), liver | | | | |
| | 4 | 2.2E+7 | 5 | 70 | 5 | 3.1E+5 |

| | | Intra-tumoral injections | | | | |
|---|---|---|---|---|---|---|
| | | Max. CCD Imaging Signal (RLU/min) in tumor (T) or liver (L) | | | | |
| LAPC-4 (AD) | days p.i. | CMV (L) | (n) | CMV (T) | (n) | PSE-BC (T) | (n) | CMV/ PSE-BC b |
| | 4 | 3.3E+5 | 3 | 7.2E+4 | 3 | 897 | 5 | |
| | 8 | 1.1E+6 | 3 | 4.3E+4 | 3 | 1798 | 5 | 24 |
| | 11 | c | | 4.2E+4 | 3 | 1309 | 4 | |

TABLE 1-continued

Table 1. Summary of CCD image signal intensities and luminometry results of luciferase expression in mice.

| | | | | | |
|---|---|---|---|---|---|
| 15 | 1.0E+6 | 3 | d | 1237 | 5 |
| 21 | 6.7E+5 | 3 | d | 1311 | 4 |

| LAPC-4 (AI) | days p.i. | PSE-BC | (n) | AI/AD e |
|---|---|---|---|---|
| | 4 | 925 | 3 | 1 |
| | 8 | 8586 | 4 | 4.8 |
| | 11 | 12803 | 4 | 9.8 |
| | 15 | 7498 | 4 | 6.1 |
| | 21 | 3291 | 4 | 2.5 | a Non-tumor bearing, naïve mice.
b Calculated by dividing average signals in the AdCMV-luc-treated group by the respective signals in the AdPSE-BC-luc-treated group.
c Incomplete data collected for this time point.
d Unable to determine. Due to the dominant signals in the liver, the signals in the tumors were below the minimum image analysis setting used.
e Calculated by dividing the average signals for the AI LAPC-4 cohort by the signals for the AD LAPC-4 cohort at the same time point post-injection.

EXAMPLE 4

The following example provides description of monitoring gene therapy with reporter gene imaging.

Advent of new techniques in molecular biology and their integration into nuclear medicine provides a great opportunity to improve the quality of diagnosis and treatment of many diseases. Methods are actively being developed for controlled gene delivery to various somatic tissues, including tumors, using novel formulations of DNA and for controlling gene expression using cell specific, replication-activated, and drug-controlled expression systems (109-111). Although various methods of gene therapy have met with very limited success, it is likely that eventually many disease processes will be successfully treated with delivery of one or more genes to target tissue(s). A major concern for the application of gene therapy is to achieve a controlled and effective delivery of genes to target cells and to avoid expression in non-target locations. Imaging the expression of a particular therapeutic gene is likely to be critical to optimizing gene therapy. Direct imaging of the expression of every therapeutic gene would require development of hundreds of different radiolabeled probes targeted against each therapeutic protein, and thus the development of a more general approach to indirectly monitor therapeutic gene expression is needed. The reporter gene approach is one such potential approach that has been well validated in pre-clinical models and is the focus of the current review.

Reporter Gene Concept

Reporter genes have long been used to study various aspects of gene expression including, promoter/regulatory elements, inducible promoters and endogenous gene expression (112, 113). The general concept is that regulatory regions of genes (e.g., promoters/enhancers) can be cloned and used to drive transcription (the process of converting DNA to mRNA) of a reporter gene. By introducing a reporter gene driven by a promoter of choice into target tissue(s), one can indirectly monitor expression of the gene whose promoter has been cloned. This avoids having to build a specific probe to evaluate the expression of every new gene. The use of a promoter of choice also allows expression of the reporter gene only in select tissues, because specific promoters are active only in specific tissues. Conventional methods used by molecular biologists to monitor gene expression take advantage of reporter genes like β-galactosidase (114, 115) and chloramphenicol-acetyltransferase (CAT) (116, 117), which require tissue samples for determining their expression levels. Other methods make use of optical reporter genes such as luciferase (118, 119), green fluorescent protein (GFP) (120-122) or β-lactamase (123). The optical reporter genes have been used in living animal models as well but are not generalizable for human applications (124).

Due to technological innovations (125, 126) such as positron emission tomography (PET) and single photon emission computed tomography (SPECT), it is now possible, using radiotracers (reporter probes), to image reporter gene expression in vivo both repeatedly and non-invasively. Radiotracer imaging techniques offer the ability to monitor the detailed location, magnitude and time-variation of reporter gene expression.

Adapting the Reporter Gene Concept for Radionuclide Imaging

In order to adapt the reporter gene concept for imaging with PET or SPECT two primary approaches are possible (FIG. 18). The reporter gene can be chosen so that it encodes for an enzyme that is capable of trapping a tracer by action of the enzyme on a chosen tracer. A second approach uses a reporter gene that encodes for an intracellular and/or extracellular receptor capable of binding a tracer (e.g., radioactive ligand). The accumulation of the tracer in both approaches is dependent on the expression of the reporter gene. Through the choice of the right tracer and optimization of it's pharmacokinetics it is possible to primarily achieve imaging signal only in those areas in which the reporter gene is expressed. The introduced reporter gene driven by a promoter of choice is sometimes referred to as a transgene. This reporter gene-imaging paradigm is independent of a particular delivery vector; it can be used with any of the several currently available vectors (e.g., retrovirus, adenovirus, adeno-associated virus, lentivirus, liposomes, etc.). The common feature for all vectors is the cDNA expression cassette containing the reporter gene(s) of interest. The promoter can be constitutive, leading to continuous transcription, or can be inducible leading to controlled expression. The promoter can also be cell specific, allowing expression of the reporter gene to be restricted to certain cells.

The ideal reporter gene would have the following characteristics: (A) When expressed, the reporter gene protein should produce specific reporter probe accumulation only in the cells in which it is expressed. (B) When the reporter gene is not expressed, there should be no accumulation of the reporter probe in cells. (C) There should be no immune response to the reporter gene product and this product should not significantly perturb the cell. Other desirable characteristics are also important and are reviewed elsewhere (127).

Specific Development of Radionuclide Reporter Genes

One of the earliest approaches investigated cytosine deaminase as a reporter gene with 5-[3H]-fluorocytosine (5-FC) as the reporter probe (128). Cytosine Deaminase (CD), which is expressed in yeasts and bacteria but not in mammalian cells, converts the antifungal agent 5-fluorocytosine to the highly toxic 5-fluorouracil (5-FU). The 5-FC does not incorporate into mammalian DNA synthesis pathway, however, its by-product 5-FU can block DNA and protein synthesis due to substitution of uracil by 5-FU in RNA and inhibition of thymidilate synthetase by 5-fluorodeoxyuridine monophosphate, resulting in impaired DNA biosynthesis. However, lack of sufficient accumulation of the probe in cytosine deaminase expressing cells (due to efflux of 5-FU) limits its use as an imaging reporter gene (128). More recently a magnetic resonance spectroscopy (MRS) based approach using some modeling has been described using this reporter gene (129). The conversion of $^{19}$F-labeled 5FC to 5FU was followed by MRS in subcutaneous human colorectal carcinoma xenografts in nude mice by using H29 cell lines stably transfected with yeast cd (ycd) gene and a three compartment model was described for non-invasive estimation of ycd transgene expression. The utility of an MRS based approach warrants further investigation.

One of the most widely used reporter gene systems to image gene expression is the herpes simplex virus type I thymidine kinase gene (HSV1-tk). Thymidine kinases are present in all mammalian cells; they phosphorylate thymidine for incorporation into DNA. Unlike mammalian thymidine kinases, HSV1-TK has relaxed substrate specificity, and is able to phosphorylate acycloguanosine and uracil derivatives which get "trapped" in their phosphorylated state inside the cell. Two main categories of substrates have been investigated as reporter probes for imaging HSV1-tk reporter gene expression: derivatives of uracil {e.g., 2'-fluoro-2'-deoxy-1-β-D-arabinofuranosyl-5-iodo-uracil (FIAU) labeled with radioactive iodine} and derivatives of guanosine {e.g., penciclovir (PCV) radiolabeled with $^{18}$F}. These two major classes of reporter probes share in common the ability to be phosphorylated by HSV1-TK, leading to their accumulation in cell (130). Further details of the HSV1-tk reporter gene approach including a comparison of various tracers, are detailed in a different review article (127). A mutant HSV1-TK enzyme (HSV1sr-39TK) that utilizes ganciclovir (GCV) and penciclovir substrates more effectively, and thymidine less effectively than the wild-type HSV1-TK enzyme, has been described and successfully applied in PET imaging (131). The HSV1-sr39tk mutant illustrates the ability to engineer the reporter protein and reporter probe to be optimized for each other, leading to a marked gain in imaging signal.

Another radionuclide reporter gene system uses the dopamine type 2 receptor ($D_2R$), which binds spiperone {(3-(2'[$^{18}$F]-fluorethyl)spiperone (FESP)} intra- and extracellulary and thus results in probe accumulation in $D_2R$ expressing cells/tissue (132, 133). The $D_2R$ receptor is a transmembrane protein expressed predominantly in stratium and pituitary and important for mediating the effects of dopamine to control movements. This receptor exerts its response through G-protein mediated signaling cascade involving adenyl cyclase as a second messenger. Spiperone, a $D_2R$ antagonist can be labeled with $^{18}$F to yield radiolabeled FESP and thus has been applied for PET imaging of the $D_2R$ reporter gene (133). Recently, we have investigated the potentiality of two mutant $D_2R$ receptors ($D_2R$80A and $D_2R$194A) for PET imaging that can uncouple the downstream cAMP dependent signaling cascade while retaining the property to bind with FESP (134). These two mutants have an advantage of overcoming the undesirable effects of ectopic expression of $D_2R$ receptors on cellular biochemistry by uncoupling signal transduction. The expression of HSV1sr-39tk and $D_2R$ reporter genes can be imaged simultaneously in living mice, with microPET, using two different tracers (e.g., [$^{18}$F]FPCV and [$^{18}$F]FESP) respectively (FIG. 19) (135).

Somatostatin receptor subtype II (SSTr2) is another reporter gene that has been extensively studied. Nuclear medicine physicians will be familiar with the use of various somatostatin analogues (e.g., radiolabeled octreotide) for imaging tumor cells expressing somatostatin receptor. SSTR2 is normally expressed primarily in the pituitary gland, and also in other tissues like thyroid, pancreas, gastroienteric tract, kidney, lung etc. When SSTr2 is used as a reporter gene, the receptor can be expressed on the surface of cells that would not normally express this gene, and therefore the use of various tracers can image SSTr2 reporter gene expression. This approach is discussed in further detail in a review article by Rogers et. al. (136). Several other radionuclide based reporter gene approaches have been preliminarily studied and are listed with appropriate references in Table 2.

Gene Therapy Studies

Precise localization and quantitative assessment of the level of gene expression is highly desirable for the evaluation of gene therapy trials. Most therapeutic transgenes lack appropriate ligands or probes that can be radiolabeled and used to generate images that define the magnitude of therapeutic gene expression. Therefore it is usually necessary to develop and validate "indirect" imaging strategies using a reporter gene in combination with a therapeutic gene. The goal of these approaches is to quantitatively image reporter gene expression and from that infer levels of therapeutic gene expression. Several approaches are currently being developed for indirect imaging of a therapeutic gene and are discussed next.

Fusion Approach

In recent years, fusion gene/protein technology has become a powerful tool in molecular biology, biochemistry, and gene therapy. A fusion gene construct contains two or more different genes joined in such a way that their coding sequences are in the same reading frame and thus a single protein with properties of both the original proteins is produced. Examples include HSV1-TK-GFP, (137-139) HSV1-TK-luciferase-Neo (140). An advantage of a fusion approach is that expression of both genes is absolutely coupled. This approach, however, cannot be generalized, as many fusion proteins do not yield functional activity for both the individual proteins or may not localize in an appropriate subcellular compartment. Every new therapeutic gene has to be fused to a reporter gene, and often the reporter protein and/or therapeutic protein activity is partially compromised. This approach is therefore not as generalizable as the approaches discussed below.

Bi-Cistronic Approach

Another approach to express multiple genes from the same vector construct is to insert an internal ribosomal entry sites (IRES) sequence between the two genes. Both the genes are transcribed into a single mRNA from the same promoter but are translated into two different proteins with the help of the IRES sequences. The discovery of cap-independent translation and existence of internal ribosomal entry sites in polioviruses and encephalomyocarditis virus opened a new gateway to construct bicistronic vectors for gene therapy purpose (141-143). IRES sequences are generally 450-800 bp long with complex RNA secondary structures that are required for initiation of translation. Several general translation initiation factors like eIF3, eIF4A, eIF4G and some specific cellular IRES transacting factors (ITAF's) are required to drive proper translation of the second cistron. We recently reported one such bi-cistronic vector where both $D_2R$ and HSV1sr-39tk genes are co-expressed from a common promoter with the aid of EMCV IRES and imaged by microPET in multiple, stably transfected tumors in living mice. (FIG. 20) (144). An approach using β-gal and HSV1-tk was also studied in mice with SPECT (145) Although IRES sequence leads to proper translation of the downstream cistron from a bicistronic vector, expression from the IRES could be cell type specific and the magnitude of expression of the gene placed distal to the IRES is often attenuated (144, 146). This can lead to a lower imaging sensitivity, and methods to improve this approach are currently under investigation. An IRES may also have different behavior in different cell types; a property yet to be fully explored.

Double Promoter Approach

Two different genes expressed from distinct promoters within a single vector (e.g., pCMV-D$_2$R-pCMV-HSV1-sr39tk) can potentially be a useful way to couple the expression of two genes. This approach may avoid some of the attenuation and tissue variation problems of an IRES based approach, and is currently under active investigation.

Co-Vector Administration Approach

Another approach to express both the therapeutic and reporter gene can also be achieved by co-administrating both the genes cloned in two different vectors but driven by same type of promoter (147). This approach has recently been tested and shows that the expression of two PET reporter transgenes, HSV1-sr39tk and D2R, driven by same CMV promoter but cloned in separate adenoviral vectors is well correlated at the multi-cell (macroscopic) and tissue level when delivered simultaneously. However, it is important to realize that trans effects between promoters on co-administered vectors carrying can potentially affect reporter gene expression.

Bi-Directional Transcriptional Approach

For many gene therapy applications it would be desirable to not only deliver the therapeutic gene to desired target(s), but to be able to regulate levels of therapeutic gene expression. We have validated an approach in a tumor model in living mice in which a simple antibiotic (doxycycline) can be used in combination with a fusion protein and a bi-directional vector in order to correlatively express two genes of choice (148). This approach leads to bi-directional transcription, two mRNAs, and two proteins. It has the unique feature that the levels of transcription can be regulated by levels of doxycycline. This approach avoids the attenuation and tissue variation problems of an IRES based approach and may prove to be one of the most robust approaches developed to date.

Non-Radionuclide Approaches to Reporter Gene Imaging

Radionuclide approaches offer a highly sensitive approach for imaging reporter gene expression that can easily be extended from animal studies to human. Nevertheless, other modalities, when used in the appropriate setting, may have desirable characteristics. Magnetic resonance imaging (MRI) techniques recently have obtained encouraging initial results. Using a substrate {(1-(2-(b-galactopyranosyloxy)propyl)-4,7,10-tris(carboxymethyl)1,4,7,10tetraazacyclododecane)gadolinium(III)-abbreviated as EgadMe} that can be enzymatically processed by β-galactosidase (β-gal) and can generate MRI signal, Louie et al (149) recently demonstrated a MRI based in vivo assay of gene expression in living *Xenopus laevis* embryos. After injecting the β-gal mRNA in one of the cells of a two cell stage *X. laevis* embryo, reporter gene expression was followed by introducing EgadMe. The MR images showed high signal intensity in the embryo with both β-gal mRNA and EgadMe in contrast to the embryo with EgadMe alone. Following image correction, it is possible to recognize the eye and branchial arches. The MR image of a live embryo correlates well with images of the same embryo after fixation and staining with X-gal. This approach for routine in vivo use is currently limited due to the delivery of the EgadMe substrate which does not have direct cellular uptake. In another study, Weissleder et al described the first non-invasive in vivo MR imaging of transgene expression (150). They implanted nude mice with 9 L gliosarcoma cells stably transfected human transferrin receptor (HETR) and control transfected (ETR−) cells followed by injection of iron oxide nanoparticles conjugated with human holo-transferrin (Tf-MION) to image the tumors with MRI. Other MRI/MRS based approaches are reviewed elsewhere (151).

Optical reporter genes such as firefly luciferase or green fluorescent protein (GFP) are currently being used to monitor gene expression in vivo (124, 152). Firefly luciferase gene expression can be imaged using a high sensitivity charged coupled device (CCD) camera. Light is produced through the interaction of luciferase with its substrate luciferin (injected peritoneally) in presence of Magnesium and ATP (152). For the green-fluorescent protein (GFP), an input wavelength must be provided and an output wavelength of light is produced which can be imaged optically by a florescence microscope (153). These optical approaches have the distinct advantage of low background signal, ease of use, and low cost; however, they are limited by light scatter and absorption, limiting studies in deep tissues. Although these optical reporter genes will be extensively used for basic research in small animals, they are not generalizable for human applications. Further examples are referenced in Table 2.

Human Imaging Studies for Gene Therapy

Studies to image reporter gene expression in human subjects are now beginning. Yaghoubi et. al. (154) reported a study to measure the kinetics, biodistribution, stability, dosimetry and safety of [$^{18}$F]FHBG in healthy human volunteers, prior to imaging patients undergoing HSV1-tk gene therapy. The study by Yaghoubi et. al. indicated that due to the properties of stability, rapid blood clearance, low background signal, biosafety and acceptable dosimetry [$^{18}$F]FHBG should be a good reporter probe for HSV1-tk imaging in humans, although [$^{18}$F]FHBG does not significantly cross the blood-brain-barrier. This may eventually allow not only imaging of gene therapy performed with HSV1-tk, but of any therapeutic gene coupled to HSV1-tk for indirect imaging of the therapeutic gene. In another study, Jacobs et al (155) have shown that [$^{124}$I]FIAU, another PET reporter probe for HSV1-tk cannot penetrate the blood brain barrier and thus is not a good marker probe for noninvasive localization of HSV1-tk in the central nervous system. However, this probe is useful for areas where the blood brain barrier is disrupted (e.g., glioblastoma). The other reporter genes also have various tracers that have been previously used in human subjects, and therefore can likely be translated to human applications in gene therapy. With the rapid progress in human gene therapy and molecular imaging it is likely that Nuclear Medicine will play a major role in optimizing gene therapy.

Other Applications of Reporter Genes

Animal applications of the reporter gene imaging assays are particularly important because they allow for the study of many important biological issues in living animals. The use of transgenic animals carrying reporter genes offers unique possibilities for tracking a single animal repeatedly over time during experimental manipulations. Transgenic animals expressing the HSV1-tk gene from tissue specific promoters have been developed to perform cell specific ablation following administration of pharmacologic levels of pro-drugs such as ganciclovir. A transgenic mouse model in which the HSV1-tk marker/reporter gene is driven by the albumin promoter has been studied (156). The albumin-HSV1-tk transgenic mice have been imaged on a microPET with both [$^{18}$F]FPCV and [$^{18}$F]FHBG and clearly demonstrate accumulation of marker/reporter probe in the mouse liver at one hour after injection. Restriction of reporter probe accumulation in the liver is the result of tissue specific transcriptional activation of the HSV1-tk marker/reporter gene by the albumin promoter. The albumin-HSV1-tk mice will be very useful for comparing alternate substrates in vivo and for assessing the reproducibility of assays. Furthermore, these transgenic mice will allow the study of albumin regulation under various manipulations (157). It would be very difficult to develop a tracer specifically targeting albumin, and therefore this indirect approach of imaging albumin gene expression (by imaging HSV1-tk reporter gene expression) illustrates the power of a reporter gene approach to study regulation of an endogenous promoter.

Other applications of reporter genes include: (1) imaging of cell trafficking by marking specific subsets of cells with a reporter gene ex vivo or through transgenic models. (2) optimization of gene delivery in animal models by studying various vectors carrying a reporter gene. (3) studies of the interaction of tumor cells and the immune system by marking each with a distinct reporter gene. (4) studies of viral infections by marking the virus of interest with a reporter gene. (5) studies of basic cancer biology by monitoring specific gene expression in various tumor models.

Conclusion

Molecular and functional imaging allows the clinician/researcher to visualize the cellular and/or molecular processes in living tissues. The development of molecular imaging probes is the key to the importance and growth of nuclear medicine. Reporter genes have emerged as a very powerful tool to monitor the delivery, magnitude, and time-variation of therapeutic gene transfer in vivo. The radionuclide based reporter genes like HSV1-tk, $D_2R$, SSTr2, etc., are currently being used for PET, SPECT and gamma camera imaging. Though still in their infancy, the non-radionuclide based reporter genes are also emerging as another tool for three dimensional, real time, noninvasive imaging of cellular and molecular processes. Nuclear Medicine should help to lead the way for molecular imaging with reporter genes and probes for use with small animal and human imaging.

TABLE 2

Summary of Reporter gene/probe systems

| Reporter gene | Mechanism | Imaging agents | Imaging | References |
|---|---|---|---|---|
| Cytosine deaminase | Deamination | $[^3H]$-5-fluorocytosine | Cell Culture study | 128 |
| | | $[^{19}F]$-5-fluorocytosine | MRS | 129 |
| Herpes-simplex virus type 1 thymidine kinase (HSV1-tk) | Phosphorylation | $[^{131}I]$FIAU, $[^{14}C]$FIAU | SPECT, gamma camera | 158 |
| | | $[^{131}I]$FIAU | SPECT, gamma camera | 159 |
| | | $[^{124}I]$FIAU | PET | 160 |
| | | $[^{123/125}I]$FIAU | Gamma camera | 161 |
| | | $[^{123}I]$IVDU, $[^{125}I]$IVFRU, $[^{125}I]$IVFAU, $[^{125}I]$IVAU | Cell Culture | 162 |
| | | $[^{125}I]$FIAU, $[^{125}I]$FIRU | Cell Culture | 163 |
| | | $[^3H]$FFUdR | Cell Culture | 164 |
| | | $[^{14}C]$GCV, $[^3H]$GCV | Autoradiography | 165, 166, 167 |
| | | $[^{18}F]$GCV | PET | 167, 168 |
| | | $[^{18}F]$PCV | PET | 135 |
| | | $[^{18}F]$FHPG | PET | 169, 170, 171, 172, 173 |
| | | $[^{18}F]$FHBG | PET | 174, 147 |
| Mutant Herpes-simplex virus type 1 thymidine kinase (HSV1-sr39-tk) | Phosphorylation | $[^{18}F]$PCV | Cell culture, PET | 131, 144, 147 |
| | | $[^{18}F]$FHBG | PET | 148 |
| Dopamine2 receptor | Receptor-ligand | $[^{18}F]$FESP | PET | 133, 144, 147, 148 |
| Mutant Dopamine2 receptor | Receptor-ligand | $[^{18}F]$FESP | PET | 134 |
| Somatostatin receptor | Affinity binding | $[^{111}In]$DTPA-D-Phe$^1$-octreotide | Gamma camera | 175 |
| | | $[^{64}Cu]$-TETA-octreotide | Tumor uptake study | 176 |
| | | $[^{188}Re]$-somatostatin analogue, $^{99\,m}Tc$ somatostatin analogue | Gamma camera | 177, 136 |
| Oxotechnetate-binding fusion proteins | Binding via transchelation | $[^{99\,m}Tc]$ Oxotechnetate | Autoradiography, Gamma camera | 151 178 |
| Gastrin releasing peptide receptor | Affinity binding | $[^{125}I]$-mIP-Des-Met$^{14}$-bombesin(7-13)NH$_2$ | Cell culture | 179, 180 |
| | | $[^{125}I]$bombesin, | Cell Culture | 181 |
| | | $[^{99\,m}Tc]$-bombesin analogue | Cell Culture | 182 |

TABLE 2-continued

Summary of Reporter gene/probe systems

| Reporter gene | Mechanism | Imaging agents | Imaging | References |
|---|---|---|---|---|
| Sodium/Iodine symporter (NIS) | Active symport | [$^{131}$I] | Gamma camera | 183, 184 |
| Tyrosinase | Metal binding to melanin | Synthetic metallomelanins [$^{111}$In], Fe | Cell culture/MRI | 185 186 |
| Green Fluorescent protein (GFP) | GFP gene expression resulting in fluorescence | Fluorescence | fluorescence microscopy | 187, 153, 188, 189, 190, 191, 192 |
| Luciferase (firefly) | Luciferase - luciferin reaction in presence of $Mg^{2+}$ | Bioluminescence | Charge coupled device (CCD) camera | 152, 193 |
| Cathepsin D | Quenched NIRF fluorochromes | Fluorescence activation | CCD camera | 194, 195, 196 |
| β-galactosidase | Hydrolysis of β-glycoside bond | {(1-(2-(b-galactopyranosyloxy)propyl)-4,7,10-tris(carboxymethyl)1,4,7,10tetra-azacyclododecane)gadolinium(III) or EgadMe | MRI | 149 |
| Engineered transferrin receptor (TfR) | Receptor-ligand, internalization | Superparamagnetic iron Tf-MION Oxide-tran | MRI | 150 |

EXAMPLE 5

The androgen-dependent (AD) phase of prostate cancer requires a functional androgen receptor (AR) and physiological levels of its ligand dihydroxytestosterone (DHT). Prostate cancer eventually transitions to androgen-independent (AI) growth after androgen withdrawal (i.e., castration). A major issue is whether AR is functional in AI cancer. We employed gene-expression based molecular imaging and chromatin immunoprecipitation (ChIP) to study AR dynamics during cancer progression in SCID mice bearing human prostate cancer xenografts. A charge-coupled device optical imaging system and an adenovirus-based, prostate-specific imaging vector were used to visualize the loss of AR activity after castration and restoration of activity upon transition to AI growth. The imaging signal in AI cancer correlated with two benchmarks of AR function in AD cancer: nuclear localization of AR and rising prostate specific antigen (PSA) levels. Chromatin immunoprecipitation (ChIP) data suggest that AR is initially bound to the endogenous PSA enhancer/promoter in AD tumors, releases from the DNA upon castration, but rebinds in the AI state. RNA polymerase II does not dissociate from the PSA gene after castration but its preferred distribution changes from coding regions to the promoter, potentially facilitating the AI transition. Our study demonstrates that AR is functional in and therefore likely to facilitate the AI phase of prostate cancer.

Prostate cancer growth is initially dependent upon the androgen receptor (AR) (Gelmann 2002), a member of the steroid receptor subfamily of nuclear receptors (Freedman 1999). In the presence of its ligand, dihydroxytestosterone (DHT), AR moves from the cytoplasm to nucleus, binds to 15-bp DNA elements (AREs) in enhancers or promoters, and activates expression of genes involved in prostate metabolism. Prostate cancer initially ceases growth with treatments that lower the concentration or effectiveness of DHT. The cancer eventually progresses from this androgen-dependent (AD) state to an androgen-independent (AI) state upon failure of androgen blockade therapies (Abate-Shen and Shen 2000; Feldman and Feldman 2001; Arnold and Isaacs 2002). AR is known to be expressed, and sometimes overexpressed, in many AI cancers (Visakorpi et al. 1995; Gregory et al. 2001) but it has not been shown to be functional. The functionality is an important issue. If AR transcriptional activity is resuscitated in the ligand-deprived environment it would provide a rationale for progression of AI cancer.

New molecular imaging technologies have made it possible to non-invasively visualize gene activity in real time in living subjects (Contag et al. 2000; Herschman et al. 2000; Contag 2002; Massoud and Gambhir 2003). The development of gene expression- and vector-based imaging approaches permits repetitive and quantitative measurements of gene regulation in a spatial and temporal fashion. These technologies include optical imaging with cooled charge coupled devices (CCD) (O'Connell-Rodwell et al. 2002) and radionuclide approaches such as positron emission tomography (PET) and single photon emission-computed tomography (SPECT) (Gambhir 2002). The pioneering studies in this area originally used potent but constitutive regulatory elements to drive levels of reporter gene expression that could be detected by CCD or radionuclide technologies.

Our goal was to monitor AR-mediated transcription during the progression of prostate cancer to the AI state in living animals. We employed CCD optical imaging of firefly luciferase because the short half-life of luciferase in conjunction with highly active reporter genes facilitates dynamic measurement of expression occurring over weeks in living animals (Wu et al. 2001a). A major challenge in creating such a system was to generate a robust, prostate-specific, reporter cassette that could detect optical signals in a tumor throughout the course of cancer and respond to changes in AR activity. A second challenge was to correlate the transcriptional activity with benchmarks such as AR nuclear localization and binding of AR to endogenous promoters. The correlation would ensure that the optical signals were accurately reporting molecular events. We focused our efforts on the prostate specific antigen (PSA) gene because of its AR-responsiveness and prostate specificity (Cleutjens et al. 1996b).

PSA is a secreted kallikrein protease widely used for evaluating treatment and progression of cancer although it has some drawbacks in prognostic utility (Bok and Small 2002). The PSA promoter and enhancer have been extensively delineated. Both the promoter and enhancer contain AREs necessary for transcriptional activity in AD cancer cell lines like LNCaP (Pang et al. 1995; Cleutjens et al. 1996a; Schuur et al. 1996; Cleutjens et al. 1997a; Cleutjens et al. 1997b; Pang et al. 1997; Zhang et al. 1997). A 440-bp core segment of the enhancer plays the major role in androgen-responsiveness (Cleutjens et al. 1997b). This core segment contains a cluster of AREs, which bind AR cooperatively and contribute synergistically to gene expression (Huang et al. 1999; Reid et al. 2001).

We previously exploited the synergistic nature of AR action to augment the AR-responsive activity of the PSA enhancer (Wu et al. 2001b). Our effort was designed to track AR activity in cancer via molecular imaging. We re-engineered the PSA regulatory region by duplicating the core portion of the PSA enhancer and by removing non-essential DNA between the enhancer and proximal promoter. This strategy generated a chimeric construct, termed PBC, which maintained low basal expression in non-prostate tissues but enhanced prostate-specific, AR-responsive activity by 20 fold.

The enhanced activity and specificity of the chimeric constructs were retained in an adenoviral vector expressing firefly luciferase. The adenovector bearing this "first generation" imaging cassette, AdPBC, was able to detect distal metastatic lesions in SCID mouse xenograft models upon intratumoral or systemic injection via tail veins, and visualization with a cooled CCD optical imaging system (Adams et al. 2002). Although the duplicated enhancer provided a significant gain in activity versus the original PSA enhancer, the overall activity was only about 1-5% that of CMV in side-by-side comparisons. This low level of activity made it difficult to dynamically monitor the androgen-response due to the extended time frames required to observe a firefly luciferase signal.

To further improve the activity we employed a strategy termed two-step transcriptional activation (TSTA). The concept of TSTA was based on an approach originally used to identify enhancers in *drosophila* (Brand and Perrimon 1993). In our TSTA system, the PSA regulatory region was used to express the potent artificial transcription activator GAL4-VP16. GAL4-VP16 acts on a GAL4-responsive firefly luciferase reporter gene, increasing expression well beyond that observed with reporter constructs bearing the PSA regulatory region alone (Iyer et al. 2001). We optimized the system by using GAL4-derivatives containing one, two and four VP16 (VP1, 2 and 4) activation domains, which acted on reporters containing one, two, five and nine GAL4 sites (G1, 2, 5 and 9) (Zhang et al. 2002). Our analysis indicated that the optimal system comprised the augmented PSA enhancer, PBC, driving GAL4-VP2 on a G5 promoter. This approach resulted in robust amplification of expression in cell culture, while maintaining prostate and ligand response. The optimal system displayed activities significantly higher than the CMV enhancer-driven firefly luciferase (Iyer et al. 2001; Zhang et al. 2002).

In this paper we incorporated the optimal TSTA system into a replication deficient adenovirus using the simplified recombination system described by Vogelstein and colleagues (He et al. 1998). We chose adenovirus as a vector because it has high infection efficiency and is widely used in gene transfer studies into animals and humans (Pfeifer and Verma 2001). We injected the virus into AD and AI tumors implanted into SCID mice. We demonstrate the ability to image activation, inactivation and reactivation of AR activity during cancer progression. We coupled the imaging with immunohistochemical staining and chromatin immunoprecipitation of AR on the PSA regulatory region in the various stages of tumorigenesis. We generate strong support for the concept that AR is fully active in AI cancer. Our ChIP data also suggest a model whereby the transcription complexes on AR-responsive genes do not disappear in the absence of androgen but remain marginally active and poised to resume full activity in the AI state.

Materials and Methods

Adenovirus Constructs

AdTSTA was generated from the optimal TSTA plasmid (Zhang et al, 2002). A second NotI site 5' from the PBC enhancer was removed to create unique NotI site in the vector. A SalI-NotI fragment containing the core BCVP2G5-Luc fragment was excised by NotI and partial SalI digestion and inserted into the SalI-NotI site of pShuttle vector (Q-Biogene, Carlsbad, Calif.), which was then incorporated into the adenovirus vector AdEasy™ through homologous recombination. AdCMV was generated as previous described (Adams et al. 2002). The viruses were packaged and propagated in 293A cells (293 cell line stably expressing the E1A gene). The virus was scaled up, purified via a CsCl gradient and titered by plaque assays on 293 monolayers (infectious units=plaque-forming units). Virus is stored at ~1011 pfu/ml in 10 mM Tris-HCl, 1 mM $MgCl_2$, and 10% glycerol.

Cell Culture and Xenografts

The human prostate cancer cell line LNCaP was grown in RPMI 1640 supplemented with 10% Fetal Bovine Serum and 1% Penicillin/Streptomycin solution. HeLa, MCF-7, and HepG cells were cultured in DMEM with 10% Fetal Bovine Serum and 1% Penicillin/Streptomycin. Prior to transfection, cells were transferred for 24 hours into medium containing 5% charcoal stripped serum (Omega Sci. Tarzana Calif.). The synthetic androgen Methylenetrienolone (R1881; NEN Life Science Products, Boston, Mass.) was added to "ligand positive" samples where indicated.

Human prostate tumor xenografts were generated on SCID mice as previously described (Klein et al. 1997). Briefly, approximately $1 \times 10^6$ LAPC-9 tumor cells generously provided by Dr. Charles Sawyers were mixed 1:1 with Matrigel (Collaborative Research, Bedford, Mass.) and implanted subcutaneously on the left flank of male SCID (scid/scid) mice. The AI sublines were passaged several rounds in castrated male mice. Single-cell suspension cultures were maintained on PreBM/GM media (Clonetics, Walkersville Md.). Alternatively, tumors were extracted from founder mice, minced into ~0.2 mm cubes, bathed in matrigel, and implanted subcutaneously onto the left flanks of SCID mice.

Virus Activity Assays

For luciferase assays, the cultured cells were infected with AdTSTA or AdCMV at an MOI of 0.1. After 48 hours, the cells were harvested and lysed using the passive lysis buffer provided in the firefly luciferase assay kit (Dual-Reporter Luciferase Assay System, Promega, Madison, Wis.). Firefly luciferase activities of 5% of the cell lysates supplemented with 100 µl of D-luciferin were measured using a luminometer (Lumat 9507, Berthod Germany) with an integration time of 10 sec.

Immunoblot Analysis of GAL4-VP16 Expression

LNCaP cells were grown in 10-cm dishes and infected with AdTSTA at MOI 10. Forty-eight hours later the cells were harvested and lysed with RIPA buffer (10 mM Tris-HCl, 150 mM NaCl, 0.1% SDS, 1% DOC, 1 mM EDTA and 1% NP40). Protein concentrations of the extracts were normalized (Bio-Rad Dc protein assay Kit), the samples were fractionated on 4-15% gradient acrylamide gels (Bio-Rad, Hercules, Calif.)

and subjected to immunoblot analysis with rabbit polyclonal antibodies generated against intact GAL4-VP16 or loading control proteins.

CCD Imaging to Detect in vivo Luciferase Expression

For the naïve mice, 107 pfu of AdTSTA or AdCMV suspended in 100 µl phosphate buffered saline (PBS) was injected via the tail vein. For the LAPC9 xenografts, a total of 107 pfu of AdTSTA or AdCMV in 40 µl PBS was injected directly into the 0.5-cm diameter tumor xenografts at multiple locations. To ensure adequate distribution throughout the tumor, the injection was carried out twice on two sequential days. The virus was allowed to express the encoded genes and distribute throughout the tissue for 3-4 days prior to imaging. At the days specified in the figures, the mice were anesthesized and injected with ~150 mg/kg D-Luciferin (approximately 3 mg/mouse). Light signals (CCD images) were obtained using a cooled IVIS CCD camera (Xenogen, Alameda, Calif.) and images were analyzed with IGOR-PRO Living Image Software, which generates a pseudoimage with an adjustable color scale. We determined the maximum photons/second of acquisition/cm2 pixel/steridian (sr) within a region of interest to be the most consistent measure for comparative analysis. The imaging results correlated closely with luminometry of tissue extracts. Typically our acquisition times ranged from 1 to 10 seconds. These acquisition times were valid in tumors injected only 2 days prior to imaging.

Tumor Immunohistochemical Analysis

Immunohistochemistry was performed on paraffin-embedded tumor sections with antigen retrieval. Tissue sections were incubated at 4° C. overnight with anti-AR 5 µg/ml (UpState, Charlottesville, Va.). After stringent blocking, washing and incubation with multi-link (BioGenex, San Ramon, Calif.) and alkaline phosphatase label for 20 min at room temperature, sections were washed and developed according to the manufacturer's instructions (BioGenex).

Tumor Chromatin Immunoprecipitation

Tumors were extracted from the mice and washed with ice cold PBS. The tumors were quickly minced and immersed in 1% formaldehyde solution, where they were further minced and homogenized using a glass dounce. The total incubation in formaldehyde solution was for 30 minutes. Prior to sonication, the cell suspensions were washed 10 minutes each in solution I containing 0.25% Triton, 10 mM EDTA, 1 mM EGTA and 10 mM HEPES, pH 7.5, and in solution II containing 0.2 M NaCl, 1 mM EDTA, 1 mM EGTA and 10 mM HEPES, pH 7.5. Extracts were obtained by 8×15 sec sonication in lysis buffer containing 1% SDS and 10 mM EDTA using a Fisher Scientific Model 550 sonicator at setting 4 with a microtip. Chromatin was purified from insoluble debris by micro-centrifugation at 15,000 rpm for 20 min.

To perform immunoprecipitation, the chromatin was diluted 1:7 in dilution buffer containing 70 mM HEPES, pH 7.5, 2.5 mM NaCl, 1.5 mM EDTA, 1.5% Triton and 0.6% deoxycholate. The extracts were pre-cleared with pre-immune IgG together with Sepharose A or G agarose beads (Amersham, Piscataway, N.J.) for 1 hour at 4° C. Pre-cleared extracts were incubated with 4 to 6 µg of specific antibodies at 4° C. overnight followed by incubation with 30 µl of agarose A or G beads for 1 hour the next day. The antibodies included the N20 and C19 AR antibodies from Santa Cruz, Biotech; the pol II CTD8WG16 monoclonal from QED Bioscience (San Diego, Calif.); and a TFIIB antibody generated in our lab. The beads were washed twice with buffer containing 50 mM HEPES, pH 7.5, 0.15 M NaCl, 1 mM EDTA, 1% Triton, 0.5% deoxycholate and 0.15% SDS followed by wash with LNDET buffer containing 0.25 M LiCl, 1% NP40, 1% DOC, 1 mM EDTA and 10 mM Tris, pH 8.0. The protein-DNA complexes were then eluted from the beads with 30 to 50 µl elution buffer containing 1% SDS and 1 mM NaHCO3. The eluates were diluted with TE and incubated at 65° C. overnight to reverse the cross-link. The samples were then treated with proteinase K at 100 ng/µl and RNAase A for 1 h at 55° C. and then extracted with phenol. The DNA was then precipitated with ethanol, resuspended in 30 µl water and subjected to PCR analysis. Typically one 1 cm tumor yielded enough material for 6 PCR reactions. The onput sample in the data shown in the ChIP experiments was typically 2% of the DNA added to a ChIP reaction.

The PCR analyses were performed with four sets of 32P-labeled primers:

```
Enhancer:
5'GGTGACCAGAGCAGTCTAGGTG3'  (SEQ ID NO:11)
and
5'TGTTTACTGTCAAGGACAATCGAT3'  (SEQ ID NO:12)

Promoter:
5'GTATGAAGAATCGGGGATCGT3'  (SEQ ID NO:13)
and
5'GCTCATGGAGACTTCATCTAG3'  (SEQ ID NO:14)

Middle:
5'TATGCTTGGGGACACCGGAT3'  (SEQ ID NO:15)
and
5'TTAGAGCTGGAGTGGAAGGATAT3'  (SEQ ID NO:16)

Exon 5:
5'TAATGGTGTGCTTCAAGGTATCACG3'  (SEQ ID NO:17)
and
5'GTGTCCTTGATCCACTTCCGGTAAT3'  (SEQ ID NO:18)
```

The PCR cycling protocol was 40 sec at 94° C., 3 minutes at 75° C., 2 minutes at 65° C., followed by 20 cycles of 40 sec at 94° C., 1 minute at 65° C. and 2 minutes at 72° C., followed by a 10 minute extension at 72° C. The PCR products were phenol-extracted, separated on 4% polyacrylamide gels and autoradiographed by exposure to XAR-5 film.

Results

The Adenovector TSTA Imaging System

FIG. 22 illustrates the adenoviral-based TSTA cassette employed in our study. A modified chimeric PSA promoter containing two copies of the AR-responsive core PSA enhancer is used to drive expression of the fusion protein GAL4-VP2, bearing two copies of the VP16 activation domain. This strategy ensures robust, AR-mediated, prostate-specific expression of GAL4-VP2. In the second step, GAL4-VP2 binds to five GAL4 binding sites positioned upstream of the adenovirus E4 core promoter and activates high levels of firefly luciferase in prostate-derived tissues. Luciferase is measured in cell culture by luminometry and in vivo in D-Luciferin-injected live animals using a cooled CCD optical imaging system (Wu et al. 2001a). The two expression cassettes were joined in a divergently-expressed orientation in the genome of Adenovirus serotype 5, with the E1 and E3 coding regions deleted, which renders the packaged virus replication deficient (He et al. 1998). To validate the ability of this imaging system to accurately detect AR activity we tested its activity, cell specificity and response to androgen in cell culture and then addressed the same criteria in SCID mice with human prostate cancer xenografts. Finally, we correlated the imaging activity with serum PSA levels, AR nuclear localization and binding of AR to the endogenous PSA gene in tumors harvested from the SCID mice.

Prostate Cancer Specificity of AdTSTA

To assess the expression and androgen responsiveness of the AdTSTA system in cell culture, we infected the model androgen dependent prostate cancer cell line, LNCaP, with AdTSTA (FIG. 23A). Expression of GAL4-VP2, and firefly luciferase were activated significantly in the presence of the synthetic androgen agonist R1881. The largest fold-increase of luciferase activity was observed at the 48-hour time point (FIG. 23A bottom), which correlated with the appearance of GAL4-VP2 by immunoblot analysis (FIG. 23A, top).

The AdTSTA system maintained cell selectivity in culture (FIG. 23B). An example of these findings is shown for cells derived from prostate cancer (LNCaP), liver (HepG) and cervical cancer (HeLa) (FIG. 23). LNCaP is an androgen-dependent prostate cancer cell line (Horoszewicz et al. 1983), which contains AR and secretes PSA (Tilley et al. 1990; Montgomery et al. 1992). AR expression is not observed in HeLa and HepG. PCR analysis demonstrated that viral infectivity was similar within a two-fold range among the cell lines we tested. The LNCaP cells displayed significantly higher firefly luciferase activity than HeLa and HepG and responded well to the androgen agonist R1881. MCF-7 cells, an AR expressing breast cancer cell line was also tested but displayed only a low basal level of TSTA expression in the presence of R1881. Thus, the AdTSTA system responds to AR specifically in prostate cells.

High levels of luciferase are necessary to observe signals from cell-specific promoters. Previous engineering of the PSA enhancer led to the adenovector, AdPBC, which expressed firefly luciferase in a prostate specific manner but with only 5% the activity of CMV. The low level of activity was suitable for initial in vivo studies but two problems limited its utility in evaluating AR function in real time: The extended time frame necessary to observe firefly luciferase expression in tumors and the long acquisition times on the CCD optical imaging system. Side-by-side comparison (FIG. 23B) demonstrated that AdTSTA displayed a ligand induced firefly luciferase activity 10-fold greater than AdCMV (FIG. 23B) and nearly 200-fold greater than AdPBC. This gain of activity reduced the time frame required to observe a robust CCD signal from a week to two days, and reduced average CCD acquisition times on average from 5 minutes to a few seconds, thereby permitting us to perform the analysis described below.

The specificity was then evaluated in vivo by tail vein injection into non-tumor bearing SCID mice. FIG. 24 shows that tail vein injection of AdCMV leads to significant expression in the liver of SCID mice lacking tumors. The figure presents CCD imaging data from a representative mouse at day 14. AdCMV generated a strong liver signal (~106 photons/sec/cm2/sr) on day 6, the signal peaked at day 14 (107 photons/sec/cm2/sr) and then decayed slightly at day 22, when the experiment was terminated. The liver signal was confirmed by imaging the individual organs after sacrifice. In contrast to the data with AdCMV, injection with the same dose of AdTSTA did not result in detectable liver signals in male mice lacking tumors.

The AdCMV and AdTSTA viruses were then injected intratumorally into mice bearing the LAPC9 xenografts (FIG. 24B). LAPC9 is a human prostate cancer derived from a bone metastasis, which was then implanted into SCID mice (Klein et al. 1997). The tumor expresses PSA and wild-type AR. LAPC9 tumors respond to androgen in vivo. Upon castration of male mice, the tumor transiently halts growth and gradually transitions into the AI state. Continued passage of the AI tumors in castrate mice generates a stable AI model, which expresses AR and PSA. We employed an adenovector because of the flexibility it offered, i.e., testing a wide variety of tumors, and because of the difficulty in establishing xenografts that express the TSTA reporter system in a stable manner.

Direct intratumoral injection of the viruses into LAPC9 AD xenografts followed by CCD imaging demonstrate that the AdTSTA is routinely twice as active as AdCMV in the tumors (FIG. 24B). Typically, injection of $10^7$ pfu of AdTSTA generated a robust signal. Therefore, we were able to reduce the amount of virus versus the 109 pfu employed in our previous imaging study with AdPBC (Adams et al. 2002).

Virus leakage of AdCMV resulted in signals emanating from the liver. The liver signal was confirmed after sacrifice by imaging the individual organs. In contrast, the specificity of the AdTSTA system, whose tissue distribution parallels that of AdCMV, precluded liver expression.

We note that the AdTSTA-injected mice did not display a signal in the prostate either by tail vein or intratumoral injection. Under the current conditions we are not achieving substantial delivery to the prostate probably due to virus sequestration in liver and lung (Wood et al. 1999). We did not pursue this issue because our goal was to study AR activity in the xenograft. However, we are currently attempting to discern the specific injection routes and protocols necessary to obtain prostate infection.

AR Signaling is Active in AI Tumors

To demonstrate the androgen responsiveness of the tumors we first castrated male mice bearing LAPC9 AD tumors and measured serum PSA levels (FIG. 25). A decrease or plateau of serum PSA is indicative of successful hormone blockade therapy in humans. The xenograft data revealed that the PSA levels ceased rising and dropped slightly beginning on day 1 and remained flat for many days post-castration, recapitulating the clinical response of androgen blockade therapy. At later time points the PSA began to rise as tumors transitioned from AD to AI, an issue that is discussed further in a later figure.

Analysis of AD and castrated AD (ADc) tumors revealed that the imaging signal responded well to castration (FIG. 26, center panels). The AdTSTA-injected tumors typically emitted >107 photons/sec/cm2/sr on day 4 after virus injection. Castration on day 4 led to a >10-fold drop in the imaging signal by day 10 (FIG. 26 left panels: AD vs. ADc, p=0.01). In contrast, AdTSTA displayed robust activity in established AI mice. Interestingly, the signal actually increased from day 4 to day 10 in AI, whereas no significant increase was observed in AD over the same time frame. These data indicate that the AR-responsive TSTA system is specifically responding to the loss of AR activity in the ADc tumor but that activity is regained in established AI tumors. We will show below that this loss and gain of activity correlates with the drop and rise of PSA in ADc and AI tumors, respectively.

The imaging activity correlates well with the subcellular locale of AR (FIG. 26 right panels). AR is known to localize predominantly to the nucleus in the presence of androgen. In the absence of androgen, AR becomes more diffuse and localizes to both the cytoplasm and nucleus (Gregory et al. 2001). Immunohistochemical analyses of tumors from the sacrificed LAPC9 animals showed that AR was tightly localized to the nucleus of AD tumors, became diffuse in ADc, but returned primarily to the nucleus in established AI tumors. The staining in ADc was heterogeneous with a small number of cells showing nuclear staining but most showing a diffuse pattern of nuclear and cytoplasmic staining.

Taken together the imaging and cytology data suggest that AR has resumed functioning in AI cancer. However, numerous other proposal have been made to explain how androgen-responsive genes might function in cells lacking physiological levels of androgen. For example, NF-κB has been proposed to bind regulatory regions of androgen-responsive genes and might substitute for AR in AI cancer (Chen and Sawyers 2002). However, the predominant nuclear location of AR in AI tumors suggest AR may be functional. One prediction of this hypothesis is that AR should be bound directly to responsive enhancers and promoters in AI cancer.

Transcription Complex Assembly in Tumors Correlates with the Imaging Signal

To address our hypothesis we measured AR binding to the endogenous PSA regulatory region using chromatin immunoprecipitation (FIG. 27). The PSA enhancer and promoter have been well delineated. Previous chromatin immunoprecipitation experiments performed in cell culture have revealed AR and RNA polymerase II (pol II) binding to the enhancer and promoter in LNCaP cells (Kang et al. 2002; Shang et al. 2002). We confirmed these results in LNCaP cells and then used that knowledge to analyze AR and pol II binding to the PSA gene in the context of AD and AI tumor samples derived from LAPC9 tumors. The tumor ChIP experiments were significantly more difficult to perform than the cell culture ones because the tumor is highly heterogeneous, solid tissue. We rapidly minced and crosslinked the tissue during tumor harvest and performed sonication in detergent containing high levels of SDS followed by ChIP in the presence of low SDS and high levels of deoxycholate.

We analyzed AR binding to four regions of the gene: The enhancer, the promoter, a region located between the enhancer and promoter, and downstream exon 5 (FIG. 27). We predicted that AR would bind only to the enhancer and promoter. FIG. 27 demonstrates that our procedure worked reasonably well and AR binding was detectable above background to the enhancer and promoter in both the AD and AI samples, although it was more evident in AD in the experiment shown. Each experiment was performed three times and specific signals were confirmed by comparing the AR-antibody signal to the background observed in a mock immunoprecipitation with IgG. The promoter signals were less reproducible than those on the enhancer region (see graph). When normalized to the signal from onput DNA in the ChIP reaction, and averaged among experiments performed with different tumors, the binding to the enhancer in AI tumors was only slightly lower than in AD tumors (see graph). In contrast, upon castration (ADc) AR binding to the enhancer and promoter decreased about 4-fold vs. AD tumors. There is still evidence of some specific AR binding in ADc as the signals on the enhancer and promoter are above the IgG background. The residual binding agrees with the cytology data in which some AR remains in the nucleus even in ADc. Furthermore, the PSA levels do not decrease to baseline in ADc but simply drop transiently as the tumor begins to transition to AI.

To analyze how preinitiation complexes respond to the presence and absence of AR we measured binding of pol II and a representative general factor TFIIB (FIG. 28). We predicted that poL II would be distributed among the promoter and downstream exon 5, and that it should disappear upon castration. However, the binding pattern was more complicated. Pol II binding was observed at both the promoter and downstream exon 5 in the AD tumors but its distribution was skewed. A scatter plot of the ratio of pol II signal at exon 5 vs. the proximal promoter shows that in AD tumors the pol II is primarily at exon 5. We interpret the binding to exon 5 as an elongating polymerase. The signal is specific because it is found only weakly at the enhancer and not in the intervening region. Binding by pol II to the enhancer was previously observed by Brown and colleagues in their LNCaP cell culture study (Shang et al. 2002). The authors interpreted this phenomenon as evidence of DNA looping between the enhancer and proximal promoter. Although we observe binding of pol II to the enhancer, the binding to promoter and exon 5 is stronger Remarkably, upon castration, pol II remained bound to the gene. However, as shown by the scatter plot, pol II was localized primarily at the promoter versus exon 5 in four separate experiments. The AI tumors were more complex; different experiments revealed more exon 5 signal and some less. This variation was in contrast to TFIIB, which was present at equal levels at the promoter in AD, ADc and AI in all experiments that we performed. Our interpretation of these findings is that the transcription complex remains intact after androgen deprivation but a greater fraction of pol II is not actively transcribing in ADc vs. AD. This observation correlates well with the drop in the ADc imaging signal measured by CCD and the drop or plateau in serum PSA levels measured by ELISA. The pol II position in AI tumors is more heterogeneous but modestly skewed towards exon 5.

Visualizing the AD-AI Transition in Real Time

In a human, the failure of androgen deprivation therapy occurs gradually over a period of time that can vary from weeks to years. The LAPC9 models were originally adapted to an androgen-rich environment in immunodeficient mice and then trained to grow in castrate or female mice. We have found that the transition time in animals occurs more rapidly as the tumor grows larger. Typically we begin an experiment when a tumor reaches 0.5 cm but it grows to 1.5 cm within two or three weeks. Usually we have to sacrifice the animals before the transition occurs to adhere to the 1.5-cm tumor size limitation set by our institutional animal care guidelines. However, some individuals transition faster and in these we are able to monitor the transition in real time, as opposed to studying established AI tumors as we described above. The data below illustrate a typical example of an animal that underwent the transition prior to sacrifice (FIG. 29).

In this animal, we injected the AdTSTA virus, imaged the mice four days later, and then castrated the animal when the tumor reached 1 cm. We found that the PSA levels initially dropped 2.4-fold by day 10, six days post-castration, and then began rising again up to day 17, when we had to sacrifice the animal because the tumor had reached the size limit.

Over this same time frame, the imaging signal was high on day 4 reached a minimum by day 10 and then gradually rose again by day 17 (FIG. 29, top). ChIP and immunohistochemical analyses on the tumor from the sacrificed animal revealed that AR had resumed its predominantly nuclear location and was bound primarily to the PSA enhancer, while pol II was found predominantly in the elongating state at exon 5 (FIG. 29, bottom). In short, we show an example, where AR has adapted to the androgen-deprived environment and resumed activity in the AI state as measured by imaging, immunohistochemistry and ChIP.

Discussion

Our study reports the development of a paradigm to study AR dynamics during prostate cancer progression. Cooled-CCD optical imaging is an emerging technology for monitoring transcriptional activity during development, differentiation and disease (Contag et al. 2000; Contag 2002; O'Connell-Rodwell et al. 2002). The ability to employ CCD imaging requires potent reporter systems that can sensitively monitor transcriptional events in living animals. We employed an adenovector-based imaging cassette, which used the TSTA scheme to measure signals that impacted the AR-signaling pathway. The TSTA system is robust and can dynamically monitor a specific androgen response in vivo in the context of a tumor.

The goal of our study was to determine whether AR was functional in AI cancer. The natural response of an AD tumor to androgen deprivation is transition to an AI state. We found that the AdTSTA imaging system could detect the decreased AR activation caused by removing the systemic source of androgen via castration. We further showed that the signal could be restored in established AI tumors. Finally, we could monitor the loss and gain of androgen responsiveness during a transitory period within an animal. While this transition is significantly more rapid than in a patient, it nevertheless demonstrates the ability of a potent but sensitive imaging system to monitor physiological changes that accompany tumorigenesis.

The imaging results paralleled several biological and mechanistic benchmarks of AR function. The optical signals paralleled the halt (or decrease) in rising PSA associated with the androgen depletion by castration. We note that castration is unable to completely block progression of well-vascularized prostate xenografts, which ultimately return to the AI state. Also, the correlation was not exact, as the PSA levels decreased on average 2 fold but the imaging signals decreased over 10 fold within the same time frame. We do not yet understand the discrepancy but it may simply reflect the relative half-lives of PSA vs. firefly luciferase. Alternatively, TSTA is an unusually sensitive reporter system designed to respond robustly to androgen. It may be responding more dramatically to changes in the cascade of events that control AR activity. There is a delay in cell culture between the administration of androgen and the appearance of a peak luciferase signal. This delay is due in part to the time required to achieve steady-state activation of the reporter and also to the two step nature of the imaging amplification system. Nevertheless, within the time frames used here, the trends of the imaging and PSA signals were remarkably consistent.

The imaging signal also correlated somewhat with the cellular distribution of AR, which was nuclear in AD and AI but became diffuse in ADc animals. We note that the levels of AR drop 2-fold in ADc mice but rise an again in the AI state. Finally, the optical signal correlated with the AR binding pattern to the endogenous PSA enhancer, which decreased in ADc but increased again in AI cancer. While the cellular localization and enhancer binding of AR clearly cycled, the effects were not absolute. As mentioned above, the PSA levels do not disappear but transiently plateau or drop while the tumors adapt. This could explain the residual AR signals in the ChIP experiments. We do not understand yet how the tumors adapt and this is the subject of much speculation and research in the field (Grossmann et al. 2001).

Indeed, one of the key issues in the prostate cancer field is whether recurrent cancer truly employs AR to drive its activity. Our study shows that AR is functional in AI cancer. Although we have only studied the PSA gene we imagine that the resuscitation of AR activity is paralleled on the other genes used by AR in AD cancer growth. Several potential mechanisms that might allow AR function in AI cancer have emerged over the last few years.

Isolation of the AR gene from tumors and cell lines suggests that certain mutations may permit it to respond to alternate ligands and even antagonists like flutamide (Barrack 1996). AR somatic mutations in the Transgenic Adenocarcimona of Mouse Prostate (TRAMP) model revealed a correlation between reduced androgen dependence and mutations in regions of AR known to interact with co-activators (Han et al. 2001).

Overexpression of AR has also been observed in AI cancer. For example, analysis of patient samples revealed that the AR gene is amplified in a subset (~30%) of AI tumors (Visakorpi et al. 1995). However, steady state levels of AR are also enhanced in patient samples, cell lines and xenografts even when the gene is not amplified (Gregory et al. 2001; Linja et al. 2001). It has been proposed that the augmented levels of AR or its co-activators can possibly drive AR function with castrate levels of ligand, in part via the principles of mass action. It has also been suggested that AR has adapted to utilize adrenal sources of androgens and possibly convert them to DHT. It is known that castration decreases circulating DHT over 10-fold but smaller effects have been observed when measuring DHT levels within the tumors (Grossmann et al. 2001).

Mitogen-activated protein kinase (MAPK) may impact AR activity. MAPK, a major signaling pathway involved in cell proliferation, has been linked to AR in numerous studies (Craft and Sawyers 1998; Abate-Shen and Shen 2000; Elo and Visakorpi 2001; Feldman and Feldman 2001; Grossmann et al. 2001; Arnold and Isaacs 2002). Elevated MAPK has been observed in advanced Prostate cancer specimens from patients and in AI xenografts (Gioeli et al. 1999; Mellinghoff et al. 2002). Also, several receptor tyrosine kinases or growth factors, which signal through MAPKs, activate AR-responsive reporter genes in an AI manner when overexpressed in cell culture (Craft and Sawyers 1998; Abate-Shen and Shen 2000; Elo and Visakorpi 2001; Feldman and Feldman 2001; Grossmann et al. 2001; Arnold and Isaacs 2002). We note that the AR in LAPC9 has not undergone mutations but its levels are slightly enhanced in AI tumors and the LAPC9 AI models used here were previously shown to display enhanced MAPK levels (Mellinghoff et al. 2002).

The relevance of AR in AI cancer is supported by several recent studies. Overexpression of murine AR from the probasin promoter in transgenic mice leads to development of high-grade prostatic intraepithelial neoplasia (PIN), which may be a precursor to prostate cancer (Stanbrough et al. 2001). Conversely, lowering AR levels by injection of a hammerhead ribozyme or antibodies targeted to AR reduces proliferation of AI LNCaP cells in culture (Zegarra-Moro et al. 2002). The effect of AR in AI cell lines apparently requires DNA binding because the PSA enhancer requires some of its natural AREs to activate reporter genes in AI LNCaP cell lines, although other transcription factors also contribute (Yeung et al. 2000). Our data provide strong direct support for the notion that AR is indeed active and bound to its target enhancers/promoters in natural tumor models of prostate cancer.

Although our data do not bear on the precise mechanism of AR function in AI cancer they provide evidence that AR is forming transcription complexes. As mentioned above, AR is bound to the PSA enhancer in AD tumors as measured by ChIP. We assume that this binding is paralleled on other AR-responsive genes but this point has not been firmly established. Castration causes much but not all AR to be removed from the PSA enhancer but it apparently rebinds in the AI state. Similarly, pol II is primarily located on exon 5 in AD and in many AI tumors, possibly indicative of an elongating polymerase. The initial loss of DHT by castration causes pol II to relocalize mainly to the promoter in ADc. This phenomenon, along with stable TFIIB binding, suggests that the transcription complexes probably remain intact in the absence of androgen, which may facilitate the reactivation of AR-mediated transcription during AI cancer.

Analysis of other genes such as á1-AT have also established that pol II can be bound with the GTFs in a quiescent state, prior to binding of activator (Cosma 2002). These data along with older studies of the heat shock locus in *drosophila* (Gilmour and Lis 1986) indicate that a pre-poised pol II may provide a mechanism for maintaining promoter accessibility during a transcriptionally inactive state. AR and pol II are known to cycle on and off the promoter during gene activation in LNCaP cells (Kang et al. 2002; Shang et al. 2002). The peaks of AR and subsequent pol II binding after androgen addition do not coincide suggesting that AR can leave while pol II is engaging the promoter. This phenomenon may be analogous to what is occurring to pol II in ADc tumors.

The chain of events that lead to the action of pol II at the PSA promoter remain to be firmly established in tumors due to the difficulty of precisely synchronizing cells in living animals. However, we have established an experimental paradigm, where we can screen tumors via gene expression-based imaging followed by detailed molecular analysis (i.e., by ChIP). We have not delved into the precise co-activators driving PSA or tumor progression because the genetic evidence linking specific co-activators to PSA expression is limited. Indeed, we have strong evidence based on RNA interference that at least one co-activator thought to allow AR function has no effect on the endogenous PSA gene. We are therefore systematically probing suspected co-activators by RNA interference to validate their roles in AR-responsiveness.

On a technical note, we have concerns about GAL4-VP16 and firefly luciferase toxicity. If the toxicity was an issue, we would predict that infected cells would die rapidly and the imaging signal would decay. However, under the conditions employed in our study we are able to obtain relatively persistent imaging signals in tumors within live animals over the course of the experiments, which can last up to a month. Also, the virus is not unusually toxic in cell culture studies, where cells appear to thrive after virus infection. We note that our ability to employ low doses of virus in the animal studies may permit a less immunogenic response and enable us to transit the system into non-SCID prostate models as well as transgenic animals. We are currently analyzing the TSTA system in lentivirus-transformed lines and in transgenic animals. One limitation of the current study is that the tumor had to be palpable to inject the virus. Lentivirus transformed tumor cell lines are expected to be more stable than adenovirus-infected cells and allow us to measure androgen-responsiveness at the earliest stages of prostate cancer growth. The use of low viral doses could also make possible the application of the system to therapeutic related research for early detection of cancer, a possibility we are currently pursuing.

EXAMPLE 6

Safe and effective prostate cancer gene therapy requires high magnitude and targeted expression in vivo. Targeted expression has the potential to minimize unwanted side effect of therapy. We improved the activity of native prostate specific antigen (PSA) promoter and enhancer by nearly 20-fold employing a chimeric enhancer manipulation strategy (Gene Ther 2001, 8:1416). Moreover, in vivo application of the prostate specific chimeric viral vector resulted in the specific localization of human prostate metastases in mouse xenograft model (Nat Med 2002, 8: 891). To accomplish efficient in vivo gene transfer we aim to improve the prostate-specific promoter activity to achieve magnitude comparable to strong viral CMV promoter. We employed a two-step transcriptional amplification (TSTA) approach, in which an artificial activator consists of GAL4 and VP16 binds upstream and activates the expression of a therapeutic or reporter gene. The specificity of TSTA is governed by the use of our modified prostate-specific promoter to express GAL4-VP16 activator. We demonstrated that TSTA system exhibits higher activity than CMV promoter but still maintained prostate specificity in cell culture transfections (Mol Ther 2002, 5:223). To optimize this system for in vivo applications, we characterized adenovirus vectors that contains the activator and the reporter component of TSTA in a single or two separate adenoviral vectors. In cell culture infection studies, we confirmed that: 1) both single and separate TSTA system exhibit higher activity than CMV, 2) both maintain androgen regulation, 3) the infection with separate vectors showed higher androgen induction than single vector in prostate cancer cells due to lower basal expression in absence of androgen and 4) high virus to cell ratio leads to diminished cell specificity and androgen regulation. Our TSTA vectors express firefly luciferase gene which can be monitored in living mice by real-time optical CCD imaging. In vivo expression of the single TSTA vector (AdTSTA-FL) exhibits cell selectivity and androgen regulation in prostate cancer xenografts and in murine prostate. Based on these promising results, we are actively investigating this TSTA transcriptionally targeted approach in gene-based therapy and diagnosis for prostate cancer.

EXAMPLE 7

Gene expression-based imaging should be a powerful tool to assess the real time response of therapy. We have applied non-invasive optical imaging to monitor HSV1 thymidine kinase suicide gene therapy in prostate cancer xenograft models. Here we report the utilization of an adenovirus-based two-step transcriptional activation (AdTSTA) system to express a potent HSV1 thymidine kinase variant (sr39tk) in the treatment of LAPC-4 prostate tumors. The TSTA system consist of an enhanced PSA promoter driving the expression of a potent synthetic transcriptional activator GAL4-VP16 which in turn activates the expression of the therapeutic gene (sr39tk) or reporter gene (firefly luciferase, FL). For in vivo applications, AdTSTA-FL and AdTSTA-tk were generated to contain the activator and the reporter/therapeutic component in a single vector. The AdTSTA mediated expression is significantly higher than comparable CMV driven vector while maintaining exquisite cell selectivity and androgen regulation. FL-based optical CCD imaging is a sensitive, facile method to sequentially monitor gene expression in living animals. Our strategy is to utilize FL mediated optical signal to measure the relative tk expression in the tumors during suicide therapy. We first demonstrated that co-infection of cells released from LAPC-4 xenografts with equivalent dosage of AdTSTA-FL and AdTSTA-tk produced luciferase activity levels that are correlated with TK protein levels. LAPC-4 tumor bearing mice were divided into 3 therapeutic groups that received intratumoral injection of equal dosage of (i) AdCMV-RL+AdTSTA-FL (control group), (ii) AdCMV-sr39tk+AdCMV-FL (CMV group), or (iii) AdTSTA-sr39tk+AdTSTA-FL (TSTA group). 7 days post viral injection, the animals were given daily intraperitoneal administration of 100 mg/kg ganciclovir (GCV) for five days. Optical imaging just prior to GCV treatment revealed that intratumoral signal in the TSTA group is more than 1 order of magnitude higher than the CMV group. Serial imaging data revealed a more precipitous loss of optical signal in the TSTA group in comparison to the CMV group in a 12 days period after GCV treatment. Detailed histological analysis revealed extensive central tumor necrosis, most dramatic in the TSTA over CMV group, and both treatment groups exhibit much greater cell death than the control group. In this report we demonstrate that TSTA system can mediate highly amplified and tissue-specific gene expression resulting in effective tumor cell killing. Moreover, non-invasive optical CCD imaging is a useful tool to monitor gene expression and therapeutic response.

EXAMPLE 8

We have previously reported the development of a Two-Step Transcriptional Amplification System (TSTA) to amplify firefly luciferase (fl) reporter gene expression in vivo (Iyer et al, PNAS, 2001). We now report the development and imaging of a novel transgenic mouse line that expresses fl transgene under the control of the Prostate-Specific promoter and VP16 transcriptional activator.

Methods

The DNA fragment PSEBCVP2-G5-fl used for injection was isolated from the plasmid vector sequence by cutting with appropriate restriction enzymes. Transgenic mice were generated in FVB mice by standard techniques. Seven founder mice carrying the transgene were outcrossed with wild-type animals to yield F1 progeny. Tails from the F1 progeny were clipped at 2 weeks of age and genotyped by PCR. The fl positive mice were imaged at different intervals of time using a cooled Charge Coupled Device (CCD) camera and D-Luciferin as the substrate (3 mg per animal, injected i.p.). The resulting bioluminescent signal was expressed as photons/sec/cm$^2$/steridian (sr).

Results

In male mice from F1 progeny, the expression of GAL4-VP16 dependent fl gene is observed to be very strong and is primarily restricted to the prostate tissue ($5 \times 10^6$ p/sec/cm$^2$/sr). In contrast, female transgenic mice show basal levels of fl expression ($5 \times 10^4$ p/sec/cm$^2$/sr). This suggests the high androgen dependency of the prostate-specific promoter. Additionally, gene expression is also observed in the ears, feet and tail of male mice ($1.7 \times 10^6$-$5 \times 10^6$ p/sec/cm$^2$/sr). Repetitive imaging over several months demonstrates persistence of the bioluminescent signal. The mice exhibit normal physical characteristics and development and do not show any deleterious effects from the transactivator.

Conclusion

We have developed a novel transgenic mouse line using the GAL4-VP16 transactivator (driven by a prostate-specific promoter) to amplify the expression of fl reporter gene and shown long-term tissue specific expression of fl. Such transgenic mouse models when coupled with other transgenic lines that spontaneously develop malignancies should play a useful role in the study of early events in cancer progression.

EXAMPLE 9

The progression of primary prostate cancer requires androgen and a functional Androgen Receptor (AR). Treatments that reduce androgen levels inhibit androgen dependent (AD) cancer progression and AR-responsive gene expression. Ultimately, the cancer regains the capacity for aggressive growth in the androgen-independent (AI) environment and AR-responsive genes are re-activated. A key issue is whether AR is directly mediating this AI response. Through extensive biochemical studies we have identified the key AR responsive elements in the Prostate Specific Antigen (PSA) enhancer. By combining enhancer modifications with two-step transcriptional activation (TSTA) approaches, we have crafted a robust, androgen-responsive optical imaging system targeted to prostate cancer cells. Our "chimeric TSTA" employs a duplicated segment of the PSA enhancer core expressing GAL4 fused to 2 VP16 activation domains. The resulting activators are targeted to reporter templates bearing 5 GAL4 binding sites upstream of firefly luciferase. The entire TSTA imaging cassette is packaged into an Adenovirus for in vivo delivery into SCID mice bearing human prostate cancer xenografts. Using cooled charge-coupled device (CCD) imaging system we observe a robust, tumor-specific luciferase signal that responds to androgen depletion in live AD animal models. Remarkably, we have also observed strong and persistent AR signaling in the AI xenografts. Following the imaging we analyzed the tumors using chromatin immunoprecipitation assays. We identified AR association with the endogenous PSA enhancer and binding of RNA polymerase II, General Transcription Factors (GTF) and the human mediator complexes to the endogenous PSA regulatory regions in both AD and AI tumors. These data combined with immunohistochemical localization studies provide mechanistic evidence that AR is fully functional in AI cancer. We have also exploited the TSTA imaging system to detect cross-talk between the AR-pathway and the MAPK signaling cascade by switching the VP16 activation domain with that of the MAPK-responsive ELK-1. Using transferrin-enhanced, liposome-assisted gene delivery, we have introduced the AdTSTA-ELK-1 into tumor xenografts through intravenous injection and obtained signals in the distally located tumors. Currently we are assessing the combined MAPK-AR effects in AD and AI xenografts. AdTSTA and AdTSTA-Elk represents a series of tools for in vivo molecular imaging and therapeutic gene targeting in prostate cancer research.

REFERENCES

1. Gambhir, S. S., Barrio, J. R., Phelps, M. E., Iyer, M., Namavari, M., Satyamurthy, N., Wu, L., Green, L. A., Bauer, E., MacLaren, D. C., et al. (1999) *Proc. Natl. Acad. Sci. USA* 96, 2333-2338
2. Tjuvajev, J. G., Avril, N., Oku, T., Sasajima, T., Miyagawa, T., Joshi, R., Safer, M., Beattie, B., DiResta, G., Daghighian, F., et al. (1998) *Cancer Res.* 58, 4333-4341
3. Tjuvajev, J. G., Finn, R., Watanabe, K., Joshi, R., Oku, T., Kennedy, J., Beattie, B., Koutcher, J., Larson, S. & Blasberg, R. G. (1996) *Cancer Res.* 56, 4087-4095
4. Zinn, K. R., Buchsbaum, D. J., Chaudhari, T. R., Mountz, J. M., Grizzle, W. E. & Rogers, B. E. (2000) *J. Nucl. Med.* 41, 887-895
5. Louie, A. H., Ahrens, E. T., Rothbacher, U., Moats, R., Jacobs, R. E., Fraser, S. E. & Meade, T. J. (2000) *Nat. Biotechnol.* 18, 321-325
6. Weissleder, R., Moore, A., Mahmood, U., Bhorade, R., Benveniste, H., Chiocca, A. & Basilion, J. P. (2000) *Nat. Med.* 6, 351-355
7. Contag, P. R., Olomu, I. N., Stevenson, D. K. & Contag, C. H. (1998) *Nat. Med.* 4, 245-247
8. Honigman, A., Zeira, E., Ohana, P., Abramovitz, R., Tavor, E., Bar, I., Zilbermman, Y., Rabinovsky, R., Gazit, D., Joseph, A., et al. (2001) *Mol. Ther.* 4, 239-249
9. Wu, J. C., Sundaresan, G., Iyer, M. & Gambhir, S. S. (2001) *Mol. Ther.* 4, 297-306
10. Yang, M., Baranov, E., Li, X. M., Wang, J. W., Jiang, P., Li, L., Moossa, A. R., Penman, S. & Hoffman, R. M. (2001) *Proc. Natl. Acad. Sci. USA* 98, 2616-2621
11. Ray, P., Bauer, E., Iyer, M., Barrio, J. R., Satyamurthy, N., Phelps, M. E., Herschman, H. & Gambhir, S. S. (2001) *Semin. Nucl. Med.* 31, 312-320

12. Cherry, S. R. & Gambhir, S. S. (2001) *Inst. Lab. Anim. Res. J.* 42, 219-232
13. Cherry, S. R., Shao, Y., Silverman, R. W., Meadors, K., Siegel, S., Cbatziioannou, A., Young, J. W., Jones, W. F., Moyers, J. C., Newport, D., et al. (1997) *IEEE. Trans. Nucl. Sci.* 44, 1161-1166
14. Gambhir, S. S., Barrio, J., Wu, L., Iyer, M., Namavari, M., Satyamurthy, N., Bauer, E., Parrish, C., MacLaren, D., Borghei, A., et al. (1998) *J. Nucl. Med.* 39, 2003-2011
15. MacLaren, D. C., Gambhir, S. S., Satyamurthy, N., Barrio, J. R., Sharfstein, S., Toyokuni, T., Wu, L., Berk, A. J., Cherry, S. R., Phelps, M. E. & Herschman, H. R. (1999) *Gene Ther.* 6, 785-791
16. Iyer, M., Barrio, J. R., Namavari, M., Bauer, E., Satyamurthy, N., Nguyen, K., Toyokuni, T., Phelps, M. E., Herschman, H. R. & Gambhir, S. S. (2001) *J. Nucl. Med.* 42, 96-105
17. Gambhir, S. S., Bauer, E., Black, M. E., Liang, Q., Kokoris, M. S., Barrio, J. R., Iyer, M., Namavari, M., Satyamurthy, N., Green, L. A., et al. (2000) *Proc. Natl. Acad. Sci. USA* 97, 2785-2790
18. Anderson, L. M. & Swaminathan, S. (1999) *Gene Ther.* 6, 854-864
19. Bui, L. A., Butterfield, L. H., Kim, J. Y., Ribas, A., Seu, P., Lau, R., Glaspy, J. A., McBride, W. H. & Economou, J. S. (1997) *Hum. Gene Ther.* 8, 2169-2170
20. Wu, L., Matherly, J., Smallwood, A., Belldegrun, A. S. & Carey, M. (2001) *Gene Ther.* 8, 1416-1426
21. Li, X., Eastman, E. M., Schwartz, R. J. & Draghia-Akli, R. (1999) *Nat. Biotechnol.* 17, 241-245
22. Choi, T., Huang, M., Gorman, C. & Jaenisch, R. (1991) *Mol. Cell. Biol.* 11, 3070-3074
23. Donello, J. E., Loeb, J. E. & Hope, T. J. (1998) *J. Virol.* 12, 5085-5092
24. Henley, D. C. & Wir, J. P. (1991) *Virus Res.* 20, 121-132
25. Emami, K. H. & Carey, M. (1992) *EMBO J.* 11, 5005-5012
26. Sadowski, I., Ma, J., Triezenberg, S. J. & Ptashne, M. (1988) *Nature (London)* 335, 563-564
27. Nettelbeck, D. M., Jerome, V. & Muller, R. (2000) *Trends Genet.* 16, 174-181
28. Sadowski, I. (1995) *Genet. Eng.* 17, 119-148
29. Pang, S., Dannull, J., Kaboo, R., Xie, Y., Tso, C. L., Michel, K., deKernion, J. B. & Belldegrun, A. S. (1997) *Cancer Res.* 57, 495-499
30. Gill, G. & Ptashne, M. (1988) *Nature (London)* 334, 721-724
31. Cleutjens, K. B., van der Korput, H. A., Ehren-van Eekelen, C. C., van Rooij, H. C., Faber, P. W. & Trapman, J. (1997) *Mol. Endocrinol.* 11, 148-161
32. Carey, M., Leatherwood, J. & Ptashne, M. (1990) *Science* 247, 710-712
33. Nettelbeck, D. M., Jerome, V. & Muller, R. (1998) *Gene Ther.* 5, 1656-1664
34. Carey, M., Lin, Y. S., Green, M. R. & Ptashne, M. (1990) *Nature (London)* 345, 361-364
35. Koster, R. W. & Fraser, S. E. (2001) *Dev. Biol.* 233, 329-346
36. Fang, B., Ji, L., Bouvet, M. & Roth, J. A. (1998) *J. Biol. Chem.* 273, 4972-4975
37. Segawa, T., Takebayashi, H., Kakehi, Y., Yoshida, O., Narumiya, S. & Kakizuka, A. (1998) *Cancer Res.* 58, 2282-2287
38. Braselmann, S., Graninger, P. & Busslinger, M. (1993) *Proc. Natl. Acad. Sci. USA* 90, 1657-1661
39. Somia, N. and Verma, I. M. (2000). Gene therapy: trials and tribulations. *Nat. Rev. Genet.* 1: 91-99
40. Shalev, M., et al. (2001). Gene therapy for prostate cancer. *Urology* 57: 8-16
41. Anderson, W. F. (1998). Human gene therapy. *Nature* 392: 25-30
42. Taneja, S. S., Pang, S., Cohan, P. and Belldegrun, A. (1995). Gene therapy: principles and potential. *Cancer Surv.* 23: 247-266
43. Rubinchik, S., et al. (2000). Adenoviral vector which delivers FasL-GFP fusion protein regulated by the tet-inducible expression system. *Gene. Ther.* 7: 875-885
44. Cleutjens, K. B., et al. (1996). Two androgen response regions cooperate in steroid hormone regulated activity of the prostate-specific antigen promoter. *J. Biol. Chem.* 271: 6379-6388
45. Schuur, E. R., et al. (1996). Prostate-specific antigen expression is regulated by an upstream enhancer. *J. Biol. Chem.* 271: 7043-7051
46. Farmer, G., Connolly, E. S., Jr., Mocco, J. and Freedman, L. P. (2001). Molecular analysis of the prostate-specific antigen upstream gene enhancer. *Prostate* 46: 76-85
47. Pang, S., et al. (1995). Prostate tissue specificity of the prostate-specific antigen promoter isolated from a patient with prostate cancer. *Hum. Gene. Ther.* 6: 1417-1426
48. Huang, W., et al. (1999). Cooperative assembly of androgen receptor into a nucleoprotein complex that regulates the prostate-specific antigen enhancer. *J. Biol. Chem.* 274: 25756-25768
49. Yeung, F., et al. (2000). Regions of prostate-specific antigen (PSA) promoter confer androgen-independent expression of PSA in prostate cancer cells. *J. Biol. Chem.* 275: 40846-40855
50. Perez-Stable, C. M., Pozas, A. and Roos, B. A. (2000). A role for GATA transcription factors in the androgen regulation of the prostate-specific antigen gene enhancer. *Mol. Cell. Endocrinol.* 167: 43-53
51. Oettgen, P., et al. (2000). PDEF, a novel prostate epithelium-specific ets transcription factor, interacts with the androgen receptor and activates prostate-specific antigen gene expression. *J. Biol. Chem.* 275: 1216-1225
52. Murphy, E. P., et al. (2001). Involvement of the nuclear orphan receptor NURR1 in the regulation of corticotropin-releasing hormone expression and actions in human inflammatory arthritis. *Arthritis Rheum.* 44: 782-793
53. Wu, L., et al. (2001). Chimeric PSA enhancers exhibit augmented activity in prostate cancer gene therapy vectors. *Gene. Ther.* 8: 1416-1426
54. Nettelbeck, D. M., Jerome, V. and Muller, R. (2000). Gene therapy: designer promoters for tumour targeting. *Trends Genet.* 16: 174-181
55. Sadowski, I., Ma, J., Triezenberg, S. and Ptashne, M. (1988). GAL4-VP16 is an unusually potent transcriptional activator. *Nature* 335: 563-564
56. Carey, M., Lin, Y. S., Green, M. R. and Ptashne, M. (1990). A mechanism for synergistic activation of a mammalian gene by GAL4 derivatives. *Nature* 345: 361-364
57. Maniatis, T., et al. (1998). Structure and function of the interferon-beta enhanceosome. *Cold Spring Harb. Symp. Quant. Biol.* 63: 609-620
58. Kim, T. K. and Maniatis, T. (1997). The mechanism of transcriptional synergy of an in vitro assembled interferon-beta enhanceosome. *Mol. Cell* 1: 119-129
59. Segawa, T., et al. (1998). Prostate-specific amplification of expanded polyglutamine expression: a novel approach for cancer gene therapy. *Cancer Res.* 58: 2282-2287

60. Iyer, M., et al. (2001). Two-step transcriptional amplification as a method for imaging reporter gene expression using weak promoters. *Proc. Natl. Acad. Sci. USA* 98:14595-14600

61. Gambhir, S. S., et al. (2000). Imaging transgene expression with radionuclide imaging technologies. *Neoplasia* 2: 118-138

62. Auclerc, G., et al. (2000). Management of advanced prostate cancer. *Oncologist* 5:36-44.

63. Sadar, M. D., Hussain, M. and Bruchovsky, N. (1999). Prostate cancer: molecular biology of early progression to androgen independence. *Endocr. Relat. Cancer* 6: 487-502

64. Lee, C., et al. (1995). Regulation of proliferation and production of prostate-specific antigen in androgen-sensitive prostatic cancer cells, LNCaP, by dihydrotestosterone. *Endocrinology* 136: 796-803

65. Joly-Pharaboz, M. O., et al. (1995). Androgens inhibit the proliferation of a variant of the human prostate cancer cell line LNCaP. *J. Steroid Biochem. Mol. Biol.* 55: 67-76

66. Gill, G. and Ptashne, M. (1988). Negative effect of the transcriptional activator GAL4. *Nature* 334: 721-724

67. Koster, R. W. and Fraser, S. E. (2001). Tracing transgene expression in living zebrafish embryos. *Dev. Biol.* 233: 329-346

68. Emami, K. H. and Carey, M. (1992). A synergistic increase in potency of a multimerized VP16 transcriptional activation domain. *Embo J.* 11: 5005-5012

69. Craft, N., Shostak, Y., Carey, M. and Sawyers, C. L. (1999). A mechanism for hormone-independent prostate cancer through modulation of androgen receptor signaling by the HER-2/neu tyrosine kinase. *Nat. Med.* 5: 280-285

70. Wu, J. C., Sundaresan, G., Iyer, M. and Gambhir, S. S. (2001). Noninvasive optical imaging of firefly luciferase reporter gene expression in skeletal muscles of living mice. *Mol. Ther.* 4: 297-306

71. Nettelbeck, D. M., Jerome, V. and Muller, R. (1998). A strategy for enhancing the transcriptional activity of weak cell type-specific promoters. *Gene. Ther.* 5: 1656-1664

72. Latham, J. P., Searle, P. F., Mautner, V. and James, N. D. (2000). Prostate-specific antigen promoter/enhancer driven gene therapy for prostate cancer: construction and testing of a tissue-specific adenovirus vector. *Cancer Res.* 60: 334-341

73. Xie, X., et al. (2001). Robust prostate-specific expression for targeted gene therapy based on the human kallikrein 2 promoter. *Hum. Gene. Ther.* 12: 549-561

74. Honigman, A., et al. (2001). Imaging transgene expression in live animals. *Mol. Ther.* 4: 239-249

75. Gambhir, S. S., et al. (1999). Imaging adenoviral-directed reporter gene expression in living animals with positron emission tomography. *Proc. Natl. Acad. Sci. USA* 96:2333-2338

76. Herschman, H. R., et al. (2000). Seeing is believing: non-invasive, quantitative and repetitive imaging of reporter gene expression in living animals, using positron emission tomography. *J. Neurosci. Res.* 59: 699-705.

77. Gambhir, S. S., et al. (1998). Imaging of adenoviral-directed herpes simplex virus type 1 thymidine kinase reporter gene expression in mice with radiolabeled ganciclovir. *J. Nucl. Med.* 39: 2003-2011.

78. Putz, T., et al. (1999). Epidermal growth factor (EGF) receptor blockade inhibits the action of EGF, insulin-like growth factor I, and a protein kinase A activator on the mitogen-activated protein kinase pathway in prostate cancer cell lines. *Cancer Res.* 59:227-233.

79. Gioeli, D., et al. (1999). Activation of mitogen-activated protein kinase associated with prostate cancer progression. *Cancer Res.* 59: 279-284.

80. Lin, J., Adam, R. M., Santiestevan, E. and Freeman, M. R. (1999). The phosphatidylinositol 3'-kinase pathway is a dominant growth factor-activated cell survival pathway in LNCaP human prostate carcinoma cells. *Cancer Res.* 59: 2891-2897.

81. Sadar, M. D. (1999). Androgen-independent induction of prostate-specific antigen gene expression via cross-talk between the androgen receptor and protein kinase A signal transduction pathways. *J. Biol. Chem.* 274: 7777-7783.

82. Carey, M., Leatherwood, J. and Ptashne, M. (1990). A potent GAL4 derivative activates transcription at a distance in vitro. *Science* 247: 710-712.

83. D'Amico, A. V. et al. Estimating the impact on prostate cancer mortality of incorporating prostate-specific antigen testing into screening. *Urology* 58, 406-10 (2001).

84. Cookson, M. M. Prostate cancer: screening and early detection. *Cancer Control* 8, 133-40 (2001).

85. Nash, A. F. & Melezinek, I. The role of prostate specific antigen measurement in the detection and management of prostate cancer. *Endocr Relat Cancer* 7, 37-51 (2000).

86. Hussain, A. & Dawson, N. Management of advanced/metastatic prostate cancer: 2000 update. *Oncology (Huntingt)* 14, 1677-88; discussion 1688, 1691-4 (2000).

87. Rini, B. I. & Small, E. J. An update on prostate cancer. *Curr Opin Oncol* 13, 204-11 (2001).

88. Bloomfield, D. J. et al. Economic evaluation of chemotherapy with mitoxantrone plus prednisone for symptomatic hormone-resistant prostate cancer: based on a Canadian randomized trial with palliative end points. *J Clin Oncol* 16, 2272-9 (1998).

89. Shalev, M. et al. Suicide gene therapy toxicity after multiple and repeat injections in patients with localized prostate cancer. *J Urol* 163, 1747-50 (2000).

90. Wu, L. et al. Chimeric PSA enhancers exhibit augmented activity in prostate cancer gene therapy vectors. *Gene Ther* 8, 1416-26 (2001).

91. Klein, K. A. et al. Progression of metastatic human prostate cancer to androgen independence in immunodeficient SCID mice. *Nat Med* 3, 402-8 (1997).

92. Craft, N. et al. Evidence for clonal outgrowth of androgen-independent prostate cancer cells from androgen-dependent tumors through a two-step process. *Cancer Res* 59, 5030-6 (1999).

93. Rehemtulla, A. et al. Rapid and quantitative assessment of cancer treatment response using in vivo bioluminescence imaging. *Neoplasia* 2, 491-5 (2000).

94. Wu, J. C., Sundaresan, G., Iyer, M. & Gambhir, S. S. Noninvasive optical imaging of firefly luciferase reporter gene expression in skeletal muscles of living mice. *Mol Ther* 4, 297-306 (2001).

95. Honigman, A. et al. Imaging transgene expression in live animals. *Mol Ther* 4, 239-49 (2001).

96. Yaghoubi, S. S. et al. Direct correlation between positron emission tomographic images of two reporter genes delivered by two distinct adenoviral vectors. *Gene Ther* 8, 1072-80 (2001).

97. Huggins, C. & Hodges, C. V. Studies on prostatic cancer. I. The effect of castration, of estrogen and androgen injection on serum phosphatases in metastatic carcinoma of the prostate. *CA Cancer J Clin* 22, 232-40 (1972).

98. Harrington, K. J., Spitzweg, C., Bateman, A. R., Morris, J. C. & Vile, R. G. Gene therapy for prostate cancer: current status and future prospects. *J Urol* 166, 1220-33 (2001).

99. Waller, A. S., Sharrard, R. M., Berthon, P. & Maitland, N. J. Androgen receptor localisation and turnover in human prostate epithelium treated with the antiandrogen, casodex. *J Mol Endocrinol* 24,339-51 (2000).

100. Zhao, X. Y. et al. Glucocorticoids can promote androgen-independent growth of prostate cancer cells through a mutated androgen receptor. *Nat Med* 6, 703-6 (2000).

101. Linja, M. J. et al. Amplification and overexpression of androgen receptor gene in hormone-refractory prostate cancer. *Cancer Res* 61,3550-5 (2001).

102. Sadar, M. D. Androgen-independent induction of prostate-specific antigen gene expression via cross-talk between the androgen receptor and protein kinase A signal transduction pathways. *J Biol Chem* 274, 7777-83 (1999).

103. Craft, N., Shostak, Y., Carey, M. & Sawyers, C. L. A mechanism for hormone-independent prostate cancer through modulation of androgen receptor signaling by the HER-2/neu tyrosine kinase. *Nat Med* 5, 280-5 (1999).

104. Gregory, C. W. et al. A mechanism for androgen receptor-mediated prostate cancer recurrence after androgen deprivation therapy. *Cancer Res* 61, 4315-9 (2001).

105. Signoretti, S. et al. Her-2-neu expression and progression toward androgen independence in human prostate cancer. *J Natl Cancer Inst* 92, 1918-25 (2000).

106. Gambhir, S. S. et al. Imaging adenoviral-directed reporter gene expression in living animals with positron emission tomography. *Proc Natl Acad Sci USA* 96, 2333-8 (1999).

107. Yaghoubi, S. et al. Human pharmacokinetic and dosimetry studies of [(18)F]FHBG: a reporter probe for imaging herpes simplex virus type-1 thymidine kinase reporter gene expression. *J Nucl Med* 42, 1225-34 (2001).

108. Leav, I. et al. Comparative studies of the estrogen receptors beta and alpha and the androgen receptor in normal human prostate glands, dysplasia, and in primary and metastatic carcinoma. *Am J Pathol* 159, 79-92 (2001).

109. Hall S J, Chen S H, Woo S L C: The promise and reality of cancer gene therapy. American Journal of Human Genetics 61:785-9, 1997.

110. Gomez-Navarro J, Curiel D T, Douglas J T: Gene therapy for cancer. European Journal of Cancer 35:867-85, 1999.

111. Cooper J M: Non-Infectious Gene Transfer and Expression systems for Cancer Gene Therapy, in Lattime E, Gerson S, (eds): Gene Therapy of Cancer. San Diego, Calif., Academic Press, 1999, pp 77-89

112. Grandaliano G, Choudhury G G, Abboud H E: Transgenic animal models as a tool in the diagnosis of kidney diseases. Seminars in Nephrology 15:43-9, 1995.

113. Ikenaka K, Kagawa T: Transgenic systems in studying myelin gene expression. Developmental Neuroscience 17:127-36, 1995.

114. Misslitz A, Mottram J C, Overath P, et al: Targeted integration into a rRNA locus results in uniform and high level expression of transgenes in *Leishmania* amastigotes. Molecular and Biochemical Parasitology 107:251-61, 2000.

115. Lee J H, Federoff H J, Schoeniger L O: G207, modified herpes simplex virus type 1, kills human pancreatic cancer cells in vitro. Journal of Gastrointestinal Surgery 3:127-31; discussion 32-3, 1999.

116. Zhou D, Zhou C, Chen S: Gene regulation studies of aromatase expression in breast cancer and adipose stromal cells. Journal of Steroid Biochemistry and Molecular Biology 61:273-80, 1997.

117. Nomura T, Takakura Y, Hashida M: [Cancer gene therapy by direct intratumoral injection: gene expression and intratumoral pharmacokinetics of plasmid DNA]. Gan To Kagaku Ryoho [japanese Journal of Cancer and Chemotherapy] 24:483-8, 1997.

118. Gnant M F, Noll L A, Irvine K R, et al: Tumor-specific gene delivery using recombinant vaccinia virus in a rabbit model of liver metastases. Journal of the National Cancer Institute 91:1744-50, 1999.

119. Karp M, Oker-Blom C: A streptavidin-luciferase fusion protein: comparisons and applications. Biomol Eng 16:101-4, 1999.

120. Kunert A, Hagemann M, Erdmann N: Construction of promoter probe vectors for *Synechocystis* sp. PCC 6803 using the light-emitting reporter systems Gfp and LuxAB. Journal of Microbiological Methods 41:185-94, 2000.

121. Seul K H, Beyer E C: Mouse connexin37: gene structure and promoter analysis. Biochimica et Biophysica Acta 1492:499-504, 2000.

122. Leffel S M, Mabon S A, Stewart C N, Jr.: Applications of green fluorescent protein in plants. Biotechniques 23:912-8, 1997.

123. Sauvonnet N, Pugsley A P: Identification of two regions of *Klebsiella oxytoca* pullulanase that together are capable of promoting beta-lactamase secretion by the general secretory pathway. Molecular Microbiology 22:1-7, 1996.

124. Contag C H, Jenkins D, Contag P R, et al: Use of reporter genes for optical measurements of neoplastic disease in vivo. Neoplasia 2:41-52, 2000.

125. Cherry S R, Shao Y, Silverman R W, et al: MicroPET: A high resolution PET scanner for imaging small animals. IEEE Transactions on Nuclear Science 44:1161-6, 1997.

126. Phelps M E: PET: A biological imaging technique. Neurochemical Research 16:929-94, 1991.

127. Gambhir S S, Herschman H R, Cherry S R, et al: Imaging transgene expression with radionuclide imaging technologies. Neoplasia 2:118-38, 2000.

128. Haberkorn U, Oberdorfer F, Gebert J, et al: Monitoring of gene therapy with cytosine deaminase: in vitro studies using 3H-5-fluorocytosine. Journal of Nuclear Medicine 37:87-94, 1996.

129. Stegman L D, Rehemtulla A, Beattie B, et al: Noninvasive quantitation of cytosine deaminase transgene expression in human tumor xenografts with in vivo magnetic resonance spectroscopy. Proceedings of the National Academy of Sciences of the United States of America 96:9821-6, 1999.

130. Gambhir S S, Barrio J R, Herschman H R, et al: Imaging gene expression: principles and assays. Journal of Nuclear Cardiology 6:219-33, 1999.

131. Gambhir S S, Bauer E, Black M E, et al: A mutant herpes simplex virus type 1 thymidine kinase reporter gene shows improved sensitivity for imaging reporter gene expression with positron emission tomography. Proceedings of the National Academy of Sciences of the United States of America 97:2785-90, 2000.

132. MacLaren D C, Gambhir S S, Cherry S R, et al: Repetitive and Non-invasive in vivo imaging of reporter gene expression using andenovirus delivered dopamine D2 receptor as a PET reporter gene and FESP as a PET reporter probe. Journal of Nuclear Medicine 39:35P, 1998.

133. MacLaren D C, Gambhir S S, Satyamurthy N, et al: Repetitive, non-invasive imaging of the dopamine $D_2$ receptor as a reporter gene in living animals. Gene Therapy 6:785-91, 1999.

134. Q Liang, N Satyamurthy, J R Barrio, et al: Noninvasive, Quantitative Imaging, in Living Animals, of a Mutant Dopamine D2 Receptor Reporter Gene in which Ligand Binding is Uncoupled from Signal Transduction. Gene Therapy, In press.
135. Iyer M, Barrio J R, Namavari M, et al: 8-[F-18]fluoropenciclovir: An improved reporter probe for imaging HSV1-tk reporter gene expression in vivo using PET. Journal of Nuclear Medicine 42:96-105, 2001.
136. Rogers B E, Zinn K R, Buchsbaum D J: Gene transfer strategies for improving radiolabeled peptide imaging and therapy. Quarterly Journal of Nuclear Medicine 44:208-23, 2000.
137. Loimas S, Wahlfors J, Jänne J: Herpes simplex virus thymidine kinase-green fluorescent protein fusion gene: new tool for gene transfer studies and gene therapy. Biotechniques 24:614-8, 1998.
138. Steffens S, Frank S, Fischer U, et al: Enhanced green fluorescent protein fusion proteins of herpes simplex virus type 1 thymidine kinase and cytochrome P450 4B1: applications for prodrug-activating gene therapy. Cancer Gene Therapy 7:806-12, 2000.
139. Jacobs A, Dubrovin M, Hewett J, et al: Functional coexpression of HSV-1 thymidine kinase and green fluorescent protein: implications for noninvasive imaging of transgene expression. Neoplasia 1:154-61, 1999.
140. Strathdee C A, McLeod M R, Underhill T M: Dominant positive and negative selection using luciferase, green fluorescent protein and beta-galactosidase reporter gene fusions. Biotechniques 28:210-2, 4, 2000.
141. Sonenberg N, Pelletier J: Poliovirus Translation—a Paradigm for a Novel Initiation Mechanism. Bioessays 11:128-32, 1989.
142. Jang S K, Kräusslich H G, Nicklin M J, et al: A segment of the 5' nontranslated region of encephalomyocarditis virus RNA directs internal entry of ribosomes during in vitro translation. Journal of Virology 62:2636-43, 1988.
143. Jang S K, Davies M V, Kaufman R J, et al: Initiation of protein synthesis by internal entry of ribosomes into the 5' nontranslated region of encephalomyocarditis virus RNA in vivo. Journal of Virology 63:1651-60, 1989.
144. Yu Y, Annala A J, Barrio J R, et al: Quantification of target gene expression by imaging reporter gene expression in living animals. Nature Medicine 6:933-7, 2000.
145. Tjuvajev J G, Joshi A, Callegari J, et al: A general approach to the non-invasive imaging of transgenes using cis-linked herpes simplex virus thymidine kinase. Neoplasia 1:315-20, 1999.
146. Kamoshita N, Tsukiyama-Kohara K, Kohara M, et al: Genetic analysis of internal ribosomal entry site on hepatitis C virus RNA: implication for involvement of the highly ordered structure and cell type-specific transacting factors. Virology 233:9-18, 1997.
147. Yaghoubi S S, Wu L, Liang Q, et al: Direct Correlation between Positron Emission Tomographic Images of Two Reporter Genes Delivered by Two Distinct Adenoviral Vectors. Gene Therapy, In press.
148. Sun X, Annala A, Yaghoubi S, et al: Quantitative imaging of gene induction in living animals. Gene Therapy, In press.
149. Louie A H, M M; Ahrens, E T; Rothbächer, U; Moats, R; Jacobs, R E; Fraser, S E; Meade, T J.: In vivo visualization of gene expression using magnetic resonance imaging. Nature Biotechnology 18:321-5., 2000.
150. Weissleder R, Moore A, Mahmood U, et al: In vivo magnetic resonance imaging of transgene expression. Nature Medicine 6:351-5, 2000.
151. Bogdanov A J, Simonova M, Weissleder R: Design of metal-binding green fluorescent protein variants. Biochimica et Biophysica Acta 1397:56-64, 1998.
152. Contag P R, Olomu I N, Stevenson D K, et al: Bioluminescent indicators in living mammals. Nature Medicine 4:245-7, 1998.
153. Yang M, Baranov E, Jiang P, et al: Whole-body optical imaging of green fluorescent protein-expressing tumors and metastases. Proceedings of the National Academy of Sciences of the United States of America 97:1206-11, 2000.
154. Yaghoubi S S, Barrio J R, Dahlbom M, et al: Human Pharmacokinetics and dosiometry studies of [18F]FHBG: A reporter Probe for Imaging Herpes Simplex Virus Type 1 Thymidine Kinase (HSV1-tk) reporter Gene Expression. Journal of Nuclear Medicine, In press.
155. Jacobs A, Braunlich I, Graf R, et al: Quantitative kinetics of [I-124]FIAU in cat and man. Journal of Nuclear Medicine 42:467-75, 2001.
156. Herschman H R, MacLaren D C, Iyer M, et al: Seeing is believing: non-invasive, quantitative and repetitive imaging of reporter gene expression in living animals, using positron emission tomography. Journal of Neuroscience Research 59:699-705, 2000.
157. Green L, Nyugen k, Bauer E, et al: Indirect monitoring of endogenous gene expression by imaging PET reporter gene in transgenic mice. Journal of Nuclear Medicine 41:81P, 2000.
158. Tjuvajev J G, Finn R, Watanabe K, et al: Noninvasive imaging of herpes virus thymidine kinase gene transfer and expression: A potential method for monitoring clinical gene therapy. Cancer Research 56:4087-95, 1996.
159. Tjuvajev J G, Chen S H, Joshi A, et al: Imaging adenoviral-mediated herpes virus thymidine kinase gene transfer expression in vivo. Cancer Research 59:5186-93, 1999.
160. Tjuvajev J G, Avril N, Oku T, et al: Imaging herpes virus thymidine kinase gene transfer and expression by positron emission tomography. Cancer Research 58:4333-41, 1998.
161. Haubner R, Avril N, Hantzopoulos P A, et al: In vivo imaging of herpes simplex virus type 1 thymidine kinase gene expression: early kinetics of radiolabelled FIAU. European Journal of Nuclear Medicine 27:283-91, 2000.
162. Morin K W, Atrazheva E D, Knaus E E, et al: Synthesis and cellular uptake of 2'-substituted analogues of (E)-5-(2-[125I]Iodovinyl-2'-deoxyuridine in tumor cells transduced with the herpes simplex type-1 thymidine kinase gene. Evaluation as probes for monitoring gene therapy. Journal of Medicinal Chemistry 40:2184-90, 1997.
163. Wiebe L I, Knaus E E, Morin K W: Radiolabelled pyrimidine nucleosides to monitor the expression of HSV-1 thymidine kinase in gene therapy. Nucleosides and Nucleotides 18:1065-6, 1999.
164. Germann C, Shields A F, Grierson J R, et al: 5-Fluoro-1-(2'-deoxy-2'-fluoro-beta-D-ribofuranosyl)uracil trapping in Morris hepatoma cells expressing the herpes simplex virus thymidine kinase gene. Journal of Nuclear Medicine 39:1418-23, 1998.
165. Haberkorn U, Altmann A, Morr I, et al: Monitoring gene therapy with herpes simplex virus thymidine kinase in hepatoma cells: uptake of specific substrates. Journal of Nuclear Medicine 38:287-94, 1997.
166. Haberkorn U, Khazaie K, Morr I, et al: Ganciclovir uptake in human mammary carcinoma cells expressing herpes simplex virus thymidine kinase. Nuclear Medicine and Biology 25:367-73, 1998.
167. Gambhir S S, Barrio J, Wu L, et al: Imaging of adenoviral directed herpes simplex virus Type 1 thymidine kinase 168. Gambhir S S, Barrio J R, Phelps M E, et al: Imaging adenoviral-directed reporter gene expression in living animals with positron emission tomography. Proceedings of the National Academy of Sciences of the United States of America 96:2333-8, 1999.
169. Alauddin M M, Conti P S, Mazza S M, et al: 9-[(3-[18F]-fluoro-1-hydroxy-2-propoxy)methyl]guanine ([18F]-FHPG): a potential imaging agent of viral infection and gene therapy using PET. Nuclear Medicine and Biology 23:787-92, 1996.
170. Alauddin M M, Shahinian A, Kundu R K, et al: Evaluation of 9-[(3-18F-fluoro-1-hydroxy-2-propoxy)methyl] guanine ([18F]-FHPG) in vitro and in vivo as a probe for PET imaging of gene incorporation and expression in tumors. Nuclear Medicine and Biology 26:371-6, 1999.
171. de Vries E F J, van Waarde A, Harmsen M C, et al: [C-11]FMAU and [F-18]FHPG as PET tracers for herpes simplex virus thymidine kinase enzyme activity and human cytomegalovirus infections]. Nuclear Medicine and Biology 27:113-9, 2000.
172. Hospers G A P, Calogero A, van Waarde A, et al: Monitoring of herpes simplex virus thymidine kinase enzyme activity using positron emission tomography. Cancer Research 60:1488-91, 2000.
173. Hustinx R, Shiue C Y, Alavi A, et al: Imaging in vivo herpes simplex virus thymidine kinase gene transfer to tumour-bearing rodents using positron emission tomography and [F-18]FHPG. European Journal of Nuclear Medicine V28:5-12, 2001.
174. Alauddin M M, Conti P S: Synthesis and preliminary evaluation of 9-(4-[18F]-fluoro-3-hydroxymethylbutyl) guanine ([18F]FHBG): a new potential imaging agent for viral infection and gene therapy using PET. Nuclear Medicine and Biology 25:175-80, 1998.
175. Rogers B E, McLean S F, Kirkman R L, et al: In vivo localization of [(111)In]-DTPA-D-Phe1-octreotide to human ovarian tumor xenografts induced to express the somatostatin receptor subtype 2 using an adenoviral vector. Clinical Cancer Research 5:383-93, 1999.
176. Buchsbaum D J, Rogers B E, Khazaeli M B, et al: Targeting strategies for cancer radiotherapy. Clinical Cancer Research 5:3048s-55s, 1999.
177. Zinn K R, Buchsbaum D J, Chaudhuri T R, et al: Non-invasive monitoring of gene transfer using a reporter receptor imaged with a high-affinity peptide radiolabeled with Tc-99m or Re-188. Journal of Nuclear Medicine 41:887-95, 2000.
178. Bogdanov A, Jr., Petherick P, Marecos E, et al: In vivo localization of diglycylcysteine-bearing synthetic peptides by nuclear imaging of oxotechnetate transchelation. Nuclear Medicine and Biology 24:739-42, 1997.
179. Rogers B E, Rosenfeld M E, Khazaeli M B, et al: Localization of iodine-125-mIP-Des-Met14-bombesin (7-13) NH2 in ovarian carcinoma induced to express the gastrin releasing peptide receptor by adenoviral vector-mediated gene transfer. Journal of Nuclear Medicine 38:1221-9, 1997.
180. Rogers B E, Curiel D T, Mayo M S, et al: Tumor localization of a radiolabeled bombesin analogue in mice bearing human ovarian tumors induced to express the gastrin-releasing peptide receptor by an adenoviral vector. Cancer 80:2419-24, 1997.
181. Rosenfeld M E, Rogers B E, Khazaeli M B, et al: Adenoviral-mediated delivery of gastrin-releasing peptide receptor results in specific tumor localization of a bombesin analogue in vivo. Clinical Cancer Research 3:1187-94, 1997.
182. Baidoo K E, Scheffel U, Stathis M, et al: High-affinity no-carrier-added 99mTc-labeled chemotactic peptides for studies of inflammation in vivo. Bioconjugate Chemistry 9:208-17, 1998.
183. Haberkor U, Henza M, Altmann A, Jiang S, Morr I, Mahmut M, Peschke P, Kubler W, Debus J nad Eisenhut M: Transfer of th Human NaI Symporter Gene Enhances Iodide Uptake in Hepatoma Cells. Journal of Nuclear Medicine 42:317-25, 2001.
184. Boland A, Ricard M, Opolon P, et al: Adenovirus-mediated transfer of the thyroid sodium/iodide symporter gene into tumors for a targeted radiotherapy. Cancer Research 60:3484-92, 2000.
185. Enochs W S, Petherick P, Bogdanova A, et al: Paramegnetic metal scavenging by melanin: MR imaging. Radiology 204:417-23, 1997.
186. Weissleder R, Simonova M, Bogdanova A, et al: MR imaging and scintigraphy of gene expression through melanin induction. Radiology 204:425-9, 1997.
187. Yang M, Baranov E, Li X M, et al: Whole-body and intravital optical imaging of angiogenesis in orthotopically implanted tumors. Proceedings of the National Academy of Sciences of the United States of America 98:2616-21, 2001.
188. Yang M, Baranov E, Moossa A R, et al: Visualizing gene expression by whole-body fluorescence imaging. Proceedings of the National Academy of Sciences of the United States of America 97:12278-82, 2000.
189. Yang M, Hasegawa S, Jiang P, et al: Widespread skeletal metastatic potential of human lung cancer revealed by green fluorescent protein expression. Cancer Research 58:4217-21, 1998.
190. Yang M, Jiang P, Sun F X, et al: A fluorescent orthotopic bone metastasis model of human prostate cancer. Cancer Research 59:781-6, 1999.
191. Hasegawa S, Yang M, Chishima T, et al: In vivo tumor delivery of the green fluorescent protein gene to report future occurrence of metastasis. Cancer Gene Therapy 7:1336-40, 2000.
192. Pfeifer A, Kessler T, Yang M, et al: Transduction of liver cells by lentiviral vectors: analysis in living animals by fluorescence imaging. Molecular Therapy 3:319-22, 2001.
193. Contag C H, Spilman S D, Contag P R, et al: Visualizing gene expression in living mammals using a bioluminescent reporter. Photochemistry and Photobiology 66:523-31, 1997.
194. Tung C H, Mahmood U, Bredow S, et al: In vivo imaging of proteolytic enzyme activity using a novel molecular reporter. Cancer Research 60:4953-8, 2000.
195. Tung C H, Bredow S, Mahmood U, et al: A cathepsin D sensitive near infrared fluorescence probe for in vivo imaging of enzyme activity. Bioconj Chem 10:892-6, 1999.
196. Weissleder R, Tung C H, Mahmood U, et al: In vivo imaging of tumors with protease-activated near-infrared fluorescent probes. Nature Biotechnology 17:375-8, 1999.

Abate-Shen, C. and M. M. Shen. 2000. Molecular genetics of prostate cancer. *Genes Dev* 14: 2410-34.

Adams, J. Y., M. Johnson, M. Sato, F. Berger, S. S. Gambhir, M. Carey, M. L. Iruela-Arispe, and L. Wu. 2002. Visualization of advanced human prostate cancer lesions in living mice by a targeted gene transfer vector and optical imaging. *Nat Med* 8: 891-7.

Arnold, J. T. and J. T. Isaacs. 2002. Mechanisms involved in the progression of androgen-independent prostate cancers: it is not only the cancer cell's fault. *Endocr Relat Cancer* 9: 61-73.

Barrack, E. R. 1996. Androgen receptor mutations in prostate cancer. *Mt Sinai J Med* 63: 403-12.

Bok, R. A. and E. J. Small. 2002. Bloodborne biomolecular markers in prostate cancer development and progression. *Nat Rev Cancer* 2: 918-26.

Brand, A. H. and N. Perrimon. 1993. Targeted gene expression as a means of altering cell fates and generating dominant phenotypes. *Development* 118: 401-15.

Chen, C. D. and C. L. Sawyers. 2002. NF-kappa B activates prostate-specific antigen expression and is upregulated in androgen-independent prostate cancer. *Mol Cell Biol* 22: 2862-70.

Cleutjens, K. B., H. A. van der Korput, C. C. Ehren-van Eekelen, R. A. Sikes, C. Fasciana, L. W. Chung, and J. Trapman. 1997a. A 6-kb promoter fragment mimics in transgenic mice the prostate-specific and androgen-regulated expression of the endogenous prostate-specific antigen gene in humans. *Mol Endocrinol* 11: 1256-65.

Cleutjens, K. B., H. A. van der Korput, C. C. van Eekelen, H. C. van Rooij, P. W. Faber, and J. Trapman. 1997b. An androgen response element in a far upstream enhancer region is essential for high, androgen-regulated activity of the prostate-specific antigen promoter. *Mol Endocrinol* 11: 148-61.

Cleutjens, K. B., C. C. van Eekelen, H. A. van der Korput, A. O. Brinkman, and J. Trapman. 1996a. Two androgen response regions cooperate in steroid hormone regulated activity of the prostate-specfic antigen promoter. *J Biol Chem* 271: 6379-88.

Cleutjens, K. B., C. C. van Eekelen, H. A. van der Korput, A. O. Brinkmann, and J. Trapman. 1996b. Two androgen response regions cooperate in steroid hormone regulated activity of the prostate-specific antigen promoter. *J Biol Chem* 271: 6379-88.

Contag, C. H., D. Jenkins, P. R. Contag, and R. S. Negrin. 2000. Use of reporter genes for optical measurements of neoplastic disease in vivo. *Neoplasia* 2: 41-52.

Contag, P. R. 2002. Whole-animal cellular and molecular imaging to accelerate drug development. *Drug Discov Today* 7: 555-562.

Cosma, M. 2002. Ordered recruitment. Gene-specific mechanism of transcription activation. *Mol Cell* 10: 227.

Craft, N. and C. L. Sawyers. 1998. Mechanistic concepts in androgendependence of prostate cancer. *Cancer Metastasis Rev* 17: 421-7.

Elo, J. P. and T. Visakorpi. 2001. Molecular genetics of prostate cancer. *Ann Med* 33: 130-41.

Feldman, B. J. and D. Feldman. 2001. The development of androgenindependent prostate cancer. *Nat Rev Cancer* 1: 34-45.

Freedman, L. P. 1999. Increasing the complexity of coactivation in nuclear receptor signaling. *Cell* 97: 5-8.

Gambhir, S. S. 2002. Molecular imaging of cancer with positron emission tomography. *Nat Rev Cancer* 2: 683-93.

Gelmann, E. P. 2002. Molecular biology of the androgen receptor. *J Clin Oncol* 20: 3001-15.

Gilmour, D. S. and J. T. Lis. 1986. RNA polymerase II interacts with the promoter region of the noninduced hsp70 gene in *Drosophila melanogaster* cells. *Mol Cell Biol* 6: 3984-9.

Gioeli, D., J. W. Mandell, G. R. Petroni, H. F. Frierson, Jr., and M. J. Weber. 1999. Activation of mitogen-activated protein kinase associated with prostate cancer progression. *Cancer Res* 59: 279-84.

Gregory, C. W., R. T. Johnson, Jr., J. L. Mohler, F. S. French, and E. M. Wilson. 2001. Androgen receptor stabilization in recurrent prostate cancer is associated with hypersensitivity to low androgen. *Cancer Res* 61: 2892-8.

Grossmann, M. E., H. Huang, and D. J. Tindall. 2001. Androgen receptor signaling in androgen-refractory prostate cancer. *J Natl Cancer Inst* 93: 1687-97.

Han, G., B. A. Foster, S. Mistry, G. Buchanan, J. M. Harris, W. D. Tilley, and N. M. Greenberg. 2001. Hormone status selects for spontaneous somatic androgen receptor variants that demonstrate specific ligand and cofactor dependent activities in autochthonous prostate cancer. *J Biol Chem* 276:11204-13.

He, T. C., S. Zhou, L. T. da Costa, J. Yu, K. W. Kinzler, and B. Vogelstein. 1998. A simplified system for generating recombinant adenoviruses. *Proc Natl Acad Sci USA* 95: 2509-14;

Herschman, H. R., D. C. MacLaren, M. Iyer, M. Namavari, K. Bobinski, L. A. Green, L. Wu, A. J. Berk, T. Toyokuni, J. R. Barrio, S. R. Cherry, M. E. Phelps, E. P. Sandgren, and S. S. Gambhir. 2000. Seeing is believing: noninvasive, quantitative and repetitive imaging of reporter gene expression in living animals, using positron emission tomography. *J Neurosci Res* 59: 699-705.

Horoszewicz, J. S., S. S. Leong, E. Kawinski, J. P. Karr, H. Rosenthal, T. M. Chu, E. A. Mirand, and G. P. Murphy. 1983. LNCaP model of human prostatic carcinoma. *Cancer Res* 43: 1809-18.

Huang, W., Y. Shostak, P. Tarr, C. Sawyers, and M. Carey. 1999. Cooperative assembly of androgen receptor into a nucleoprotein complex that regulates the prostate-specific antigen enhancer. *J Biol Chem* 274: 25756-68.

Iyer, M., L. Wu, M. Carey, Y. Wang, A. Smallwood, and S. S. Gambhir. 2001. Two-step transcriptional amplification as a method for imaging reporter gene expression using weak promoters. *Proc. Natl. Acad. Sci. USA* 98:14595-14600.

Kang, Z., A. Pirskanen, O. A. Janne, and J. J. Palvimo. 2002. Involvement of proteasome in the dynamic assembly of the androgen receptor transcription complex. *J Biol Chem* 277: 48366-71.

Klein, K. A., R. E. Reiter, J. Redula, H. Moradi, X. L. Zhu, A. R. Brothman, D. J. Lamb, M. Marcelli, A. Beildegrun, O. N. Witte, and C. L. Sawyers. 1997. Progression of metastatic human prostate cancer to androgen independence in immunodeficient SCID mice. *Nat Med* 3: 402-8.

Linja, M. J., K. J. Savinainen, O. R. Saramaki, T. L. Tammela, R. L. Vessella, and T. Visakorpi. 2001. Amplification and overexpression of androgen receptor gene in hormone-refractory prostate cancer. *Cancer Res* 61: 3550-5.

Massoud, T. and S. S. Gambhir. 2003. Molecular imaging in living subjects: Seeing fundamental biological processes in a new light. *Genes Dev* (in press).

Mellinghoff, I. K., C. Tran, and C. L. Sawyers. 2002. Growth Inhibitory Effects of the Dual ErbB1/ErbB2 Tyrosine Kinase Inhibitor PKI-166 on Human Prostate Cancer Xenografts. *Cancer Res* 62: 5254-9.

Montgomery, B. T., C. Y. Young, D. L. Bilhartz, P. E. Andrews, J. L. Prescott, N. F. Thompson, and D. J. Tindall. 1992. Hormonal regulation of prostate-specific antigen (PSA) glycoprotein in the human prostaticadenocarcinoma cell line, LNCaP. *Prostate* 21: 63-73.

O'Connell-Rodwell, C. E., S. M. Burns, M. H. Bachmann, and C. H. Contag. 2002. Bioluminescent indicators for in vivo measurements of gene expression. *Trends Biotechnol* 20: S19-23.

Pang, S., J. Dannull, R. Kaboo, Y. Xie, C. L. Tso, K. Michel, J. B. deKernion, and A. S. Belldegrun. 1997. Identification of a positive regulatory element responsible for tissue-specific expression of prostate-specific antigen. *Cancer Res* 57: 495-9.

Pang, S., S. Taneja, K. Dardashti, P. Cohan, R. Kaboo, M. Sokoloff, C. L. Tso, J. B. Dekernion, and A. S. Belldegrun. 1995. Prostate tissue specificity of the prostate-specific antigen promoter isolated from a patient with prostate cancer. *Hum Gene Ther* 6: 1417-26.

Pfeifer, A. and I. M. Verma. 2001. Gene therapy: promises and problems. *Annu Rev Genomics Hum Genet* 2: 177-211.

Reid, K. J., S. C. Hendy, J. Saito, P. Sorensen, and C. C. Nelson. 2001. Two classes of androgen receptor elements mediate cooperativity through allosteric interactions. *J Biol Chem* 276: 2943-52.

Schuur, E. R., G. A. Henderson, L. A. Kmetec, J. D. Miller, H. G. Lamparski, and D. R. Henderson. 1996. Prostate-specific antigen expression is regulated by an upstream enhancer. *J Biol Chem* 271: 7043-51.

Shang, Y., M. Myers, and M. Brown. 2002. Formation of the androgen receptor transcription complex. *Mol Cell* 9: 601-10.

Stanbrough, M., 1. Leav, P. W. Kwan, G. J. Bubley, and S. P. Balk. 2001. Prostatic intraepithelial neoplasia in mice expressing an androgen receptor transgene in prostate epithelium. *Proc Natl Acad Sci USA* 98: 10823-8.

Tilley, W. D., C. M. Wilson, M. Marcelli, and M. J. McPhaul. 1990. Androgen receptor gene expression in human prostate carcinoma cell lines. *Cancer Res* 50: 5382-6.

Visakorpi, T., E. Hyytinen, P. Koivisto, M. Tanner, R. Keinanen, C. Palmberg, A. Palotie, T. Tammela, J. Isola, and O. P. Kallioniemi. 1995. In vivo amplification of the androgen receptor gene and progression of human prostate cancer. *Nat Genet* 9: 401-6.

Wood, M., P. Perrotte, E. Onishi, M. E. Harper, C. Dinney, L. Pagliaro, and D. R. Wilson. 1999. Biodistribution of an adenoviral vector carrying the luciferase reporter gene following intravesical or intravenous administration to a mouse. *Cancer Gene Ther* 6: 367-72.

Wu, J. C., G. Sundaresan, M. Iyer, and S. S. Gambhir. 2001a. Noninvasive optical imaging of firefly luciferase reporter gene expression in skeletal muscles of living mice. *Mol Ther* 4: 297-306.

Wu, L., J. Matherly, A. Smallwood, J. Y. Adams, E. Billick, A. Belldegrun, and M. Carey. 2001b. Chimeric PSA enhancers exhibit augmented activity in prostate cancer gene therapy vectors. *Gene Ther* 8: 1416-26.

Yeung, F., X. Li, J. Ellett, J. Trapman, C. Kao, and L. W. Chung. 2000. Regions of prostate-specific antigen (PSA) promoter confer androgen-independent expression of PSA in prostate cancer cells. *J Biol Chem* 275: 40846-55.

Zegarra-Moro, O. L., L. J. Schmidt, H. Huang, and D. J. Tindall. 2002. Disruption of androgen receptor function inhibits proliferation of androgen-refractory prostate cancer cells. *Cancer Res* 62: 1008-13.

Zhang, L., J. Y. Adams, E. Billick, R. Ilagan, M. Iyer, K. Le, A. Smallwood, S. S. Gambhir, M. Carey, and L. Wu. 2002. Molecular engineering of a two-step transcription amplification (TSTA) system for transgene delivery in prostate cancer. *Mol Ther* 5: 223-32.

Zhang, S., P. E. Murtha, and C. Y. Young. 1997. Defining a functional androgen responsive element in the 5' far upstream flanking region of the prostate specific antigen gene. *Biochem Biophys Res Commun* 231: 784-8.

What is claimed is:

1. An expression vector comprising:
   a first expression cassette, comprising
   a. a mammalian tissue-specific enhancer sequence,
   b. a mammalian tissue-specific promoter sequence operably linked to the tissue specific enhancer sequence; and
   c. a nucleotide sequence encoding a chimeric transactivator operably linked to the tissue-specific promoter sequence, wherein the encoded transactivator comprises a GAL4 DNA binding domain and two to four copies of a VP16 viral transcription activation domain; and
   a second expression cassette, comprising
   a. at least two GAL4 binding sequences;
   b. an adenoviral early promoter sequence operatively linked to said at least two GAL4 binding sequences, and
   c. a heterologous gene sequence operatively linked to said adenoviral early promoter sequence.

2. The expression vector of claim 1, wherein the first cassette further comprises a second tissue-specific enhancer sequence operably linked to the tissue-specific promoter.

3. The expression vector of claim 1, wherein the tissue specific enhancer sequence is from blood, prostate, brain, lung, stomach, bladder, pancreas, colon, breast, ovary, uterus, cervix, liver, muscle, skin, or bone.

4. The expression vector of claim 1, wherein the tissue specific enhancer sequence is a Prostate Specific Antigen (PSA) enhancer sequence and the tissue specific promoter is a prostate specific promoter, wherein the PSA enhancer sequence is operably linked to the prostate specific promoter.

5. The expression vector of claim 1, wherein the at least two GAL4 binding sequences consist of 5 GAL4 binding sequences.

6. The expression vector of claim 1, wherein the Adenoviral early promoter sequence is from serotypes selected from a group consisting of Ad 1, 2, 3, 4, and 5.

7. The expression vector of claim 1, wherein the Adenoviral early promoter sequence comprises an E1a, E1b, E2a, E2b, E3, or E4 sequence.

8. The expression vector of claim 1, wherein the Adenoviral early promoter sequence comprises a TATA box sequence.

9. The expression vector of claim 1 further comprising a second heterologous gene sequence operably linked to the first heterologous gene sequence.

10. The vector of claim 1 which is a plasmid, cosmid, or phagemid.

11. The vector of claim 1 which is a bacterial vector, yeast vector, adenoviral vector, adenoviral-associated vector, lentiviral vector, or retroviral vector.

12. A host-vector system, comprising the vector system of claim 1 and a host cell.

13. The host-vector system of claim 12, wherein the host cell is a prokaryote or eukaryote.

14. A method for expressing a polypeptide, comprising growing the host-vector system of claim 12 so as to express the polypeptide wherein the polypeptide is encoded by the heterologous gene sequence of the host vector system.

15. A method for expressing a polypeptide in a subject, comprising implanting the host-vector system of claim 12 in the subject so as to express the polypeptide wherein the polypeptide is encoded by the heterologous gene sequence of the host-vector system.

16. A method for detecting expression of a polypeptide in a subject, comprising administering the host-vector system of claim 12 to a subject under suitable conditions so as to express the polypeptide, wherein the polypeptide is encoded by the heterologous gene sequence of the host-vector system and detecting the polypeptide so expressed.

17. The method of claim 15 or 16 comprising administering to the subject an agent to induce expression of the polypeptide encoded by the heterologous gene sequence.

18. The method of claim 17, wherein the tissue-specific enhancer sequence is a prostate specific enhancer sequence and the tissue specific promoter sequence is a prostate specific promoter sequence and the agent is an androgen.

19. The method of claim 16, wherein the detecting is effected by positron emission tomography, single photon emission computed tomography, cooled charged coupled device (CCD) camera optical imaging, magnetic resonance imaging, bioluminescent optical imaging, fluorescence optical imaging, radionuclide imaging, or non-radionuclide imaging.

20. The expression vector of claim 1, wherein the chimeric transactivator is a GAL4-VP16 fusion protein containing two VP16 transactivation domains.

21. The expression vector of claim 1, wherein the chimeric transactivator is a GAL4-VP16 fusion protein containing four VP16 transactivation domains.

22. The expression vector of claim 1, wherein second cassette has five copies of a GAL4 binding sequence.

23. The expression vector of claim 1, wherein said expression cassettes are arranged in a head to tail orientation.

24. The expression vector of claim 1, wherein the heterologous gene sequence encodes a therapeutic protein.

25. The expression vector of claim 4, wherein prostate specific enhancer is a PSA enhancer having a duplication of a PSE androgen response element.

26. The expression vector of claim 4, wherein prostate specific enhancer is a PSA enhancer having an insertion of ARE4 and a duplication of the PSA enhancer core.

27. The expression vector of claim 4, wherein intervening sequences (−3744 to −2855) between the enhancer and promoter are removed.

28. The expression vector of claim 4, wherein the enhancer is a PSE-BA, PSE-BC or PSE-BAC enhancer.

29. The expression vector of claim 1, wherein the tissue-specific promoter and tissue-specific enhancer are each specific to melanocytes, oligodendrocytes, glial cells, neurons, liver tumors, adenocarcinomas, pancreatic cancer, breast cancer, osteosarcoma, prostate cancer, ovarian cancer or cervical cancer.

30. A method of imaging tissue in a mammalian subject, said method comprising administering an expression vector of claim 1 to the subject and expressing the heterologous protein within the tissue, wherein the expression of the heterologous protein in the tissue is detected in the subject.

31. A method of delivering a heterologous protein to a tissue of a mammalian subject, said method comprising administering an expression vector of claim 1 to the subject, thereby transducing cells of the tissue with the vector and expressing the protein in the tissue.

32. An expression vector for expressing a protein in a tissue comprising:
   a first cassette capable of expressing in the tissue a transactivator fusion protein comprising a GAL4 DNA binding domain and two copies of a VP16-viral transcription activation domain; and
   a second expression cassette, comprising
     a. five GAL4 binding sequences;
     b. an Adenoviral early promoter sequence operatively linked to said at least five GAL-4 binding sequences, and
     c. a heterologous gene sequence operatively linked to said adenoviral early promoter sequence.

* * * * *